US007883715B2

(12) United States Patent
Abraham et al.

(10) Patent No.: US 7,883,715 B2
(45) Date of Patent: *Feb. 8, 2011

(54) PESTICIDE COMPOSITIONS CONTAINING DICARBOXYLIC ACIDS

(75) Inventors: William Abraham, Wildwood, MO (US); Michael K. Stern, Clayton, MO (US); Jeffrey Alan Graham, Chesterfield, MO (US); Xiaodong Chris Xu, Valley Park, MO (US); Ronald J. Brinker, Ellisville, MO (US); Jeffrey N. Travers, Chesterfield, MO (US); Tracey L. Reynolds, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1982 days.

This patent is subject to a terminal disclaimer.

(21) Appl. No.: 10/653,049

(22) Filed: Aug. 29, 2003

(65) Prior Publication Data

US 2004/0097372 A1 May 20, 2004

Related U.S. Application Data

(60) Provisional application No. 60/407,180, filed on Aug. 31, 2002.

(51) Int. Cl.
| | |
|---|---|
| A61K 38/16 | (2006.01) |
| A61K 31/66 | (2006.01) |
| A01N 57/16 | (2006.01) |
| A01N 57/00 | (2006.01) |
| A01N 37/00 | (2006.01) |
| A01N 25/00 | (2006.01) |

(52) U.S. Cl. ................ 424/405; 504/206; 514/7; 514/75; 514/574

(58) Field of Classification Search ............ None
See application file for complete search history.

(56) References Cited

U.S. PATENT DOCUMENTS

| | | | |
|---|---|---|---|
| 3,799,758 A | 3/1974 | Franz | |
| 4,159,901 A | 7/1979 | Beestman et al. | |
| 4,405,531 A | 9/1983 | Franz | |
| 5,070,197 A | 12/1991 | Chin et al. | |
| 5,389,598 A | 2/1995 | Berk et al. | |
| 5,436,220 A | 7/1995 | Hickey | |
| 5,525,576 A | 6/1996 | Medina-Vega et al. | |
| 5,563,111 A | 10/1996 | Hioki et al. | |
| 5,614,468 A | 3/1997 | Kramer et al. | |
| 5,622,911 A | 4/1997 | Hasebe et al. | |
| 5,633,397 A | 5/1997 | Gillespie et al. | |
| 5,665,409 A * | 9/1997 | Drewry | 426/132 |
| 5,703,015 A | 12/1997 | Berger et al. | |
| 5,750,468 A | 5/1998 | Wright et al. | |
| 5,795,847 A | 8/1998 | Nielsen et al. | |
| 5,849,663 A | 12/1998 | Hasebe et al. | |
| 5,863,863 A | 1/1999 | Hasebe et al. | |
| 5,863,909 A | 1/1999 | Kurita et al. | |
| 5,948,421 A | 9/1999 | Okano et al. | |
| 5,985,794 A | 11/1999 | Hasebe et al. | |
| 5,985,798 A | 11/1999 | Crudden | |
| 5,998,332 A | 12/1999 | Sato et al. | |
| 6,008,158 A | 12/1999 | Hasebe et al. | |
| 6,030,923 A | 2/2000 | Okano et al. | |
| 6,051,533 A | 4/2000 | Kajikawa et al. | |
| 6,063,733 A | 5/2000 | Berger et al. | |
| 6,083,875 A * | 7/2000 | Sato et al. | 504/127 |
| 6,093,679 A | 7/2000 | Azuma et al. | |
| 6,117,820 A | 9/2000 | Cutler et al. | |
| 6,180,566 B1 | 1/2001 | Nielsen et al. | |
| 6,218,336 B1 | 4/2001 | Coleman | |
| 6,245,713 B1 | 6/2001 | Brinker et al. | |
| 6,313,074 B1 | 11/2001 | Suzuki et al. | |
| 6,448,434 B1 | 9/2002 | Kramer | |
| 6,475,954 B2 | 11/2002 | Hamroll et al. | |
| 6,599,858 B1 | 7/2003 | Kramer | |
| 2002/0123430 A1* | 9/2002 | Xu et al. | 504/206 |

FOREIGN PATENT DOCUMENTS

| | | |
|---|---|---|
| EP | 0 394 211 A1 | 10/1990 |
| EP | 1 203 532 A1 | 5/2002 |
| WO | WO 90/07275 A1 | 7/1990 |
| WO | WO 92/12637 A1 | 8/1992 |
| WO | WO 94/10844 A1 | 5/1994 |
| WO | WO 95/17817 A1 | 7/1995 |
| WO | WO 01/08480 A1 | 2/2001 |
| WO | WO 01/08492 | 2/2001 |

(Continued)

OTHER PUBLICATIONS

Research Disclosure Publication No. RD 15334, Industrial Opportunities Ltd., Jan. 1977, Homewell-Havant-Hampshire P09 1EF, United Kingdom.

(Continued)

*Primary Examiner*—Ernst V Arnold
(74) *Attorney, Agent, or Firm*—Senniger Powers LLP; Joseph A. Schaper

(57) ABSTRACT

Solid and liquid pesticidal concentrate and spray compositions are described which exhibit enhanced efficacy due to the addition thereto of a compound which increases EPSPS enzyme inhibition by the pesticide, cell membrane permeability, or expression of hydroxyproline-rich glycoproteins.

78 Claims, No Drawings

FOREIGN PATENT DOCUMENTS

| WO | WO 01/30157 A1 | 5/2001 |
|---|---|---|
| WO | WO 01/89302 A2 | 11/2001 |
| WO | WO 02/069718 A2 | 9/2002 |

OTHER PUBLICATIONS

Turner, D.J. et al., "Complexing agents as herbicide additives", *Weed Research*, 1978, pp. 199-207, vol. 18, Blackwell Scientific Publications.

Turner, D.J., "Polybasic acids and their salts and esters", The Herbicide Glyphosate, 1985, pp. 229-230, Chapter 15, Butterworths.

Annex to Form PCT/ISA/206 Communication Relating to the Results of the Partial International Search pertaining to International Application No. PCT/US 03/27229.

International Search Report for PCT/US 03/27195 dated Jan. 27, 2004.

* cited by examiner

PESTICIDE COMPOSITIONS CONTAINING DICARBOXYLIC ACIDS

BACKGROUND OF THE INVENTION

The present invention relates to a method for enhancing pesticidal efficacy with dicarboxylic acids. More particularly, the present invention relates to a method of enhancing the herbicidal effectiveness of glyphosate concentrates and tank mix formulations optionally containing one or more surfactants through the addition of a dicarboxylic acid or another component which increases EPSPS enzyme inhibition by glyphosate, cell membrane permeability or hydroxyproline-rich glycoprotein expression.

Polycarboxylic acids have been added to glyphosate compositions. For example, Prill et al. WO 92/12637 discloses water soluble tablets containing glyphosate acid, an acid acceptor such as sodium oxalate, and an optional anionic surfactant. The acid acceptor is said to solubilize glyphosate acid through glyphosate salt formation upon exposure to water.

U.S. Patent Application Pub. No. US2002/0049140 A1 discloses herbicide tablets containing 20 wt % of glyphosate acid, 10 wt % surfactant, a base such as ammonium hydrogen carbonate or carbonate, and 11 wt % oxalic acid. Upon exposure to water the base reacts with the organic acid to generate carbon dioxide and improve tablet disintegration via effervescence.

U.S. Pat. No. 5,948,421 to Okano et al. describes aqueous concentrate formulations containing 37.8 wt. % (a.e.) isopropylamine glyphosate, chelating agents including 1.9 wt % (a.e.) potassium oxalate, and 8-10% surfactant.

U.S. Pat. Nos. 5,795,847 and 6,180,566 to Nielsen et al. disclose an aqueous suspension containing solid glyphosate acid, a synergistic amount of a dissolved electrolyte, most preferably ammonium sulphate, and surfactant. Optionally polycarboxylic acids may be added as pH buffers and to activate surfactant amino groups.

WO95/17817 to Hasabe et al. discloses an enhancer composition for agricultural chemicals which comprises at least one nitrogen containing surfactant and a chelating agent and the use of said composition in tank mixes with the isopropylamine salt of glyphosate in a weight ratio of 4.8:1 glyphosate to oxalic acid on an a.e. basis.

Polycarboxylic acids have been used as chelators to enhance glyphosate efficacy in tank mix compositions. For example, D. J. Turner reported in Butterworths (1985), at pages 229-230, that 2% concentrations of polycarboxylic acids in glyphosate (Roundup®) tank mixes gave efficacy enhancement. Further, Research Disclosure publication number RD15334, Industrial Opportunities Ltd., Homewell-Havant-Hampshire P09 1EF, United Kingdom (January 1977), disclosed that glyphosate tank mixes formulated with water containing calcium and/or magnesium ions in concentrations greater than 200 ppm (hard water) had diminished herbicidal activity. Herbicidal activity was restored by adding oxalic acid to the tank mix in weight ratios to glyphosate of between about 1:10 to about 10:1.

U.S. Pat. No. 5,863,863 to Hasabe et al. teaches tank mix and liquid concentrate formulations containing IPA glyphosate and oxalic acid salts in a weight ratio of 15:1 on an a.e. basis.

U.S. Pat. No. 5,525,576 to Medina-Vega et al. discloses a process for preparing a seed hull extract containing a mixture of polycarboxylic acids for use as a herbicide assimilation agent. 0.25% of the extract was added to tank mixes containing the trimethylsulfonium (TMS) salt of glyphosate (sold commercially as Touchdown®) or the isopropylamine (IPA) salt of glyphosate (sold commercially as Roundup®). U.S. Pat. No. 5,436,220 to Hickey teaches an efficacy enhancing formulation comprising a seed hull extract containing tricarboxylic acids and Roundup® herbicide, with glyphosate application rates of 64 to 191 g/ha in combination with 82 g/ha of a seed hull extract containing about 5 wt % tricarboxylic acid.

U.S. Pat. Nos. 5,849,663, 6,093,679, and 6,008,158 describe spray compositions containing TMS or IPA glyphosate, oxalic acid or potassium or diethyl oxalate, and surfactant in a weight ratio of glyphosate to oxalic acid of 4:1 to 11:1 on an a.e. basis.

U.S. Pat. No. 6,218,336 to Coleman discloses tank mixes containing up to 1.25 wt % Roundup® Ultra IPA glyphosate and 2.5 wt % of succinic, tartaric or malic acids or their ammonium salts. Sylgard 309® (ethoxylated organosilicone) and Emsorb 6900® (polyoxyethylenated sorbitol ester) surfactants may be added to the tank mixes.

It would be desirable to enhance the efficacy of solid or liquid glyphosate concentrates. Greater efficacy affords lower application rates of the herbicide to achieve the same degree of weed control. Application of less herbicide is cost effective to the consumer since less product provides equivalent weed control. Moreover, such an enhanced efficacy formulation is environmentally responsible because packaged volume is reduced, less storage space is required, shipping cost savings may be realized, and most importantly, environmental burden is minimized through reduced application rate requirements. As will be clear from the disclosure that follows, these and other benefits are provided by the present invention.

SUMMARY OF THE INVENTION

Among the several features of the invention, therefore, may be noted the provision of a pesticidal composition useful in agriculture wherein the bioefficacy of the water-soluble pesticide in the plant is increased by formulating the composition so as to include a compound which increases EPSPS enzyme inhibition by the pesticide; the provision of a pesticidal composition useful in agriculture wherein cellular uptake of the water-soluble pesticide into the foliage of a plant is increased by formulating the composition so as to include a compound which increases cell membrane permeability; the provision of a pesticidal composition which includes a compound which increases expression of hydroxyproline-rich glycoproteins; the provision of herbicidal compositions exhibiting improved control of a broad spectrum of broadleaf plants including velvetleaf and morningglory; the provision of a pesticidal composition comprising two or more co-herbicides wherein antagonism between the co-herbicides is reduced; the provision of storage stable herbicidal concentrates which can be formulated with reduced surfactant to reduce the aquatic toxicity of the formulation without reducing its performance; and the provision of storage-stable solid or liquid concentrates that are relatively easy to dilute and use.

DETAILED DESCRIPTION OF THE PREFERRED EMBODIMENTS

Oxalic acid is known to enhance the efficacy of glyphosate in controlling weeds. However, the enhancement was attributed to the ability of oxalic acid to sequester bivalent metal ions from hard water. Relatively low levels of oxalic acid and relatively high levels of surfactant were formulated as an enhancer composition to be added to a commercial glyphosate formulation to enhance its performance by increasing the amount of glyphosate delivered into the plant. More specifically, the surfactant enhances the delivery of glyphosate across the leaf cuticle.

Oxalates are also known in the art as acid acceptors for use in solid glyphosate concentrates. When the solid concentrate is dissolved in water, the oxalate reacts with glyphosate acid to form a glyphosate salt and oxalic acid. The oxalate solubilizes the glyphosate to improve dissolution of the solid concentrate.

It has been discovered that oxalic acid and derivatives thereof enhance the pesticidal activity of a pesticide by acting as either an allosteric or cooperative effecter of the inhibition of the target enzyme 5-enolpyruvylishikimate-3-phosphate synthase (hereinafter referred to as EPSP synthase or EPSPS). For example, oxalic acid increases the inhibition of EPSPS enzyme by glyphosate to enhance the physiological response of plants at the enzyme level. The oxalic acid does not affect uptake of glyphosate, but it does enhance movement of glyphosate from a leaf into the plant once the glyphosate is inside the leaf. In other words, the oxalic acid is absorbed and systemically transported throughout the plant. The enhancement is not substantially caused by the ability of oxalic acid to chelate calcium and other metal ions in hard water, although it is an effective chelant for use in hard or brackish water. In fact, oxalic acid improves efficacy significantly more than conventional chelators such as EDTA or sodium citrate. The oxalic acid efficacy advantage over EDTA is present even though EDTA possesses a chelating capability about five orders of magnitude greater than oxalic acid.

The addition of a dicarboxylic acid component can reduce the amount of surfactant needed in the composition which, upon dilution and application to foliage of a plant, provides the desired plant growth control. It also significantly improves the performance of many surfactants which otherwise provide only marginal growth control, enabling the use of a broader range of surfactants in herbicidal formulations. The compositions of the invention have been effective in controlling a broad spectrum of broadleaf plants including velvetleaf, sicklepod, morningglory, dandelion, and marestail.

Furthermore, it has been discovered that weed control can be maintained when dicarboxylic acids are substituted for pesticide in the formulation. When oxalic acid is substituted at a 1:1 (wt./wt.) ratio for glyphosate, herbicidal efficacy of the formulation is maintained. Efficacy is also maintained at relatively low surfactant levels as compared to conventional enhancer compositions. Dicarboxylic acid substitution for pesticide results in a significant reduction in the pesticide and surfactant content of a formulation which improves aquatic toxicity.

It has further been discovered that dicarboxylic acids can reduce the herbicidal antagonistic effect associated with some formulations comprising two or more co-herbicides. Antagonism typically results where the co-herbicides represent several different classes of chemistry and modes of action. Antagonism reduction thereby increases the spectrum of both co-herbicides that can be efficaciously formulated as well as the number of plant species on which the formulation is commercially effective. Moreover, antagonism reduction enables higher weed control at lower application rates.

While not wishing to be bound to any particular theory, there are several mechanisms by which a dicarboxylic acid such as oxalic acid and other compounds are likely to improve pesticide bioefficacy. First, the dicarboxylic acid increases inhibition of EPSPS target enzyme by the pesticide. Second, the dicarboxylic acid component increases cell membrane permeability in a plant by chelating calcium in the cell walls and/or apoplast which compromises calcium dependent defense responses. Third, enhanced expression of hydroxyproline-rich glycoproteins (HRGPs) enhances pesticide movement to the phloem.

Glyphosate inhibits the shikimic acid pathway which leads to the biosynthesis of aromatic compounds including amino acids, plant hormones and vitamins. Specifically, glyphosate curbs the conversion of phosphoenolpyruvic acid (PEP) and 3-phosphoshikimic acid to 5-enolpyruvyl-3-phosphoshikimic acid by inhibiting the EPSPS enzyme. It is believed that oxalic acid and other dicarboxylic acids enhance the binding efficiency of glyphosate to the S3P-EPSPS complex, resulting in a whole plant response to the oxalate at a given glyphosate concentration. The oxalic acid is believed to act as a molecular staple whereby through a combination of electrostatic interactions with basic amino acid residues around the active site, the closed conformation of the enzyme is made more stable. This would lower the $K_d$ of the S3P-EPSPS-glyphosate ternary complex. Data reported in the literature from x-ray crystallography have clearly identified the 427 amino acid side chains. Each of the six $\alpha$-helices in the top domain and four of the six $\alpha$-helices in the lower domain are capped with basic amino acid residues. Electrostatic interaction of a dicarboxylic acid or other compound of the proper stearic requirement with these basic amino acid residues on the surface of the two domains of the enzyme are believed to produce a stapling action. Such stapling action is possible only on at least a partially closed conformation of the ternary complex of S3P-EPSPS-glyphosate. Based on enzyme studies and whole plant response, oxalic acid by itself does not have any herbicidal property. Thus, it appears that oxalic acid molecules act as molecular staple(s), making the S3P-EPSPS-glyphosate complex tighter and more stable, and do not have any inhibitory effect on the enzyme per se. Any compound with stapling action to close the ternary complex tighter, thereby enhancing the inhibition of the enzyme is a suitable enhancer component of the invention.

In an embodiment of the invention, a solid pesticidal concentrate composition is provided which comprises the pesticide and an enhancer component which increases inhibition of EPSPS target enzyme by the pesticide, cell membrane permeability in a plant, or expression of hydroxyproline-rich glycoproteins (HRGPs) as compared to a similarly loaded water-soluble solid pesticide composition which includes the same surfactant system without the enhancer component. The surfactant component is an optional component of the solid concentrate compositions. In some jurisdictions, aquatic toxicity or other environmental regulatory issues such as caution or warning labeling may dictate how much, if any, surfactant is incorporated in the solid concentrates of the invention.

In another embodiment of the invention, an aqueous pesticidal concentrate composition is provided which comprises a water-soluble pesticide dissolved in water. The water-soluble pesticide is present in a concentration that is biologically effective when the composition is diluted in a suitable volume of water and applied to the foliage of a susceptible plant. The composition also comprises a surfactant component in solution or stable suspension, emulsion, or dispersion in the water. The surfactant component comprises one or more surfactants. The surfactant component is present in a concentration sufficient to provide acceptable temperature stability of the composition such that the composition has a cloud point of at least about 50° C. and a crystallization point not greater than about 0° C. The composition also includes an enhancer component which increases inhibition of EPSPS target enzyme by the pesticide, cell membrane permeability in a plant, or expression of hydroxyproline-rich glycoproteins (HRGPs) as compared to a similarly loaded water-soluble pesticide composition which includes the same surfactant system without the enhancer component.

In another embodiment of the invention, a solid adjuvant for a pesticide composition is provided which comprises a surfactant component and an enhancer component which increases inhibition of EPSPS target enzyme by the pesticide, cell membrane permeability in a plant, or expression of hydroxyproline-rich glycoproteins (HRGPs) as compared to a similarly loaded solid enhancer which includes the same surfactant system without the enhancer component. An inorganic salt is an optional component of the solid adjuvant compositions.

Although oxalic acid has proven most effective in improving the performance of the compositions of the invention, other components are also effective in enhancing the pesticide formulations. Dicarboxylic acids, their salts or derivatives, may be added to the compositions to enhance herbicidal effectiveness. Suitable dicarboxylic acids that may be added to the formulations include oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors, with oxalic acid being preferred. Suitable salts include, for example, alkali metal salts such as sodium and potassium salts, alkanolamine salts and alkylamine salts such as IPA. Preferred salts include potassium oxalate, dipotassium oxalate, sodium oxalate, disodium oxalate, ammonium oxalate, diammonium oxalate, diethanolamine oxalate, dimethylamine oxalate, alkanolamine salts of oxalic acid, and lower alkylamine salts of oxalic acid. Suitable derivatives of dicarboxylic acid include the aforementioned as well as esters of any of said acids (e.g., methyl, ethyl, propyl, butyl esters) including alkylamine and alkoxylated alkylamine esters (e.g. cocoamine oxalate, stearylamine oxalate, tallowamine oxalate, alkoxylated cocoamine oxalate, alkoxylated stearylamine oxalate, alkoxylated tallowamine oxalate). Alkoxylated groups include, for example, methoxy, ethoxy and propoxy. Formulations contain such compounds in an amount sufficient to enhance the resulting efficacy of the formulation. In dry formulations, the weight ratio of total surfactant to dicarboxylic acid compound is between about 10:1 and about 1:10, more preferably between about 5:1 and about 1:3, and most preferably between about 3:1 and about 1:2 on an acid equivalent basis. Preferably, the weight ratio of glyphosate in the free acid, or a.e., form to oxalic acid is between about 20:1 and about 1:2, more preferably about 15:1 to about 1:1.25, and most preferably between about 13:1 to about 1.2:1 on an acid equivalent basis. The molar ratio of glyphosate a.e. to oxalic acid is between about 11:1 and about 1:4, more preferably about 8:1 to about 1:3, and most preferably between about 7:1 to about 1:1.5 on an acid equivalent basis. One skilled in the art can extrapolate the above molar ratios derived for oxalic acid to determine the appropriate weight ratio for any other dicarboxylic acid component.

Precursors of dicarboxylic acids can be used as the dicarboxylic acid component of the compositions of the invention. Terminally functionalized hydroxyacids, oxoacids, α,ω-dihydroxyalkanes, dinitriles, and dioxoalkanes are easily oxidized to dioic acids. α,ω-Aminoacids, haloacids, and dihalides are hydrolyzable to hydroxyacids or dihydroxides which are then oxidized. Precursors for use in the invention include, for example, oxalic acid precursors (glycolic acid, glyoxylic acid (and salts, e.g., oxaloacetate), glyoxal sodium bisulfite, oxalyl halides, ethylene glycol, glyoxal, 1,2-dihaloethane), adipic acid precursors (e.g., α-aminoadipic acid, cyclohexanol, cyclohexanone, cyclohexane), malonic acid precursors (e.g., malic acid, malonic dialdehyde, methylmalonic acid, cyanoacetic acid, diethyl malonate, malonyl Coenzyme A, acetyl CoA, acetate, butyrate), malic acid precursors (ketoglutaric acid, 2-oxoglutaric), succinic acid precursors (e.g., malic acid, malate, maleic acid, ketoglutaric acid, succinic acid dimethyl ester, succinic dialdehyde, L-glutamate, oxaloacetate, fumarate), and glutaric acid precursors (e.g., glutaric dialdehyde, glutaronitrile, cyclopentane, cyclopentanone, lysine, tryptophan, hemiamido glutarate, amidomethyl glutarate).

In a preferred embodiment, solid concentrate compositions of the invention contain oxalic acid or an anhydride, ester, amide, halide, salt or precursor thereof in combination with at least one salt of a polycarboxylic acid, such as sodium citrate or the sodium salt of EDTA. Such mixtures are especially preferred for use in solid concentrate compositions containing a relatively low concentration of glyphosate to reduce any eye irritancy which may otherwise result from relatively high concentrations of oxalic acid.

The solid concentrate compositions of the invention preferably comprise a water-soluble herbicide in a concentration between about 10 and about 90% by weight of the composition, a surfactant component in a concentration up to about 50% by weight of the composition, and a dicarboxylic acid in a concentration between about 1 and about 60% by weight of the composition. More preferably, the compositions comprise the water-soluble herbicide in a concentration between about 30 and about 80% by weight of the composition, a surfactant component in a concentration between about 5 and about 25% by weight of the composition, and a dicarboxylic acid in a concentration between about 3 and about 50% by weight of the composition. In another embodiment, the compositions comprise the water-soluble herbicide in a concentration between about 30 and about 80% by weight of the composition, a surfactant component in a concentration between about 5 and about 25% by weight of the composition, and a dicarboxylic acid in a concentration between about 5 and about 50% by weight of the composition. More preferably, the compositions comprise glyphosate or a salt or ester thereof in a concentration between about 35 and about 80% by weight a.e. of the composition, a surfactant component in a concentration between about 5 and about 25% by weight of the composition, and a dicarboxylic acid in a concentration between about 5 and about 40% by weight a.e. of the composition. Even more preferably, the compositions comprise glyphosate or a salt or ester thereof in a concentration between about 50 and about 80% by weight a.e. of the composition, a surfactant component in a concentration between about 7.5 and about 25% by weight of the composition, and a dicarboxylic acid in a concentration between about 10 and about 30% by weight a.e. of the composition. Most preferably, the compositions comprise glyphosate or a salt or ester thereof in a concentration between about 50 and about 80% by weight a.e. of the composition, a surfactant component in a concentration between about 7.5 and about 20% by weight of the composition, and oxalic acid or a salt or ester thereof in a concentration between about 10 and about 25% by weight of the composition, or the compositions comprise glyphosate or a salt or ester thereof in a concentration between about 50 and about 72% by weight a.e. of the composition, a surfactant component in a concentration between about 7.5 and about 20% by weight of the composition, and oxalic acid or a salt or ester thereof in a concentration between about 10 and about 25% by weight of the composition. In yet another embodiment, the compositions comprise glyphosate or a salt or ester thereof in a concentration between about 35 and about 80% by weight a.e. of the composition, a surfactant component in a concentration between about 5 and about 25% by weight of the composition, and a dicarboxylic acid in a concentration between about 3 and about 40% by weight a.e. of the composition. Even more preferably, the compositions comprise glyphosate or a salt or ester thereof in a concentration between about 50 and about 80% by weight a.e. of the composition, a surfactant component in a concentration between about 7.5 and about 25% by weight of the composition, and a dicarboxylic acid in a concentration between about 3 and about 30% by weight a.e. of the composition. Most preferably, the compositions comprise glyphosate or a salt or ester thereof in a concentration between about 50 and about 80% by weight a.e. of the composition, a surfactant component in a concentration between about 7.5 and about 20% by weight of the composition, and oxalic acid or a salt or ester thereof in a concentration between about 3 and about 25% by weight of the composition, or the compositions comprise glyphosate or a salt or ester thereof in a concentration between about 50 and about 77% by weight a.e. of the composition, a surfactant component in a concentration between about 7.5 and about 20% by weight of the composition, and oxalic acid or a salt or ester thereof in a concentration between about 3 and about 25% by weight of the composition.

In one embodiment of the invention, dry formulations include between 30 and 70 wt. % of at least one water-soluble pesticide, as well as at least one enhancer component and at least one anionic surfactant, wherein the weight ratio of enhancer component to anionic surfactant is greater than 4.8:1, or greater than 5.0:1, 5.5:1, 6.0:1, 6.5:1, 7.0:1, 7.5:1, 8.0:1, 8.5:1, 9.0:1, or 9.5:1, on an acid equivalent basis. In such formulations, the molar ratio of the pesticide to the enhancer component is between about 0.1 and about 16 on an acid equivalent basis, preferably between about 0.18 and about 16 or between about 0.2 and about 16.

In other embodiment, the dry formulations include between 30 and 70 wt. % of at least one water-soluble pesticide, as well as at least one enhancer component and at least one anionic surfactant, wherein the weight ratio of the enhancer component to anionic surfactant is less than 0.25:1, or less than 0.24:1, 0.23:1, 0.22:1, 0.21:1, 0.20:1, 0.19:1, 0.18:1, 0.17:1, 0.16:1, 0.15:1, 0.14:1, 0.13:1, 0.12:1, 0.11:1, 0.10:1, 0.09:1, 0.08:1, 0.07:1, 0.06:1, 0.05:1, 0.04:1, 0.03:1, 0.02:1, 0.01:1, on an acid equivalent basis. In such formulations, the molar ratio of the pesticide to the enhancer component is between about 0.1 and about 16 on an acid equivalent basis, preferably between about 0.18 and about 16 or between about 0.2 and about 16.

In another embodiment of the invention, dry formulations include between 33 and 70 wt. % of at least one water-soluble pesticide, as well as at least one enhancer component and at least one anionic surfactant, wherein the weight ratio of enhancer component to anionic surfactant is greater than 1.1:1, or greater than 1.2:1, 1.3:1, 1.4:1, 1.5:1, 1.6:1, 1.7:1, 1.8:1, 1.9:1, 2.0:1, 2.5:1, 3.0:1, 4.0:1, or 4.5:1, on an acid equivalent basis. In such formulations, the molar ratio of the pesticide to the enhancer component is between about 0.1 and about 16 on an acid equivalent basis, preferably between about 0.18 and about 16 or between about 0.2 and about 16.

In yet another embodiment of the invention, the dry formulation comprises at least one enhancer component as described above and between 30-70 wt. % of at least one water-soluble pesticide. However, the formulation includes no more than 22 wt. % anionic surfactant, or no more than 21, 20, 19, 18, 17, 16, 15, 14, 13, 12, 11, 10, 9, 8, 7, 6, 5.7, 5, 4, 3, 2 or 1 wt. % anionic surfactant.

In another embodiment of the invention, the dry formulation comprises at least one enhancer component and at least one water-soluble pesticide wherein either the molar ratio of the pesticide to the enhancer component is no more than 0.4 on an acid equivalent basis (or no more than 0.35, 0.3, 0.25, 0.2, 0.15 or 0.1), or the weight ratio of the pesticide to the enhancer component is no more than 0.8 on an acid equivalent basis (or no more than 0.75, 0.7, 0.65, 0.6, 0.55, 0.5, 0.45, 0.4, 0.35, or 0.3). In one embodiment, the concentration of water-soluble pesticide is between 33 and 70 wt. % and either the molar ratio of the pesticide to the enhancer component is no more than 0.8 on an acid equivalent basis (or no more than 0.75, 0.7, 0.65, 0.6, 0.55, 0.5, 0.45, 0.4, 0.35, or 0.3), or the weight ratio of the pesticide to the enhancer component is no more than 1.6 on an acid equivalent basis (or no more than 1.5, 1.4, 1.3, 1.2, 1.1, or 1.0).

In another embodiment of the invention, the dry formulation comprises at least one enhancer component and at least one water-soluble pesticide wherein either the molar ratio of the pesticide to the enhancer component is at least 3.6 on an acid equivalent basis (or at least 3.7, 3.8, 3.9, 4.0, 4.1, 4.2, 4.3, 4.4, 4.5 or 5.0), or the weight ratio of the pesticide to the enhancer component is at least 6.7 on an acid equivalent basis (or at least 6.8, 6.9, 7.0, 7.1, 7.2, 7.3, 7.4, 7.5, 8.0, 8.5, 9.0, 9.5, 10.0, 10.5, 11.0, 11.5, 12.0, 12.5 or 13.0).

In other embodiment, the dry formulations include between 30 and 70 wt. % of at least one water-soluble pesticide, as well as at least one enhancer component and at least one anionic surfactant, wherein the weight ratio of the pesticide to anionic surfactant is less than 1.7:1, or less than 1.6:1, 1.5:1, 1.4:1, 1.3:1, 1.2:1, 1.1:1, 1.0:1, 0.9:1, 0.8:1, 0.7:1, 0.6:1, 0.5:1, 0.4:1, 0.3:1, 0.2:1 or 0.1:1, on an acid equivalent basis. In such formulations, the molar ratio of the pesticide to the enhancer component is between about 0.1 and about 16 on an acid equivalent basis, preferably between about 0.18 and about 16 or between about 0.2 and about 16.

In another embodiment, the dry formulations include between 30 and 70 wt. % of at least one water-soluble pesticide, as well as at least one enhancer component and at least one anionic surfactant, wherein the weight ratio of the pesticide to anionic surfactant is greater than 5.7:1, or greater than 5.8:1, 5.9:1, 6:1, 7:1, or 8:1, on an acid equivalent basis. In such formulations, the molar ratio of the pesticide to the enhancer component is between about 0.1 and about 16 on an acid equivalent basis, preferably between about 0.18 and about 16 or between about 0.2 and about 16. In one embodiment, the concentration of water-soluble pesticide is between 33 and 70 wt. % and the weight ratio of the pesticide to anionic surfactant is greater than 2.1:1, or greater than 2.2:1, 2.3:1, 2.4:1, 2.5:1, 2.6:1, 2.7:1, 2.8:1, 2.9:1 or 3.0:1, on an acid equivalent basis.

In another embodiment, the dry formulations include at least one water-soluble pesticide, as well as at least one enhancer component and at least one surfactant other than an anionic surfactant, and either:
 (a) the pesticide is present in a concentration greater than 30 wt. %, or greater than 35, 40, 45, 50, 55, 60, or 65 wt. %;
 (b) the enhancer component is present in a concentration greater than 20 wt. %;
 (c) the surfactant component is present in an amount greater than 10 wt. %;
 (d) the molar ratio of the pesticide to the enhancer component is greater than 1.1:1 on an acid equivalent basis (or greater than 1.5:1, 2:1, 2.5:1, 3:1, 3.5:1, 4:1. 4.5:1 or 5:1), or the weight ratio of the pesticide to the enhancer component is greater than 1.25:1 on an acid equivalent basis (or greater than 1.5:1, 2:1, 2.5:1, 3:1, 3.5:1, 4:1. 4.5:1 or 5:1);

(e) the molar ratio of the pesticide to the enhancer component is less than 0.9:1 on an acid equivalent basis, or the weight ratio of the pesticide to the enhancer component is less than 1.8 on an acid equivalent basis;

(f) the weight ratio of pesticide to surfactant component is greater than 2:1 on an acid equivalent basis (or greater than 2.5:1, 3:1, 3.5:1, 4:1, 4.5:1, 5:1, 5.5:1, or 6:1); or (g) the weight ratio of pesticide to surfactant component is less than 2:1 on an acid equivalent basis (or less than 1.9:1, 1.8:1, 1.7:1, 1.6:1, or 1.5:1).

Typically, in liquid systems the weight ratio of total surfactant to dicarboxylic acid compound may be from 50:1 to 1:50, preferably from about 1:1 to about 50:1, even more preferably 5:1 to 40:1 and most preferably from about 5:1 to about 20:1 on an acid equivalent basis. This ratio of total surfactant to dicarboxylic acid significantly enhances the herbicidal performance of the resulting formulation. When the dicarboxylic acid component is present in the form of a surface-active ester, such as tallowamine-oxalate ester, little or no additional surfactant needs to be added to the formulation. Preferably, the weight ratio of glyphosate in the free acid, or a.e., form to dicarboxylic acid is between about 1:1 and about 500:1, more preferably about 2:1 to about 100:1, and most preferably between about 2:1 to about 50:1 on an acid equivalent basis.

The liquid concentrate compositions of the invention preferably comprise a water-soluble herbicide in a concentration between about 20 and about 45% by weight acid equivalent of the composition, a surfactant component in a concentration between about 0.1 and about 25% by weight of the composition, and a dicarboxylic acid in a concentration between about 0.01 and about 20% by weight of the composition. More preferably, the compositions comprise glyphosate or a salt or ester thereof in a concentration between about 25 and about 40% by weight of the composition, a surfactant component in a concentration between about 0.1 and about 20% by weight of the composition, and a dicarboxylic acid in a concentration between about 0.01 and about 18% by weight of the composition. Even more preferably, the compositions comprise glyphosate or a salt or ester thereof in a concentration between about 30 and about 40% by weight of the composition, a surfactant component in a concentration between about 0.1 and about 15% by weight of the composition, and a dicarboxylic acid in a concentration between about 0.01 and about 10% by weight of the composition. Most preferably, the compositions comprise glyphosate or a salt or ester thereof in a concentration between about 31 and about 40% by weight of the composition, a surfactant component in a concentration between about 0.1 and about 12% by weight of the composition, and oxalic acid or a salt or ester thereof in a concentration between about 0.01 and about 5% by weight of the composition.

In one embodiment, an aqueous pesticidal composition is formed that is biologically effective to control growth of a susceptible plant when applied to the foliage of a susceptible plant. In one embodiment, the pesticide is present in a concentration between about 2% and 30% by weight. In another embodiment the composition comprises at least one water-soluble pesticide in a concentration between about 0.0001% and about 3% by weight (or between about 0.001 and 3%, or 0.01 and 3%), a surfactant component, and an enhancer component present in an acid equivalent concentration between 2% by weight and maximum percent by weight dictated by the solubility of the enhancer component present, preferably at least 3, 3.5, 4, 4.5, 5, 5.5, 6, 7, 8, 9 or 10% by weight.

Liquid concentrate compositions of the invention have a viscosity of not greater than about 1000 cPs at 10° C., preferably not greater than about 900 cPs at 10° C., more preferably not greater than about 800, 700, 600, 500, 400 or 300 cPs at 10° C., and even more preferably not greater than about 200 cPs at 10° C., at 45/s shear rate.

The term "water-soluble" as used herein in relation to a herbicide or salt or ester thereof means having a solubility in deionized water at 20° C. of not less than about 2 g/l, and preferably not less than about 50 g/l for concentrates. Preferred water-soluble herbicides have a solubility in deionized water at 20° C. of not less than about 200 g/l. Particularly preferred water-soluble herbicides have a herbicidal active acid or anionic moiety and are most usefully present in a composition of the invention in the form of one or more water-soluble salts. The aqueous phase of the composition can optionally contain, in addition to the water-soluble herbicide, other salts contributing to the ionic strength of the aqueous phase.

A particularly preferred group of water-soluble herbicides are those that are normally applied post-emergence to the foliage of plants. While the invention is not limited to any particular class of foliar-applied water-soluble herbicide, it has been found to provide useful benefits for compounds that rely at least in part for their herbicidal effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected symplastically by plasmodesmata, or via both apoplastic and symplastic pathways. For foliar-applied systemic herbicides, the most important pathway is the phloem, and the present invention is believed to provide the greatest benefits where the water-soluble herbicide is phloem-mobile. However, compositions of the invention can also be useful where the water-soluble herbicide is non-systemic, as in the case of paraquat.

Water-soluble herbicides suitable for use in compositions of the invention include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

Phloem-mobile herbicides that are preferred for use in compositions of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr. A particularly preferred group of water-soluble herbicides are salts of bialaphos, glufosinate and glyphosate. Another particularly preferred group of water-soluble herbicides are salts of imidazolinone herbicides.

Compositions of the invention can optionally contain more than one water-soluble herbicide in solution in the aqueous phase.

An especially preferred water-soluble herbicide useful in a composition of the present invention is glyphosate, the acid form of which is alternatively known as N-(phosphonomethyl)glycine. For example, glyphosate salts useful in compositions of the present invention are disclosed in U.S. Pat. Nos. 3,799,758 and 4,405,531. Glyphosate salts that can be used according to the present invention include but are not restricted to alkali metal, for example sodium and potassium, salts; ammonium salt; $C_{1-6}$ alkylammonium, for example dimethylammonium and isopropylammonium, salts; $C_{1-6}$ alkanolammonium, for example monoethanolammonium, salt; $C_{1-6}$ alkylsulfonium, for example trimethylsulfonium, salts; and mixtures thereof. The N-phosphonomethylglycine molecule has three acid sites having different pKa values; accordingly mono-, di- and tribasic salts, or any mixture thereof, or salts of any intermediate level of neutralization, can be used. Especially preferred glyphosate salts include the potassium salt, isopropylamine salt, ammonium salt, diammonium salt, monoethanolamine salt, and trimethylsulfonium salt. The ammonium and sodium salts are most preferred for solid formulations as they are the least hygroscopic. The potassium salt is most preferred for liquid formulations.

It has been discovered that dicarboxylic acids enhance the performance of formulations containing glyphosate or a salt or ester thereof in combination with another herbicide, such as a pre-or post-emergent foliar applied herbicide. For example, some post-emergent foliar applied herbicides reduce the performance of glyphosate in a formulation. This reduction in performance is not observed when the formulation includes oxalic acid or a derivative thereof.

The relative amount of glyphosate loading in the pesticidal compositions of the present invention will vary depending upon many factors including the surfactant system employed, the rheological characteristics of the composition, and the temperature range at which the composition will be exposed. The glyphosate loading in the herbicidal compositions of the invention is preferably at least 320 g a.e./L, and more preferably at least 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 g a.e./L.

Compositions of the invention can optionally contain one or more water-insoluble herbicides in solution in an organic solvent or in suspension in a concentration that is biologically effective when the composition is diluted in a suitable volume of water and applied to the foliage of a susceptible plant. Preferred water-insoluble herbicide is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzfendizone, benzofenap, bromobutide, bromofenoxim, butachlor, butafenacil, butamifos, butralin, butroxydim, butylate, cafenstrole, carfentrazone-ethyl, carbetamide, chlorbromuron, chloridazon, chlorimuron-ethyl, chlorotoluron, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluazifop-P-butyl, fluazoate, fluchloralin, flumetsulam, flumiclorac-pentyl, flumioxazin, fluometuron, fluorochloridone, flupoxam, flurenol, fluridone, fluroxypyr-1-methylheptyl, flurtamone, fluthiacet-methyl, graminicides, halosulfuron, haloxyfop, hexazinone, imazosulfuron, indanofan, isoproturon, isouron, isoxaben, isoxaflutole, isoxapyrifop, lenacil, linuron, mefenacet, metamitron, metazachlor, methabenzthiazuron, methyldymron, metobenzuron, metobromuron, metolachlor, S-metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, profluazol, prometon, prometryn, propachlor, propanil, propaquizafop, propazine, propham, propisochlor, propyzamide, prosulfocarb, prosulfuron, pyraflufen-ethyl, pyrazogyl, pyrazolynate, pyrazosulfuronethyl, pyrazoxyfen, pyributicarb, pyridate, pyriminobac-methyl, quinclorac, quinmerac, quizalofop, quizalofop-P, rimsulfuron, sethoxydim, siduron, simazine, simetryn, sulcotrione, sulfentrazone, sulfometuron, sulfosulfuron, tebutam, tebuthiuron, tepraloxydim, terbacil, terbumeton, terbuthylazine, terbutryn, thenylchlor, thiazopyr, thidiazimin, thifensulfuron, thiobencarb, tiocarbazil, tralkoxydim, triallate, triasulfuron, tribenuron, trietazine, trifluralin, triflusulfuron and vernolate.

Compositions of the invention can optionally contain two or more water-insoluble co-herbicides, two or more water-soluble co-herbicides or one or more water-insoluble co-herbicides in combination with one or more water-soluble co-herbicides. In one embodiment glyphosate or an ester or a salt thereof is combined with one or more water-insoluble co-herbicides and/or one or more water-soluble co-herbicides. Examples of co-herbicide classes include sulfonylurea, triazolopyrimidine, diphenyl ether, chlorophenoxy, chloroacetanilide, triazine, imidazolinone, urea, amino acid derivative, chlorophenoxy, benzoic acid, DNA (dinitroaniline), pyridinecarboxylic acid, pyridine, oxadiazole and acetamide. Examples of co-herbicides include nicosulfuron, fluazifop-p, oxyfluorfen, diuron, acetochlor, atrazine, imazathapyr, imazpyr, diquat, glufosinate, 2-4D, paraquat, dicamba, trifluralin, triclopyr, clomazone, dithiopyr, imazaquin, imazapic, oxadiazon and propanil.

In some cases co-herbicides can be antagonistic. A method of the invention includes reducing antagonism of glyphosate acid or an ester or a salt thereof and a coherbicide by using a dicarboxylic acid source in preparation of an aqueous herbicidal mixture for application to unwanted vegetation. The aqueous herbicidal mixture may optionally further comprise a surfactant.

The surfactant component of the composition of the present invention when applied with the above-mentioned herbicidal components of the invention is of the type and present in a sufficient concentration to allow the plant to cellularly uptake and translocate a herbicidally effective amount of herbicide such as glyphosate. One way to accomplish this is to provide more intimate contact between the applied herbicidal composition and the microtopographically rough surface of the plant, for example by flattening the contact angle of the composition, so as to permit the composition to spread into crevices and pores in the plant. For example, the surfactant composition should preferably also enhance sticking or adhesion to a plant surface when used in aqueous solution, and it should allow the solution to dry on a time scale that is effective to permit penetration.

Various surfactants have been found to be effective in formulating pesticidal compositions and concentrates of the invention. Any surfactant can be incorporated in the compositions of the invention. When formulating solid concentrates, the surfactant concentration should be less than the concentration at which the composition becomes sticky or waxy or at which the composition is difficult to dissolve.

Cationic surfactants effective in forming herbicide formulations include:

(a) aminated alkoxylated alcohol having the formula:

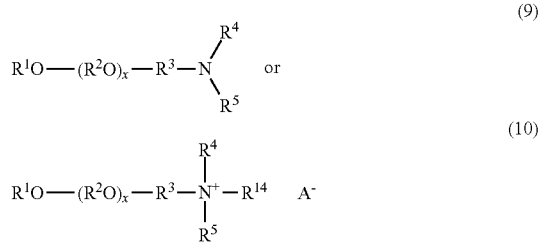

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, —$C(=S)NR^{12}R^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, —$C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, —$(R^6)_n$—$(R^2O)_yR^7$, —$C(=NR^{11})NR^{12}R^{13}$, —$C(=O)NR^{12}R^{13}$, or —$C(=S)NR^{12}R^{13}$, n is 0 or 1, x and y are independently an average number from 1 to about 60, and A- is an agriculturally acceptable anion. In this context, preferred $R^1$, $R^3$, $R^4$, $R^5$, $R^6$, $R^{11}$, $R^{12}$ and $R^{13}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^3$ is linear alkylene, preferably ethylene, and $R^1$, $R^2$, $R^4$ and $R^5$ are as previously defined. In another embodiment, $R^4$ is H, alkyl, or —$R^2OR^7$ and $R^1$, $R^2$, $R^3$, $R^5$ and $R^7$ are as previously defined. In yet another embodiment, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene group having from 1 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 1 to about 4 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are methyl, and x is an average number from about 4 to about 20. Compounds of formula (10) have the preferred groups as described above and $R^{14}$ is preferably hydrogen or a linear or branched alkyl or alkenyl group, more preferably alkyl, and most preferably methyl. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah).

(b) hydroxylated amides having the formula:

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl. In this context, preferred $R^1$ and $R^2$ hydrocarbyl groups are linear or branched alkyl, linear or branched alkenyl, linear or branched alkynyl, aryl, or aralkyl groups. Preferably, the hydroxylated amides have the formula:

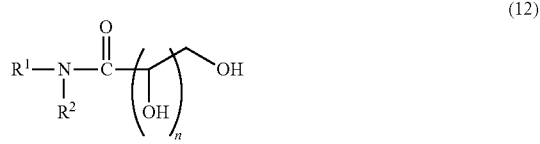

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and n is 1 to about 8. In this context, preferred $R^1$ and $R^2$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ is hydrogen, a linear or branched alkyl or linear or branched alkenyl group having from 1 to about 30 carbon atoms, and n is about 4 to about 8; or $R^1$ and $R^2$ are independently linear or branched alkyl or linear or branched alkenyl groups having from about 4 to about 30 carbon atoms and n is about 4 to about 8. More preferably, $R^1$ is a linear or branched alkyl or linear or branched alkenyl group having from about 8 to about 22 carbon atoms, $R^2$ is hydrogen or a linear or branched alkyl or linear or branched alkenyl group having from 1 to about 6 carbon atoms, and n is about 4 to about 8; or $R^1$ and $R^2$ are independently linear or branched alkyl or linear or branched alkenyl groups having from about 4 to about 8 carbon atoms, and n is about 4 to about 8.

(c) diamines having the formula:

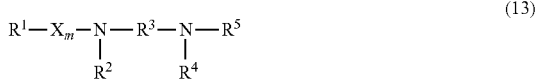

(13)

wherein $R^1$, $R^2$ and $R^5$ are independently hydrogen or hydrocarbyl or substituted hydrocarbyl having from 1 to about 30 carbon atoms or —$R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is —C(O)— or —SO$_2$—. In this context, preferred $R^1$, $R^2$, $R^3$, $R^4$, $R^5$ and $R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$ and $R^5$ are independently hydrogen, a linear or branched alkyl or alkenyl group having from 1 to about 6 carbon atoms, and $R^3$ is a linear or branched alkylene having from 2 to about 6 carbon atoms. More preferably, $R^1$, $R^2$, $R^4$ and $R^5$ are independently hydrogen, or a linear or branched alkyl group having from 1 to about 6 carbon atoms, and $R^3$ is a linear or branched alkylene having from 2 to about 6 carbon atoms. Most preferably, $R^1$, $R^2$, $R^4$, and $R^5$ are independently hydrogen or methyl, and $R^3$ is ethylene or propylene.

(d) mono- or di-ammonium salts having the formula:

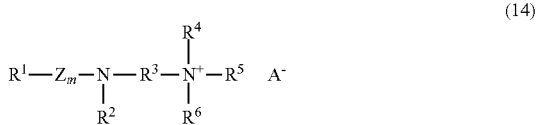

(14)

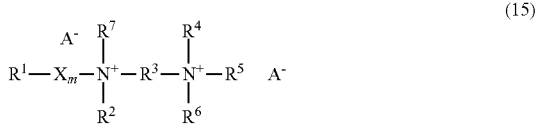

(15)

wherein $R^1$, $R^2$, $R^4$, $R^5$ and $R^7$ are independently hydrogen or hydrocarbyl or substituted hydrocarbyl having from 1 to about 30 carbon atoms or —$R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A$^-$ is an agriculturally acceptable anion. In this context, preferred $R^1$-$R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$, $R^5$ and $R^7$ are independently hydrogen, or a linear or branched alkyl or alkenyl group having from 1 to about 6 carbon atoms, $R^6$ is a linear or branched alkyl or alkenyl group having from about 8 to about 30 carbon atoms, m is 0 or 1, and $R^3$ is a linear or branched alkylene having from 2 to about 22 carbon atoms. More preferably, $R^1$, $R^2$, $R^4$, $R^5$ and $R^7$ are independently hydrogen, or a linear or branched alkyl group having from 1 to about 6 carbon atoms, $R^6$ is a linear or branched alkyl group having from about 8 to about 22 carbon atoms, m is 0 or 1, and $R^3$ is a linear or branched alkylene having from 2 to about 20 carbon atoms. Most preferably, $R^1$, $R^2$, $R^4$, $R^5$ and $R^7$ are independently hydrogen or methyl, $R^6$ is a linear or branched alkyl group having from about 8 to about 18 carbon atoms, m is 0 or 1, and $R^3$ is ethylene or propylene.

(e) poly(hydroxyalkyl)amines having the formula:

(16)

(17)

wherein $R^1$ is hydrocarbyl or substituted hydrocarbyl having from about 4 to about 30 carbon atoms or —$R^4OR^8$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, $R^8$ is hydrogen or hydrocarbyl or substituted hydrocarbyl having from 1 to about 30 carbon atoms, $R^5$ is —$(R^6O)_yR^7$; $R^6$ in each of the y ($R^6O$) groups is independently $C_2$-$C_4$ alkylene; $R^7$ is hydrogen or a linear or branched alkyl group having 1 to about 4 carbon atoms; and y is an average number from 0 to about 30. Preferably, the poly (hydroxyalkyl)amines have the formula:

(18)

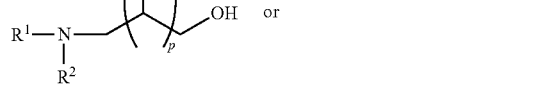

(19)

wherein $R^1$ is hydrocarbyl or substituted hydrocarbyl having from about 4 to about 30 carbon atoms or —$R^3OR^4$; $R^2$ is hydrogen or hydrocarbyl or substituted hydrocarbyl having from 1 to about 30 carbon atoms, $R^3$ is hydrocarbylene or substituted hydrocarbylene having from 2 to about 18 carbon atoms, $R^4$ is hydrogen or hydrocarbyl or substituted hydrocarbyl having from 1 to about 30 carbon atoms, m and n are independently integers from 0 to about 7, the sum of m and n is not greater than about 7, and p is an integer from 1 to about 8. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 30 carbon atoms or —$R^3OR^4$, $R^2$ is hydrogen, a linear or branched alkyl or linear or branched alkenyl group having from 1 to about 30 carbon atoms, $R^3$ is a linear or branched alkylene or alkenylene group having from 2 to about 6 carbon atoms, $R^4$ is a linear or branched alkyl or alkenyl group having from about 8 to about 22 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 30 carbon atoms, m and n are independently integers from 0 to about 7, the sum of m and n is from about 3 to 7, and p is an integer from about 4 to about 8. More preferably, $R^1$ is a linear or branched alkyl or linear or branched alkenyl group having from about 8 to about 22 carbon atoms or —$R^3OR^4$, $R^2$ is hydrogen or a linear or branched alkyl or linear or branched alkenyl group having from 1 to about 6 carbon atoms, $R^3$ is a linear or branched alkylene or alkenylene group having from 2 to about 6 carbon atoms, $R^4$ is a linear or branched alkyl or alkenyl group having from about 8 to about 18 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms or —$R^3OR^4$, $R^2$ is hydrogen or methyl, m and n are independently integers from 0 to about 4, $R^3$ is a linear or branched alkylene group having from 2 to about 6 carbon atoms, $R^4$ is a linear or branched alkyl group having from about 8 to about 18 carbon atoms, the sum of m and n is about 4, and p is an integer of about 4. Most preferably, $R^1$ is a linear or branched alkyl group having from about 8 to about 18 carbon atoms or —$R^3OR^4$, $R^2$ is methyl, $R^3$ is ethylene, propylene, hydroxyethylene or 2-hydroxypropylene, $R^4$ is a linear or branched alkyl group having from about 8 to about 18 carbon atoms, m and n are independently integers from 0 to about 4, the sum of m and n is about 4, and p is an integer of about 4. Such compounds are commercially available from Aldrich and Clariant.

(f) alkoxylated poly(hydroxyalkyl)amines having the formula:

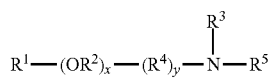

(20)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$-$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferred alkoxylated poly(hydroxyalkyl)amines have the formula:

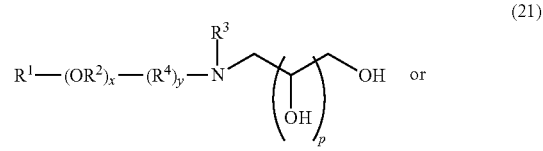

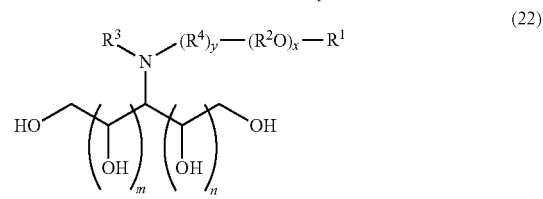

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$-$C_4$ alkylene; $R^4$ is hydrocarbylene or substituted hydrocarbylene having from 1 to about 30 carbon atoms, m and n are independently integers from 0 to about 7, the sum of m and n is not greater than about 7, p is an integer from 1 to about 8, x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferably, $R^1$ is a linear or branched alkyl or linear or branched alkenyl group having from about 8 to about 30 carbon atoms; $R^2$ in each of the x ($R^2O$) groups is independently $C_2$-$C_4$ alkylene; $R^3$ is hydrogen, a linear or branched alkyl or linear or branched alkenyl group having from 1 to about 30 carbon atoms; $R^4$ is a linear or branched alkylene having from 1 to about 30 carbon atoms, m and n are independently integers from 0 to about 7, the sum of m and n is from about 3 to 7, p is an integer from 1 to about 8, x is an average number from 0 to about 30, and y is 0 or 1. More preferably, $R^1$ is a linear or branched alkyl group having from about 8 to about 22 carbon atoms; $R^2$ in each of the x ($R^2O$) groups is independently ethylene or propylene; $R^3$ is hydrogen, or a linear or branched alkyl group having from 1 to about 6 carbon atoms; $R^4$ is a linear or branched alkylene having from 1 to about 6 carbon atoms, m and n are independently integers from 0 to about 7, the sum of m and n is from about 3 to 7, p is an integer from 1 to about 8, x is an average number from 0 to about 30, and y is 0 or 1. Most preferably, $R^1$ is a linear or branched alkyl group having from about 8 to about 18 carbon atoms; $R^2$ in each of the x ($R^2O$) groups is independently ethylene or propylene; $R^3$ is hydrogen or methyl; m and n are independently integers from 0 to about 7, the sum of m and n is from about 3 to 7, p is an integer from 1 to about 8, x is an average number from 0 to about 30, and y is 0.

(g) di-poly(hydroxyalkyl)amine having the formula:

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, the di-poly(hydroxyalkyl)amine has the formula:

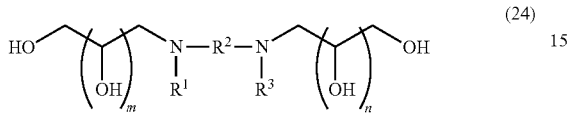

(24)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ are independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(h) quaternary poly(hydroxyalkyl)amine salts having the formula:

(25)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, and X— is an agriculturally acceptable anion. In this context, preferred $R^1$, $R^2$, and $R^3$ hydrocarbyl groups are linear or branched alkyl, linear or branched alkenyl, linear or branched alkynyl, aryl, or aralkyl groups. Preferably, the quaternary poly(hydroxyalkyl)amine salts have the formula:

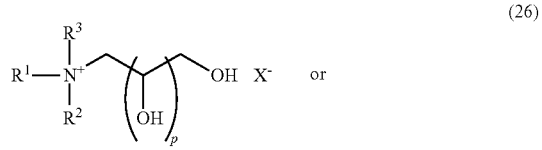

(26)

or

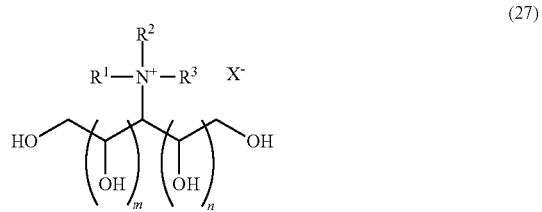

(27)

wherein $R^1$ is $-X_m-(R^4O)_yR^5$, hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, m and n are independently integers from 0 to about 7, the sum of m and n is not greater than about 7, p is an integer from 1 to about 8, X— is an agriculturally acceptable anion, $R^4$ in each of the y ($R^4O$) groups is independently $C_2$-$C_4$ alkylene; $R^5$ is hydrogen or a linear or branched alkyl group having 1 to about 4 carbon atoms; X is hydrocarbylene or substituted hydrocarbylene having from 2 to about 18 carbon atoms; m is 0 or 1; and y is an average number from 0 to about 30. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ and $R^3$ are independently hydrogen or a linear or branched alkyl or linear or branched alkenyl group having from 1 to about 30 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 30 carbon atoms, m and n are independently integers from 0 to about 7, the sum of m and n is not greater than about 7, and p is an integer from about 4 to about 8. More preferably, $R^1$ is a linear or branched alkyl or linear or branched alkenyl group having from about 8 to about 22 carbon atoms, $R^2$ and $R^3$ are independently hydrogen or a linear or branched alkyl or linear or branched alkenyl group having from 1 to about 6 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms, $R^2$ and $R^3$ are independently hydrogen or methyl, m and n are independently integers from 0 to about 4, the sum of m and n is about 4, and p is an integer of about 4. Most preferably, $R^1$ is a linear or branched alkyl group having from about 8 to about 18 carbon atoms, $R^2$ and $R^3$ are methyl, m and n are independently integers from 0 to about 4, the sum of m and n is about 4, and p is an integer of about 4.

(i) triamines having the formula:

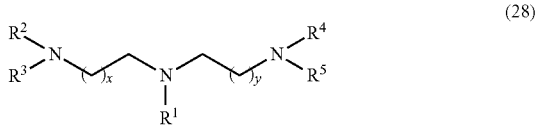

(28)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or —$(R^8)_s(R^7O)_nR^6$; $R^6$ is hydrogen or a linear or branched alkyl group having from 1 to about 4 carbon atoms, $R^7$ in each of the n $(R^7O)$ groups is independently $C_2$-$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4. In this context, preferred $R^1$, $R^2$, $R^3$, $R^4$, $R^5$, and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or —$(R^7O)_nR^6$, $R^6$ is hydrogen, methyl or ethyl; $R^7$ in each of the n $(R^7O)$ groups is independently $C_2$-$C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or —$(R^7O)_nR^6$, $R^6$ is hydrogen or methyl, $R^7$ in each of the n $(R^7O)$ groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or —$(R^7O)_nR^6$, $R^6$ is hydrogen, $R^7$ in each of the n $(R^7O)$ groups is independently ethylene or propylene, n is an average number from 1 to about 5, and x and y are independently an integer from 1 to about 4. Commercially available triamines include Acros and Clariant Genamin 3119.

(j) diamines having the formula:

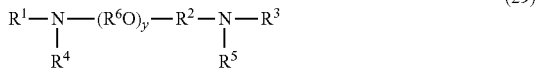

(29)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $C(=NR^{11})NR^{12}R^{13}$—, —$C(=O)NR^{12}R^{13}$—, —$C(=S)NR^{12}R^{13}$—, —$C(=NR^{12})$—, —$C(S)$—, or —$C(O)$—, $R^6$ in each of the x $(R^6O)$ and y $(R^6O)$ groups is independently $C_2$-$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60. In this context, preferred $R^1$, $R^2$, $R^3$, $R^4$, and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$ and $R^5$ are independently hydrogen or a linear or branched alkyl or linear or branched alkenyl group having from 1 to about 22 carbon atoms or —$(R^6O)_xR^7$, $R^2$ is a linear or branched alkylene or linear or branched alkenylene group having from 1 to about 6 carbon atoms, $R^6$ in each of the x$(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, and y is an average number from 0 to about 60. More preferably, $R^1$, $R^3$, $R^4$ and $R^5$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 15, and y is an average number from 0 to about 60. Most preferably, $R^1$ and $R^3$ are independently linear or branched alkyl groups having from about 8 to about 18 carbon atoms and $R^4$ and $R^5$ are independently hydrogen, $R^2$ is a linear or branched alkylene group having from about 1 to about 6 carbon atoms, $R^6$ in each of the x $(R^6O)$ and y $(R^6O)$ groups is independently ethylene or propylene, $R^7$ is hydrogen, or a linear or branched alkyl group having from 1 to about 4 carbon atoms, x is an average number from 1 to about 10, and y is an average number from 0 to about 50.

(k) mono- or di-quaternary ammonium salts having the formula:

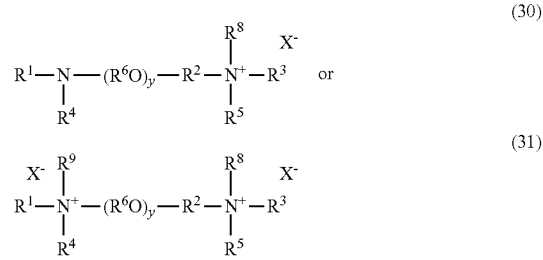

wherein $R^1$, $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $R^6$ in each of the x $(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion. In this context, preferred $R^1$, $R^2$, $R^3$, $R^4$, $R^5$, $R^8$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$, $R^5$, $R^8$ and $R^9$ are independently hydrogen or a linear or branched alkyl or alkenyl group having from about 1 to about 22 carbon atoms or —$(R^6O)_xR^7$, $R^2$ is a linear or branched alkylene or alkenylene group having from about 1 to about 6 carbon atoms, $R^6$ in each of the x ($R^6O$) and y ($R^6O$) groups is independently $C_2$-$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$, $R^5$, $R^8$ and $R^9$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$, $R^5$, $R^8$ and $R^9$ are independently hydrogen or methyl, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 10 to about 50.

(l) a secondary or tertiary amine having the formula:

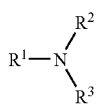

(32)

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl or ethyl. In one embodiment of the amine of formula (32), $R^1$ is a linear or branched alkyl group having from about 12 to about 22 carbon atoms, and $R^2$ and $R^3$ are independently linear or branched hydroxyalkyl groups having from 1 to about 6 carbon atoms.

In one embodiment, the surfactant has the formula (32) wherein $R^1$ is hydrocarbyl or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or poly(hydroxyalkyl)alkyl. In this context, preferred $R^1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

(m) monoalkoxylated amines having the formula:

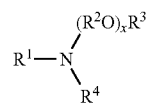

(33)

wherein $R^1$ and $R^4$ are independently hydrocarbyl or substituted hydrocarbyl groups having from 1 to about 30 carbon atoms or —$R^5SR^6$, $R^2$ in each of the x ($R^2O$) groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^5$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x ($R^2O$) groups is independently $C_2$-$C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear or branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

(n) dialkoxylated quaternary ammonium salts having the formula:

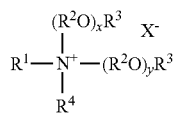

(34)

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2$-$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x any y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and x is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and x is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and x is an average number from about 5 to about 15. Preferred dialkoxylated quaternary ammonium surfactants include Ethoquad™ C12 (a PEG 2 coco methyl ammonium chloride from Akzo Nobel), PEG 5 coco methyl ammonium chloride, PEG 5 tallow methyl ammonium chloride, PEG 5 ditallow ammonium bromide, and PEG 10 ditallow ammonium bromide.

(o) monoalkoxylated quaternary ammonium salts having the formula:

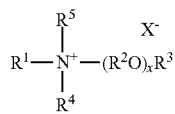

(8)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2O$) groups is independently $C_2$-$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(p) quaternary ammonium salts having the formula:

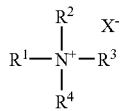

(35)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion. In this context, preferred $R^1$, $R^2$, $R^3$, and $R^4$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(q) etheramines having the formula:

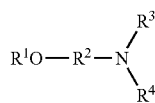

(7)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or $-(R^5O)_xR^6$, $R^5$ in each of the x ($R^5-O$) groups is independently $C_2$-$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or $-(R^5O)_xR^6$, $R^5$ in each of the x ($R^5O$) groups is independently $C_2$-$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or $-(R^5O)_xR^6$, $R^5$ in each of the x ($R^5O$) groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or $-(R^5O)_xR^6$, $R^5$ in each of the x ($R^5O$) groups is independently ethylene or propylene, $R^6$ is hydrogen, and x is an average number from 1 to about 5.

(r) diamines having the formula:

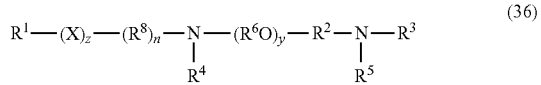

(36)

wherein $R^1$, $R^3$, $R^4$ and $R^5$ are independently hydrogen, hydrocarbyl or substituted hydrocarbyl having from 1 to about 30 carbon atoms, or $-(R^6O)_xR^7$; $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$-$C_4$ alkylene, $R^7$ is hydrogen, or a linear or branched alkyl group having from 1 to about 30 carbon atoms, x is an average number from 1 to about 30, X is $-O-$, $-N(R^6)-$, $-C(O)-$, $-C(O)O-$, $-OC(O)-$, $-N(R^9)C(O)-$, $-C(O)N(R^9)-$, $-S-$, $-SO-$, or $-SO_2-$, y is 0 or an average number from 1 to about 30, n and z are independently 0 or 1, and $R^9$ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^6$ in each of the y ($R^6O$) groups is independently $C_2$-$C_4$ alkylene, y is an average number from 1 to about 20 and n and z are 0; or $R^1$ and $R^3$ are independently a linear alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or $-(R^6O)_xR^7$, $R^6$ in each of the x ($R^6O$) groups is independently $C_2$-$C_4$ alkylene, $R^7$ is hydrogen, or a linear or branched alkyl group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is $-C(O)-$ or $-SO_2-$, n and y are 0 and z is 1. More preferably, $R^1$ and $R^4$ are independently a linear or branched alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or —$(R^6O)_xR^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is —C(O)— or —$SO_2$—, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{10}$, $C_{14}$ or $C_{16}$ ethylene, propylene or butylene N-methyl diamines from Monsanto), Ethoduomeens™, and Jeffamine™ EDR-148.

(s) amine oxides having the formula:

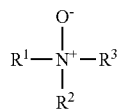

(37)

wherein $R^1$, $R^2$ and $R^3$ are independently hydrogen, hydrocarbyl or substituted hydrocarbyl having from 1 to about 30 carbon atoms, —$(R^4O)_xR^5$, or —$R^6(OR^4)_xOR^5$; $R^4$ in each of the x ($R^4O$) groups is independently $C_2$-$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8. In this context, preferred $R^1$, $R^2$, $R^3$, $R^5$ and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or —$(R^4O)_xR^5$; $R^3$ is a linear or branched alkyl or linear or branched alkenyl group having from 8 to about 30 carbon atoms, $R^4$ in each of the x ($R^4O$) groups is independently $C_2$-$C_4$ alkylene; $R^5$ is hydrogen or a linear or branched alkyl or linear or branched alkenyl group having from 1 to about 30 carbon atoms, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently —$(R^4O)_xR^5$, $R^3$ is a linear or branched alkyl group having from about 8 to about 22 carbon atoms, $R^4$ in each of the x ($R^4O$) groups is ethylene or propylene, $R^5$ is hydrogen or a linear or branched alkyl or linear or branched alkenyl group having from 1 to about 30 carbon atoms, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently —$(R^4O)_xR^5$, $R^3$ is a linear or branched alkyl group having from about 8 to about 18 carbon atoms, $R^4$ in each of the x ($R^4O$) groups is ethylene or propylene, $R^5$ is hydrogen or an alkyl group having from about 8 to about 18 carbon atoms, and x is an average number from 1 to about 5. Commercially available amine oxide surfactants include Chemoxide L70.

(t) alkoxylated amine oxides having the formula:

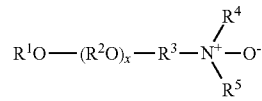

(38)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene or alkenylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene, propylene, or 2-hydroxypropylene group, $R^4$ and $R^5$ are methyl, and x is an average number from about 4 to about 20.

(u) dialkoxylated amines having the formula:

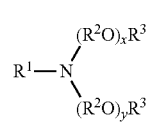

(39)

wherein $R^1$ is hydrogen or hydrocarbyl or substituted hydrocarbyl having from 1 to about 30 carbon atoms, —$R^4SR^5$, or —$(R^2O)_zR^3$, $R^2$ in each of the x ($R^2O$), y ($R^2O$) and z ($R^2O$) groups is independently $C_2$-$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40. In this context, preferred $R^1$ hydrocarbyl groups are hydrogen, linear or branched alkyl, linear or branched alkenyl, linear or branched alkynyl, aryl, or aralkyl groups. Preferably, $R^1$ is hydrogen, a linear or branched alkynyl, aryl, or aralkyl group having from about 1 to about 30 carbon atoms, $R^2$ in each of the x ($R^2O$), y ($R^2O$) and z ($R^2O$) groups is independently $C_2$-$C_4$ alkylene, $R^3$ is hydrogen, methyl or ethyl, and x and y are independently an average number from 1 to about 20. More preferably, $R^1$ is hydrogen or a linear or branched alkynyl, aryl, or aralkyl group having from about 8 to about 25 carbon atoms, $R^2$ in each of the x ($R^2O$), y ($R^2O$) and z ($R^2O$) groups is independently ethylene or propylene, $R^3$ is hydrogen or methyl, and x and y are independently an average number from 1 to about 30. Even more preferably, $R^1$ is hydrogen or a linear or branched alkynyl, aryl, or aralkyl group having from about 8 to about 22 carbon atoms, $R^2$ in each of the x ($R^2O$), y ($R^2O$) and z ($R^2O$) groups is independently ethylene or propylene, $R^3$ is hydrogen or methyl, and x and y are independently an average number from 1 to about 5. Preferred commercially available dialkoxylated amines include Trymeen™ 6617 (from Cognis) and Ethomeen™ C/12, C/15, C/20, C/25, T/12, T/15, T/20 and T/25 (from Akzo Nobel).

(v) aminated alkoxylated alcohols having the following chemical structure:

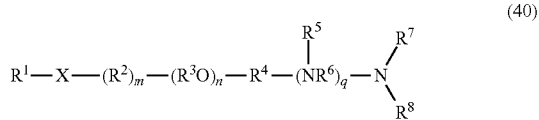

(40)

wherein $R^1$, $R^7$, $R^8$, and $R^9$ are each independently hydrogen, hydrocarbyl or substituted hydrocarbyl having from 1 to about 30 carbon atoms, or —$(R^{11})_s(R^3O)_vR^{10}$; X is —O—, —OC(O)—, —C(O)O—, —N($R^{12}$)C(O)—, —C(O)N ($R^{12}$)—, —S—, —SO—, —$SO_2$— or —N($R^9$)—; $R^3$ in each of the n ($R^3O$) groups and the v ($R^3O$) groups is independently $C_2$-$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=$NR^{12}$)—, —C(S)—, or —C(O)—; q is an integer from 0 to 5; and $R^5$ is hydrogen or hydrocarbyl or substituted hydrocarbyl having from 1 to about 30 carbon atoms. In this context, preferred $R^1$, $R^2$, $R^4$, $R^5$, $R^6$, $R^7$, $R^8$, $R^9$, $R^{11}$ and $R^{12}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups; and (w) fatty imidazolines to be used herein are represented by the formula:

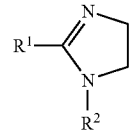

(41)

wherein $R^1$ and $R^2$ are independently H or a substituted or unsubstituted $C_1$-$C_{22}$ fatty acid.

In one embodiment, any of the amine or quaternary ammonium surfactants as described in sections (a)-(w) above are included in liquid glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain at least about 10 wt. % glyphosate a.e., more preferably at least about 15%, 20%, 25%, 30%, 35%, 40% or more wt. % a.e., or at least about 120 g a.e. glyphosate per liter, more preferably at least 130, 140, 150, 160, 170, 180, 190, 200, 210, 220, 230, 240, 250, 260, 270, 280, 290, 300, 310, 320, 330, 340, 350, 360, 370, 380, 390, or 400 g a.e./l or more.

In another embodiment, any of the cationic surfactants as described in (a)-(w) above are preferably formulated in concentrates that are free of alkyl polyglycosides, or that only contain alkyl polyglycosides having a light color of less than 10, preferably less than 9, 8, 7, 6, or 5 as measured using a Gardner colorimeter. When dye is added to a formulated glyphosate product having a Gardner color greater than about 10, the concentrate remains dark brown in color. Concentrates having a Gardner color value of 10 are difficult to dye blue or green as is often desired to distinguish the glyphosate product from other herbicidal products.

A subclass of such cationic surfactants described above includes a monoalkoxylated amine having the formula:

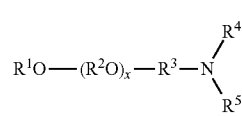

(42)

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2O$) groups is independently $C_2$-$C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2O$) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is ethylene or propylene, $R^4$ and $R^5$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is ethylene, $R^4$ and $R^5$ are methyl, and x is an average number from about 4 to about 20. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 13, 15, 20 or 25 $C_{14-18}$ ether dimethyl propylamines (from Tomah) and Surfonic™ AGM-550 from Huntsman.

Quaternary ammonium, sulfonium and sulfoxonium salts are also effective cationic surfactants in forming potassium glyphosate concentrates and have a chemical structure:

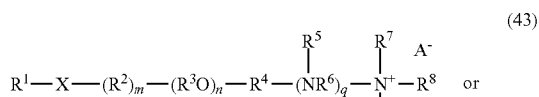
(43)

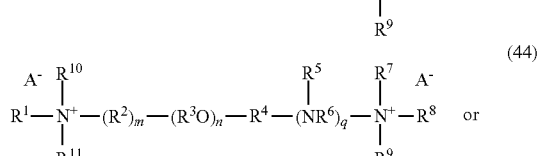
(44)

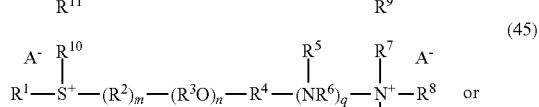
(45)

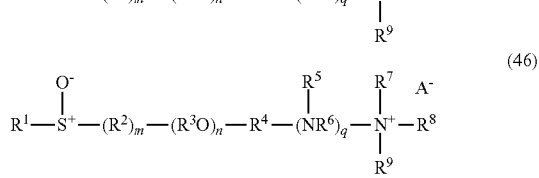
(46)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —($R^{13}$)$_s$($R^3O$)$_v$$R^{12}$; X is —O—, —OC(O)—, —N($R^{14}$)C(O)—, —C(O)N($R^{14}$)—, —C(O)O—, or —S—; $R^3$ in each of the n ($R^3O$) groups and v ($R^3O$) groups is independently $C_2$-$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=N$R^{12}$)—, —C(S)—, or —C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion. In this context, preferred $R^1$, $R^2$, $R^4$, $R^5$, $R^6$, $R^7$, $R^8$, $R^9$, $R^{10}$, $R^{11}$, $R^{13}$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Another cationic surfactant effective in the formulations of the invention is a diamine or diammonium salt having the formula:

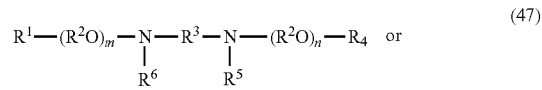
(47)

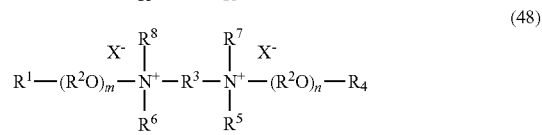
(48)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m ($R^2O$) and n ($R^2O$) groups and $R^9$ are independently $C_2$-$C_4$ alkylene, $R^3$ is hydrocarbylene or substituted hydrocarbylene having from about 2 to about 6 carbon atoms or —($R^2O$)$_p$$R_9$—, m and n are individually an average number from 0 to about 50, and p is an average number from 0 to about 60. In this context, preferred $R^1$, $R^3$, $R^4$, $R^5$, $R^6$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (47) or (48), $R^3$ is hydrocarbylene having from about 2 to about 6 carbon atoms, and the remaining groups are as defined above.

Some preferred cationic surfactants include alkylamine ethoxylates (including etheramines and diamines) such as tallowamine ethoxylate, cocoamine ethoxylate, etheramine ethoxylate, N-tallow ethylenediamine ethoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl) cocoamine N-oxide), nonethoxylated amine oxides (e.g., cethyldimethylamine N-oxide) and amidoamine oxides.

Preferred nonionic surfactants suitable for use in formulating the herbicidal compositions and concentrates of the invention include:

(a) alkoxylated alcohols having the formula:

(49)

wherein $R^1$ is hydrocarbyl or substituted hydrocarbyl having from 1 to about 30 carbon atoms, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x ($R^2O$) groups is independently $C_2$-$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x ($R^2O$) groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, $R^2$ in each of the x ($R^2O$) groups is independently ethylene or propylene, $R^3$ is hydrogen or methyl, and x is an average number from about 8 to about 30. Preferred commercially available alkoxylated alcohols include Procol™ LA-15 (from Protameen), Brij™ 35, Brij™ 76, Brij™ 78, Brij™ 97 and Brij™ 98 (from Sigma Chemical Co.), Neodol™ 25-12 (from Shell), Hetoxol™ CA-10, Hetoxol™ CA-20, Hetoxol™ CS-9, Hetoxol™ CS-15, Hetoxol™ CS-20, Hetoxol™ CS-25, Hetoxol™ CS-30, and Plurafac™ A38 (from BASF), ST-8303 (from Cognis), and Arosurf™ 66 E20 (from Goldschmidt).

(b) dialkoxylated alcohols having the formula:

$$R^1(OR^2)_xO\text{—}R^3\text{—}O\text{—}(R^2O)_yR^1 \tag{50}$$

wherein $R^1$ is independently hydrogen, or a linear or branched alkyl group having from 1 to about 4 carbon atoms, $R^2$ in each of the x ($R^2O$) and the y ($R^2O$) groups is independently $C_2$-$C_4$ alkylene, $R^3$ is hydrocarbylene or substituted hydrocarbylene having from 2 to about 30 carbon atoms, and x and y are independently an average number from 1 to about 60. In this context, preferred $R^3$ hydrocarbylene groups are linear or branched alkylene, linear or branched alkenylene, linear or branched alkynylene, arylene, or aralkylene groups. Preferably, $R^1$ is hydrogen, methyl or ethyl, $R^2$ in each of the x ($R^2O$) and the y ($R^2O$) groups is independently $C_2$-$C_4$ alkylene, $R^3$ is a linear or branched alkylene or linear or branched alkenylene group having from about 8 to about 25 carbon atoms, and x and y are independently an average number from about 1 to about 20. More preferably, $R^1$ is hydrogen or methyl, $R^2$ in each of the x ($R^2O$) and the y ($R^2O$) groups is independently ethylene or propylene, $R^3$ is a linear or branched alkylene or linear or branched alkenylene group having from about 8 to about 18 carbon atoms, and x and y are independently an average number from 1 to about 10. Even more preferably, $R^1$ is hydrogen, $R^2$ in each of the x ($R^2O$) and the y ($R^2O$) groups is independently ethylene or propylene, $R^3$ is a linear or branched alkylene group having from about 8 to about 18 carbon atoms, and x and y are independently an average number from 1 to about 5.

(c) alkoxylated dialkylphenols having the formula:

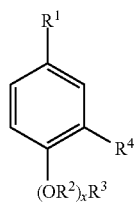
(51)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$-$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2O$) groups is independently $C_2$-$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

(d) alkoxylated alkylphenols having the formula:

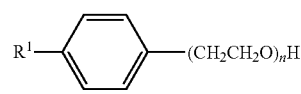
(52)

wherein $R^1$ is a substituted or unsubstituted $C_1$-$C_{22}$ group, and n is from 1 to about 20.

(e) alkoxylated mercaptans having the formula:

$$R^1S(R^2)_nH \tag{53}$$

wherein $R^1$ is a substituted or unsubstituted $C_1$-$C_{22}$ group; $R^2$ is methoxy, ethoxy or propoxy; and n is from 1 to about 20.

(f) alkyl pyrrolidones having the formula:

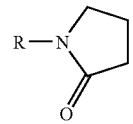
(54)

wherein R is a substituted or unsubstituted $C_1$-$C_{22}$ group.

(g) alkoxylated alkanolamides having the formula:

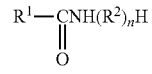
(55)

wherein $R^1$ is a substituted or unsubstituted $C_1$-$C_{22}$ group; $R^2$ is methoxy, ethoxy or propoxy; and n is from 1 to about 20; and (h) alkoxylated glycols having the formula:

$$R^1\text{—}(R^2)_n\text{—}R^3\text{—}OH \tag{56}$$

wherein $R^1$ is H, —OH, or a substituted or unsubstituted $C_1$-$C_{22}$ group; $R^2$ is methoxy, ethoxy or propoxy; $R^3$ is H, —OH, or a substituted or unsubstituted $C_1$-$C_{22}$ group; and n is from 1 to about 20.

(i) alkyl amine oxalate esters having the formulae:

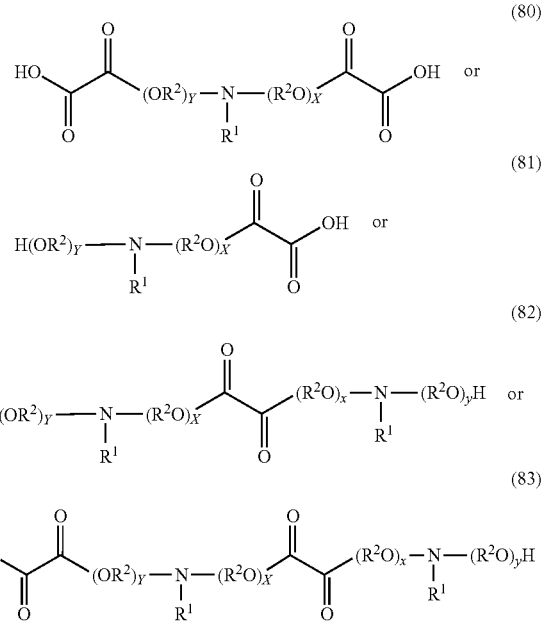

wherein $R^1$ is independently hydrocarbyl or substituted hydrocarbyl having from 1 to about 22 carbon atoms; $R^2$ in each of the x ($R^2O$) and y ($R^2O$) groups is independently $C_2$-$C_4$ alkylene; x is independently 0 to 50; y is independently 0 to 50; and the sum of x and y is 1 to 100. In this context, preferred $R^1$ hydrocarbyl groups are linear or branched alkyl, linear or branched alkenyl, linear or branched alkynyl, aryl, or aralkyl groups. Preferably, $R^1$ is independently a linear or branched alkyl or alkenyl group having from 1 to about 22 carbon atoms; $R^2$ in each of the x ($R^2O$) and y ($R^2O$) groups is independently $C_2$-$C_4$ alkylene; x is independently 0 to 10; y is independently 0 to 10; and the sum of x and y is 2 to 20. More preferably, $R^1$ is independently a linear or branched alkyl group having from 8 to about 18 carbon atoms; $R^2$ in each of the x ($R^2O$) and y ($R^2O$) groups is $C_2$ alkylene; x is independently 0 to 5; y is independently 0 to 5; and the sum of x and y is 5 to 10.

Other suitable nonionic surfactants include alkylpolyglucosides; glycerol esters such as glyceryl monolaurate, and ethyoxylated glyceryl monocococate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol ethoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as Neodols and oxoalcohol ethoxylates; and ethylene oxide/propylene oxide copolymers such as Pluronic type, Tetronic type, or Tergitol XH type.

Additional nonionic surfactants for inclusion in surfactant compositions that may be used in the invention are polyoxyethylene (5-30) $C_{8-22}$ alkylethers and polyoxyethylene (5-30) $C_{8-12}$ alkylphenylethers, wherein "(5-30)" means that the average number of ethylene oxide units in the polyoxyethylene chains of these surfactants is from about 5 to about 30. Examples of such nonionic surfactants include polyoxyethylene nonylphenols, octanols, decanols and trimethylnonanols. Particular nonionic surfactants that have proved useful include NEODOL™ 91-6 of Shell (a polyoxyethylene (6) $C_{9-11}$ linear primary alcohol), NEODOL™ 1-7 of Shell (a polyoxyethylene (7) $C_{11}$ linear primary alcohol), TERGITOL™ 15-S-9 of Union Carbide (a polyoxyethylene (9) $C_{12-15}$ secondary alcohol) and SURFONIC™ NP95 of Huntsman (a polyoxyethylene (9.5) nonylphenol). Suitable polyalkoxylated silicone surfactants include those described in U.S. Pat. No. 6,051,533, the disclosures of which are incorporated herein by reference.

In a preferred embodiment of the invention, the herbicidal compositions include at least one nonionic surfactant and at least one cationic surfactant. Any of the cationic and nonionic surfactants described herein can be used in combination in the herbicidal compositions of the invention. Preferred cationic surfactants include an alkylamine, an alkyl diamine, an alkyl polyamine, a mono- or di-quaternary ammonium salt, a monoalkoxylated amine, a dialkoxylated amine such as ethoxylated tallow amines, a monoalkoxylated quaternary ammonium salt, a dialkoxylated quaternary ammonium salt, an etheramine, an amine oxide, an alkoxylated amine oxide, and a fatty imidazoline. Preferred nonionic surfactants include an alkoxylated alcohol, a dialkoxylated alcohol, an alkoxylated dialkylphenol, an alkylpolyglycoside, an alkoxylated alkylphenol, an alkoxylated glycol, an alkoxylated mercaptan, a glyceryl or polyglyceryl ester of a natural fatty acid, an alkoxylated glycol ester, an alkoxylated fatty acid, an alkoxylated alkanolamide, a polyalkoxylated silicone, and an N-alkyl pyrrolidone. Examples of such surfactants include polyoxyethylene (5-30) $C_{8-22}$ amines or polyoxyethylene (5-30) polyoxypropylene (2-10) $C_{8-22}$ amines in combination with alkylpolyglucosides, alkoxylated or dialkoxylated alcohols such as polyoxyethylene (5-30) $C_{8-22}$ alkylethers, or methoxy, ethoxy or propoxy substituted glycol esters with a degree of substitution between 1 and about 20. Suitable cationic and nonionic surfactants for use in the compositions of the invention include those described in U.S. Pat. No. 6,245,713, which is incorporated herein by reference. When the surfactant component of the compositions of the present invention includes both cationic and nonionic surfactants, the weight ratio of nonionic surfactant(s) to cationic surfactant(s) is from about 1:10 to about 10:1, preferably from about 1:5 to about 5:1, more preferably from about 1:3 to about 3:1, and most preferably from about 1:1.5 to 1.5:1.

The herbicidal compositions of the invention may also include a compound capable of reducing eye irritancy. Such compounds are generally effective in combination with the alkylamine surfactants described herein, and have the formula:

wherein $R_1$ is a hydrocarbyl group having from about 8 to about 22 carbon atoms, each of the n ($R^2O$) groups is independently $C_2$-$C_4$ alkylene, n is a number from 0 to about 60, and $X_1$ is a carboxylate, sulfate or phosphate. These compounds are described in U.S. Pat. No. 6,063,733, which is incorporated herein by reference.

Suitable amphoteric surfactants include betaines such as simple betaines (e.g., cocodimethylbetaine), sulfobetaines, amidobetaines, and cocoamidosulfobetaines; imidazolinium compounds such as disodium lauroamphodiacetate, sodium cocoamphoacetate, sodium cocoamphopropionate, disodium cocoaminodipropionate, and sodium cocoamphohydoxypropyl sulfonate; and other amphoteric surfactants such as N-alkyl, N,-bis(2-hydroxyethyl)glycine and alkylaminedipropionates.

Other surfactants for use in herbicidal compositions and concentrates of the invention include compounds of the formula:

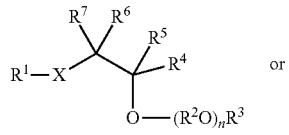

(58)

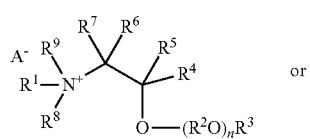

(59)

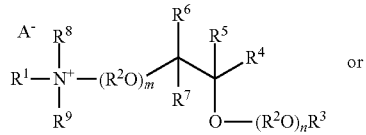

(60)

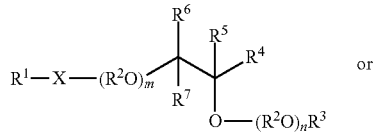

(61)

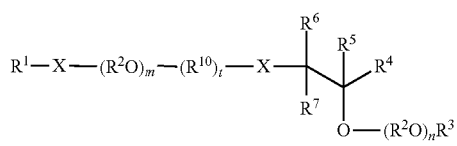

(62)

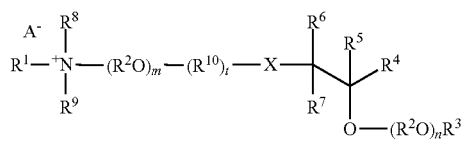

(63)

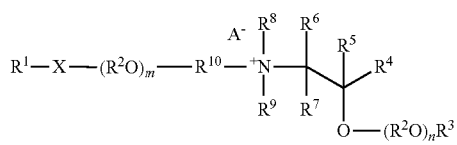

(64)

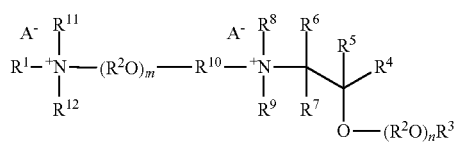

(65)

-continued

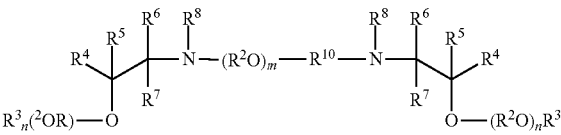

(66)

wherein $R^1$, $R^9$, and $R^{12}$ are independently hydrocarbyl or substituted hydrocarbyl having from 1 to about 30 carbon atoms, or —$(R^2O)_pR^{13}$; $R^2$ in each of the m ($R^2O$), n ($R^2O$), p ($R^2O$) and q ($R^2O$) groups is independently $C_2$-$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —$(CH_2)_yOR^{13}$ or —$(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrogen, hydrocarbyl or substituted hydrocarbyl having from 1 to about 30 carbon atoms, or —$(CH_2)_zO(R^2O)_pR^3$; m, n, p and q are independently an average number from 1 to about 50; X is independently —O—, —N($R^{14}$)—, —C(O)—, —C(O)O—, —OC(O)—, —N($R^{15}$)C(O)—, —C(O)N($R^{15}$)—, —S—, —SO—, or —$SO_2$—; t is 0 or 1; A— is an agriculturally acceptable anion; and y and z are independently an integer from 0 to about 30. In this context, preferred $R^1$, $R^3$, and $R^5$—$R^{15}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^9$, and $R^{12}$ are independently linear or branched alkyl or alkenyl groups having from 1 to about 22 carbon atoms, or —$(R^2O)_pR^{13}$; $R^2$ in each of the m ($R^2O$), n ($R^2O$), p ($R^2O$) and q ($R^2O$) groups is independently $C_2$-$C_4$ alkylene; $R^3$ is hydrogen, methyl or ethyl; $R^4$ is —$(CH_2)_yOR^{13}$ or —$(CH_2)_yO(R^2O)_qR^3$; $R^5$, $R^6$ and $R^7$ are independently hydrogen, linear or branched alkyl or alkenyl groups having from 1 to about 22 carbon atoms, or $R^4$; $R^8$, $R^{11}$, $R^{13}$ and $R^{15}$ are independently hydrogen, or linear or branched alkyl or alkenyl groups having from 1 to about 22 carbon atoms; $R^{10}$ is a linear or branched alkylene or alkenylene group having from 2 to about 18 carbon atoms; $R^{14}$ is a linear or branched alkyl or alkenyl group having from 1 to about 22 carbon atoms, or —$(CH_2)_zO(R^2O)_pR^3$; m, n, p and q are independently an average number from 1 to about 30; X is independently —O—, —N($R^{14}$)—, —C(O)—, —C(O)O—, —OC(O)—, —N($R^{15}$)C(O)—, —C(O)N($R^{15}$)—, —S—, —SO—, or —$SO_2$—, t is 0 or 1; A- is an agriculturally acceptable anion; and y and z are independently an integer from 0 to about 30. More preferably, $R^1$ is a linear or branched alkyl or alkenyl groups having from about 8 to about 18 carbon atoms, or —$(R^2O)_pR^{13}$; $R^9$ and $R^{12}$ are independently linear or branched alkyl or alkenyl groups having from 1 to about 22 carbon atoms, or —$(R^2O)_pR^{13}$; $R^2$ in each of the m ($R^2O$), n ($R^2O$), p ($R^2O$) and q ($R^2O$) groups is independently ethylene or propylene; $R^3$ is hydrogen or methyl; $R^4$ is —$(CH_2)_yOR^{13}$ or —$(CH_2)_yO(R^2O)_qR^3$; $R^8$, $R^{11}$, $R^{15}$ are independently hydrogen, or linear or branched alkyl or alkenyl groups having from 1 to about 22 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or —$(CH_2)_z$ $O(R^2O)_pR^3$; m, n, p and q are independently an average number from 1 to about 20; X is independently —O—, —$N(R^{14})$—, —C(O)—, —C(O)O—, —OC(O)—, —$N(R^{15})$C(O)—, —$C(O)N(R^{15})$—, —S—, —SO—, or —$SO_2$—, t is 0 or 1; $A^-$ is an agriculturally acceptable anion; and y and z are independently an integer from 0 to about 10. Most preferably, $R^1$ is a linear or branched alkyl or alkenyl groups having from about 12 to about 18 carbon atoms, or —$(R^2O)_p$ $R^{13}$; $R^9$ and $R^{12}$ are independently linear or branched alkyl or alkenyl groups having from 1 to about 6 carbon atoms, or —$(R^2O)_pR^{13}$; $R^2$ in each of the m ($R^2O$), n ($R^2O$), p ($R^2O$) and q ($R^2O$) groups is independently ethylene or propylene; $R^3$ is hydrogen; $R^4$ is —$(CH_2)_yOR^{13}$ or —$(CH_2)_yO(R^2O)_qR^3$; $R^8$, $R^{11}$, $R^{15}$ are independently hydrogen, or linear or branched alkyl or alkenyl groups having from 1 to about 6 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or —$(CH_2)_zO(R^2O)_pR^3$; m, n, p and q are independently an average number from 1 to about 5; X is independently —O— or —$N(R^{14})$—, t is 0 or 1; $A^-$ is an agriculturally acceptable anion; and y and z are independently an integer from 1 to about 3.

Preferred anionic surfactants effective in forming formulations of the invention include saturated carboxylic acids such as butyric, caproic, caprylic, capric, lauric, palmitic, myristic or stearic acid, and unsaturated carboxylic acids such as palmitoleic, oleic, linoleic or linolenic acid. Preferred carboxylic acids include palmitic, oleic or stearic acid. Other preferred anionic surfactants include alkyl sulfates such as sodium lauryl sulfate, and phosphate esters or diesters and their salts having the formulae:

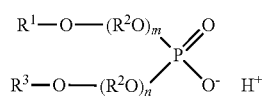

(6)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2O$) and the n ($R^2O$) groups is independently $C_2$-$C_4$ alkylene; and m and n are independently from 1 to about 30; or

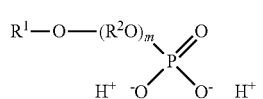

(5)

wherein $R^1$ is a linear or branched alkyl, linear or branched alkenyl, linear or branched alkynyl, aryl, or aralkyl group having from about 8 to about 30 carbon atoms; $R^2$ in each of the m ($R^2O$) groups is independently $C_2$-$C_4$ alkylene; and m is from 1 to about 30. Representative phosphate esters include oleth-10 phosphate, oleth-20 phosphate and oleth-25 phosphate.

Preferred phosphate ester surfactants include mono- and dialcohol phosphates, mono- and di-(polyoxyalkylene alcohol) phosphates and the mono- and dialcohol phosphates, (polyoxyalkylene alkylphenol) phosphates, and are represented by the formula:

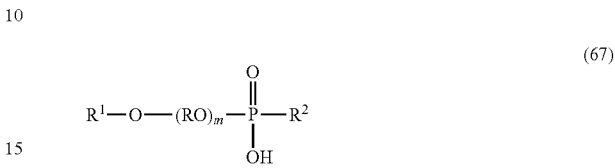

(67)

wherein $R^1$ is $C_8$-$C_{20}$ alkyl or $C_8$-$C_{20}$ alkylphenyl; R is an alkylene having from 2 to about 4 carbon atoms, usually ethylene or propylene, m is zero or a number up to about 60, preferably less than 10 and more preferably about 4, and $R^2$ is hydroxyl or $R^1$—O—$(RO)_m$— radical wherein $R^1$ and R are as just indicated and m is 0 to about 30. If $R^2$ is hydroxyl, then the compound is monoester. If $R^2$ is a $R^1$—O—$(RO)_m$-radical, then the compound is a diester. Mixtures of phosphate esters or diesters of formula (5), (6), and/or (67) and a cationic surfactant, particularly the alkylamine surfactants of formula (3), (33), (34), (39), (42) or (57) are preferred for use in the compositions of the invention. Mixtures of monoesters and diesters are also useful, together with the polyoxyalkylene alkylamines. Where mixtures of monoesters and diesters are present, the weight percentage of the monoester, or monoesters, exceeds that of the diester or diesters.

Other suitable anionic surfactants include fatty soaps such as ammonium tallowate and sodium stearate; alkyl sulfates such as sodium $C_{8-10}$ alcohol sulfate, and sodium oleyl sulfate; sulfated oils such as sulfated castor oil; ether sulfates such as sodium lauryl ether sulfate, ammonium lauryl ether sulfate, and ammonium nonylphenol ether sulfate; sulfonates such as petroleum sulfonates, alkylbenzene sulfonates (e.g., sodium (linear) dodecylbenzene sulfonate or sodium (branched) dodecylbenzene sulfonate), alkylnapthalene sulfonates (e.g., sodium dibutylnapthalene sulfonate), alkyl sulfonates (e.g., alpha olefin sulfonates), sulfosuccinates such as dialkylsulfosuccinates (e.g., sodium dioctylsulfosuccinate) and monoalkylsulfosuccinates and succinamides (e.g., disodium laurylsulfosuccinate and disodium N-alkylsulfosuccinamate); sulfonated amides such as sodium N-methyl N-coco taurate; isethionates such as sodium cocoyl isethionate; sarcosinates such as N-lauroyl sarcosine; and phosphates such as alkylether ethoxylate phosphates and alkylarylether ethoxyated phosphates.

Exemplary cationic surfactants that may be used in accordance with the present invention include the following species:

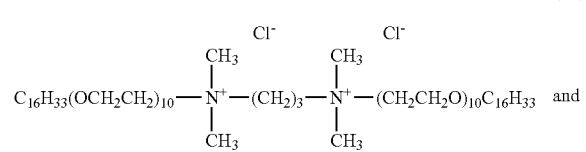

(68)

and

-continued

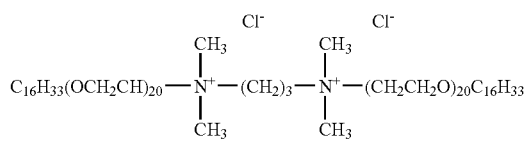

(69)

Other surfactants for use in herbicidal compositions and concentrates of the invention include N-acyl sarcosinates, which are described in U.S. Pat. No. 5,985,798, which is incorporated herein by reference. Such surfactants are represented by the formula:

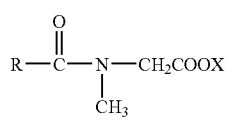

(70)

wherein R is $C_8$ to $C_{22}$ N-acyl, preferably a fatty acid of chain length $C_{10}$ to $C_{18}$, and X is salt forming cation including alkali metal, ammonia or alkanolamine. More preferably R is lauroyl, cocoyl, palmitoyl, myristoyl or oleoyl, and X is sodium, potassium, ammonium, an isopropylamine, or an amino alcohol. Preferred sarcosinates include sodium lauroyl sarcosinate, sodium cocoyl sarcosinate and sodium myristoyl sarcosinate, which are commercially available under the trademark HAMPOSYL from Hampshire Chemical Corp.

Alkylpolyglycosides are also suitable for use in the compositions and concentrates of the invention, and are described, for example, in U.S. Pat. No. 6,117,820. As used herein the term "alkylglycoside" includes mono- and poly-alkylglycosides. Glycosides are represented by the formula:

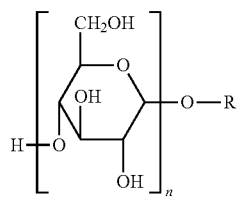

(71)

wherein n is the degree of polymerization, or number of glycose groups, and R is a branched or straight chain alkyl group preferably having from 4 to 18 carbon atoms, or a mixture of alkyl groups having an average value within the given range. The number of glycose groups per alkyl group may vary and alkyl mono- or di-, or polyglucose or saccharide derivatives are possible. Commercial alkylpolyglycosides usually contain a mixture of derivatives with n expressed as an average. Preferably n is between 1 and about 5, and more preferably between 1 and about 3. Typical of alkylglycosides is the product commercially available under the trade names AL2042 (Imperial Chemical Industries PLC) wherein n is an average of 1.7 and R is a mixture of octyl (45%) and decyl (55%), the product commercially available under the trade name AGRIMUL PG2069 (Henkel Corp) wherein n is an average of 1.6 and R is a mixture of nonyl (20%), decyl (40%) and undecyl (40%), and the product commercially available under the trade name BEROL AG6202 (Akzo Nobel) which is 2-ethyl-1-hexylglycoside.

Representative surfactants of the type mentioned above are described in U.S. Pat. Nos. 5,703,015, 5,750,468 and 5,389,598, the entirety of each being incorporated herein by reference.

The surfactant component of the compositions of the present invention may optionally contain a glycol or glycol ester of formula:

$$HO-(R^4O)_x-R^5 \tag{75}$$

wherein $R^4$ in each of the x ($R^4O$) groups is independently a linear or branched $C_{2-6}$ alkylene group, x is 1 to about 4, and $R^5$ is hydrogen or a $C_1$-$C_4$ hydrocarbyl group. Contemplated glycols and glycol esters include but are not limited to monoethylene glycol, diethylene glycol, propylene glycol or the methyl, ethyl, n-propyl, -butyl or t-butyl ethers thereof, dipropylene glycol or the methyl, ethyl, n-propyl, -butyl or t-butyl ethers thereof, tripropylene glycol, or the methyl, ethyl, n-propyl, -butyl or t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol.

Other nonionic surfactants may likewise be found useful, including without restriction polyoxyethylene polyoxypropylene block copolymers and alkyl polyglucosides. Cationic, anionic or amphoteric surfactants may also be included if desired.

In one embodiment of the invention, the herbicidal compositions include at least one nonionic surfactant and at least one cationic surfactant such as those described herein. Such surfactant combinations are described in U.S. Pat. No. 5,998,332, which is incorporated herein by reference.

Additional cationic surfactants suitable for use in the herbicidal compositions of the invention are those described in U.S. Pat. Nos. 5,563,111, 5,622,911, 5,849,663, 5,863,909, 5,985,794, 6,030,923 and 6,093,679, which are incorporated herein by reference.

The surfactant compositions typically are intended for mixing with a water soluble herbicide composition. It is preferred that there be substantially no water present in the surfactant composition.

A surfactant composition of the invention comprises any combination of the surfactants as described above. The surfactant composition is particularly preferred for use in formulating compositions or concentrates containing potassium, di-ammonium, ammonium, sodium, monoethanolamine, n-propylamine, methylamine, ethylamine, hexamethylenediamine, dimethylamine and/or trimethylsulfonium glyphosate.

The density of any glyphosate-containing formulation of the invention is preferably at least 1.050 grams/liter, more preferably at least about 1.055, 1.060, 1.065, 1.070, 1.075, 1.080, 1.085, 1.090, 1.095, 1.100, 1.105, 1.110, 1.115, 1.120, 1.125, 1.130, 1.135, 1.140, 1.145, 1.150, 1.155, 1.160, 1.165, 1.170, 1.175, 1.180, 1.185, 1.190, 1.195, 1.200, 1.205, 1.210, 1.215, 1.220, 1.225, 1.230, 1.235, 1.240, 1.245, 1.250, 1.255, 1.260, 1.265, 1.270, 1.275, 1.280, 1.285, 1.290, 1.295, 1.300, 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.410, 1.415, 1.420, 1.425, 1.430, 1.435, 1.440, 1.445, or 1.450 grams/liter.

Other additives, adjuvants, or ingredients may be introduced into the formulations of the present invention to improve certain properties of the resulting formulations.

Although the formulations of the present invention generally show good overall stability and viscosity properties without the addition of any further additives, the addition of a solubilizer (also commonly referred to as a cloud point enhancer or stabilizer) can significantly improve the properties of the formulations of the present invention. Suitable solubilizers for use with the novel formulations of the present invention include, for example, cocoamine (Armeen C), dimethylcocoamine (Armeen DMCD), cocoammonium chloride (Arquad C), PEG 2 cocoamine (Ethomeen C12), and PEG 5 cocoamine (Ethomeen C15), all of which are manufactured by Akzo Nobel (California).

Additionally, it has been found that the addition of a $C_4$ to $C_{16}$ alkyl or aryl amine compound, or the corresponding quaternary ammonium compound, greatly enhances the compatibility of certain glyphosate salts (e.g., potassium or isopropylamine) with surfactants that otherwise exhibit low or marginal compatibility at a given glyphosate loading. Suitable stabilizers include primary, secondary or tertiary $C_4$ to $C_{16}$ alkyl or aryl amine compounds, or the corresponding quaternary ammonium compounds. Such stabilizers greatly enhance the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 $C_2$-$C_4$ alkylene oxide groups, preferably ethylene oxide groups. Preferred alkylamine compounds include $C_6$ to $C_{12}$ alkylamines having 0 to 2 ethylene oxide groups. Similarly, etheramine compounds having 4 to 12 carbons and 0 to about 5 ethylene oxide groups, as well as the corresponding quaternary ammonium compounds, also enhance the compatibility of such formulations. In one embodiment, the compounds which enhance the compatibility of such surfactants include amines or quaternary ammonium salts having the formula:

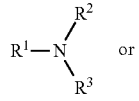

(76)

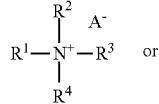

(77)

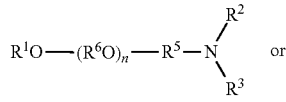

(78)

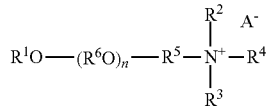

(79)

wherein $R^1$ is linear or branched alkyl or aryl having from about 4 to about 16 carbon atoms, $R^2$ is hydrogen, methyl, ethyl, or —$(CH_2CH_2O)_xH$, $R^3$ is hydrogen, methyl, ethyl, or —$(CH_2CH_2O)_yH$ wherein the sum of x and y is not more than about 5; $R^4$ is hydrogen or methyl; $R^6$ in each of the n ($R^6O$) groups is independently $C_2$-$C_4$ alkylene; $R^5$ is hydrocarbylene or substituted hydrocarbylene having from 2 to about 6 carbon atoms; and A- is an agriculturally acceptable anion.

Ammonium sulfate, citric acid or ethylendiaminetetraacetic acid (EDTA) can also be added to the formulations of the invention to reduce the amount of dicarboxylic acid component otherwise needed to maintain herbicidal efficacy of the formulation. The weight ratio of ammonium sulfate to oxalic acid is preferably from about 10:1 to about 1:10, more preferably from about 5:1 to about 1:5 and most preferably from about 3:1 to about 1:3 on an a.e. basis.

The glyphosate compositions of the invention can be prepared in liquid or solid form as tank mixes, liquid concentrates, water soluble powders, water soluble solid concentrates, and other water soluble forms including flakes, pellets and tablets.

Liquid concentrates and tank mixes of the invention can be prepared by conventional methods of mixing the components including the dicarboxylic acid component, with water.

Water soluble solid concentrate pesticidal mixtures may be prepared in a mixing step by combining a glyphosate component as described above which includes: glyphosate acid, a salt of glyphosate acid or mixtures thereof; and a dicarboxylate component as described above which includes a dicarboxylic acid, derivatives of dicarboxylic acid or mixtures thereof; and optionally water and an adjuvant component or co-herbicide. If a portion or all of the glyphosate component is glyphosate acid and/or if a portion or all of the dicarboxate composition is a dicarboxylic acid, a base may be added to the mixture such that at least a portion of the glyphosate acid and/or dicarboxylic acid is neutralized by the base in a neutralizing step. The mixing and neutralization steps may be carried out separately or in combination to form a water soluble pesticidal mixture as described in greater detail below. Finally, the water soluble pesticidal mixture may be further processed in one or more material processing steps to form a powder, granular or flake product.

In general, for preparation of a water soluble solid concentrate pesticidal mixture, a water soluble salt of glyphosate acid is used and may be, for example, a mono-, di- or tri-basic salt of glyphosate acid including an ammonium salt of glyphosate, an alkali metal salt of glyphosate (e.g., sodium glyphosate or potassium glyphosate), an alkylamine salt of glyphosate (e.g. mono-isopropylamine glyphosate) or an alkanolamine salt of glyphoste (e.g. monoethanolamine glyphosate) or a mixture of one or more of the previously described salts of glyphosate. Typically the glyphosate component is added as glyphosate acid, an ammonium salt of glyphosate acid, more typically a mono-ammonium salt of glyphosate acid, or mixtures thereof.

The glyphosate component may be added as a dry solid, a moist solid (e.g. glyphosate acid wet cake) or as part of a slurry. The water soluble salt of glyphosate acid may be a single water soluble salt of glyphosate or may be a combination of two or more water soluble salts of glyphosate acid. Where two or more water soluble salts of glyphosate are added, they may be added separately to the mixture or they may first blended together and the blend may then be added to the mixture.

The amount of glyphosate component added to the mixture is typically from about 30% to about 80%, in one embodiment from about 40% to about 72% and in another embodiment from about 55% to about 68% by weight of the total mixture on an acid equivalent basis.

In general, the dicarboxylic acid component for use in water soluble solid concentrate pesticidal mixtures is as described above. The dicarboxylate component may also be a combination of two or more dicarboxylic components. Where two or more dicarboxylic components are added, they may be added separately to the mixture or they may first blended together and the blend may then be added to the mixture. The dicarboxylate component may be added as a solid, a melt, or a slurry. Solid dicarboxylic acids typically have poor solubility in water, therefore when all or a portion of the dicarboxylic acid component is a dicarboxylic acid it may be combined with a base component to form an acid salt.

Where the dicarboxylate component is added as a melt, it should be noted that the melt will typically crystallize upon cooling. Accordingly, it may be preferable to maintain the temperature of the mixture above the melt temperature of the dicarboxylate component until a substantially homogeneous mixture is formed.

Where the dicarboxylate component is added as a slurry, the dicarboxylate component is typically mixed with water and/or an adjuvant component to form the slurry. While not narrowly critical to the present invention, the concentration of the slurry may be varied depending on the desired total quantity of water and/or adjuvant component melt in the mixture as well as the amount of water and/or adjuvant that is to be added with one or more of the other components.

The molar ratio of the dicarboxylate component to the water soluble salt of glyphosate acid added to the mixture is typically from about 4:1 to about 1:11, from about 3:1 to about 1:8 and in one embodiment from about 1.5:1 to about 1:7 on an acid equivalent basis.

The water may be added separately or in combination with one or more of the other components. In general the amount of water present in the mixture is at least about 2% by weight of all of the components added to the mixture. Typically some amount of water will be present via dicarboxylic acid hydration. Further, in embodiments where glyphosate acid slurry is used, water will be introduced with that component. Therefore, in some embodiments, water content of about 2% by weight or greater may be achieved through only glyphosate and/or dicarboxylic addition. The amount of water, when added, typically added is from about 2% to about 25% and may vary depending on the neutralization and/or material processing steps as discussed in more detail below.

An adjuvant component may be optionally included in the mixture of the glyphosate component and the dicarboxylate component. The adjuvant component may be a single adjuvant or it may comprise two or more adjuvant materials. Where two or more adjuvant materials are used, they may be added separately to the mixture or they may first blended together and the blend may then be added to the mixture. A portion or all of the adjuvant may be added as a solid, melt or slurry and may be added separately or in combination with one or more of the other components of the mixture.

The adjuvant component may be added prior to neutralization, during neutralization, or after neutralization. In general, all of the adjuvant is added prior to the material processing steps, e.g., pan granulation, drum drying, spray drying and extrusion. In one embodiment a portion of the adjuvant is added during the neutralization step with the remainder being added after neutralization.

In general, the adjuvant added to the reaction mixture may be a nonionic surfactant, cationic surfactant, anionic surfactant, amphoteric surfactant, silicone surfactant, fluorocarbon surfactant, anti-foaming agent, filler, humectant, desiccant, lubricant or mixtures thereof. Suitable surfactants are described above. Examples of suitable anti-foaming agents include silicones and fatty acids. Examples of suitable fillers include diammonium phosphate, sodium phosphate, ammonium sulfate, sodium chloride, sodium sulfate, dyes or pigments, urea, sucrose and potassium phosphate. Examples of suitable humectants include ethylene glycol, propylene glycol and glucose. Examples of suitable lubricants include fatty acids such as oleic acid; silicon oils such as polydimethylsiloxane; fatty esters such as corn oil, sugars and reduced sugars. Examples of suitable scavengers include sodium sulfite and ascorbic acid.

The adjuvant component is typically added to the mixture such that the total amount of adjuvant component, based on contained surfactant, in the water soluble pesticidal mixture is generally no greater than about 25% by weight, typically from about 5% to about 25% and more typically from about 7.5% to about 20% by weight of the water soluble pesticidal mixture. Typically the weight ratio of the adjuvant component, based on contained surfactant, to the dicarboxylic acid component is from about 10:1 to about 1:10, more typically from about 5:1 to about 1:3, and still more typically from about 3:1 to about 1:2.

Co-Herbicides may be optionally added to the mixture in addition to the glyphosate component. The co-herbicide, if included, may be an acid which may be neutralized in the presence of a base during the neutralization step, may be added after the neutralization, or may be added as a salt. Herbicides salts are generally water-soluble and the end-product of the process is a water-soluble granular formulation. Optionally, a water-insoluble herbicidal active ingredient can be included in the mix, in which case the end-product of the process is a water-dispersible granular formulation. Suitable water-soluble and water-insoluble co-herbicides are described above.

The glyphosate acid and/or the di-carboxylic acid may be neutralized by reacting the acid(s) with a base to form a water soluble salt of glyphosate acid and a salt of di-carboxylic acid, respectively. Typically, a portion or all of the glyphosate component is added as glyphosate acid and neutralized to form a water soluble salt thereof. The dicarboxylate component may be added as dicarboxylic acid or a derivative thereof. If the dicarboxylate component is added as a derivative of dicarboxylic acid, it may be added in part or in whole prior to, during and/or after the neutralization of the glyphosate acid. If added as dicarboxylic acid, the acid may be neutralized to form the salt thereof and subsequently added during the neutralization of glyphosate acid, co-neutralized with the glyphosate acid, or added to the neutralized glyphosate acid and subsequently neutralized.

In general, the base component used in the neutralization step may be an alkali metal hydroxide such as sodium hydroxide or potassium hydroxide, an alkali earth metal hydroxide such as magnesium hydroxide or calcium hydroxide, carbonates of alkali metals or alkali earth metals such as sodium carbonate or sodium bicarbonate, alkali metal phosphates such as sodium phosphate, disodium phosphate, trisodium phosphate, potassium phosphate, ammonium phosphate or diammonium phosphate, or ammonia, ammonium carbonate, ammonium bicarbonate, ammonium hydroxide or mixtures thereof. In general, the amount of base component added to the reactor in which the neutralization step is carried out is determined based on the desired degree of neutralization of the glyphosate acid and/or dicarboxylic acid present in the components fed to the process and can be readily determined. Typically, in the case of neutralizing glyphosate acid, the amount of base component added is approximately the stoichiometric amount required to neutralize a substantial portion of the first proton of glyphosate acid such that the pH is at least about 3, typically from about 3 to about 6 and more typically from about 3.5 to about 4.5. That is, at least about 50%, at least about 70%, at least about 80%, at least 90% or even 100% by weight or greater of the glyphosate acid is neutralized and, if present, a portion or all of any dicarboxylic acid present in the mixture is also neutralized. As stated earlier, the amount of base component added may be varied to over or under neutralize the glyphosate and/or dicarboxylic acids present without departing from the scope of the present invention.

A water soluble salt of glyphosate acid may be formed by combining glyphosate acid, a base and water to form a reaction mass and allowing at least a portion of the glyphosate screens acid to react with the base to form a water soluble salt of the glyphosate acid. The amount of water added to the reaction mass may be varied such that the reaction mass formed is either in a liquid state or a solid state. In the liquid state reaction, water is added to the reaction mass such that the reaction mass forms an aqueous solution as described in U.S. patent application Ser. No. 09/624,949, filed Jul. 25, 2000 and U.S. patent application Ser. No. 09/703,077, filed Jul. 25, 2000, the entire disclosures of which are incorporated herein by reference. The reaction product is a concentrated solution or slurry which may then be spray dried to form a powder, dried and then pan granulated to form granules, or drum dried to form flakes. In the solid state reaction, the total amount of water added is typically no greater than 25% by weight of all of the glyphosate acid, base and water added to the reaction mass thereby forming a wet solid state reaction mixture. Advantageously, the heat of reaction of the glyphosate acid and the base causes the evaporation of water from the reaction mass thereby reducing the water content. Depending on initial amount of water added to the reaction mass and the amount of water evaporated from the reaction mass, the reaction product may be a substantially dry, free flowing powder having a moisture content of no greater than about 2% by weight or a downstream processable paste having a moisture content of from about 2% to about 20% by weight, as described in U.S. Pat. Nos. 5,633,397 and 5,614,468, U.S. patent application Ser. No. 10/150,030 filed on May 17, 2002 and PCT publication no. WO 01/08492, the entire disclosures of which are incorporated herein by reference. An adjuvant component may be added to the reaction mixture prior to and/or during the reaction. In addition, the reaction product, whether as a dry powder or a paste may be further combined with an adjuvant component and/or additional water to form an extrudable mixture. The extrudable mixture may then be extruded to form a granular product.

In general the process for mixing the glyphosate component, dicarboxylate component, water and optionally the adjuvant component and/or co-herbicide may be carried out as a batch or continuous process in either a solid or liquid state. The mixing step may be carried out prior to neutralization of one or more of the components such that the glyphosate component and/or the dicarboxylate component includes an acid form or after neutralization of both components. That is, in one embodiment a glyphosate component, a portion or all of which is glyphosate acid may be combined with a derivative of dicarboxylic acid. In another embodiment, a water soluble salt of glyphosate acid may be combined with a dicarboxylate component, a portion or all of which is a dicarboxylic acid. In another embodiment, a glyphosate component, a portion or all of which is glyphosate acid may be combined with a dicarboxylate component, a portion or all of which is a dicarboxylic acid. In another embodiment, a water soluble salt of glyphosate acid may be combined with a dicarboxylic acid derivative.

The mixture of water-soluble salts of glyphosate acid and dicarboxylate component may be further processed to form dry ammonium glyphosate granules. According to this embodiment, additional adjuvant component may be added to the paste mixture and mixed until a homogeneous wet mix, preferably having a dough-like consistency, herein referred to as an extrudable glyphosate/dicarboxylic acid mixture is formed. It is generally preferred to add the adjuvant to the glyphosate paste mixture after the paste has cooled to a temperature of from about 25° C. to about 75° C., more preferably about 50° C. to about 70° C. and more preferably about 70° C.

The extrudable mixture of glyphosate component and dicarboxylate component may be extruded through screens having apertures which typically have a nominal diameter about 0.5 to about 3 mm, more typically from about 0.5 mm to about 2 mm, and in one embodiment from about 0.6 to about 1.5 mm.

Finally, the moist granules may be dried to further reduce the moisture concentration if desired. Any known drying method can be used, such as fluid bed drying. In one embodiment, a continuous fluid bed dryer is used with continuous inward feed from the extruder and continuous outward feed, for example to a holding vessel or packaging unit, optionally via a classifying step as indicated below. The granules are may be dried to a moisture content below about 1%, or even below about 0.5%, by weight.

After drying, the granules can be packaged or held in a hopper or other storage vessel until ready for packaging, but it is generally preferred to first classify the granules, for example by sieving, to retain only those in a desired size range. This is optional step (e) of the process of the present invention. An illustrative size range to be retained is larger than 40 mesh (about 0.6 mm) and smaller than 5 mesh (about 5 mm). Over- and under-sized granules or fragments or aggregates thereof can be recycled by adding them to the wet mix prior to extrusion.

Although various steps in the process may be performed as either a batch process or a continuous process, it is preferred that some or all of the process steps are performed continuously. In addition, if one or more of the components are added as an acid and neutralized and in particular if the glyphosate acid and dicarboxylic acid are co-neutralized, it is preferred that the reaction of glyphosate acid and base and the dicarboxylic acid and base be carried out in a continuous reactor capable of both mixing the reaction components and conveying the reaction mass to the discharge of the reactor.

Solid adjuvants for a pesticide composition of the invention consist essentially of a surfactant component comprising one or more surfactants and an enhancer component. When the adjuvant is diluted in a suitable volume of water to form an enhanced application mixture and applied to the foliage of a susceptible plant, increased efficacy of a pesticide may result from a number of mechanisms depending on the enhancer. Without being bound to any particular mechanism, and based on experimental evidence to date, the inhibition of the plant EPSPS enzyme by the pesticide within the plant treated is increased with the enhanced application mixture as compared to a plant treated with a reference application mixture devoid of the enhancer component but otherwise having the same composition as the enhanced application mixture. Under another theory, cell membrane permeability within the plant is increased thereby increasing cellular uptake of the pesticide in the plant treated with the enhanced application mixture as compared to a plant treated with the reference application mixture. Under still another theory, expression of hydroxyproline-rich glycoproteins is increased thereby increasing the movement of the pesticide to the phloem in the plant treated with the enhanced application mixture as compared to a plant treated with the reference application mixture. Suitable pesticides are discussed above. In one embodiment the pesticide comprises glyphosate acid or an ester or salt thereof.

The solid adjuvant preferably contains an enhancer component comprising a dicarboxylic acid source as described above. In some embodiments the dicarboxylic acid source is not a surfactant or a pesticide. In one embodiment the dicarboxylic source is an acid or an anhydride, ester, amide, halide, salt or precursor thereof having two carboxyl functional groups joined by a covalent bond or an alkylene or alkenylene moiety having 1 to about 10 carbon atoms. In another embodiment the dicarboxylic acid source comprises oxalic acid or an anhydride, ester, amide, halide, salt or precursor thereof.

The surfactant component is as described above and may comprise a nonionic, cationic, anionic, amphoteric or zwitterionic surfactant or mixtures thereof. In one embodiment the surfactant component is selected from cationic, nonionic, anionic and amphoteric surfactants, and mixtures thereof. In another embodiment the surfactant component comprises at least one cationic surfactant and at least one nonionic surfactant. In yet another embodiment the surfactant component consists of cationic and nonionic surfactants or mixtures thereof. In another embodiment, the surfactant component comprises a cationic surfactant other than an organic quaternary ammonium salt. In still another embodiment the weight ratio of the surfactant component to the enhancer component is preferably less than 3:1 on an acid equivalent basis, or less than 2.9:1, 2.8:1, 2.7:1, 2.6:1, 2.5:1, 2.4:1, 2.3:1, 2.2:1, 2.1:1, 2.0:1, 1.9:1, 1.8:1, 1.7:1, 1.6:1, 1.5:1, 1.4:1, 1.3:1, 1.2:1, 1.1:1, or 1.0:1.

The solid adjuvant may further include an inorganic salt (which may also function as an inorganic filler), organic fillers or a polycarboxylate salt. Examples of suitable inorganic salts and fillers include diammonium phosphate, sodium phosphate, potassium phosphate, ammonium sulfate, sodium chloride, sodium sulfate, and inorganic dyes or pigments. Examples of organic fillers include, urea, sucrose and organic dyes or pigments. Examples of polycarboxylate salts include sodium citrate, potassium citrate, sodium ethylendiaminetetraacetate (EDTA) and potassium EDTA.

The solid adjuvant of the invention preferably comprise an enhancer component in a concentration ranging from about 34% to about 90% by weight and typically from about 70% to about 90% by weight, a surfactant component in a concentration ranging from about 5% to about 50% by weight and typically from about 5% to about 20% by weight, and optionally, a filler in a concentration generally no greater than about 34% by weight and typically from about 5% to about 10% by weight.

In a process for the preparation of solid adjuvants, wherein the adjuvant comprises a dicarboxylic acid source, the dicarboxylic acid may be combined with a base component such that the dicarboxylic acid is neutralized by the base component to form a salt of dicarboxylic acid. One or more components may be combined with the dicarboxylic acid source before, during or after the neutralization to form the solid adjuvant composition. Preferably, the other components added to the dicarboxylic acid source to form the solid adjuvant composition comprises one or more surfactant(s) and may optionally include, for example, an inorganic salt (which may also function as an inorganic filler), organic fillers or a polycarboxylate salt. The amounts of the dicarboxylic acid source and the surfactant, and optionally a base component and/or filler, to be combined are determined such that the solid adjuvant, when formed, has the concentrations as set forth above. The solid adjuvant composition may be combined with a pesticide, for example a glyphosate component, to form a water-soluble pesticidal composition or may be optionally subjected to further material processing and/or packaged separately as a solid adjuvant composition. When co-formulated with a pesticide or when applied with a pesticide, the preferred weight ratio of pesticide to dicarboxylic acid is between 3:1 and 6:1, and the preferred weight ratio of pesticide to surfactant is between 2:1 and 5:1.

While not necessary in the practice of the present invention, it may be desirable to prepare the solid adjuvant composition such that the bulk density of the solid adjuvant composition is roughly the same as the bulk density of a pesticide component or a water-soluble pesticidal composition, to which the solid adjuvant composition is to be subsequently combined. The amount of filler present in the solid adjuvant composition may be selected based on the desired bulk density of the solid adjuvant composition.

In one embodiment a solid adjuvant comprising a dicarboxylic acid or an anhydride, ester, amide, halide, salt or precursor thereof and at least one surfactant in a concentration sufficient to increase the dissolution rate of the solid and reduce dusting may be packaged for use in a pesticidal tank mix. The particle size of the solid is generally sufficient to dissolve in a suitable volume of water containing the pesticide without formation of crystals therein to form a biologically effective enhanced application mixture for application to the foliage of a susceptible plant. The application mixture preferably can be applied to the foliage of a susceptible plant using a conventional applicator without clogging the nozzles of said applicator during application. The solid adjuvant of the invention is generally tankmixed with a pesticide to form an enhanced application mixture in an amount of about 30 to about 100 pounds per 100 acres.

In a method of using the liquid or solid pesticidal compositions of the inventions to control unwanted vegetation, an aqueous tank mixture is prepared containing a source of glyphosate anions and a dicarboxylic acid source. Preferred glyphosate sources and dicarboxylic acid sources are as describe above and include glyphosate acid or a salt or ester thereof and dicarboxylic acids, or an anhydride, ester, amide, halide, salt or precursors thereof. In particular, the present invention includes a method for killing or controlling weeds or unwanted vegetation comprising the steps of diluting a liquid concentrate in a convenient amount of water to form a tank mix and applying a herbicidally effective amount of the tank mix to the foliage of the weeds or unwanted vegetation. Similarly included in the invention is a method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

If desired, the user can mix one or more adjuvants with a composition of the invention and the water of dilution when preparing the application composition. Such adjuvants can include, for example, a surfactant with the aim of further enhancing herbicidal efficacy. However, under most conditions a herbicidal method of use of the present invention gives acceptable efficacy in the absence of such adjuvants.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, at least 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

The method of the present invention where the water-soluble herbicide is glyphosate, more particularly a water-soluble glyphosate salt, is applicable to any and all plant species on which glyphosate is biologically effective as a herbicide. This encompasses a very wide variety of plant species worldwide. Likewise, compositions of the invention containing a glyphosate salt can be applied to any and all plant species on which glyphosate is biologically effective. Therefore, for example, and in one method, compositions of the invention containing a glyphosate source as an herbicidal active ingredient and a dicarboxylic acid source can be applied to a plant in a herbicidally effective amount.

In another method of the invention an aqueous tank mix is formed containing between 0.01% and about 3% by weight glyphosate anions and conjugate anions of a dicarboxylic acid source at a concentration between about 2% by weight and the maximum percent by weight dictated by the solubility of the dicarboxylic acid source.

The tank mix is then used to control unwanted vegetation.

In another method of the invention an aqueous tank mix is formed wherein the molar ratio of glyphosate to dicarboxylic acid in said aqueous mixture is between about 0.1 and about 16 on an acid equivalent basis. The tank mix is then used to control unwanted vegetation.

Contemplated methods for forming a tank mixes containing between 0.01% and about 3% by weight glyphosate anions and conjugate anions of the dicarboxylic acid source at a concentration between about 2% by weight and the maximum percent by weight dictated by the solubility of the dicarboxylic acid source, or a molar ratio of glyphosate to dicarboxylic acid in said aqueous mixture is between about 0.1 and about 16 on an acid equivalent basis, include diluting a liquid or solid herbicidal concentrate or directly forming a tank mix by combining a glyphosate source and the dicarboxylic acid source in said weight percent or in said molar ratio.

In yet another method of the invention, unwanted vegetation is controlled in a plurality of areas wherein other application mixtures comprising a glyphosate component in the absence of any dicarboxylic acid component were previously administered. Efficacy is enhanced by forming and applying to said areas an application mixture containing the glyphosate source and the one or more sources of the dicarboxylic acid source.

In a particular contemplated method of use of a composition of the invention, the composition, following dilution in water or following direct formulation as a tank mix, is applied to foliage of crop plants genetically transformed or selected to tolerate glyphosate, and simultaneously to foliage of weeds or undesired plants growing in close proximity to such crop plants. This method of use results in control of the weeds or undesired plants while leaving the crop plants substantially unharmed. Crop plants genetically transformed or selected to tolerate glyphosate include those whose seeds are sold by Monsanto Company or under license from Monsanto Company bearing the Roundup Ready® trademark. These include, without restriction, varieties of cotton, soybean, canola, sugar beet, wheat and corn.

Methods of marketing glyphosate and/or dicarboxylic acids sources for use in mixtures for application to vegetation to be controlled are also contemplated by the invention. In one method: (1) sources of glyphosate and/or dicarboxylic acid are offered or designated; (2) information for preparing aqueous herbicidal mixtures from said glyphosate source and/or said dicarboxylic acid source are made available, supplied or referenced; (3) information regarding desired molar and/or weight ratios of the glyphosate component to the dicarboxylic acid component for achieving increased herbicidal efficacy are made available, supplied or referenced; and (4) information regarding application rates and schedules to unwanted vegetation are made available, supplied or referenced thereby enabling the preparation and use of the inventive herbicidal aqueous mixtures.

Also contemplated are methods for preparation of an herbicidal composition for control of unwanted vegetation. In one embodiment a dicarboxylic acid source and a glyphosate source are obtained, and mixed with water to form an aqueous herbicidal mixture containing between 0.01% and about 3% by weight glyphosate a.e. and between 2% by weight and the maximum percent by weight dictated by the solubility of the dicarboxylic acid source. The aqueous herbicidal mixture is then applied to the vegetation to be controlled. In another embodiment, a crude dicarboxylic acid source is milled to produce a refined dicarboxylic acid source of reduced average particle size, the refined dicarboxylic acid source is transported to a mixing site for mixing with a glyphosate acid, salt or ester thereof.

Application of plant treatment compositions to foliage is preferably accomplished by spraying, using any conventional means for spraying liquids, such as spray nozzles, atomizers or the like. Compositions of the invention can be used in precision farming techniques, in which apparatus is employed to vary the amount of pesticide applied to different parts of a field, depending on variables such as the particular plant species present, soil composition, etc. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl ($-CH_2OH$), and hydroxyethyl ($-C_2H_4OH$), bis(hydroxymethyl)methyl ($-CH(CH_2OH)_2$), and tris(hydroxymethyl)methyl ($-C(CH_2OH)_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number." The presence in a composition of individual surfactant molecules having an integer number of such units outside the stated range in "average number" does not remove the composition from the scope of the present invention, so long as the "average number" is within the stated range and other requirements are met.

By "storage-stable," in the context of a liquid concentrate of the invention, is meant not exhibiting phase separation on exposure to temperatures up to about 50° C. for 14-28 days, and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate aqueous solution concentrate. Ideally the cloud point should be 60° C. or more, and the composition should withstand temperatures as low as about −10° C., preferably as low as about −20° C., for up to about 7 days without crystal growth, even in the presence of seed crystals of the glyphosate salt.

As used herein, the term "surfactant" means any compound that reduces surface tension when dissolved in water or water solutions, or that reduces interfacial tension between two liquids or between a liquid and a solid. Examples of surface active agents include detergents, wetting agents and emulsifiers.

A surfactant that is described herein as "compatible" with a glyphosate salt at specified surfactant and glyphosate a.e. concentrations is one that enables incorporation without promotion of glyphosate crystal formation during the granulation or drying process, one that will not precipitate or adversely impact the granulation or drying process as by, for example, separating from the composition thereby preventing a homogeneous composite or by adhering to process equipment, or one that will not react with other components or otherwise degrade thus altering its physical properties.

An "agronomically useful surfactant content" means containing one or more surfactants of such a type or types and in such an amount that a benefit is realized by the user of the composition in terms of herbicidal effectiveness by comparison with an otherwise similar composition containing no surfactant.

By "fully loaded" is meant having a sufficient concentration of a suitable surfactant to provide, upon conventional dilution in water and application to foliage, herbicidal effectiveness on one or more important weed species without the need for further surfactant to be added to the diluted composition.

EXAMPLES

The following Examples are provided for illustrative purposes only and are not intended to limit the scope of the present invention. The Examples will permit better understanding of the invention and perception of its advantages and certain variations of execution.

Spray compositions of the Examples contained an exogenous chemical, such as glyphosate potassium salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

Because the commercially most important herbicidal derivatives of N-phosphonomethylglycine are certain salts thereof, the glyphosate compositions useful in the present invention will be described in more detail with respect to such salts. These salts are well known and include ammonium, IPA, alkali metal (such as the mono-, di-, and tripotassium salts), and trimethylsulfonium salts. Salts of N-phosphonomethylglycine are commercially significant in part because they are water soluble. The salts listed immediately above are highly water soluble, thereby allowing for highly concentrated solutions that can be diluted at the site of use. In accordance with the method of this invention as it pertains to glyphosate herbicide, an aqueous solution containing a herbicidally effective amount of glyphosate and other components in accordance with the invention is applied to foliage of plants. Such an aqueous solution can be obtained by dilution of a concentrated glyphosate salt solution with water, or dissolution or dispersion in water of a dry (i.e., granular, powder, tablet or briquette) glyphosate formulation.

Exogenous chemicals should be applied to plants at a rate sufficient to give the desired biological effect. These application rates are usually expressed as amount of exogenous chemical per unit area treated, e.g. grams per hectare (g/ha). What constitutes a "desired effect" varies according to the standards and practice of those who investigate, develop, market and use a specific class of exogenous chemicals. For example, in the case of a herbicide, the amount applied per unit area to give 85% control of a plant species as measured by growth reduction or mortality is often used to define a commercially effective rate.

Herbicidal effectiveness is one of the biological affects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The herbicidal effectiveness data set forth herein report "inhibition" as a percentage following a standard procedure in the art which reflects a visual assessment of plant mortality and growth reduction by comparison with untreated plants, made by technicians specially trained to make and record such observations. In all cases, a single technician makes all assessments of percent inhibition within any one experiment or trial. Such measurements are relied upon and regularly reported by Monsanto Company in the course of its herbicide business.

The selection of application rates that are biologically effective for a specific exogenous chemical is within the skill of the ordinary agricultural scientist. Those of skill in the art will likewise recognize that individual plant conditions, weather and growing conditions, as well as the specific exogenous chemical and formulation thereof selected, will affect the efficacy achieved in practicing this invention. Useful application rates for exogenous chemicals employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Such compositions can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium, and Zea.

Particularly important species for which glyphosate compositions are used are exemplified without limitation by the following:

Annual broadleaves:
velvetleaf (*Abutilon theophrasti*)
pigweed (Amaranthus spp.)
buttonweed (Borreria spp.)
oilseed rape, canola, indian mustard, etc. (Brassica spp.)
commelina (Commelina spp.)
filaree (Erodium spp.)
sunflower (Helianthus spp.)
morningglory (Ipomoea spp.)
kochia (*Kochia scoparia*)
mallow (Malva spp.)
wild buckwheat, smartweed, etc. (Polygonum spp.)
purslane (Portulaca spp.)
russian thistle (Salsola spp.)
sida (Sida spp.)
wild mustard (*Sinapis arvensis*)
cocklebur (Xanthium spp.)
Annual narrowleaves:
wild oat (*Avena fatua*)
carpetgrass (Axonopus spp.)
downy brome (*Bromus tectorum*)
crabgrass (Digitaria spp.)
barnyardgrass (*Echinochloa crus-galli*)
goosegrass (*Eleusine indica*)
annual ryegrass (*Lolium multiflorum*)
rice (*Oryza sativa*)
ottochloa (*Ottochloa nodosa*)
bahiagrass (*Paspalum notatum*)
canarygrass (Phalaris spp.)
foxtail (Setaria spp.)
wheat (*Triticum aestivum*)
corn (*Zea mays*)
Perennial broadleaves:
mugwort (Artemisia spp.)
milkweed (Asclepias spp.)
canada thistle (*Cirsium arvense*)
field bindweed (*Convolvulus arvensis*)
kudzu (Pueraria spp.)
Perennial narrowleaves:
brachiaria (Brachiaria spp.)
bermudagrass (*Cynodon dactylon*)
yellow nutsedge (*Cyperus esculentus*)
purple nutsedge (*C. rotundus*)
quackgrass (*Elymus repens*)
lalang (*Imperata cylindrica*)
perennial ryegrass (*Lolium perenne*)
guineagrass (*Panicum maximum*)
dallisgrass (*Paspalum dilatatum*)
reed (Phragmites spp.)
johnsongrass (*Sorghum halepense*)
cattail (Typha spp.)
Other perennials:
horsetail (Equisetum spp.)
bracken (*Pteridium aquilinum*)
blackberry (Rubus spp.)
gorse (*Ulex europaeus*)

Thus, the method of the present invention, as it pertains to glyphosate herbicide, can be useful on any of the above species.

Plants evaluated in the following Examples include the following:

| Bayer Code | Common Name |
|---|---|
| ABUTH | velvetleaf |
| AGRRR | rhizome quackgrass |
| ALRTE | apaga-fogo |
| AMAQU | pigweed |
| AMATA | common waterhemp |
| AMAVI | slender amaranth |
| AMBTR | giant ragweed |
| AVESA | oats |
| AVESS | oats |
| AVESX | oats |
| BIDPI | hairy beggarticks |
| BLARH | none |
| BOILF | broadleaf buttonweed |
| BRADC | surinam grass |
| BRSJU | Indian mustard |
| CAPSS | shepherd's purse |
| CASOB | sicklepod |
| CENME | Malta starthistle |
| CHEAL | common lambsquarters |
| CMIRA | trumpetcreeper |
| COMBE | tropical spiderwort |
| COMSS | commelina species |
| COPDI | swine cress |
| CRUNU | musk thistle |
| CYNDA | bermudagrass |
| CYPCP | annual sedge |
| CYPES | yellow nutsedge |
| CYPRO | purple nutsedge |
| CYPSS | sedge, sp. |
| DACGL | orachardgrass |
| DIGHO | digitaria horizontalis |
| DIGIN | capim-amargoso |
| DIGSA | large crabgrass |
| ECHCF | Japanese millet, barnyardgrass |
| ECHCG | barnyardgrass |
| ECHCO | junglerice |
| ELEIN | goosegrass |
| EPHHL | wild poinsettia |
| EPHHT | prostrate spurge |
| ERIBO | hairy fleabane |

-continued

| Bayer Code | Common Name |
|---|---|
| ERICA | canadian horseweed |
| ERICG | marestail/horseweed |
| EROCI | redstem filaree |
| FESAR | tall fescue |
| GERCA | carolina geranium |
| GLXMV | volunteer soybean |
| GERDI | cutleaf geranium |
| IPOAC | blue morningglory |
| IPOAO | ipomoea arist. |
| IPOHI | none |
| IPOLA | pitted morningglory |
| IPOPD | introduled morningglory |
| IPOSS | ipomoea sp. |
| LACSE | prickly lettuce |
| LAMAM | henbit |
| LOLMG | annual ryegrass |
| LOLMU | Italian ryegrass |
| LOLPE | perennial ryegrass |
| MEUSS | clover |
| OEOLA | cutleaf eveningprimrose |
| ORYSA | red rice |
| POLAV | knotweed |
| POLCO | wild buckwheat |
| POROL | common purslane |
| PYHCA | carolina false dandelion |
| RUMCR | curly dock |
| SEBEX | hemp sesbania |
| SECCW | secale cereale |
| SECCX | rye |
| SECSS | volunteer secale |
| SIDRH | arrowleaf sida |
| SIDSP | prickly sida |
| SORHR | rhizome johsongrass |
| SPRAR | corn spurry |
| STDSS | stippa species |
| TAROF | common dandelion |
| TRZAV | volunteer wheat |
| TRZAW | winter wheat |
| TRZVX | wheat |
| VERPG | purslane speedwell |
| XANSI | Italian cocklebur |
| YZZZZ | misc. non crops |
| ZZZZZ | (includes CYNDA, RAROF, LOLMG, MEUSS) |

Effectiveness in greenhouse tests, usually at exogenous chemical rates lower than those normally effective in the field, is a proven indicator of consistency of field performance at normal use rates. However, even the most promising composition sometimes fails to exhibit enhanced performance in individual greenhouse tests. As illustrated in the Examples herein, a pattern of enhancement emerges over a series of greenhouse tests; when such a pattern is identified this is strong evidence of biological enhancement that will be useful in the field.

The compositions of the present invention can be applied to plants by spraying, using any conventional means for spraying liquids, such as spray nozzles, atomizers, or the like. Compositions of the present invention can be used in precision farming techniques, in which apparatus is employed to vary the amount of exogenous chemical applied to different parts of a field, depending on variables such as the particular plant species present, soil composition, and the like. In one embodiment of such techniques, a global positioning system operated with the spraying apparatus can be used to apply the desired amount of the composition to different parts of a field.

The composition at the time of application to plants is preferably dilute enough to be readily sprayed using standard agricultural spray equipment. Preferred application rates for the present invention vary depending upon a number of factors, including the type and concentration of active ingredient and the plant species involved. Useful rates for applying an aqueous composition to a field of foliage can range from about 25 to about 1,000 liters per hectare (l/ha) by spray application. The preferred application rates for aqueous solutions are in the range from about 50 to about 300 l/ha.

Many exogenous chemicals (including glyphosate herbicide) must be taken up by living tissues of the plant and translocated within the plant in order to produce the desired biological (e.g., herbicidal) effect. Thus, it is important that a herbicidal composition not be applied in such a manner as to excessively injure and interrupt the normal functioning of the local tissue of the plant so quickly that translocation is reduced. However, some limited degree of local injury can be insignificant, or even beneficial, in its impact on the biological effectiveness of certain exogenous chemicals.

A large number of compositions of the invention are illustrated in the Examples that follow. Many concentrate compositions of glyphosate have provided sufficient herbicidal effectiveness in greenhouse tests to warrant field testing on a wide variety of weed species under a variety of application conditions.

The spray compositions of Examples 1-63 contained an exogenous chemical, such as glyphosate ammonium or potassium salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

In the following Examples illustrative of the invention, greenhouse and field tests were conducted to evaluate the relative herbicidal effectiveness of glyphosate compositions. Standard compositions included for comparative purposes include the following:

STD1: Dry formulation containing 68% glyphosate a.e. with 5.7% tallowamine ethoxylate, 7.9% alcohol ethoxylate, and 8.3% diammonium oxalate.

STD2: 725 g/l of glyphosate potassium salt in aqueous solution with no added surfactant.

STD3: 50% by weight of glyphosate IPA salt in aqueous solution together with a surfactant. This formulation is sold by Monsanto Company under the ROUNDUP ULTRAMAX® trademark.

STD4: Roundup MAX®.

STD5: Ammonium salt of glyphosate.

STD6: Roundup WeatherMax®.

STD7: 472 g a.e./l of glyphosate potassium salt in aqueous solution together with 117 g/l cocoamine (5 EO) surfactant and iso-stearyl (10 EO) surfactant and 13 g/l cocoamine.

STD8: 570 g/l of glyphosate IPA salt in an aqueous solution with no added surfactant.

STD9: Roundup WG®.

STD10: Roundup ProDry®.

STD11: 480 g a.e./l glyphosate IPA salt with 120 g/l Ethoxylated etheramine surfactant.

STD12: Dry formulation containing 68% glyphosate, 5.7% tallowamine ethoxylate, 7.9% alcohol ethoxylate and 8.3% diammonium oxalate.

Cationic Surfactants:

| CIS1 | | ethoxylated stearylamine |
|---|---|---|
| CIS2 | Ethomeen T25 | Ethoxylated (15) tallow alkyl amine |
| CIS3 | Witcamine 405 | PEG5 Tallowamine |
| CIS4 | MON 0818 | Tallowamine |

-continued

| | | |
|---|---|---|
| CIS5 | Ethoquad C25 | Ethoxylated (15EO) cocoalkyl methyl quaternary ammonium chloride |
| CIS6 | 151R5T | Blended alkoxylated alkylamine |
| CIS7 | Witcamine TAM105 | Ethoxylated (10.5) tallowamine |
| CIS8 | Ethomeen C12 | Ethoxylated (2) cocoamine |
| CIS9 | Witcamine TAM 150 | PEG 15 tallow amine |
| CIS10 | 816Y7N | Ethoxylated (15) cetyl/stearyl etheramine |
| CIS11 | 091Q2C | $C_{9-11}$ alkoxylated propylamine (3PO)(10EO) |
| CIS12 | Ethodquad T/25 | tallow ethoxylate (15EO) quaternary ammonium chloride |
| CIS13 | 271C6G | monoethoxylated tallow amine (11EO) |
| CIS14 | 096W5B | monoethoxylated cocoamine (7EO) |
| CIS15 | 632P4B | monoethoxylated tallowamine (15EO) |
| CIS16 | 633Q3X | Tallowamine ethoxylate (15EO) |
| CIS17 | 265Z5F | Ethoxylated cocoamine (11EO) |
| CIS19 | Surfonic T-15 | PEG 15 tallow amine |
| CIS20 | PF8000 | ethoxylated phosphate ester |
| CIS21 | FloMo 1407 | ethoxylated (20) tallowamine |
| CIS22 | | Hexadecyl-eicosa (ethylene oxide) dimethylamine |
| CIS23 | 121A6M | $C_{12-14}$ ethoxylated (5EO) etheramine |
| CIS24 | 275E3H | Monoethoxylated stearylamine (11EO) |
| CIS25 | Witcamine 302 | PEG 2 cocoamine |
| CIS26 | Witcamine 305 | PEG 5 cocoamine |
| CIS28 | Flomo ® TD-20 | ethoxylated Tallowamine |
| CIS29 | Witcamine 105 | PEG-10 tallowamine |
| CIS36 | Surfonic AGM-550 | Alkoxylated alkyl etheramine. |

Nonionic Surfactants:

| | | |
|---|---|---|
| NIS1 | Hetoxol CS20 | C16/18 alcohol ethoxylate (20EO) |
| NIS2 | Agrimul PG2069 | Alkypolyglycoside (Henkel) |
| NIS3 | Triton TX-100 | Octylphenoxypolyethoxy-ethanol |
| NIS4 | Alcodet HS1000 | Mercaptan ethoxylate (Rhodia) |
| NIS5 | Emerest 2622 | PEG200 dilaurate (Cognis) |
| NIS6 | Tween 80 | Polysorbate 80 (Sigma) |
| NIS7 | Agrimul 2067 | Alkylpolyglucoside (Cognis) |
| NIS8 | 119E4F | citric acid-PEG5 tallowamine ester |
| NIS9 | 119G6V | adipic acid-PEG5 tallowamine ester |
| NIS10 | 119H8M | succinic acid-PEG5 tallowamine ester |
| NIS11 | 119I7T | oxalic acid-PEG5 tallowamine ester |
| NIS12 | Procol SA-20 | PEG20 Stearyl Alcohol |
| NIS13 | L68-20 | $C_{16-18}$ alcohol ethoxylate (20EO) |
| NIS14 | 014R56 | Alkoxylated alcohol 20EO |
| NIS15 | Hetoxol CAWS | $C_{16}$ alcohol alkoxylate (PO5)(EO20) |
| NIS16 | Neodol 23-5 | $C_{12-15}$ ethoxylated (5 EO) alcohol |
| NIS17 | Emthox 5888 | PEG 20 $C_{18}$ alcohol |
| NIS18 | 412E3S | Alkoxylated alcohol |
| NIS19 | 933T4M | $C_{12-14}$ alcohol alkoxylate (1.5PO)(8EO) |
| NIS20 | Agrimul 225 | $C_{8-10}$ alkylpolyglucoside |
| NIS21 | 986B3F | Experimental PEG 7 tallowamine |
| NIS22 | 158P9X | alkoxylated linear alcohol |
| NIS23 | 840L9J | $C_{12}$(5PO)(5EO) alkoxylated alcohol |
| NIS24 | 2250R3U | Alkoxylated alcohol |
| NIS25 | 119D8J | PEG 4.5 tallowamine-oxalate ester |
| NIS26 | 119S4T | PEG 20 tallowamine-oxalate ester |
| NIS27 | Hetoxol CS15 | C16/18 alcohol ethoxylate (15EO) |
| NIS28 | APG 3399 | Branched C8 alkylpolyglucoside |
| NIS29 | TX-100 | Octylphenoxyethoxy-ethanol |
| NIS30 | | Tallowamine 10-oxalate ester. Tallowamine: oxalate mole ratio estimated to be about 1:1. |
| NIS31 | | Tallowamine 6-oxalate ester. Tallowamine: oxalate mole ratio estimated to be about 1:1. |
| NIS32 | | Tallowamine 5-oxalate ester. Tallowamine: oxalate mole ratio estimated to be about 1.3:1. |
| NIS33 | | Tallowamine 10-oxalate ester Tallowamine: oxalate mole ratio estimated to be about 1.3:1. |
| NIS34 | | Tallowamine 5-oxalate ester. Tallowamine: oxalate mole ratio estimated to be about 2:1. |
| NIS35 | | ethoxylated tallowamine-oxalate ester |
| NIS36 | | organosilicone surfactant |
| NIS37 | Toximul 8240 | PEG-36 Castor Oil |
| NIS38 | | POE 40 Stearate |
| NIS39 | Toximul 8242 | POE 40 Castor oil |
| NIS40 | Cognis 33811 | |

Other Components:

| | | |
|---|---|---|
| OTH1 | Di-ammonium Oxalate | |
| OTH2 | Hydrochloric Acid | |
| OTH3 | Propylene Glycol | |
| OTH4 | Citric Acid | |
| OTH5 | Oxalic Acid | |
| OTH6 | TCI H0083 | Hexyldecyl trimethylammonium hydroxide |
| OTH7 | BTAH | Benzyltrimethylammonium hydroxide |
| OTH8 | Formic Acid | |
| OTH9 | Benzolic Acid | |
| OTH10 | Phosphoric Acid | |
| OTH11 | Ascorbic Acid | |
| OTH12 | Succinic Acid | |
| OTH13 | Malonic Acid | |
| OTH14 | Adipic Acid | |
| OTH15 | EDTA sodium salt | |
| OTH16 | Potassium Hydroxide | |
| OTH17 | Sodium Sulfite | |
| OTH18 | Agnique DF6889 | Silicone dispersion antifoam |
| OTH19 | Glutaric Acid | |
| OTH20 | Ammonium Sulfate | |
| OTH21 | Sodium Citrate | |
| OTH22 | Crop Oil Concentrate | mineral and vegetable oil with 15–17% added nonionic surfactant |
| OTH23 | 125T7X | alkoxylated linear alcohol |
| OTH24 | n-methyl glucamine | |
| OTH25 | Urea | |
| OTH26 | Ammonium iron II sulfate hexahydrate | |
| OTH27 | Ammonium iron III oxalate | |
| OTH28 | Ammonium oxalate hydrate | |
| OTH29 | Isopar L | Isoparaffinic solvent |
| OTH30 | Dipotassium oxalate | |
| OTH31 | Ferric sulfate | |
| OTH32 | L-malic acid | |
| OTH33 | Glyoxylic acid | |
| OTH34 | Glyoxalic acid | |
| OTH35 | Glycolic acid | |
| OTH36 | Kemp's triacid | |
| OTH37 | Sodium nitrate | |
| OTH38 | Sodium bicarbonate | |
| OTH39 | EDTA | |
| OTH40 | Witconate AOS | $C_{14-16}$ Alphaolefin sulfonate |
| OTH41 | Sodium oxalate | |
| OTH42 | Sodium formate | |
| OTH43 | Bio-Terge AS-90 | $C_{14-16}$ alpha olefin sulfonate sodium salt |
| OTH44 | Breakthru AF-9903 | |
| OTH45 | | Blend of 44% tallowamine ethoxylate and 56% alcohol ethoxylate |
| OTH47 | Triethylene glycol | |
| OTH48 | Maltrin M180 | Reduced malto-oligosaccharide |
| OTH49 | | PEG 900 |

The following greenhouse testing procedure was used for evaluating compositions of the Examples to determine herbicidal effectiveness, except where otherwise indicated.

Seeds of the plant species indicated were planted in 88 mm square pots in a soil mix which was previously sterilized and prefertilized with a 14-14-14 NPK slow release fertilizer at a rate of 3.6 kg/m3. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 29° C. during the day and about 21° C. during the night. Plants were sub-irrigated throughout the test to ensure adequate soil moisture levels.

Pots were assigned to different treatments in a fully randomized experimental design with 6 replications. A set of pots was left untreated as a reference against which affects of the treatments could later be evaluated.

Application of glyphosate compositions was made by spraying with a track sprayer fitted with a 9501E nozzle calibrated to deliver a spray volume of 93 liters per hectare (l/ha) at a pressure of 165 kilopascals (kPa). After treatment, pots were returned to the greenhouse until ready for evaluation.

Treatments were made using dilute aqueous compositions. These could be prepared as spray compositions directly from their ingredients, or by dilution with water of preformulated concentrate compositions.

Adjuvant and active compositions were formulated as indicated in Table 1A below. Ammonium glyphosate concentrations in formulations 082BD1 and 082BE9 were 62 grams acid equivalent per liter. Formulation 082AD6 comprised STD3 diluted to 62 grams acid equivalent per liter.

TABLE 1A

| Comp. | Gly. | Cmpnt. 1 | wt % | Cmpnt. 2 | wt % | Cmpnt. 3 | wt % |
|---|---|---|---|---|---|---|---|
| 082BC4 | — | CIS1 | 0.36 | NIS1 | 0.25 | OTH1 | 0.77 |
| 082BZ3 | — | CIS1 | 0.36 | NIS1 | 0.25 | OTH1 | 1.54 |
| 082CZ7 | — | CIS1 | 0.36 | NIS1 | 0.25 | OTH1 | 2.31 |
| 082DZ5 | — | CIS1 | 0.36 | NIS1 | 0.25 | OTH1 | 3.08 |
| 082BD1 | $NH_4$-gly | CIS1 | 0.36 | NIS1 | 0.25 | — | — |
| 082BE9 | $NH_4$-gly | CIS1 | 0.36 | NIS1 | 0.25 | OTH1 | 0.77 |
| 082AD6 | IPA-gly | — | — | — | — | OTH1 | 0.77 |

The compositions, and composition combinations, of Table 1A were applied to 5 leaf stage ABUTH. Spray applications of the formulated compositions were separately and sequentially applied via a track sprayer onto single source leaves of whole plants. Glyphosate application rates of 150, 300 and 500 g a.e./ha were evaluated. Plastic wrap was used to shield selected leaves. Trials 1-10 were conducted as follows with the ABUTH % inhibition at 14 days after treatment reported in Table 1B.

TABLE 1B

| Trial | Composition 1 | Glyphosate Application Rate (g a.e./ha) | Composition 2 | Oxalate Application Rate (g a.i./ha) | ABUTH % Inhibition |
|---|---|---|---|---|---|
| 1 | 082BD1 | 150, 300, 500 | — | — | 11, 63, 83 |
| 2 | 082BE9 | 150, 300, 500 | — | — | 28, 70, 86 |
| 3 | 082BD1 | 150, 300, 500 | 082BC4 | 34, 69, 115 | 3, 63, 78 |
| 4 | 082BD1 | 150, 300, 500 | 082BZ3 | 54, 110, 179 | 0, 60, 74 |
| 5 | 082BD1 | 150, 300, 500 | 082DZ5 | 93, 185, 309 | 11, 68, 78 |
| 6 | STD3 | 150, 300, 500 | — | — | 23, 60, 75 |
| 7 | 082AD6 | 150, 300, 500 | — | — | 61, 73, 93 |
| 8 | STD3 | 150, 300, 500 | 082BC4 | 34, 69, 115 | 15, 61, 79 |
| 9 | STD3 | 150, 300, 500 | 082BZ3 | 54, 110, 179 | 25, 65, 85 |
| 10 | STD3 | 150, 300, 500 | 082CZ7 | 93, 185, 309 | 21, 75, 75 |

Trial 1: Glyphosate was applied to leaf 3.
Trial 2: Glyphosate and oxalate were applied to leaf 3.
Trial 3: Glyphosate was applied to leaf 3 and 1X oxalate was applied to leaf 4.
Trial 4: Glyphosate was applied to leaf 3 and 2X oxalate was applied to leaf 4.
Trial 5: Glyphosate was applied to leaf 3 and 3X oxalate was applied to leaf 4.
Trial 6: STD3 was applied to Leaf 3.
Trial 7: STD3 and oxalate were applied to leaf 3.
Trial 8: STD3 was applied to leaf 3 and 1X oxalate was applied to leaf 4.
Trial 9: STD3 was applied to leaf 3 and 2X oxalate was applied to leaf 4.
Trial 10: STD3 was applied to leaf 3 and 3X oxalate was applied to leaf 4.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. The reported % control values represent the average for all replicates of each treatment.

Example 1

An adjuvant system containing a cationic surfactant, a nonionic surfactant and oxalate was evaluated in combination with glyphosate by sequential spray application of the components onto separate leaves to determine if increasing the level of oxalate in the sequential sprays could retrieve lost efficacy due to the separation of spray components.

Where the composition components are separately applied, the data indicate performance recovery with increasing levels of sequentially applied oxalate.

The compositions, and composition combinations, of Table 1A were applied to 5 leaf stage ABUTH. Spray applications of the formulated compositions were separately and sequentially applied via a track sprayer onto single source leaves of whole plants. Glyphosate application rates of 200, 400 and 600 g a.e./ha were evaluated. Plastic wrap was used to shield selected leaves. Trials 1-8 were conducted as follows with the ABUTH % inhibition at 15 days after treatment reported in Table 1C.

TABLE 1C

| Trial | Composition 1 | Glyphosate Application Rate (g a.e./ha) | Composition 2 | Oxalate Application Rate (g a.i./ha) | ABUTH % Inhibition |
|---|---|---|---|---|---|
| 1 | 082BD1 | 200, 400, 600 | — | — | 70, 84, 91 |
| 2 | 082BE9 | 200, 400, 600 | — | — | 80, 92, 94 |
| 3 | 082BD1 | 200, 400, 600 | 082BC4 | 47, 92, 138 | 70, 84, 88 |
| 4 | STD3 | 200, 400, 600 | — | — | 70, 83, 86 |
| 5 | 082AD6 | 200, 400, 600 | — | — | 56, 81, 85 |
| 6 | STD3 | 200, 400, 600 | 082BC4 | 66, 133, 200 | 56, 81, 85 |
| 7 | 082BD1 | 200, 400, 600 | 082BZ3 | 66, 133, 200 | Not Reported, 81, 90 |
| 8 | STD3 | 200, 400, 600 | 082BZ3 | 66, 133, 200 | 71, 83, 90 |

Trial 1: Glyphosate was applied to leaf 3.
Trial 2: Glyphosate and oxalate were applied to leaf 3.
Trial 3: Glyphosate was applied to leaf 3 and oxalate was applied to leaf 4.
Trial 4: STD3 was applied to leaf 3.
Trial 5: STD3 and oxalate were applied to leaf 3.
Trial 6: STD3 was applied to leaf 3 and oxalate was applied to leaf 4.
Trial 7: Glyphosate was applied to leaf 3 and 2X oxalate was applied to leaf 4.
Trial 8: STD3 was applied to leaf 3 and 2X oxalate was applied to leaf 4.

The data indicate that separation of glyphosate and oxalate applications results in the loss of oxalate induced performance enhancement. However, doubling the oxalate concentration application to leaf 4, with glyphosate application to leaf 3, appeared to result in partial recovery of the oxalate enhancement effect. The dose dependence of the oxalate effect therefore suggests that there may be a physiological effect and not simply a leaf cuticle effect.

The compositions, and composition combinations, of Table 1A were applied to 7 leaf stage ABUTH. Spray applications of the formulated compositions were applied sequentially via a track sprayer onto the leaves of the whole plants. The oxalate composition was applied (1) immediately following glyphosate application or (2) two hours after glyphosate application. Glyphosate application rates of 200, 300 and 400 g a.e./ha of were evaluated. Trials 1-8 were conducted as follows with the ABUTH % inhibition at 15 days after treatment reported in Table 1D.

Co-application of glyphosate and oxalate provided the greatest ABUTH % inhibition. Sequential application (at 0 or 120 minutes) gave better ABUTH % inhibition than did glyphosate alone.

Some of the compositions, and composition combinations, of Table 1A and additional compositions given in Table 1E below were applied to 5 leaf stage ABUTH. Spray applications of the formulated compositions were separately and sequentially applied via a track sprayer onto single source leaves of whole plants. Glyphosate application rates of 200, 400 and 600 g a.e./ha were evaluated. Plastic wrap was used to shield selected leaves. Trials 1-16 were conducted as follows with the ABUTH % inhibition at 15 days after treatment reported in Table 1F.

Trial 1: Glyphosate was applied to leaf 3.
Trial 2: Glyphosate and oxalate were applied to leaf 3.
Trial 3: Glyphosate was applied to leaf 3 and 1× oxalate was applied to leaf 4.

TABLE 1D

| Trial | Composition 1 | Glyphosate Application Rate (g a.e./ha) | Composition 2 | Oxalate Application Rate (g a.i./ha) | ABUTH % Inhibition |
|---|---|---|---|---|---|
| 1 | 082BD1 | 200, 300, 400 | — | — | 80, 88, 95 |
| 2 | 082BE9 | 200, 300, 400 | — | — | 85, 93, 96 |
| 3 | 082BD1 | 200, 300, 400 | 082BC4 | 47, 71, 94 | 85, 91, 96 |
| 4 | 082BD1 | 200, 300, 400 | 082BC4 | 47, 71, 94 | 88, 91, 96 |
| 5 | STD3 | 200, 300, 400 | — | — | 78, 85, 89 |
| 6 | 082AD6 | 200, 300, 400 | — | — | 88, 93, 96 |
| 7 | STD3 | 200, 300, 400 | 082BC4 | 47, 71, 94 | 83, 88, 91 |
| 8 | STD3 | 200, 300, 400 | 082BC4 | 47, 71, 94 | 83, 89, 93 |

Trial 1: Glyphosate was applied.
Trial 2: Glyphosate and oxalate were co-applied.
Trial 3: Glyphosate was applied immediately followed by oxalate.
Trial 4: Glyphosate was applied followed 2 hours later by oxalate.
Trial 5: STD3 was applied.
Trial 6: STD3 and oxalate were co-applied.
Trial 7: STD3 was applied immediately followed by oxalate.
Trial 8: STD3 was applied followed 2 hours later by oxalate.

Trial 4: Glyphosate was applied to leaf 3 and 2× oxalate was applied to leaf 4.
Trial 5: Glyphosate was applied to leaf 3 and 1× citrate was applied to leaf 4.
Trial 6: Glyphosate was applied to leaf 3 and 2× citrate was applied to leaf 4.
Trial 7: Glyphosate was applied to leaf 3 and 1× oxalate and 1× citrate were applied to leaf 4.
Trial 8: Glyphosate was applied to leaf 3 and 1× oxalate and 2× citrate were applied to leaf 4.
Trial 9: STD3 was applied to leaf 3.
Trial 10: STD3 and oxalate were applied to leaf 3.
Trial 11: STD3 was applied to leaf 3 and 1× oxalate was applied to leaf 4.
Trial 12: STD3 was applied to leaf 3 and 2× oxalate was applied to leaf 4.
Trial 13: STD3 was applied to leaf 3 and 1× citrate was applied to leaf 4.
Trial 14: STD3 was applied to leaf 3 and 2× citrate was applied to leaf 4.
Trial 15: STD3 was applied to leaf 3 and 1× oxalate and 1× citrate were applied to leaf 4.
Trial 16: STD3 was applied to leaf 3 and 1× oxalate and 2× citrate were applied to leaf 4.

TABLE 1E

| Comp. | Cmpnt 1 | wt % | Cmpnt. 2 | wt % | Cmpnt. 3 | wt % | Cmpnt. 4 | wt % |
|---|---|---|---|---|---|---|---|---|
| 082SA8 | CIS1 | 0.36 | NIS1 | 0.25 | OTH4 | 0.77 | — | — |
| 082SB2 | CIS1 | 0.36 | NIS1 | 0.25 | OTH4 | 1.54 | — | — |
| 082SC5 | CIS1 | 0.36 | NIS1 | 0.25 | OTH4 | 0.77 | OTH1 | 0.77 |
| 082SD7 | CIS1 | 0.36 | NIS1 | 0.25 | OTH4 | 1.54 | OTH1 | 0.77 |

TABLE 1F

| Trial | Composition 1 | Glyphosate Application Rate (g a.e./ha) | Composition 2 | Oxalate Application Rate (g a.i./ha) | ABUTH % Inhibition |
|---|---|---|---|---|---|
| 1 | 082BD1 | 200, 400, 600 | — | — | 63, 73, 81 |
| 2 | 082BE9 | 200, 400, 600 | — | — | 68, 77, 85 |
| 3 | 082BD1 | 200, 400, 600 | 082BC4 | 47, 93, 140 | 33, 84, 88 |
| 4 | 082BD1 | 200, 400, 600 | 082BZ3 | 71, 143, 214 | 45, 67, 81 |
| 5 | 082BD1 | 200, 400, 600 | 082SA8 | 47, 93, 140 | 52, 65, 74 |
| 6 | 082BD1 | 200, 400, 600 | 082SB2 | 71, 143, 214 | 33, 66, 76 |
| 7 | 082BD1 | 200, 400, 600 | 082SC5 | 71, 143, 214 | 30, 73, 78 |
| 8 | 082BD1 | 200, 400, 600 | 082SD7 | 100, 200, 300 | 69, 68, 85 |
| 9 | STD3 | 200, 400, 600 | — | — | 23, 71, 76 |
| 10 | STD3 | 200, 400, 600 | 082AD6 | 47, 93, 140 | 73, 73, 80 |
| 11 | STD3 | 200, 400, 600 | 082BC4 | 47, 93, 140 | 62, 68, 78 |
| 12 | STD3 | 200, 400, 600 | 082BZ3 | 71, 143, 214 | 45, 71, 74 |
| 13 | STD3 | 200, 400, 600 | 082SA8 | 47, 93, 140 | 59, 68, 77 |
| 14 | STD3 | 200, 400, 600 | 082SB2 | 71, 143, 214 | 23, 68, 74 |
| 15 | STD3 | 200, 400, 600 | 082SC5 | 71, 143, 214 | 17, 63, 81 |
| 16 | STD3 | 200, 400, 600 | 082SD7 | 100, 200, 300 | 48, 64, 77 |

Statistically significant efficacy performance trends in relation to late loading levels could not be noted. Generally co-application of glyphosate oxalate gave the greatest % inhibition and sequential application gave slightly er, but statistically insignificant, results.

The compositions, and composition combinations, of Table 1A were applied to 6 leaf stage ABUTH. Spray applications of the formulated compositions were separately applied via a track sprayer onto single source leaves of whole plants. Glyphosate application rates of 200, 400 and 600 g a.e./ha were evaluated. Plastic wrap was used to shield selected leaves. Trials 1-10 were conducted as follows with the ABUTH % inhibition at 14 days after treatment reported in Table 1G.

Trial 1: Glyphosate was applied to leaf 3.
Trial 2: Glyphosate and oxalate were applied to leaf 3.
Trial 3: Glyphosate was applied to leaf 3 and 1× oxalate was applied to leaf 4.

Trial 4: Glyphosate was applied to leaf 3 and 2× oxalate was applied to leaf 4.
Trial 5: Glyphosate was applied to leaf 3 and 3× oxalate was applied to leaf 4.
Trial 6: STD3 was applied to Leaf 3.
Trial 7: STD3 and oxalate were applied to leaf 3.
Trial 8: STD3 was applied to leaf 3 and 1× oxalate was applied to leaf 4.
Trial 9: STD3 was applied to leaf 3 and 2× oxalate was applied to leaf 4.
Trial 10: STD3 was applied to leaf 3 and 3× oxalate was applied to leaf 4.

TABLE 1G

| Trial | Composition 1 | Glyphosate Application Rate (g a.e./ha) | Composition 2 | Oxalate Application Rate (g a.i./ha) | ABUTH % Inhibition |
|---|---|---|---|---|---|
| 1 | 082BD1 | 200, 400, 600 | — | — | 60, 78, 84 |
| 2 | 082BE9 | 200, 400, 600 | — | — | 59, 82, 80 |
| 3 | 082BD1 | 200, 400, 600 | 082BC4 | 47, 93, 140 | 12, 75, 78 |
| 4 | 082BD1 | 200, 400, 600 | 082BZ3 | 71, 143, 214 | 10, 77, 83 |
| 5 | 082BD1 | 200, 400, 600 | 082CZ7 | 100, 200, 300 | 35, 78, 84 |
| 6 | 082BD1 | 200, 400, 600 | 082DZ5 | 125, 250, 375 | 6, 73, 80 |
| 7 | STD3 | 200, 400, 600 | — | — | 1, 73, 72 |
| 8 | STD3 | 200, 400, 600 | 082AD6 | 47, 93, 140 | 15, 77, 80 |
| 9 | STD3 | 200, 400, 600 | 082BC4 | 47, 93, 140 | 5, 62, 78 |
| 10 | STD3 | 200, 400, 600 | 082BZ3 | 71, 143, 214 | 0, 70, 78 |
| 11 | STD3 | 200, 400, 600 | 082CZ7 | 100, 200, 300 | 15, 54, 79 |
| 12 | STD3 | 200, 400, 600 | 082DZ5 | 125, 250, 375 | 43, 72, 80 |

The data show a complete recovery of the oxalate effect as seen by the % inhibition results wherein separately applied 4× oxalate and oxalate preformed similarly to glyphosate co-application with 1× oxalate. The % inhibition decreased as the amount of separately applied oxalate was decreased. Oxalate, whether co-applied to the same leaf or separately applied to two leafs gave % inhibition higher than that of glyphosate alone. The data suggest that the loss of oxalate effect upon spatial separation is partial and the total recovery of this loss appears asymptotic, with marginal gain over the 1×, 2×, 3× and 4× range of oxalic used.

Examples 2-5

Various dicarboxylic acids and chelators were tested for their ability to enhance glyphosate performance.

Example 2

Adjuvant and ammonium glyphosate compositions were formulated as indicated in Table 2A below. Ammonium glyphosate concentration in each formulation was 20.0 g a.e./l. Four different dicarboxylic acids were formulated with a cationic surfactant and a nonionic surfactant and compared to oxalic acid for ability to enhance glyphosate efficacy.

TABLE 2A

| Comp. | Cmpnt. 1 | wt % | Cmpnt. 2 | wt % | Cmpnt. 3 | wt % |
|---|---|---|---|---|---|---|
| 056A2C | CIS1 | 0.25 | NIS1 | 0.25 | — | — |
| 056B7U | CIS1 | 0.25 | NIS1 | 0.25 | OTH5 | 0.50 |
| 056C6G | CIS1 | 0.25 | NIS1 | 0.25 | OTH13 | 0.41 |
| 056D4F | CIS1 | 0.25 | NIS1 | 0.25 | OTH12 | 0.47 |
| 056E0P | CIS1 | 0.25 | NIS1 | 0.25 | OTH19 | 0.52 |
| 056F4C | CIS1 | 0.25 | NIS1 | 0.25 | OTH14 | 0.58 |
| 056G7N | CIS1 | 0.25 | NIS1 | 0.25 | — | — |
| 056H1M | CIS1 | 0.25 | NIS1 | 0.25 | OTH5 | 2.00 |
| 056I6B | CIS1 | 0.25 | NIS1 | 0.25 | OTH13 | 1.65 |
| 056J5A | CIS1 | 0.25 | NIS1 | 0.25 | OTH12 | 1.87 |
| 056K8K | CIS1 | 0.25 | NIS1 | 0.25 | OTH19 | 2.10 |
| 056L4V | CIS1 | 0.25 | NIS1 | 0.25 | OTH14 | 2.32 |

The compositions, and composition combinations, of Table 2A were applied to ABUTH and ECHCF at glyphosate application rates of 75, 100, 200 and 400 g a.e./ha and TRZVX at glyphosate application rates of 75, 100, 150 and 300 g a.e./ha evaluated versus STD4, STD5 and STD6 standards with the % inhibition results reported in Table 2B below.

TABLE 2B

| Composition | ABUTH % inhibition | ECHCF % inhibition | TRZVX % inhibition |
|---|---|---|---|
| 056A2C | 21, 42, 72, 96 | 62, 67, 84, 98 | — |
| 056B7U | 68, 77, 88, 98 | 63, 69, 87, 99 | — |
| 056C6G | 50, 53, 75, 90 | 58, 73, 78, 98 | — |
| 056D4F | 23, 53, 75, 94 | 59, 73, 90, 100 | — |
| 056E0P | 44, 58, 77, 92 | 68, 73, 85, 99 | — |
| 056F4C | 13, 53, 78, 97 | 68, 77, 85, 99 | — |
| 056G7N | 52, 57, 80, 95 | 60, 66, 84, 94 | 58, 60, 73, 81 |
| 056H1M | 70, 87, 92, 98 | 65, 66, 87, 97 | 59, 64, 75, 81 |
| 056I6B | 33, 45, 73, 90 | 65, 68, 75, 92 | 53, 55, 65, 79 |
| 056J5A | 23, 58, 77, 99 | 63, 70, 86, 98 | 53, 58, 65, 81 |
| 056K8K | 31, 53, 75, 95 | 68, 68, 81, 98 | 55, 58, 62, 76 |
| 056L4V | 53, 55, 79, 95 | 63, 68, 88, 97 | 48, 55, 67, 80 |
| STD5 | 3, 9, 54, 78 | 15, 39, 49, 74 | 10, 35, 40, 60 |
| STD6 | 1, 13, 63, 83 | 60, 68, 75, 91 | 45, 59, 65, 85 |
| STD4 | 6, 37, 74, 88 | 59, 65, 74, 94 | 50, 55, 73, 88 |

Oxalic acid gave the greatest efficacy on velvetleaf. The other dicarboxylic acids, succinic, adipic, malonic and glutaric, gave marginal efficacy advantages for control of either ABUTH or ECHCF. Adipic acid was shown to provide some efficacy enhancement on ECHCF. Overall efficacy for the oxalic acid formulation was superior to STD3 or STD6 for velvetleaf control and equal to or slightly superior to these standards for ECHCF control.

As applied to TRZVX, no formulation was more efficacious than STD4 or STD6.

Example 3

Adjuvant and ammonium glyphosate compositions were formulated as indicated in Table 3A below. Ammonium glyphosate concentration in each formulation was 62.0 g a.e./l.

TABLE 3A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 071N1Q | CIS1 | 0.73 | NIS1 | 0.49 | — | — | — | — |
| 071P9M | CIS1 | 0.73 | NIS1 | 0.49 | OTH1 | 0.80 | — | — |
| 009A3V | CIS1 | 0.73 | NIS1 | 0.49 | OTH4 | 0.80 | — | — |
| 009B8J | CIS1 | 0.73 | NIS1 | 0.49 | OTH4 | 0.40 | OTH1 | 0.40 |
| 009EA5G | CIS1 | 0.73 | NIS1 | 0.49 | OTH4 | 0.40 | OTH1 | 0.80 |
| 009EB6Y | CIS1 | 0.73 | NIS1 | 0.49 | OTH4 | 0.80 | OTH1 | 0.40 |
| 009EC4B | CIS1 | 0.73 | NIS1 | 0.49 | OTH15 | 0.80 | — | — |
| 009ED2L | CIS1 | 0.73 | NIS1 | 0.49 | OTH15 | 0.40 | OTH1 | 0.40 |
| 009EE7K | CIS1 | 0.73 | NIS1 | 0.49 | OTH15 | 0.40 | OTH1 | 0.80 |
| 009EF8H | CIS1 | 0.73 | NIS1 | 0.49 | OTH15 | 0.80 | OTH1 | 0.40 |

The compositions, and composition combinations, of Table 3A were applied to ABUTH, ECHCF and TRZVX plants. Glyphosate application rates of 100, 150, 200 and 400 g a.e./ha were evaluated versus STD4 and STD5 standards with the % inhibition results reported in Table 3B below.

TABLE 3B

| | % inhibition 15 days after treatment | | |
|---|---|---|---|
| Composition | Rate (g a.e./ha) | ABUTH | ECHCF | TRZVX |
| 071N1Q | 100, 150, 200, 400 | 67, 88, 91, 95 | 63, 79, 87, 94 | 67, 73, 85, 92 |
| 071P9M | 100, 150, 200, 400 | 80, 93, 95, 97 | 60, 74, 88, 95 | 62, 75, 80, 93 |
| 009A3V | 100, 150, 200, 400 | 70, 88, 89, 95 | 63, 73, 80, 93 | 57, 73, 83, 96 |
| 009B8J | 100, 150, 200, 400 | 79, 88, 94, 97 | 59, 72, 84, 97 | 64, 78, 83, 89 |
| 009EA5G | 100, 150, 200, 400 | 78, 88, 93, 96 | 63, 73, 81, 89 | 60, 75, 80, 89 |
| 009EB6Y | 100, 150, 200, 400 | 68, 88, 93, 97 | 60, 74, 85, 96 | 67, 73, 81, 85 |
| 009EC4B | 100, 150, 200, 400 | 67, 85, 91, 96 | 61, 72, 75, 89 | 63, 74, 80, 96 |
| 009ED2L | 100, 150, 200, 400 | 74, 87, 93, 97 | 59, 74, 89, 95 | 65, 74, 83, 94 |
| 009EE7K | 100, 150, 200, 400 | 75, 92, 94, 97 | 62, 76, 87, 97 | 65, 77, 85, 95 |
| 009EF8H | 100, 150, 200, 400 | 75, 87, 91, 96 | 60, 72, 88, 97 | 67, 78, 85, 98 |
| STD5 | 100, 150, 200, 400 | —, —, —, — | —, —, —, — | 10, 27, 35, 56 |
| STD4 | 100, 150, 200, 400 | 32, 78, 84, 90 | 58, 72, 82, 92 | 62, 68, 78, 91 |

The addition of a second chelating agent such as EDTA or citric acid to an oxalate containing formulation did not give improved efficacy versus ammonium oxalate alone and a synergistic effect was not observed. The efficacy ranked, in order, ammonium oxalate>EDTA-sodium>citric acid blends>glyphosate alone. Efficacy generally increased with oxalate concentration.

Example 4

A trial was conducted to determine if alternate acids in combination with oxalic acid affects the efficacy of systems containing glyphosate, a cationic surfactant, a nonionic surfactant and oxalic acid. Adjuvant and potassium glyphosate compositions were formulated as indicated in Table 4A below. Potassium glyphosate concentration in each formulation was 62.0 g a.e./l.

TABLE 4A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 808A0L | CIS6 | 0.75 | NIS7 | 1.00 | — | — | — | — |
| 808B7D | CIS6 | 0.75 | NIS7 | 1.00 | OTH5 | 0.18 | — | — |
| 808C5T | CIS6 | 0.75 | NIS7 | 1.00 | OTH5 | 0.18 | OTH8 | 0.30 |
| 808D3S | CIS6 | 0.75 | NIS7 | 1.00 | OTH5 | 0.18 | OTH9 | 0.30 |
| 808E8I | CIS6 | 0.75 | NIS7 | 1.00 | OTH5 | 0.18 | OTH4 | 0.30 |
| 808F1Q | CIS6 | 0.75 | NIS7 | 1.00 | OTH5 | 0.18 | OTH10 | 0.30 |
| 808G7J | CIS6 | 0.75 | NIS7 | 1.00 | OTH5 | 0.18 | OTH11 | 0.30 |
| 808H4C | CIS6 | 0.75 | NIS7 | 1.00 | OTH5 | 0.18 | OTH12 | 0.30 |

The compositions, and composition combinations, of Table 4A were applied to ABUTH, ECHCF, LOLMG and BRSJU plants and evaluated versus STD2, STD3 and STD6 standards. ABUTH and ECHCF were evaluated at glyphosate application rates of 100, 200, 300 and 400 g a.e./ha, LOLMG was evaluated at glyphosate application rates of 100, 200, 400 and 600 g a.e./ha, and BRSJU was evaluated at glyphosate application rates of 150, 250, 400 and 800 g a.e./ha. The % inhibition results are reported in Table 4B below.

TABLE 4B

| | % inhibition | | | |
|---|---|---|---|---|
| Comp. | ABUTH | ECHCF | LOLMG | BRSJU |
| 808A0L | 23, 75, 84, 88 | 26, 60, 65, 68 | 40, 70, 84, 93 | 40, 60, 74, 81 |
| 808B7D | 77, 88, 91, 94 | 38, 65, 68, 73 | 40, 74, 88, 94 | 50, 64, 74, 80 |
| 808C5T | 79, 86, 94, 98 | 46, 63, 66, 72 | 60, 73, 86, 96 | 46, 68, 79, 77 |
| 808D3S | 68, 87, 90, 93 | 51, 63, 70, 76 | 42, 78, 86, 93 | 59, 69, 73, 79 |
| 808E8I | 77, 87, 91, 96 | 50, 66, 68, 73 | 64, 76, 85, 95 | 57, 69, 75, 80 |
| 808F1Q | 68, 84, 93, 96 | 49, 65, 68, 74 | 43, 76, 88, 93 | 54, 70, 77, 82 |
| 808G7J | 63, 84, 91, 92 | 51, 65, 68, 73 | 62, 75, 87, 91 | 62, 72, 75, 83 |
| 808H4C | 68, 85, 89, 93 | 54, 64, 68, 75 | 50, 75, 85, 92 | 58, 70, 71, 81 |
| STD2 | 0, 2, 59, 63 | 1, 30, 48, 48 | 0, 40, 62, 76 | 8, 14, 42, 55 |
| STD6 | 7, 63, 83, 87 | 11, 63, 68, 69 | 45, 71, 83, 95 | 53, 67, 74, 81 |
| STD3 | 17, 84, 86, 91 | 13, 61, 66, 70 | 45, 72, 85, 90 | 52, 67, 75, 80 |

Significant efficacy enhancement was not provided by the addition of acids to formulations containing glyphosate, a cationic surfactant, a nonionic surfactant and oxalic acid. Hence addition of acids did not result in any significant reduction in overall efficacy.

Example 5

A trial was conducted to determine the efficacy effect of oxalate, EDTA and citric acid chelators on glyphosate systems containing a cationic surfactant. Adjuvant and IPA glyphosate compositions were formulated as indicated in Table 5A below. STD3 was used as the source of IPA glyphosate and concentrations are indicated in g a.e./l.

TABLE 5A

| Comp. | gly g a.e./l | Cmpnt 1 | wt % | Cmpnt. 2 | wt % |
|---|---|---|---|---|---|
| 027A3G | 62 | — | — | — | — |
| 027B5F | 62 | — | — | OTH1 | 0.80 |
| 027C8K | 62 | — | — | OTH4 | 0.80 |
| 027D5J | 62 | — | — | OTH15 | 0.80 |
| 027AA1C | 1.07 | — | — | — | — |
| 027AB9L | 2.14 | — | — | — | — |
| 027AC4Z | 4.28 | — | — | — | — |
| 027E7N | 1.07 | CIS5 | 0.071 | OTH1 | 0.018 |
| 027H0S | 2.14 | CIS5 | 0.143 | OTH1 | 0.036 |
| 027K7R | 4.28 | CIS5 | 0.285 | OTH1 | 0.071 |
| 027G3P | 1.07 | CIS5 | 0.071 | OTH15 | 0.018 |
| 027J2W | 2.14 | CIS5 | 0.143 | OTH15 | 0.036 |
| 027M6Y | 4.28 | CIS5 | 0.285 | OTH15 | 0.071 |
| 027F3S | 1.07 | CIS5 | 0.071 | OTH4 | 0.018 |
| 027I9E | 2.14 | CIS5 | 0.143 | OTH4 | 0.036 |
| 027L7U | 4.28 | CSI5 | 0.285 | OTH4 | 0.071 |
| 027BA2T | 0.21 | — | — | — | — |
| 027BB6G | 0.43 | — | — | — | — |
| 027BC5O | 0.86 | — | — | — | — |
| 027N7W | 0.21 | CIS5 | 0.014 | OTH1 | 0.004 |
| 027Q2K | 0.43 | CIS5 | 0.029 | OTH1 | 0.007 |
| 027T5B | 0.86 | CIS5 | 0.057 | OTH1 | 0.014 |
| 027P4K | 0.21 | CIS5 | 0.014 | OTH15 | 0.004 |
| 027S1J | 0.43 | CIS5 | 0.029 | OTH15 | 0.007 |
| 027V6L | 0.86 | CIS5 | 0.057 | OTH15 | 0.014 |
| 027O2D | 0.21 | CIS5 | 0.014 | OTH4 | 0.004 |
| 027R4Y | 0.43 | CIS5 | 0.029 | OTH4 | 0.007 |
| 027U3E | 0.86 | CIS5 | 0.057 | OTH4 | 0.014 |

The compositions, and composition combinations, of Table 5A were applied to ABUTH and ECHCF plants. ABUTH and ECHCF were evaluated at glyphosate application rates of 100, 200 and 400 g a.e./ha (at a spray volume of 93 l/ha), and 200, 400 and 800 g a.e./ha (at a spray volume of 930 l/ha). The % inhibition results are reported in Table 5B below.

TABLE 5B

| % inhibition 16 days after treatment | | | |
|---|---|---|---|
| Composition | Rate (g a.e./ha) | ABUTH | ECHCF |
| 027A3G | 100, 200, 400 | 0, 60, 85 | 20, 75, 87 |
| 027B5F | 100, 200, 400 | 53, 86, 92 | 58, 78, 89 |
| 027C8K | 100, 200, 400 | 5, 60, 85 | 40, 73, 82 |
| 027D5J | 100, 200, 400 | 25, 68, 87 | 53, 78, 80 |
| 027AA1C | 100 | 3 | 38 |
| 027AB9L | 200 | 70 | 75 |
| 027AC4Z | 400 | 89 | 85 |
| 027E7N | 100 | 58 | 63 |
| 027H0S | 200 | 85 | 76 |
| 027K7R | 400 | 93 | 89 |
| 027G3P | 100 | 31 | 60 |
| 027J2W | 200 | 75 | 80 |
| 027M6Y | 400 | 89 | 83 |
| 027F3S | 100 | 5 | 60 |

TABLE 5B-continued

% inhibition 16 days after treatment

| Composition | Rate (g a.e./ha) | ABUTH | ECHCF |
|---|---|---|---|
| 027I9E | 200 | 73 | 80 |
| 027L7U | 400 | 91 | 84 |
| 027BA2T | 200 | 17 | 47 |
| 027BB6G | 400 | 73 | 70 |
| 027BC5O | 800 | 88 | 93 |
| 027N7W | 200 | 58 | 65 |
| 027Q2K | 400 | 79 | 76 |
| 027T5B | 800 | 93 | 96 |
| 027P4K | 200 | 45 | 44 |
| 027S1J | 400 | 72 | 78 |
| 027V6L | 800 | 88 | 80 |
| 027O2D | 200 | 10 | 48 |
| 027R4Y | 400 | 70 | 73 |
| 027U3E | 800 | 88 | 90 |

The efficacy results at 93 l/ha were higher than at 930 l/ha. Generally efficacy efficiency for ammonium oxalate formulations was the greatest followed by EDTA-sodium salt and citric acid formulations.

Examples 6-10

An efficacy evaluation was done to determine preferred glyphosate:surfactant molar ratios in compositions comprising glyphosate, a cationic surfactant, a nonionic surfactant and oxalate.

Example 6

Adjuvant and ammonium glyphosate compositions were formulated as indicated in Table 6A below. The ammonium glyphosate concentrations in each composition was 62 grams acid equivalent per liter.

TABLE 6A

| Comp. | Cmpnt 1 | wt % | Cmpnt. 2 | wt % | Cmpnt. 3 | wt % | gly:surf | gly:oxalate |
|---|---|---|---|---|---|---|---|---|
| 018A3C | CIS1 | 0.50 | NIS7 | 0.70 | OTH1 | 0.73 | 5:1 | 8.2:1 |
| 018B8J | CIS2 | 0.50 | NIS7 | 0.70 | OTH1 | 0.73 | 5:1 | 8.2:1 |
| 018I7N | CIS1 | 0.50 | NIS1 | 0.70 | OTH1 | 0.73 | 5:1 | 8.2:1 |
| 018J7Q | CIS2 | 0.50 | NIS1 | 0.70 | OTH1 | 0.73 | 5:1 | 8.2:1 |
| 018C9V | CIS1 | 0.74 | NIS1 | 0.74 | OTH1 | 0.83 | 4.1:1 | 7.2:1 |
| 018D3E | CIS2 | 0.74 | NIS1 | 0.74 | OTH1 | 0.83 | 4.1:1 | 7.2:1 |
| 018E5Y | CIS1 | 0.77 | NIS1 | 0.77 | OTH1 | 1.21 | 3.9:1 | 5:1 |
| 018F6S | CIS2 | 0.77 | NIS1 | 0.77 | OTH1 | 1.21 | 3.9:1 | 5:1 |
| 018G3P | CIS1 | 0.80 | NIS1 | 0.80 | OTH1 | 1.50 | 3.75:1 | 4:1 |
| 018H5Z | CIS2 | 0.80 | NIS1 | 0.80 | OTH1 | 1.50 | 3.75:1 | 4:1 |

The compositions, and composition combinations, of Table 6A were applied to ABUTH, ECHCF, TRZVX, LOLMG and SIDSP plants and evaluated versus glyphosate STD2, STD3, STD4 and STD5 standards. ABUTH and ECHCF were evaluated at glyphosate application rates of 100, 200, 300 and 400 g a.e./ha, TRZVX and SIDSP were evaluated at glyphosate application rates of 150, 200, 400 and 800 g a.e./ha, and LOLMG was evaluated at glyphosate application rates of 300, 600, 800 and 1000 g a.e./ha. The % inhibition results are reported in Table 6B below.

TABLE 6B

| | % inhibition | | | | |
|---|---|---|---|---|---|
| Composition | ABUTH | ECHCF | TRZVX | SIDSP | LOLMG |
| 018A3C | 82, 90, 92, 99 | 30, 61, 70, 79 | 78, 84, 98, 99 | 74, 75, 91, 98 | 80, 92, 98, 99 |
| 018B8J | 75, 90, 94, 95 | 43, 61, 75, 79 | 78, 83, 97, 99 | 72, 77, 89, 98 | 80, 89, 97, 99 |
| 018I7N | 82, 91, 93, 97 | 27, 63, 78, 84 | 78, 87, 99, 100 | 71, 78, 90, 98 | 87, 97, 99, 99 |
| 018J7Q | 83, 91, 96, 99 | 38, 64, 77, 84 | 80, 90, 99, 99 | 75, 84, 91, 97 | 91, 97, 99, 99 |
| 018C9V | 86, 93, 99, 97 | 28, 67, 76, 89 | 80, 85, 98, 99 | 76, 88, 94, 98 | 83, 96, 98, 99 |
| 018D3E | 88, 91, 99, 100 | 43, 64, 78, 84 | 83, 86, 97, 99 | 76, 85, 90, 98 | 83, 95, 99, 99 |
| 018E5Y | 88, 95, 94, 99 | 43, 62, 82, 83 | 83, 86, 98, 99 | 76, 85, 93, 98 | 83, 98, 99, 99 |
| 018F6S | 84, 96, 99, 100 | 38, 68, 83, 92 | 79, 88, 98, 99 | 76, 87, 91, 98 | 85, 96, 99, 99 |
| 018G3P | 91, 96, 97, 100 | 53, 75, 80, 97 | 81, 86, 99, 98 | 74, 84, 93, 98 | 83, 97, 98, 99 |
| 018H5Z | 93, 99, 99, 99 | 43, 79, 85, 92 | 80, 85, 100, 100 | 78, 85, 93, 98 | 87, 98, 98, 98 |
| STD4 | 80, 85, 88, 92 | 60, 65, 73, 79 | 75, 78, 90, 99 | 51, 68, 89, 98 | — |
| STD5 | — | — | 3, 30, 35, 60 | 0, 33, 49, 70 | — |
| STD2 | — | — | — | — | 40, 63, 72, 78 |
| STD3 | — | — | — | — | 82, 90, 95, 99 |

In this example both the surfactant and the oxalate concentrations were increased concurrently. The data indicate that across the different species studied, the NIS/CIS/oxalate platform was more effective in weed control that the commercial standard for all the compositions. The data did not show any consistent dependence on the surfactant or oxalate concentration, with the formulations with high surfactant and oxalate content often outperforming the rest. There was no difference in performance between the two cationic surfactants used in the NIS/CIS/oxalate platform Example 7

To optimize glyphosate:oxalate and glyphosate:surfactant ratios in compositions containing glyphosate, a cationic surfactant, a nonionic surfactant and oxalate adjuvant and ammonium glyphosate compositions were formulated as indicated in Table 7A below. The ammonium glyphosate concentration in each composition was 62 grams acid equivalent per liter.

TABLE 7A

| Comp. | Cmpnt 1 | wt % | Cmpnt. 2 | wt % | Cmpnt. 3 | wt % | gly:surf | gly:oxalate |
|---|---|---|---|---|---|---|---|---|
| 018I8H | CIS1 | 0.50 | NIS1 | 0.70 | OTH1 | 0.73 | 5:1 | 8.2:1 |
| 030A3N | CIS1 | 0.74 | NIS1 | 0.74 | OTH1 | 0.73 | 4.1:1 | 8.2:1 |
| 030C4R | CIS1 | 0.80 | NIS1 | 0.80 | OTH1 | 0.73 | 3.75:1 | 8.2:1 |
| 030E1A | CIS1 | 0.74 | NIS1 | 0.74 | OTH1 | 0.83 | 4.1:1 | 7.2:1 |
| 030G9L | CIS1 | 0.80 | NIS1 | 0.80 | OTH1 | 0.83 | 3.75:1 | 7.2:1 |
| 030I7W | CIS1 | 0.74 | NIS1 | 0.74 | OTH1 | 1.21 | 4.1:1 | 5:1 |
| 030K4J | CIS1 | 0.80 | NIS1 | 0.80 | OTH1 | 1.21 | 3.75:1 | 5:1 |
| 030M6P | CIS1 | 0.74 | NIS1 | 0.74 | OTH1 | 1.50 | 4.1:1 | 4:1 |
| 030O1R | CIS1 | 0.80 | NIS1 | 0.80 | OTH1 | 1.50 | 3.75:1 | 4:1 |

The compositions, and composition combinations, of Table 7A were applied to ABUTH, ECHCF, TRZVX and LOLMG plants. ABUTH and ECHCF were evaluated at glyphosate application rates of 100, 200, 300 and 400 g a.e./ha, TRZVX was evaluated at glyphosate application rates of 100, 200, 300 and 600 g a.e./ha, and LOLMG was evaluated at glyphosate application rates of 100, 200, 300 and 500 g a.e./ha. Efficacy was evaluated versus glyphosate STD4 and STD5 standards. The % inhibition results are reported in Table 7B below.

TABLE 7B

| | % inhibition | | | |
|---|---|---|---|---|
| Comp | ABUTH | ECHCF | TRZVX | LOLMG |
| 018I8H | 76, 90, 95, 97 | 63, 78, 86, 94 | 82, 93, 98, 99 | 77, 88, 97, 97 |
| 030A3N | 79, 91, 95, 97 | 63, 80, 90, 90 | 83, 95, 98, 100 | 78, 88, 94, 98 |
| 030C4R | 80, 93, 97, 98 | 67, 85, 93, 96 | 83, 91, 98, 99 | 73, 89, 94, 99 |
| 030E1A | 80, 92, 96, 97 | 64, 88, 94, 96 | 82, 95, 98, 99 | 74, 86, 95, 99 |
| 030G9L | 83, 96, 98, 98 | 65, 87, 95, 97 | 79, 95, 98, 100 | 68, 86, 93, 98 |
| 030I7W | 85, 93, 98, 98 | 61, 88, 88, 97 | 77, 96, 97, 99 | 66, 85, 92, 97 |
| 030K4J | 80, 95, 97, 98 | 63, 85, 87, 92 | 83, 95, 98, 100 | 73, 81, 93, 97 |
| 030M6P | 85, 94, 95, 97 | 63, 85, 89, 94 | 86, 95, 98, 99 | 66, 86, 95, 99 |
| 030O1R | 84, 93, 97, 99 | 64, 85, 90, 93 | 84, 95, 99, 99 | 73, 83, 96, 98 |
| STD5 | 2, 19, 67, 79 | 8, 59, 65, 68 | 36, 51, 71, 75 | 48, 63, 85, 91 |
| STD4 | 21, 72, 82, 92 | 62, 72, 81, 90 | 68, 83, 96, 99 | 68, 88, 97, 97 |

Trends for ABUTH and ECHCF efficacy indicate that more total surfactant provides slightly higher performance across weed species. Ranking of formulation performance versus total surfactant loading (glyphosate:surfactant ratios) was generally as follows: 3.75:1>4.1:1>5.1:1. All formulations outperformed the standards. Efficacy performance trends for TRZVX and LOLMG were not found. However all formulations performed equivalent to or better than the standards.

Example 8

To optimize glyphosate:oxalate and glyphosate:surfactant ratios in compositions containing glyphosate, a cationic surfactant, a nonionic surfactant and oxalate adjuvant and ammonium glyphosate compositions were formulated as indicated in Table 8A below. The ammonium glyphosate concentration in each composition was 62 grams acid equivalent per liter.

TABLE 8A

| Comp. | Cmpnt 1 | wt % | Cmpnt. 2 | wt % | Cmpnt. 3 | wt % | gly:surf | gly:oxalate |
|---|---|---|---|---|---|---|---|---|
| 018J7B | CIS2 | 0.50 | NIS1 | 0.70 | OTH1 | 0.73 | 5:1 | 8.2:1 |
| 030B2U | CIS2 | 0.74 | NIS1 | 0.74 | OTH1 | 0.73 | 4.1:1 | 8.2:1 |
| 030D9V | CIS2 | 0.80 | NIS1 | 0.80 | OTH1 | 0.73 | 3.75:1 | 8.2:1 |
| 030F8T | CIS2 | 0.74 | NIS1 | 0.74 | OTH1 | 0.83 | 4.1:1 | 7.2:1 |
| 030H7L | CIS2 | 0.80 | NIS1 | 0.80 | OTH1 | 0.83 | 3.75:1 | 7.2:1 |
| 030J1P | CIS2 | 0.74 | NIS1 | 0.74 | OTH1 | 1.21 | 4.1:1 | 5:1 |
| 030L2S | CIS2 | 0.80 | NIS1 | 0.80 | OTH1 | 1.21 | 3.75:1 | 5:1 |
| 030N6G | CIS2 | 0.74 | NIS1 | 0.74 | OTH1 | 1.50 | 4.1:1 | 4:1 |
| 030P0L | CIS2 | 0.80 | NIS1 | 0.80 | OTH1 | 1.50 | 3.75:1 | 4:1 |

The compositions, and composition combinations, of Table 8A were applied to ABUTH, ECHCF and TRZVX. ABUTH and ECHCF were evaluated at glyphosate application rates of 100, 200, 300 and 400 g a.e./ha, and TRZVX was evaluated at glyphosate application rates of 100, 150, 200 and 400 g a.e./ha. Efficacy was evaluated versus glyphosate STD4 and STD5 standards. The % inhibition results are reported in Table 8B below.

TABLE 8B

| | % inhibition | | |
|---|---|---|---|
| Comp | ABUTH | ECHCF | TRZVX |
| 018J7B | 88, 97, 99, 100 | 64, 75, 89, 96 | 63, 81, 85, 98 |
| 030B2U | 86, 95, 97, 100 | 68, 78, 91, 93 | 67, 78, 87, 98 |
| 030D9V | 89, 99, 100, 100 | 64, 80, 90, 95 | 63, 73, 83, 98 |
| 030F8T | 89, 99, 98, 100 | 68, 83, 91, 92 | 55, 70, 87, 95 |
| 030H7L | 87, 99, 99, 100 | 68, 86, 90, 96 | 53, 68, 86, 96 |
| 030J1P | 88, 98, 99, 100 | 64, 84, 93, 97 | 55, 73, 88, 92 |
| 030L2S | 89, 94, 98, 100 | 69, 83, 93, 93 | 52, 69, 78, 96 |
| 030N6G | 91, 96, 97, 100 | 65, 87, 91, 93 | 60, 66, 79, 97 |
| 030P0L | 88, 98, 99, 100 | 66, 88, 92, 94 | 60, 68, 82, 95 |
| STD5 | 36, 65, 80, 87 | 33, 58, 65, 68 | 12, 35, 40, 65 |
| STD4 | 45, 80, 87, 97 | 62, 77, 82, 90 | 55, 70, 85, 97 |

All test formulations showed high level of activity on all plant species tested with performance levels superior to the standards. Efficacy trends generally indicate higher performance with increasing total surfactant. Ranking of surfactant performance versus surfactant loading (gly:surf ratios) generally followed the trend of 3.75:1>4.1:1>5.1:1. Performance increase on ABUTH and ECHCF was noted with increasing levels of oxalate. To the contrary, performance decrease on TRZVX was noted with increasing levels of oxalate.

Example 9

To determine the efficacy effect of different nonionic surfactants in glyphosate systems containing a cationic surfactant, a nonionic surfactant and a dicarboxylic acid wherein the mole ratio of oxalate:cationic surfactant is greater than 10:1, compositions containing ammonium glyphosate, a cationic surfactant, a nonionic surfactant and oxalate adjuvant were formulated as indicated in Table 9A below. The ammonium glyphosate concentration in each composition was 62 grams acid equivalent per liter.

TABLE 9A

| Composition | Cmpnt 1 | wt % | Cmpnt. 2 | wt % | Cmpnt. 3 | wt % |
|---|---|---|---|---|---|---|
| 095A4D | CIS6 | 0.73 | NIS1 | 0.49 | OTH1 | 0.77 |
| 095I9M | CIS6 | 0.49 | NIS1 | 0.73 | OTH1 | 0.77 |
| 095C3W | CIS6 | 0.73 | NIS2 | 0.49 | OTH1 | 0.77 |

TABLE 9A-continued

| Composition | Cmpnt 1 | wt % | Cmpnt. 2 | wt % | Cmpnt. 3 | wt % |
|---|---|---|---|---|---|---|
| 095J7R | CIS6 | 0.73 | NIS1 | 0.49 | — | — |
| 095K7L | CIS6 | 0.73 | NIS2 | 0.49 | — | — |
| 095F4K | CIS2 | 0.73 | NIS1 | 0.49 | OTH1 | 0.77 |

The compositions, and composition combinations, of Table 9A were applied to LOLMG. Efficacy was evaluated versus glyphosate STD1, STD2, STD3 and STD4 standards. The % inhibition results are reported in Table 9B below.

TABLE 9B

| | % inhibition 16 days after treatment | |
|---|---|---|
| Comp | Rate (g a.e./ha) | LOLMG |
| 095A4D | 200, 400, 600, 800 | 73, 97, 98, 99 |
| 095I9M | 200, 400, 600, 800 | 76, 94, 96, 98 |
| 095C3W | 200, 400, 600, 800 | 72, 95, 97, 99 |
| 095J7R | 200, 400, 600, 800 | 88, 99, 99, 100 |
| 095K7L | 200, 400, 600, 800 | 83, 98, 99, 100 |
| 095F4K | 200, 400, 600, 800 | 86, 98, 98, 1005 |
| STD2 | 200, 400, 600, 800 | 1, 3, 28, 47 |
| STD3 | 200, 400, 600, 800 | 78, 96, 97, 99 |
| STD4 | 200, 400, 600, 800 | 81, 97, 98, 100 |
| STD1 | 200, 400, 600, 800 | 75, 97, 98, 100 |

All compositions exhibited greater efficacy than the STD3 standard. This example showed very high activity on ryegrass and the differences were noted only at the lowest rate. At the lowest rate used, there was no beneficial effect noted from the oxalate-containing formulations. Also, there were no differences between the two nonionic surfactants used in this example.

Example 10

To determine the efficacy effect of different nonionic surfactants in glyphosate systems containing a cationic surfactant, a nonionic surfactant and a dicarboxylic acid, compositions containing potassium glyphosate, a cationic surfactant, a nonionic surfactant and oxalate adjuvant were formulated as indicated in Table 10A below. The potassium glyphosate concentration in each composition was 62 grams acid equivalent per liter.

TABLE 10A

| Composition | Cmpnt 1 | wt % | Cmpnt. 2 | wt % | Cmpnt. 3 | wt % |
|---|---|---|---|---|---|---|
| 697A2J | CIS2 | 0.40 | NIS4 | 1.10 | — | — |
| 697B9K | CIS2 | 0.40 | NIS4 | 1.10 | OTH5 | 0.45 |

TABLE 10A-continued

| Composition | Cmpnt 1 | wt % | Cmpnt. 2 | wt % | Cmpnt. 3 | wt % |
|---|---|---|---|---|---|---|
| 697C1X | CIS2 | 0.40 | NIS5 | 1.10 | — | — |
| 697D0H | CIS2 | 0.40 | NIS5 | 1.10 | OTH5 | 0.45 |
| 697E2W | CIS2 | 0.40 | NIS6 | 1.10 | — | — |
| 697F8U | CIS2 | 0.40 | NIS6 | 1.10 | OTH5 | 0.45 |
| 697G3R | CIS2 | 0.40 | NIS1 | 1.10 | — | — |
| 697H9J | CIS2 | 0.40 | NIS1 | 1.10 | OTH5 | 0.45 |

The compositions, and composition combinations, of Table 10A were applied to BRSJU. Efficacy was evaluated versus glyphosate STD2, STD3, STD7 standards. The % inhibition results are reported in Table 10B below.

TABLE 10B

% inhibition 16 days after treatment

| Comp | Rate (g a.e./ha) | BRSJU |
|---|---|---|
| 697A2J | 100, 200, 400, 800 | 62, 70, 79, 87 |
| 697B9K | 100, 200, 400, 800 | 75, 79, 86, 88 |
| 697C1X | 100, 200, 400, 800 | 62, 73, 77, 85 |
| 697D0H | 100, 200, 400, 800 | 70, 77, 86, 90 |
| 697E2W | 100, 200, 400, 800 | 70, 76, 83, 88 |
| 697F8U | 100, 200, 400, 800 | 75, 79, 86, 89 |
| 697G3R | 100, 200, 400, 800 | 71, 78, 85, 93 |
| 697H9J | 100, 200, 400, 800 | 75, 83, 88, 91 |
| STD2 | 100, 200, 400, 800 | 17, 48, 62, 74 |
| STD3 | 100, 200, 400, 800 | 68, 78, 83, 88 |
| STD7 | 100, 200, 400, 800 | 55, 77, 84, 89 |

All compositions exhibited greater efficacy than the STD3 standard. Nonionic surfactant efficacy performance gave the following trend in order of effectiveness: Hetoxol 20>Tween 80>Aldocet HS1000>Emerest 2622.

Example 11

A trial was conducted to determine efficacy of formulations comprising monoethoxylated alkylamine cationic surfactant, hetoxol nonionic surfactant, citric acid and ammonium glyphosate on ABUTH and ECHCF. Adjuvant and ammonium glyphosate compositions were formulated as indicated in Table 11A below. Ammonium glyphosate concentration in each formulation was 62.0 g a.e./l.

TABLE 11A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 082BD4 | CIS1 | 0.36 | NIS1 | 0.25 | — | — | — | — |
| 082BE8 | CIS1 | 0.36 | NIS1 | 0.25 | OTH1 | 0.77 | — | — |
| 009AA1 | CIS1 | 0.36 | NIS1 | 0.25 | OTH4 | 0.77 | — | — |
| 009AB9 | CIS1 | 0.36 | NIS1 | 0.25 | OTH4 | 0.40 | OTH1 | 0.40 |
| 009AC2 | CIS1 | 0.36 | NIS1 | 0.25 | OTH4 | 0.60 | OTH1 | 0.20 |
| 009AD6 | CIS7 | 0.36 | NIS1 | 0.25 | OTH4 | 0.40 | OTH1 | 0.40 |
| 009AE8 | CIS7 | 0.36 | NIS1 | 0.25 | OTH4 | 0.60 | OTH1 | 0.20 |

The compositions, and composition combinations, of Table 11A were applied to ABUTH, ECHCF, SIDSP and BRSJU plants and evaluated versus STD3, STD5 and STD8 standards. ABUTH and ECHCF were evaluated at glyphosate application rates of 100, 200, 300 and 400 g a.e./ha, SIDSP was evaluated at glyphosate application rates of 200, 400, 600 and 800 g a.e./ha, and BRSJU was evaluated at glyphosate application rates of 100, 200, 400 and 800 g a.e./ha. The % inhibition results are reported in Table 11B below.

TABLE 11B

% inhibition

| Comp. | ABUTH | ECHCF | SIDSP | BRSJU |
|---|---|---|---|---|
| 082BD4 | 28, 85, 90, 93 | 2, 63, 65, 72 | 71, 91, 93, 98 | 62, 69, 85, 93 |
| 082BE8 | 80, 86, 95, 96 | 3, 59, 66, 74 | 81, 91, 95, 97 | 70, 82, 90, 93 |
| 009AA1 | 75, 83, 88, 90 | 7, 61, 64, 71 | 84, 92, 96, 97 | 65, 74, 88, 91 |
| 009AB9 | 77, 90, 93, 97 | 3, 63, 64, 76 | 75, 88, 96, 97 | 52, 78, 92, 94 |
| 009AC2 | 80, 88, 91, 97 | 8, 65, —, — | 79, 91, 96, 97 | 59, 77, 88, 94 |
| 009AD6 | 81, 88, 93, 97 | 18, 64, 68, 74 | 82, 90, 96, 97 | 50, 80, 88, 93 |
| 009AE8 | 78, 87, 91, 95 | 22, 62, 69, 76 | 84, 88, 96, 98 | 73, 80, 90, 96 |
| STD5 | 0, 3, 44, 69 | 0, 3, 18, 46 | 50, 58, 65, 68 | 10, 33, 69, 71 |
| STD8 | 0, 2, 43, 77 | 0, 24, 45, 50 | 55, 70, 76, 83 | 27, 53, 61, 81 |
| STD3 | 3, 80, 85, 92 | 4, 62, 65, 75 | 74, 88, 95, 98 | 43, 69, 87, 96 |

The presence of citric acid in the formulations containing CIS, NIS and citric acid or CIS, NIS, citric acid and oxalate did not appear to provide any statistically significant efficacy affects on weed control.

Example 12

A trial was conducted to determine if alternate acids in combination with oxalic acid affects the efficacy of systems containing glyphosate, a cationic surfactant, a nonionic surfactant and oxalic acid. Adjuvant and ammonium glyphosate compositions were formulated as indicated in Table 12A below. Ammonium glyphosate concentration in each formulation was 62.0 g a.e./l.

TABLE 12A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 071N5C | CIS1 | 0.73 | NIS1 | 0.49 | — | | — | |
| 071P0J | CIS1 | 0.73 | NIS1 | 0.49 | OTH1 | 0.80 | — | |
| 009A4S | CIS1 | 0.73 | NIS1 | 0.49 | OTH4 | 0.80 | — | |
| 009B1D | CIS1 | 0.73 | NIS1 | 0.49 | OTH4 | 0.40 | OTH1 | 0.40 |
| 009C5H | CIS1 | 0.30 | NIS1 | 0.25 | OTH1 | 0.80 | — | |
| 009D2N | CIS1 | 0.30 | NIS1 | 0.25 | OTH4 | 0.40 | OTH1 | 0.40 |
| 009E8J | CIS2 | 0.30 | NIS1 | 0.25 | OTH4 | 0.40 | OTH1 | 0.40 |

The compositions, and composition combinations, of Table 12A were applied to ABUTH and ECHCF and evaluated versus STD2, STD3 and STD8 standards. The % inhibition results are reported in Table 12B below.

TABLE 12B

| | | % inhibition | |
|---|---|---|---|
| Composition | Rate (g a.e./ha) | ABUTH | ECHCF |
| 071N5C | 100, 200, 300, 400 | 78, 88, 94, 95 | 63, 75, 80, 88 |
| 071P0J | 100, 200, 300, 400 | 88, 92, 95, 96 | 63, 78, 92, 92 |
| 009A4S | 100, 200, 300, 400 | 77, 85, 92, 93 | 63, 73, 84, 87 |
| 009B1D | 100, 200, 300, 400 | 82, 90, 95, 96 | 62, 83, 92, 95 |
| 009C5H | 100, 200, 300, 400 | 81, 91, 94, 97 | 41, 68, 80, 88 |
| 009D2N | 100, 200, 300, 400 | 80, 89, 93, 96 | 50, 69, 84, 85 |
| 009E8J | 100, 200, 300, 400 | 78, 88, 92, 98 | 48, 71, 75, 87 |
| STD2 | 100, 200, 300, 400 | 0, 47, 75, 78 | 36, 44, 51, 58 |
| STD8 | 100, 200, 300, 400 | 50, 68, 76, 79 | 33, 46, 53, 58 |
| STD3 | 100, 200, 300, 400 | 77, 82, 89, 93 | 53, 72, 81, 89 |

The incorporation of citric acid in blends containing a cationic surfactant and a nonionic surfactant, or a cationic surfactant, a nonionic surfactant and oxalate did not provide significant efficacy enhancement. The data suggest that citrate does not have a positive or negative effect on efficacy. Most formulations were slightly superior to STD3 for ABUTH control. Compositions containing oxalate provided greater ECHCF control than did compositions not containing oxalate.

Example 13

A trial was conducted to determine the efficacy effect of ammonium sulfate on compositions containing glyphosate, a cationic surfactant, a nonionic surfactant and, optionally, oxalate. Adjuvant and ammonium glyphosate compositions were formulated as indicated in Table 13A below. Ammonium glyphosate concentration in each formulation was 62.0 g a.e./l.

TABLE 13A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 817A3K | — | | — | | OTH5 | 1.20 | — | |
| 817B6G | — | | — | | OTH20 | 6.00 | — | |
| 817C1W | CIS4 | 0.40 | NIS12 | 0.80 | OTH5 | 1.20 | — | |
| 817D9H | CIS4 | 0.40 | NIS12 | 0.80 | OTH20 | 6.00 | — | |
| 817E4Z | CIS4 | 0.40 | NIS12 | 0.80 | OTH5 | 0.60 | OTH20 | 0.60 |
| 817F0U | CIS4 | 0.40 | NIS12 | 0.80 | OTH5 | 0.80 | OTH20 | 0.40 |
| 817G6R | CIS4 | 0.40 | NIS12 | 0.80 | OTH5 | 0.40 | OTH20 | 0.80 |
| 817H4Y | CIS4 | 0.40 | NIS12 | 0.80 | OTH20 | 1.20 | — | |

The compositions, and composition combinations, of Table 13A were applied to ABUTH, ECHCF, SIDSP, BRSJU and SEBEX plants. ABUTH and ECHCF were evaluated at glyphosate application rates of 75, 170, 255 and 340 g a.e./ha, SIDSP and SEBEX were evaluated at glyphosate application rates of 100, 200, 400 and 800 g a.e./ha, and BRSJU was evaluated at glyphosate application rates of 150, 250, 400 and 800 g a.e./ha. Efficacy was evaluated versus glyphosate STD3, STD5 and STD6 standards. The % inhibition results are reported in Table 13B below.

TABLE 13B

| | % inhibition | | | | |
|---|---|---|---|---|---|
| Comp | ABUTH | ECHCF | SIDSP | SEBEX | BRJSU |
| 817A3K | 28, 66, 88, 88 | 0, 8, 35, 46 | 47, 64, 74, 83 | 18, 33, 43, 83 | 45, 72, 77, 83 |
| 817B6G | 0, 30, 80, 87 | 0, 9, 26, 44 | 40, 63, 73, 885 | 0, 34, 35, 19 | 50, 60, 76, 84 |
| 817C1W | 79, 89, 91, 94 | 1, 50, 65, 69 | 63, 76, 88, 96 | 13, 63, 74, 87 | 58, 65, 78, 85 |
| 817D9H | 81, 90, 92, 95 | 2, 52, 66, 68 | 73, 88, 95, 99 | 13, 65, 80, 90 | 45, 60, 75, 89 |

TABLE 13B-continued

| | % inhibition | | | | |
|---|---|---|---|---|---|
| Comp | ABUTH | ECHCF | SIDSP | SEBEX | BRJSU |
| 817E4Z | 84, 90, 93, 96 | 8, 61, 63, 68 | 75, 86, 93, 99 | 0, 51, 60, 76 | 60, 70, 79, 85 |
| 817F0U | 87, 93, 96, 97 | 0, 58, 66, 68 | 75, 85, 92, 97 | 5, 72, 81, 99 | 60, 68, 83, 89 |
| 817G6R | 80, 91, 93, 96 | 1, 54, 66, 69 | 77, 83, 96, 99 | 48, 84, 89, 92 | 60, 71, 78, 89 |
| 817H4Y | 72, 88, 89, 93 | 2, 53, 64, 70 | 68, 85, 90, 99 | 35, 82, 91, 89 | 53, 67, 77, 88 |
| STD5 | 0, 0, 41, 65 | 0, 5, 31, 48 | 49, 60, 76, 80 | 0, 2, 3, 44 | 32, 54, 57, 70 |
| STD6 | 0, 46, 82, 86 | 0, 53, 63, 68 | 57, 78, 85, 98 | 10, 68, 81, 85 | 45, 65, 73, 86 |
| STD3 | 0, 75, 88, 91 | 0, 56, 67, 68 | 50, 75, 85, 99 | 45, 79, 86, 91 | 58, 68, 79, 86 |

The data show that ammonium sulfate and oxalic acid are synergistic for overall efficacy on both ABUTH and ECHCF. Of three ratios of oxalic acid:ammonium sulfate evaluated (1:1, 2:1 and 1:2), the 1:1 and 2:1 ratios gave slightly higher ABUTH and ECHCF efficacies than did the 1:2 ratio. The data did not show a synergistic relationship between ammonium sulfate and oxalic acid for SIDSP or BRSJU efficacy. All compositions containing surfactants and ammonium sulfate or oxalic acid, or a combination thereof, provided better SIDSP and BRSJU control than the standards. STD3, 817G6R and 817H4Y gave the highest efficacy on SEBEX. 817G6R and 817H4Y each contained a cationic surfactant, a nonionic surfactant, oxalate and ammonium sulfate.

The compositions, and composition combinations, of Table 13A were applied to ABUTH and ECHCF in a second trial at application rates of 75, 100, 150 and 300 g a.e./ha. Efficacy was evaluated versus glyphosate STD3, STD5 and STD6 standards. The % inhibition results are reported in Table 13C below.

TABLE 13C

| | % inhibition | |
|---|---|---|
| Comp | ABUTH | ECHCF |
| 817A3K | 17, 48, 69, 84 | 9, 16, 18, 55 |
| 817B6G | 9, 20, 53, 84 | 7, 8, 34, 53 |
| 817C1W | 78, 85, 88, 95 | 39, 60, 68, 88 |
| 817D9H | 75, 78, 88, 95 | 35, 57, 68, 85 |
| 817E4Z | 78, 83, 88, 95 | 38, 60, 68, 91 |
| 817F0U | 80, 85, 91, 96 | 44, 58, 70, 91 |
| 817G6R | 81, 87, 92, 98 | 45, 65, 75, 85 |
| 817H4Y | 70, 73, 85, 95 | 37, 63, 69, 86 |
| STD5 | 0, 0, 0, 49 | 0, 5, 35, 58 |
| STD6 | 0, 0, 41, 75 | 20, 51, 68, 78 |
| STD3 | 0, 10, 67, 86 | 15, 50, 70, 86 |

The compositions containing surfactant, ammonium sulfate and oxalic acid provided the greatest ABUTH and ECHCF control. All compositions containing surfactants and ammonium sulfate or oxalic acid, or a combination thereof, provided better ABUTH and ECHCF control than the standards. The three oxalic acid to ammonium sulfate ratios of 1:1, 2:1 and 1:2 appeared statistically equivalent.

Example 14

A trial was conducted to determine the efficacy effect of ammonium sulfate on compositions containing glyphosate, a cationic surfactant, a nonionic surfactant and, optionally, oxalate. Adjuvant and ammonium glyphosate compositions were formulated as indicated in Table 14A below. Ammonium glyphosate concentration in each formulation was 62.0 g a.e./l.

TABLE 14A

| Comp. | Cmpnt 1 | wt % | Cmpnt. 2 | wt % | Cmpnt. 3 | wt % | Cmpnt. 4 | wt % |
|---|---|---|---|---|---|---|---|---|
| 830A2J | — | — | — | — | OTH1 | 1.00 | — | — |
| 830B8R | — | — | — | — | OTH20 | 1.00 | — | — |
| 830C6G | — | — | — | — | OTH1 | 0.50 | OTH20 | 0.50 |
| 830D5V | CIS4 | 0.4 | NIS12 | 0.80 | OTH1 | 1.00 | — | — |
| 830E3P | CIS4 | 0.4 | NIS12 | 0.80 | — | — | OTH20 | 1.00 |
| 830F1T | CIS4 | 0.4 | NIS12 | 0.80 | OTH1 | 0.50 | OTH20 | 0.50 |
| 830G0K | CIS4 | 0.4 | NIS12 | 0.80 | OTH1 | 0.75 | OTH20 | 0.25 |
| 830H7N | CIS4 | 0.4 | NIS12 | 0.80 | OTH1 | 0.25 | OTH20 | 0.75 |

The compositions, and composition combinations, of Table 14A were applied to ABUTH, ECHCF and SIDSP. ABUTH and ECHCF were evaluated at glyphosate application rates of 75, 100, 200 and 400 g a.e./ha, SIDSP was evaluated at glyphosate application rates of 150, 250, 400 and 800 g a.e./ha. Efficacy was evaluated versus glyphosate STD4, STD5 and STD6 standards. The % inhibition results are reported in Table 14B below.

TABLE 14B

| | % inhibition | | |
|---|---|---|---|
| Comp | ABUTH | ECHCF | SIDSP |
| 830A2J | 43, 61, 81, 89 | 22, 35, 45, 65 | 67, 79, 84, 93 |
| 830B8R | 2, 8, 38, 76 | 6, 14, 32, 63 | 70, 78, 81, 88 |
| 830C6G | 12, 18, 79, 88 | 5, 15, 29, 66 | 72, 77, 79, 91 |
| 830D5V | 65, 78, 88, 98 | 38, 59, 71, 92 | 85, 91, 93, 98 |
| 830E3P | 64, 71, 78, 93 | 40, 58, 70, 95 | 88, 92, 96, 97 |
| 830F1T | 62, 76, 88, 94 | 33, 60, 73, 98 | 85, 89, 94, 97 |
| 830G0K | 68, 73, 83, 99 | 44, 60, 74, 93 | 83, 88, 90, 97 |
| 830H7N | 63, 77, 84, 97 | 48, 62, 82, 98 | 82, 90, 93, 98 |
| STD5 | 0, 0, 28, 75 | 2, 5, 40, 72 | 40, 48, 65, 80 |
| STD6 | 1, 3, 60, 85 | 43, 62, 72, 90 | 65, 78, 82, 97 |
| STD4 | 3, 57, 74, 88 | 45, 60, 71, 92 | 69, 83, 92, 98 |

The data show that compositions containing a cationic and nonionic surfactant plus ammonium sulfate and oxalate, oxalate or ammonium sulfate showed efficacy performance for ABUTH, ECHCF and SIDSP equal or superior to the standards. The surfactant+oxalate and ammonium sulfate blends in ratios of 2:1 and 1:2 showed the greatest overall ABUTH, ECHCF and SIDSP efficacy.

Example 15

To determine the efficacy effect of surfactant esters of dicarboxylic acid compositions were formulated with potassium glyphosate as indicated in Table 15A below. The potassium glyphosate concentration in each composition was 62 grams acid equivalent per liter.

TABLE 15A

| Composition | Cmpnt 1 | wt % | Cmpnt. 2 | wt % |
|---|---|---|---|---|
| 824A4C | CIS3 | 1.00 | — | — |
| 824B8U | CIS3 | 1.00 | OTH5 | 0.20 |
| 824C7H | NIS11 | 1.00 | — | — |
| 824D5L | NIS11 | 1.20 | — | — |
| 824E4S | CIS3 | 1.00 | OTH12 | 0.25 |
| 824F3C | NIS10 | 1.00 | — | — |
| 824G9R | NIS10 | 1.25 | — | — |

The compositions, and composition combinations, of Table 15A were applied to ABUTH, ECHCF, SIDSP and TRZVX. The ABUTH and ECHCF application rates were 100, 200, 300 and 400 g a.e./ha. The SIDSP and TRZVX application rates were 100, 200, 400 and 800 g a.e./ha. Efficacy was evaluated versus glyphosate STD2, STD3, STD4 and STD6. The % inhibition results are reported in Table 15B below.

TABLE 15B

| | % inhibition | | | |
|---|---|---|---|---|
| Comp | ABUTH | ECHCF | SIDSP | TRZVX |
| 824A4C | 10, 67, 73, 83 | 60, 78, 86, 95 | 57, 85, 95, 99 | 53, 79, 97, 98 |
| 824B8U | 23, 70, 84, 88 | 62, 77, 89, 99 | 71, 93, 98, 99 | 58, 79, 96, 98 |
| 824C7H | 26, 54, 79, 89 | 64, 87, 88, 98 | 70, 93, 97, 99 | 58, 80, 97, 100 |
| 824D5L | 35, 76, 89, 90 | 63, 83, 90, 98 | 72, 92, 96, 100 | 63, 84, 98, 99 |
| 824E4S | 57, 73, 77, 86 | 64, 79, 82, 95 | 68, 88, 96, 99 | 63, 80, 98, 98 |
| 824F3C | 13, 71, 77, 81 | 53, 73, 86, 91 | 72, 85, 97, 98 | 65, 80, 96, 99 |
| 824G9R | 50, 67, 74, 84 | 57, 75, 80, 89 | 60, 93, 97, 98 | 66, 82, 97, 99 |

TABLE 15B-continued

| | % inhibition | | | |
|---|---|---|---|---|
| Comp | ABUTH | ECHCF | SIDSP | TRZVX |
| STD2 | 0, 0, 43, 66 | 3, 45, 53, 70 | 32, 63, 80, 87 | 2, 23, 45, 57 |
| STD4 | — | — | 70, 84, 93, 99 | 50, 75, 95, 99 |
| STD6 | 5, 67, 73, 81 | 60, 73, 88, 95 | 65, 80, 93, 97 | 52, 71, 96, 99 |
| STD3 | 13, 70, 79, 92 | 56, 75, 82, 94 | 71, 90, 97, 98 | 66, 76, 97, 100 |

Overall, for ABUTH, ECHCF, SIDSP and TRZVX control, each acid formulated as an ester showed no strong advantages or disadvantages over the straight acids when formulated with a cationic surfactant. The compositions performed better than or similar to the standards for ABUTH, ECHCF, SIDSP and TRZVX control.

The stability of tallowamine-oxalate esters versus compositions containing varying amounts of tallowamine in conjunction with oxalate was evaluated in glyphosate solutions containing 40% acid equivalent of potassium glyphosate salt as reported in Table 16C below. In the table component 1 is PEG 4.5 tallowamine-oxalate ester, component 2 is PEG 4.5 tallowamine and component 3 is dipotassium oxalate. Comparative compositions are reported as a or b. Compositions 2a and b provide direct comparison on an equimolar basis. For example, PEG 4.5 tallowamine-oxalate was prepared in a 1:1 molar ratio thus 100 g of 10% by weight PEG 4.5 tallowamine-oxalate is calculated to contain 0.018 moles each of PEG 4.5 tallowamine (or 8.3 g; 8.3%) and oxalic acid (or 1.7 g; 1.7%). Hence comparative composition 2b contains 8.3% PEG 4.5 tallowamine and 3.2% $K_2$ oxalate (0.018 mol). Composition 1b evaluates lower tallowamine and oxalate loading, 3b evaluates a lower oxalate loading, and 4b evaluates a higher tallowamine loading. All components are reported on a % w/w basis.

TABLE 15C

| Comp. | Component 1 | Component 2 | Component 3 | 25° C. Stability | 60° C. Stability |
|---|---|---|---|---|---|
| 1a | 10% | — | — | Stable | Stable |
| 1b | — | 7% | 3% | Unstable | Unstable |
| 2a | 10% | — | — | Stable | Stable |
| 2b | — | 8.3% | 3.2% | Unstable | Unstable |
| 3a | 10% | — | — | Stable | Stable |
| 3b | — | 8.3% | 1.7% | Stable | Unstable |
| 4a | 10% | — | — | Stable | Stable |
| 4b | — | 10% | 3.2% | Unstable | Unstable |

The oxalate ester surfactants exhibit greater stability in highly concentrated glyphosate formulations than do tallowamine in conjunction with oxalate.

Example 16

To determine the efficacy effect of surfactant esters of acids with two or more carboxylic acid groups, potassium glyphosate compositions were formulated as indicated in Table 16A below. In the trial each of four acids were formulated with an amine surfactant and compared to the same acid formulated as a PEG5 tallowamine ester. The potassium glyphosate concentration in each composition was 62 grams acid equivalent per liter.

TABLE 16A

| Composition | Cmpnt 1 | wt % | Cmpnt. 2 | wt % |
|---|---|---|---|---|
| 814A4R | CIS3 | 0.87 | OTH5 | 0.17 |
| 814B7H | NIS11 | 1.00 | — | — |
| 814C0R | CIS3 | 0.83 | OTH12 | 0.21 |
| 814D3O | NIS10 | 1.00 | — | — |
| 814E6Y | CIS3 | 0.79 | OTH14 | 0.24 |
| 814F9K | NIS9 | 1.00 | — | — |
| 814G8E | CIS3 | 0.73 | OTH4 | 0.30 |
| 814H3J | NIS8 | 1.00 | — | — |

The compositions, and composition combinations, of Table 16A were applied to ABUTH, ECHCF and SIDSP. The ABUTH and ECHCF application rates were 100, 200, 300 and 400 g a.e./ha. The SIDSP application rate was 100, 200, 400 and 800 g a.e./ha. Efficacy was evaluated versus glyphosate STD2, STD3 and STD6 standards. The % inhibition results are reported in Table 16B below.

TABLE 16B

| | % inhibition | | |
|---|---|---|---|
| Comp | ABUTH | ECHCF | SIDSP |
| 814A4R | 73, 87, 89, 96 | 54, 68, 70, 77 | 54, 60, 83, 94 |
| 814B7H | 53, 82, 88, 94 | 52, 65, 75, 78 | 54, 58, 75, 92 |
| 814C0R | 53, 78, 87, 88 | 48, 60, 66, 71 | 45, 53, 71, 88 |
| 814D3O | 25, 80, 85, 88 | 30, 65, 68, 79 | 33, 45, 63, 83 |
| 814E6Y | 57, 79, 85, 88 | 46, 68, 69, 74 | 39, 47, 65, 88 |
| 814F9K | 17, 62, 82, 89 | 28, 68, 70, 71 | 32, 44, 64, 86 |
| 814G8E | 40, 65, 85, 87 | 49, 67, 68, 78 | 40, 48, 64, 84 |
| 814H3J | 24, 75, 83, 85 | 28, 68, 72, 75 | 43, 45, 67, 86 |
| STD2 | 0, 27, 68, 76 | 3, 41, 53, 59 | 13, 32, 45, 53 |
| STD6 | 0, 58, 84, 86 | 48, 65, 68, 81 | 47, 53, 60, 86 |
| STD3 | 26, 78, 86, 92 | 49, 72, 80, 81 | 45, 48, 69, 91 |

The compositions containing oxalic acid and the oxalic acid-PEG5 tallowamine ester provided the greatest ABUTH, ECHCF and SIDSP control. The other acids and their esters provided marginal efficacy enhancement. Each acid formulated as an ester showed no efficacy advantage over the straight acid blend formulation. The efficacy for the oxalic formulations was superior to STD3 and STD6 for ABUTH and SIDSP control and equal to those standards for ECHCF control.

Example 17

A trial was conducted to determine the efficacy of the IPA salt of 2,4-D plus potassium glyphosate in compositions containing a cationic surfactant, a nonionic surfactant and oxalic acid. Compositions were formulated as indicated in Table 17A below with potassium glyphosate and 2,4-D concentrations in g a.e./l indicated as [gly] and [2,4-D].

TABLE 17A

| Comp. | [gly] | [2,4-D] | Cmpnt. 1 | wt % | Cmpnt. 2 | wt % | Cmpnt. 3 | wt % |
|---|---|---|---|---|---|---|---|---|
| 820A2X | 62.0 | — | CIS23 | 0.75 | NIS7 | 1.00 | — | — |
| 820B8J | — | 60.0 | CIS23 | 0.75 | NIS7 | 1.00 | — | — |
| 820C5P | 62.0 | 2.0 | CIS23 | 0.75 | NIS7 | 1.00 | OTH5 | 0.30 |
| 820D2T | 62.0 | 2.0 | CIS23 | 0.75 | NIS7 | 1.00 | — | — |
| 820E9M | 62.0 | 6.0 | CIS23 | 0.75 | NIS7 | 1.00 | OTH5 | 0.30 |
| 820F1R | 62.0 | 6.0 | CIS23 | 0.75 | NIS7 | 1.00 | — | — |
| 820G4N | 62.0 | 4.0 | CIS23 | 0.75 | NIS7 | 1.00 | OTH5 | 0.60 |
| 820H2I | 62.0 | 6.0 | CIS23 | 0.75 | NIS7 | 1.00 | OTH5 | 0.60 |

The compositions, and composition combinations, of Table 17A were applied to ABUTH with % inhibition determined at 4 and 14 days after treatment. The test compositions were evaluated against STD2, STD3 and STD6 standards. The % inhibition results are reported in Table 17B below.

TABLE 17B

| | | % inhibition | |
|---|---|---|---|
| Composition | Rate (g a.e./ha) | ABUTH (4 DAT) | ABUTH (14 DAT) |
| 820A2X | 150, 250, 400, 800 | 5, 5, 10, 10 | 41, 75, 84, 94 |
| 820B8J | 150, 250, 400, 800 | 20, 25, 35, 40 | 67, 77, 81, 82 |
| 820C5P | 150, 250, 400, 800 | 5, 5, 5, 10 | 79, 85, 95, 99 |
| 820D2T | 150, 250, 400, 800 | 5, 5, 5, 10 | 26, 77, 85, 92 |
| 820E9M | 150, 250, 400, 800 | 5, 5, 10, 10 | 78, 81, 91, 97 |
| 820F1R | 150, 250, 400, 800 | 5, 5, 10, 10 | 23, 65, 83, 95 |
| 820G4N | 150, 250, 400, 800 | 10, 15, 20, 25 | 79, 85, 94, 100 |
| 820H2I | 150, 250, 400, 800 | 10, 15, 20, 25 | 79, 85, 96, 99 |
| STD2 | 150, 250, 400, 800 | 0, 5, 5, 5 | 0, 27, 71, 84 |
| STD6 | 150, 250, 400, 800 | 5, 5, 10, 10 | 25, 81, 85, 97 |
| STD3 | 150, 250, 400, 800 | 5, 5, 10, 10 | 70, 85, 90, 99 |

All formulations containing glyphosate, 2,4-D and oxalic acid gave the greatest efficacy and outperformed the standards. The composition containing glyphosate, 2,4-D and no oxalic acid did not perform as well as the standards. All compositions containing 2,4-D exhibited typical early symptomology with epinasty at 2 DAT.

Example 18

A trial was conducted to determine the efficacy of the IPA salt of 2,4-D plus potassium glyphosate in compositions containing a cationic surfactant, a nonionic surfactant and oxalic acid. Compositions were formulated as indicated in Table 18A below with potassium glyphosate and 2,4-D concentrations in g a.e./l indicated as [gly] and [2,4-D].

TABLE 18A

| Comp. | [gly] | [2,4-D] | Cmpnt. 1 | wt % | Cmpnt. 2 | wt % | Cmpnt. 3 | wt % |
|---|---|---|---|---|---|---|---|---|
| 806A9K | — | 60.0 | — | — | — | — | — | — |
| 806B2W | — | 60.0 | CIS23 | 0.75 | NIS7 | 1.00 | — | — |
| 806C7B | — | 60.0 | CIS23 | 0.75 | NIS7 | 1.00 | OTH5 | 0.30 |
| 806D1L | 62.0 | — | CIS23 | 0.75 | NIS7 | 1.00 | — | — |
| 806E6X | 62.0 | — | CIS23 | 0.75 | NIS7 | 1.00 | OTH5 | 0.30 |
| 806F3J | 62.0 | 2.0 | CIS23 | 0.75 | NIS7 | 1.00 | — | — |
| 806G5J | 62.0 | 2.0 | CIS23 | 0.75 | NIS7 | 1.00 | OTH5 | 0.30 |

The compositions, and composition combinations, of Table 18A were applied to ABUTH with % inhibition determined at 15 days after treatment. The test compositions were evaluated against STD2, STD3, STD6 and STD7 standards. The % inhibition results are reported in Table 18B below.

TABLE 18B

| | % inhibition | |
|---|---|---|
| Composition | Rate (g a.e./ha) | ABUTH |
| 806A9K | 100, 200, 300, 400 | 59, 76, 78, 80 |
| 806B2W | 100, 200, 300, 400 | 67, 75, 80, 80 |
| 806C7B | 100, 200, 300, 400 | 75, 78, 80, 83 |
| 806D1L | 100, 200, 300, 400 | 24, 59, 85, 88 |
| 806E6X | 100, 200, 300, 400 | 78, 88, 96, 98 |
| 806F3J | 100, 200, 300, 400 | 25, 75, 81, 87 |
| 806G5J | 100, 200, 300, 400 | 68, 89, 96, 97 |
| STD2 | 100, 200, 300, 400 | 0, 2, 44, 78 |
| STD6 | 100, 200, 300, 400 | 10, 64, 85, 90 |
| STD3 | 100, 200, 300, 400 | 13, 82, 90, 95 |
| STD7 | 100, 200, 300, 400 | 17, 63, 85, 90 |

Oxalic acid did not provide a statistically significant performance enhancement when combined with 2,4-D on ABUTH. Compositions containing glyphosate, 2,4-D and oxalate outperformed compositions containing glyphosate and 2,4-D. The compositions containing glyphosate and oxalic acid, with and without 2,4-D, provided the greatest control.

Example 19

Evaluations were done to determine if the efficacy of various herbicide classes with differing modes of action are affected in tank mixes containing 1 w/v % of ammonium oxalate.

In this trial, diammonium oxalate was tank mixed with each of four different commercial postemergent herbicides representing several different classes of chemistry and different modes of action. Tables 19A provides efficacy results for nicosulfuron (ACCENT®), fluazifop-p (FUSILADE® DX), imazethapyr (PURSUIT®) and diquat (REWARD®) in combination with ammonium oxalate (OTH1) when applied to ABUTH, ECHCF and TRZVX. Nicosulfuron was applied at rates of 1, 3, 5 and 10 g a.e. per hecatre and the remainder of the compositsions were applied at 30, 70, 100 and 200 g a.e. per hectare. Comparative standard STD3 was used.

TABLE 19A

| | 16 days after treatment | | | |
|---|---|---|---|---|
| Composition | OTH1 Rate % v/v | ABUTH | ECHCF | TRZVX |
| nicosulfuron | — | 0.8, 12, 14, 28 | 0.8, 13, 40, 51 | 5, 15, 50, 65 |
| nicosulfuron | 1, 1, 1, 1 | 6, 8, 10, 58 | 4, 10, 37, 42 | 3, 25, 47, 67 |
| fluazifop-p | — | 0, 0, 0, 0 | 98, 100, 100, 100 | 70, 85, 91, 97 |
| fluazifop-p | 1, 1, 1, 1 | 0, 0, 0, 0 | 97, 100, 100, 100 | 73, 83, 93, 98 |
| imazethapyr | — | 73, 80, 82, 85 | 68, 72, 75, 87 | 14, 41, 52, 73 |
| imazethapyr | 1, 1, 1, 1 | 72, 81, 85, 89 | 66, 71, 74, 80 | 25, 33, 50, 67 |
| diquat | — | 5, 15, 20, 32 | 19, 33, 43, 46 | 3, 7, 27, 46 |
| diquat | 1, 1, 1, 1 | 10, 30, 41, 57 | 11, 24, 33, 50 | 14, 16, 19, 47 |
| STD3 | — | 0, 13, 42, 68 | 23, 61, 65, 90 | 25, 53, 68, 82 |
| STD3 | 1, 1, 1, 1 | 46, 79, 82, 93 | 37, 63, 65, 87 | 32, 53, 68, 87 |

Results indicate that oxalate at 1% of spray volume was highly effective for increasing the efficacy of STD3 on ABUTH with little or no effect on ECHCF or TRZVX. The results also show that oxalate may have some significant broadleaf weed efficacy when tankmixed with Reward® (diquat) herbicide. Results with Fusilade® and Pursuit® showed no efficacy enhancement at any application rate on ABUTH and ECHCF. Oxalate did not appear to be antagonistic for control of ECHCF or TRZVX. Slight efficacy improvements were found for Pursuit® and Reward® at the lowest application rates. Early symptomology data was taken 2 days after treatment. Only Reward® herbicide showed early necrotic spotting on ABUTH and ECHCF leaves. Overall only glyphosate and diquat showed consistent and significant efficacy enhancements on ABUTH when tank mixed with diammonium oxalate.

Table 19B provides efficacy results trials wherein diammonium oxalate was tank mixed with each of four different commercial postemergent herbicides representing several different classes of chemistry and several different modes of herbicidal action. Glufosinate (FINALE®), oxyfluorfen (GOAL®), diuron (DIREX®) and ATRAZINE® in were evaluated when applied to ABUTH and ECHCF. The application rate was 75, 100, 150 and 200 g a.e. per hectare. Comparative standard STD3 was used.

TABLE 19B

| % inhibition 17 days after treatment | | | | |
|---|---|---|---|---|
| Composition | OTH22 Rate % v/v | OTH1 Rate % v/v | ABUTH | ECHCF |
| glufosinate | — | — | 22, 43, 74, 89 | 94, 95, 98, 99 |
| glufosinate | — | 1, 1, 1, 1 | 68, 82, 90, 98 | 95, 96, 99, 100 |
| oxyfluorfen | — | — | 81, 82, 84, 91 | 0, 0, 0, 3 |
| oxyfluorfen | — | 1, 1, 1, 1 | 80, 82, 87, 92 | 0, 0, 0, 2 |
| diuron | — | — | 0, 0, 5, 17 | 0, 0, 0, 0 |
| diuron | — | 1, 1, 1, 1 | 0, 0, 2, 10 | 0, 0, 0, 0 |
| ATRAZINE ® | 1, 1, 1, 1 | — | 85, 90, 90, 93 | 80, 82, 83, 84 |
| ATRAZINE ® | 1, 1, 1, 1 | 1, 1, 1, 1 | 91, 91, 93, 93 | 80, 81, 83, 83 |
| STD3 | — | — | 13, 38, 71, 71 | 63, 70, 83, 87 |
| STD3 | — | 1, 1, 1, 1 | 84, 88, 93, 95 | 68, 79, 85, 89 |

Diammonium oxalate at 1% of spray volume was highly effective for increasing the efficacy of STD3 on velvetleaf. Slight enhancement on ECHCF at low application rates was also noted. Results indicate that oxalate may have some significant broadleaf weed efficacy benefits when tank mixed with glufosinate, a glutamine synthesis inhibitor. Results with oxyfluorfen (a protoporphyrinogen oxidase inhibitor), Atrazine and duron (both photosystem III inhibitors) showed no efficacy enhancement at any application rate tested on ABUTH and ECHCF. Oxalate did not appear to be antagonistic for control of ECHCF. The data indicate that oxalate performance enhancement may be dependent on certain inhibitory pathways.

Table 19C provides efficacy results for glyphosate+acetochlor+atrazine (Field Master®) and glyphosate+2,4-D (RT MASTER®) in combination with oxalic acid (OTH5) when applied to ABUTH and ECHCF. Comparative standards STD2 and STD3 were used.

TABLE 19C

| 16 days after treatment | | | | | |
|---|---|---|---|---|---|
| Composition | Rate g a.e./ha | OTH5 g a.i./ha | gly:OA ratio | ABUTH | ECHCF |
| RT MASTER ® | 75, 100, 200 | — | — | 48, 62, 78 | 55, 78, 91 |
| RT MASTER ® | 75, 100, 200 | 38, 50, 100 | 2:1 | 75, 83, 95 | 65, 85, 96 |
| RT MASTER ® | 75, 100, 200 | 8, 10, 20 | 10:1 | 67, 78, 92 | 63, 83, 95 |
| RT MASTER ® | 75, 100, 200 | 2, 3, 7 | 30:1 | 54, 76, 90 | 60, 81, 94 |
| Field Master ® | 75, 100, 200 | — | — | 41, 54, 85 | 28, 49, 50 |
| Field Master ® | 75, 100, 200 | 38, 50, 100 | 2:1 | 77, 88, 91 | 48, 60, 62 |
| Field Master ® | 75, 100, 200 | 8, 10, 20 | 10:1 | 65, 77, 80 | 35, 53, 54 |
| Field Master ® | 75, 100, 200 | 2, 3, 7 | 30:1 | 48, 74, 79 | 21, 48, 50 |
| STD3 | 75, 100, 200 | — | — | 41, 76, 86 | 58, 78, 92 |
| STD3 | 75, 100, 200 | 38, 50, 100 | 2:1 | 78, 88, 98 | 62, 81, 95 |
| STD3 | 75, 100, 200 | 8, 10, 20 | 10:1 | 71, 86, 98 | 62, 79, 98 |
| STD3 | 75, 100, 200 | 2, 3, 7 | 30:1 | 66, 81, 96 | 55, 81, 93 |
| STD2 | 75, 100, 200 | — | — | 7, 46, 64 | 3, 30, 49 |

The di-ammonium oxalate as a tankmix with STD3, RT MASTER® and FieldMaster® appeared to provide consistent efficacy enhancements for each of these products on velvetleaf. Some significant efficacy enhancements were also noted on barnyardgrass but levels were lower and less consistent compared to velvetleaf. Of the three total molar ratios of glyphosate:oxalate, namely 2:1, 10:1 and 30:1, the higher oxalate levels present at 2:1 provided the best efficacy. The overall ranking of the glyphosate premix formulations tested, both with and without oxalic acid, showed STD3>=RT MASTER®>FieldMaster®. Both RT MASTER® and FieldMaster® caused some slight early symptoms.

Table 19D provides efficacy results for glyphosate+atrazine (ReadyMaster ATZ®) and glyphosate+oxyfluorfen (FirePower®) in combination with oxalic acid when applied to ABUTH and ECHCF. The application rate was 75, 100 and 200 g a.e. per hectare. Comparative standards STD2 and STD3 were used.

TABLE 19D

| 18 days after treatment | | | | |
|---|---|---|---|---|
| Composition | OTH5 Rate g a.i./ha | gly: OA ratio | ABUTH | ECHCF |
| ReadyMaster ATZ ® | — | — | 8, 31, 63 | 8, 49, 71 |
| ReadyMaster ATZ ® | 38, 50, 100 | 2:1 | 14, 65, 85 | 9, 58, 71 |

TABLE 19D-continued 18 days after treatment

| Composition | OTH5 Rate g a.i./ha | gly: OA ratio | ABUTH | ECHCF |
|---|---|---|---|---|
| ReadyMaster ATZ ® | 8, 10, 20 | 10:1 | 4, 26, 83 | 8, 50, 68 |
| ReadyMaster ATZ ® | 2, 3, 7 | 30:1 | 0, 26, 74 | 5, 50, 68 |
| FirePower ® | — | — | 8, 15, 38 | 8, 29, 80 |
| FirePower ® | 38, 50, 100 | 2:1 | 30, 59, 75 | 22, 68, 83 |
| FirePower ® | 8, 10, 20 | 10:1 | 13, 38, 74 | 15, 44, 82 |
| FirePower ® | 2, 3, 7 | 30:1 | 7, 38, 66 | 5, 48, 83 |
| STD3 | — | — | 0, 42, 74 | 38, 58, 83 |
| STD3 | 38, 50, 100 | 2:1 | 35, 68, 88 | 38, 60, 84 |
| STD3 | 8, 10, 20 | 10:1 | 20, 60, 82 | 30, 60, 86 |
| STD3 | 2, 3, 7 | 30:1 | 6, 68, 79 | 33, 63, 81 |
| STD2 | — | — | 0, 0, 18 | 0, 15, 47 |

Di-ammonium oxalate as a tankmix with STD3, Fire-Power® and ReadyMaster ATZ® appeared to provide efficacy enhancements for each of these products on ABUTH. Some significant enhancements on ECHCF were also noted but enhancement levels were less consistent and significantly lower compared to ABUTH. Although not completely alleviated, a 2:1 ratio of glyphosate to diammonium oxalate appeared to reduce the antagonistic effect typically associated with these co-herbicides. Of the three total molar ratios of glyphosate:oxalate, namely 2:1, 10:1 and 30:1, the higher oxalate levels present at 2:1 provided the best efficacy. The overall ranking of the glyphosate premix formulations tested, both with and without oxalic acid, showed STD3>FirePower®=ReadyMaster ATZ®. Both FirePower® and ReadyMaster ATZ® caused some early efficacy symptoms.

Table 19E provides efficacy results for tank mixtures of glyphosate+dicamba (Fallow Master®) and glyphosate+diquat in combination with oxalic acid (OTH5) at each of three glyphosate a.e.:oxalate ratios (2:1, 10:1 and 30:1) when applied to ABUTH and ECHCF. Application rates of 75, 100 and 200 g a.e. per hectare were used. Comparative standards STD2 and STD3 were used.

TABLE 19E

| Composition | OTH5 Rate g a.i./ha | gly: OA ratio | ABUTH | ECHCF |
|---|---|---|---|---|
| glyphosate + diquat | — | — | 6, 17, 35 | 6, 22, 62 |
| glyphosate + diquat | 38, 50, 100 | 2:1 | 23, 28, 38 | 2, 7, 57 |
| glyphosate + diquat | 8, 10, 20 | 10:1 | 5, 10, 38 | 0.8, 8, 50 |
| Fallow Master ® | — | — | 60, 70, 84 | 64, 67, 82 |
| Fallow Master ® | 38, 50, 100 | 2:1 | 68, 78, 88 | 65, 68, 90 |
| Fallow Master ® | 8, 10, 20 | 10:1 | 67, 82, 85 | 66, 68, 90 |
| Fallow Master ® | 2, 3, 7 | 30:1 | 67, 78, 86 | 65, 71, 92 |
| STD3 | — | — | 11, 40, 77 | 64, 65, 73 |
| STD3 | 38, 50, 100 | 2:1 | 52, 80, 90 | 68, 68, 76 |
| STD3 | 8, 10, 20 | 10:1 | 52, 77, 86 | 64, 68, 73 |
| STD3 | 2, 3, 7 | 30:1 | 47, 68, 85 | 60, 68, 72 |
| STD2 | — | — | 3, 8, 32 | 21, 41, 59 |

The efficacy results generally show the glyphosate co-herbicide premixes to perform more effectively when tank mixed with oxalate. Diammonium oxalate provided some velvetleaf efficacy benefits for each of the products tested. The 2:1 ratio of glyphosate:oxalate appeared to reduce the antagonistic effects typically associated with the tested co-herbicide package premixes. Moreover, the 2:1 ratio provided the best efficacy. The overall ranking of the glyphosate premix formulations with and without oxalic acid gave an efficacy effectiveness order of Fallow Master®>STD3>glyphosate+diquat Example 20

The rainfastness properties of compositions containing a cationic surfactant, a nonionic surfactant, oxalic acid and potassium glyphosate were evaluated. The compositions were formulated as indicated in Table 20A below. The potassium glyphosate concentration in each composition was 62 g a.e./l.

TABLE 20A

| Comp. | Cmpnt. 1 | wt % | Cmpnt. 2 | wt % | Cmpnt. 3 | wt % | Cmpnt. 4 | wt % |
|---|---|---|---|---|---|---|---|---|
| 699A4W | CIS7 | 1.5 | NIS1 | 0.0 | — | — | — | — |
| 699B7Q | CIS7 | 0.0 | NIS1 | 1.5 | — | — | — | — |
| 699C5T | CIS7 | 0.75 | NIS1 | 0.75 | — | — | — | — |
| 699D3K | CIS7 | 0.75 | NIS1 | 0.75 | OTH5 | 0.3 | — | — |
| 699E4V | CIS7 | 0.75 | NIS1 | 0.75 | OTH5 | 0.3 | OTH6 | 2.5 |
| 699F1O | CIS7 | 0.75 | NIS1 | 0.75 | OTH5 | 0.3 | OTH7 | 0.9 |
| 699G0I | — | — | — | — | OTH5 | 0.3 | OTH6 | 4.5 |

The compositions, and composition combinations, of Table 20A were applied to ABUTH and ECHCF at rates of 300 and 400 g a.e. per hectare. One set of compositions was then subjected to a simulated 0.25 inch (6.4 mm) total rain over 1 hour. These results were compared to a set of compositions that was not subjected to rain. Efficacy was evaluated versus a glyphosate STD3 standard. The % inhibition results 15 days after treatment are reported in Table 20B below.

TABLE 20B

| | % inhibition | | | |
|---|---|---|---|---|
| Comp | ABUTH No Rain | ABUTH 0.25# Rain/1 hr | ECHCF No Rain | ECHCF 0.25# Rain/1 hr |
| 699A4W | 83, 89 | 45, 60 | 66, 77 | 58, 62 |
| 699B7Q | 84, 90 | 77, 78 | 65, 73 | 41, 59 |
| 699C5T | 91, 94 | 73, 79 | 68, 75 | 52, 65 |
| 699D3K | 92, 98 | 65, 75 | 68, 80 | 57, 60 |
| 699E4V | 93, 98 | 73, 76 | 76, 81 | 56, 61 |
| 699F1O | 93, 99 | 70, 75 | 72, 83 | 60, 63 |
| 699G0I | 80, 88 | 33, 48 | 65, 73 | 57, 58 |
| STD3 | 83, 88 | 58, 68 | 65, 73 | 50, 62 |

The cationic/nonionic surfactant compositions containing oxalic acid with or without organic bases did not provide any efficacy improvements in ABUTH or ECHCF rainfast properties over the cationic+nonionic system alone. Formulations containing the cationic and nonionic surfactants improved rainfast efficacy on ABUTH, with some improvement noted on ECHCF.

Example 21

Water soluble granules (WSG) containing ammonium glyphosate, a cationic surfactant, a nonionic surfactant and ammonium oxalate were formulated. The WSG compositions were formulated as indicated in Table 21A below with the ammonium glyphosate concentration expressed in g a.e./composition. Composition 049F1F additionally contained 10.6 wt % ammonium sulfate. The glyphosate formulations were prepared at decreasing glyphosate a.e. concentrations (50%, 45%, 40% and 34%) but applied as if fully loaded at 68% a.e. Thus the formulations were actually compared to their fully loaded counterpart formulations at reduced acid equivalent application rates.

TABLE 21A

| Comp. | [gly] | Cmpnt. 1 | wt % | Cmpnt. 2 | wt % | Cmpnt. 3 | wt % |
|---|---|---|---|---|---|---|---|
| 049A3K | 500 | CIS19 | 8.0 | NIS13 | 8.0 | OTH1 | 26.4 |
| 049B7E | 450 | CIS19 | 8.0 | NIS13 | 8.0 | OTH1 | 32.1 |
| 049C8I | 400 | CIS19 | 8.0 | NIS13 | 8.0 | OTH1 | 37.8 |
| 049D3X | 340 | CIS19 | 11.0 | NIS13 | 11.0 | OTH1 | 38.6 |
| 049E6L | 400 | CIS19 | 10.0 | NIS13 | 10.0 | OTH1 | 33.8 |
| 049F1F | 340 | CIS19 | 8.0 | NIS13 | 8.0 | OTH1 | 34.0 |
| 049G8J | 400 | CIS19 | 8.0 | NIS13 | 8.0 | OTH1 | 37.8 |
| 049H3N | 340 | CIS19 | 11.0 | NIS13 | 11.0 | OTH1 | 38.6 |

The compositions, and composition combinations, of Table 21A formulated as a tank mix and were applied to ABUTH and ECHCF. The test compositions were evaluated against STD4, STD5 and STD9 standards. The % inhibition results are reported in Table 21B below.

TABLE 21B

| | | % inhibition | |
|---|---|---|---|
| Composition | Rate (g a.e./ha) | ABUTH | ECHCF |
| 049A3K | 55, 73, 147, 294 | 73, 78, 92, 99 | 65, 73, 94, 99 |
| 049B7E | 50, 66, 132, 264 | 70, 74, 91, 98 | 58, 71, 91, 99 |
| 049C8I | 44, 59, 118, 235 | 60, 70, 88, 98 | 58, 70, 89, 97 |
| 049D3X | 38, 50, 100, 200 | 64, 77, 90, 98 | 60, 73, 91, 98 |
| 049E6L | 44, 59, 118, 235 | 75, 84, 88, 98 | 62, 73, 98, 99 |
| 049F1F | 38, 50, 100, 200 | 54, 74, 87, 97 | 60, 71, 94, 99 |
| 049G8J | 75, 100, 200, 400 | 85, 87, 99, 100 | 73, 91, 100, 100 |
| 049H3N | 75, 100, 200, 400 | 83, 85, 98, 100 | 86, 97, 1000, 100 |
| STD5 | 75, 100, 200, 400 | 3, 8, 78, 91 | 21, 52, 69, 85 |
| STD9 | 75, 100, 200, 400 | 23, 23, 72, 90 | 62, 71, 94, 99 |
| STD4 | 75, 100, 200, 400 | 24, 28, 84, 94 | 63, 70, 93, 99 |

Compositions containing 8% cationic surfactant, 8% nonionic surfactant and 38% oxalate, and 11% cationic surfactant, 11% nonionic surfactant and 39% oxalate were evaluated. Both were applied at their full label strengths of 40% a.e. and 34% a.e., respectively. A comparison of the remaining formulations at reduced application rates (i.e., lower a.e. loaded) to the full rate applications showed some significant efficacy reductions across the ABUTH and ECHCF weed species. Although the efficacy reductions were statistically significant at the lower application rates, the differences among these formulations were small and overall efficacy was at least equal to or superior to dry standards STD9 and STD4. Hence a range of lower a.e. loaded dry glyphosate products may be commercially acceptable for overall weed control versus current dry standards.

Several dry glyphosate were prepared at decreasing glyphosate a.e. concentrations (50%, 45%, 40% and 34% a.e.) but were applied as if fully loaded at 68% a.e. The compositions, and composition combinations, of Table 21A formulated as a tank mix and were applied to ABUTH and ECHCF. The test compositions were evaluated against STD4, STD5 and STD9 standards. The % inhibition results are reported in Table 21C below.

TABLE 21C

| | % inhibition 15 days after treatment | | |
|---|---|---|---|
| Composition | Rate (g a.e./ha) | ABUTH | ECHCF |
| 049A3K | 55, 74, 147, 294 | 55, 73, 85, 99 | 55, 68, 80, 91 |
| 049B7E | 50, 66, 132, 264 | 75, 77, 86, 100 | 51, 66, 81, 96 |
| 049C8I | 44, 59, 118, 235 | 75, 78, 83, 100 | 51, 66, 77, 92 |
| 049D3X | 38, 50, 100, 200 | 31, 40, 71, 92 | 54, 61, 81, 94 |
| 049E6L | 44, 59, 118, 235 | 33, 47, 75, 93 | 63, 65, 76, 91 |
| 049F1F | 38, 50, 100, 200 | 22, 42, 77, 91 | 53, 63, 73, 94 |
| 049G8J | 75, 100, 200, 400 | 73, 78, 92, 100 | 68, 76, 88, 97 |
| 049H3N | 75, 100, 200, 400 | 75, 79, 98, 100 | 67, 75, 97, 99 |
| STD5 | 75, 100, 200, 400 | 0, 0, 60, 83 | 41, 57, 65, 70 |
| STD9 | 75, 100, 200, 400 | 5, 28, 69, 86 | 60, 70, 73, 89 |
| STD4 | 75, 100, 200, 400 | 23, 38, 73, 92 | 63, 70, 77, 86 |

The two highest efficacy performers across both weed species were 049G8J (8% CIS, 8% NIS and oxalate at 38%) and 049H$_3$N (11% CIS, 11% NIS and oxalate at 39%). The remaining formulations at reduced application rates (or lower a.e. loaded) showed significant efficacy reduction for most formulations on both weed species. However, overall efficacy was at least equal to or superior to dry standards STD4 and STD9 on both weeds, but primarily on ABUTH. Thus a range of lower a.e. loaded dry glyphosate products may give acceptable overall weed control versus current dry standards.

Several dry glyphosate formulations were prepared at decreasing glyphosate a.e. concentrations (50%, 45%, 40% and 34% a.e.) but were applied as if fully loaded at 68% a.e. The compositions, and composition combinations, of Table 21A formulated as a tank mix and were applied to TRZVX. The test compositions were evaluated against STD4, STD5 and STD9 standards. The % inhibition results are reported in Table 21D below.

TABLE 21D

| | % inhibition | |
|---|---|---|
| Composition | Rate (g a.e./ha) | TRZVX |
| 049A3K | 55, 74, 110, 220 | 53, 55, 61, 67 |
| 049B7E | 50, 66, 99, 198 | 50, 55, 63, 68 |
| 049C8I | 44, 59, 88, 176 | 49, 50, 63, 65 |
| 049D3X | 38, 50, 75, 150 | 53, 53, 63, 68 |
| 049E6L | 44, 59, 88, 176 | 53, 55, 63, 70 |
| 049F1F | 38, 50, 75, 150 | 47, 52, 63, 63 |
| 049G8J | 75, 100, 150, 300 | 58, 59, 64, 84 |
| 049H3N | 75, 100, 150, 300 | 53, 55, 62, 83 |
| STD5 | 75, 100, 150, 300 | 0, 0, 8, 37 |
| STD9 | 75, 100, 150, 300 | 50, 54, 63, 65 |
| STD4 | 75, 100, 150, 300 | 52, 55, 61, 67 |

The two highest efficacy performers across both weed species were 049G8J (8% CIS, 8% NIS and oxalate at 38%) and 049H$_3$N (11% CIS, 11% NIS and oxalate at 39%). The remaining formulations at reduced application rates (or lower a.e. loaded) showed significant efficacy reduction for most formulations on both weed species. However, overall efficacy was at least equal to or superior to dry standards STD4 and STD9 on both weeds, but primarily on ABUTH. Thus a range of lower a.e. loaded dry glyphosate products may give acceptable overall weed control versus current dry standards.

The compositions, and composition combinations, of Table 21A formulated as a tank mix and were applied to SIDSP. The test compositions were evaluated against STD4, STD5 and STD9 standards. The % inhibition results are reported in Table 21E below.

TABLE 21E

| | % inhibition | |
|---|---|---|
| Composition | Rate (g a.e./ha) | SIDSP |
| 049A3K | 55, 74, 110, 220 | 57, 75, 82, 92 |
| 049B7E | 50, 66, 99, 198 | 68, 74, 80, 93 |
| 049C8I | 44, 59, 88, 176 | 59, 74, 79, 89 |
| 049D3X | 38, 50, 75, 150 | 51, 69, 80, 93 |
| 049E6L | 44, 59, 88, 176 | 69, 73, 79, 93 |
| 049F1F | 38, 50, 75, 150 | 53, 67, 78, 93 |
| 049G8J | 75, 100, 150, 300 | 78, 81, 89, 98 |
| 049H3N | 75, 100, 150, 300 | 78, 83, 91, 98 |
| STD5 | 75, 100, 150, 300 | 20, 37, 53, 68 |
| STD9 | 75, 100, 150, 300 | 61, 73, 78, 90 |
| STD4 | 75, 100, 150, 300 | 53, 75, 82, 92 |

The two highest efficacy performing compositions on SIDA in this trial were CIS@8%+NIS@8%+oxalate38% and CIS@11%+NIS@11%+oxalate39%. Comparing the remaining formulations at reduced application rates (or lower a.e. loaded) to the full application rates showed significant efficacy reductions for most formulations. Although the reductions were statistically significant compared to their fully loaded counterparts, overall efficacy for some select formulations was at least equal to or superior to dry standards STD4 and STD9. Thus a range of lower a.e. loaded dry glyphosate products may be commercially acceptable for overall weed control versus current dry standards.

Example 22

The purpose of this example was to determine the efficacy of stabilized high load surfactant formulations in combination with oxalic acid and/or alkylpolyglucoside on SIDSP. High load compositions containing potassium glyphosate (n.b., composition 079DR3 was instead formulated with IPA glyphosate), a cationic surfactant and other constituents were formulated as indicated in Table 22A below. The glyphosate concentration is expressed in g a.e./l composition. Composition 079AQ7 additionally contained propylene glycol.

TABLE 22A

| Comp. | [gly] | Cmpnt. 1 | wt % | Cmpnt. 2 | wt % | Cmpnt. 3 | wt % |
|---|---|---|---|---|---|---|---|
| 687A4K | 540 | CIS23 | 10.0 | — | — | — | — |
| 687C5G | 540 | CIS23 | 10.0 | — | — | OTH5 | 1.0 |
| 687D9W | 540 | — | — | NIS7 | 10.0 | OTH5 | 1.0 |
| 687E2B | 540 | CIS23 | 6.0 | NIS7 | 4.0 | OTH5 | 1.0 |
| 687F7F | 540 | CIS23 | 4.0 | NIS7 | 6.0 | OTH5 | 1.0 |
| 687G8J | 540 | CIS23 | 6.0 | NIS7 | 5.0 | OTH5 | 1.0 |
| 079AQ7 | 480 | CIS14 | 5.0 | CIS8 | 6.0 | OTH23 | 2.0 |
| 083DR3 | 365 | CIS24 | 2.3 | NIS20 | 5.0 | OTH1 | 3.0 |

The compositions, and composition combinations, of Table 22A formulated as a tank mix and were applied to SIDSP at rates of 100, 200, 400 and 800 g a.e./ha. The test compositions were evaluated against STD2, STD3 and STD7 standards. The % inhibition results are reported in Table 22B below.

TABLE 22B

| | % inhibition 15 days after treatment | |
|---|---|---|
| Composition | Rate (g a.e./ha) | SIDSP |
| 687A4K | 100, 200, 400, 800 | 49, 78, 85, 92 |
| 687C5G | 100, 200, 400, 800 | 65, 79, 91, 95 |
| 687D9W | 100, 200, 400, 800 | 47, 67, 78, 88 |
| 687E2B | 100, 200, 400, 800 | 62, 73, 85, 94 |
| 687F7F | 100, 200, 400, 800 | 53, 58, 78, 93 |
| 687G8J | 100, 200, 400, 800 | 57, 79, 88, 96 |
| 079AQ7 | 100, 200, 400, 800 | 63, 70, 85, 93 |
| 083DR3 | 100, 200, 400, 800 | 66, 78, 93, 97 |
| STD2 | 100, 200, 400, 800 | 20, 58, 66, 79 |
| STD3 | 100, 200, 400, 800 | 55, 77, 84, 94 |
| STD7 | 100, 200, 400, 800 | 47, 78, 83, 94 |

Formulations 687C5G and 083DR3 were the two best efficacy performers on SIDSP and outperformed STD3 and STD7. Formulations 687A4K, 687G8J, 687E2B and 079AQ7 provided similar control as STD3 and STD7. Overall, the addition of oxalic acid to these formulations provided some SIDSP efficacy enhancement. Blends containing alkylpolyglucoside surfactant showed that efficacy increased as its concentration was decreased. Thus compositions with higher cationic amine surfactant:alkylpolyglucoside surfactant ratios generally provided increased SIDSP efficacy.

Example 23

The purpose of this example was to determine the efficacy of stabilized high load IPA glyphosate formulations containing monoethoxylated alkylamine. High load compositions containing IPA glyphosate, a cationic surfactant and other constituents were formulated as indicated in Table 23A below. The glyphosate concentration is expressed in g a.e./l composition.

TABLE 23A

| Comp. | [gly] | Cmpnt. 1 | wt % | Cmpnt. 2 | wt % | Cmpnt. 3 | wt % | Cmpnt. 4 | wt % |
|---|---|---|---|---|---|---|---|---|---|
| 095BA6 | 360 | CIS13 | 1.5 | NIS2 | 3.0 | NIS19 | 2.0 | OTH1 | 2.5 |
| 095BB3 | 360 | CIS14 | 1.0 | NIS2 | 2.5 | NIS19 | 1.5 | OTH1 | 2.5 |
| 083DA1 | 360 | CIS13 | 2.0 | NIS2 | 3.0 | NIS19 | 2.0 | — | — |
| 083DD7 | 360 | CIS14 | 2.0 | NIS2 | 2.5 | NIS19 | 1.5 | OTH1* | 2.5 |
| 083BS9 | 360 | CIS14 | 2.0 | NIS2 | 2.5 | NIS19 | 1.5 | OTH1 | 2.5 |
| 083BV3 | 360 | CIS13 | 2.0 | NIS2 | 2.5 | NIS19 | 1.5 | OTH1 | 2.5 |

*Additionally contained 0.15 g hydrochloric acid

The compositions, and composition combinations, of Table 23A were applied to ABUTH and ECHCF at rates of 100, 200, 300, and 400 g a.e./ha. The test compositions were evaluated against STD1, STD2, STD3 and STD7 standards. The % inhibition results are reported in Table 23B below.

TABLE 23B

% inhibition 14 days after treatment

| Composition | Rate (g a.e./ha) | ABUTH | ECHCF |
|---|---|---|---|
| 095BA6 | 100, 200, 300, 400 | 84, 89, 94, 97 | 29, 64, 74, 91 |
| 095BB3 | 100, 200, 300, 400 | 84, 90, 97, 97 | 29, 66, 73, 77 |
| 083DA1 | 100, 200, 300, 400 | 79, 83, 89, 90 | 38, 63, 73, 85 |
| 083DD7 | 100, 200, 300, 400 | 84, 92, 97, 98 | 35, 63, 68, 78 |
| 083BS9 | 100, 200, 300, 400 | 83, 94, 98, 99 | 32, 66, 66, 73 |
| 083BV3 | 100, 200, 300, 400 | 85, 93, 97, 99 | 33, 63, 67, 80 |
| STD1 | 100, 200, 300, 400 | 85, 91, 95, 98 | 53, 73, 81, 95 |
| STD2 | 100, 200, 300, 400 | 27, 52, 75, 80 | 1, 29, 48, 54 |
| STD3 | 100, 200, 300, 400 | 65, 83, 90, 93 | 45, 66, 68, 88 |
| STD7 | 100, 200, 300, 400 | 30, 78, 86, 90 | 41, 63, 68, 83 |

Formulations 095BA6, 095BB3, 083DD7, 083BS9 and 083BV3 were superior in ABUTH efficacy than were STD3 and STD7 standards. STD1 provided the best ECHCF control. Oxalic acid provided a significant efficacy benefit for control of ABUTH, but ECHCF performance levels were approximately equal with STD3. Compositions containing lower aklypolyglucoside levels were slightly more performant on ABUTH than were those with higher alkylpolyglucoside levels. Efficacy was approximately equal for cationic surfactants with 7EO and 10EO.

Example 24

The purpose of this example was to determine the prickly sida efficacy of high load potassium glyphosate formulations containing polyglucoside surfactants and oxalic acid. High load compositions containing 540 g a.e./l potassium glyphosate and other constituents were formulated as indicated in Table 24A below. The glyphosate concentration is expressed in g a.e./l composition.

The compositions, and composition combinations, of Table 24A were applied to SIDSP at rates of 150, 250, 400, and 800 g a.e./ha. The test compositions were evaluated against STD2, STD3, STD6, STD7 and STD8 standards. The % inhibition results are reported in Table 24B below.

TABLE 24B

% inhibition 16 days after treatment

| Composition | Rate (g a.e./ha) | SIDSP |
|---|---|---|
| 801A3C | 150, 250, 400, 800 | 44, 61, 75, 87 |
| 801B1U | 150, 250, 400, 800 | 41, 52, 68, 79 |
| 801C1K | 150, 250, 400, 800 | 48, 54, 73, 83 |
| 801D0N | 150, 250, 400, 800 | 50, 63, 76, 90 |
| 801E8J | 150, 250, 400, 800 | 43, 58, 72, 86 |
| 801F2L | 150, 250, 400, 800 | 47, 57, 73, 88 |
| STD2 | 150, 250, 400, 800 | 0, 8, 42, 63 |
| STD3 | 150, 250, 400, 800 | 42, 53, 74, 85 |
| STD6 | 150, 250, 400, 800 | 38, 50, 65, 83 |
| STD7 | 150, 250, 400, 800 | 9, 51, 65, 85 |
| STD8 | 150, 250, 400, 800 | 7, 28, 55, 70 |

Composition SIDSP efficacy followed the trend of 801D0N>801A3C>801F2L>801E8J. These formulations were superior in SIDSP efficacy than STD3, STD6 and STD7 standards. Formulation 801B1U, which did not contain oxalic acid, was the worst performer. The best performing composition, 801D0N, had the highest cationic surfactant:alkypolyglucoside ratio and did not contain potassium hydroxide.

Example 25

A trial was done to compare the efficacy of formulations containing glyphosate, a non-ionic surfactant (NIS), a cationic surfactant (CIS) and oxalate versus glyphosate formulations containing oxalate and a single non-ionic, cationic or anionic surfactant (AIS). Compositions were prepared containing glyphosate acid (compsoitions 060A3C, 060B7R and 060C4T)or ammonium glyphosate salt (the remainder of the compositions), reported in g a.e. per liter and excipient ingredients, reported as w/w % unless otherwise indicated, as shown in Table 25A. In each composition, the glyphosate to surfactant weight ratio is 2:1.

TABLE 24A

| Comp. | Cmpnt. 1 | wt % | Cmpnt. 2 | wt % | Cmpnt. 3 | wt % | Cmpnt. 4 | wt % |
|---|---|---|---|---|---|---|---|---|
| 801A3C | CIS23 | 8.0 | NIS7 | 3.0 | OTH5 | 1.0 | — | — |
| 801B1U | CIS23 | 8.0 | NIS7 | 3.0 | — | — | — | — |
| 801C1K | CIS23 | 6.0 | NIS7 | 5.0 | OTH5 | 1.0 | OTH16 | 1.4 |
| 801D0N | CIS23 | 9.0 | NIS7 | 2.5 | OTH5 | 1.0 | — | — |
| 801E8J | CIS23 | 4.0 | NIS7 | 8.0 | OTH5 | 1.0 | OTH16 | 2.0 |
| 801F2L | CIS23 | 8.0 | NIS7 | 3.0 | OTH5 | 1.0 | OTH16 | 2.0 |

TABLE 25A

| Comp. | [GLY] | Cmpnt. 1 | wt % | Cmpnt. 2 | wt % | Cmpnt. 3 | wt % | % oxalate a.e. | Gly a.e.: oxalate a.e. | Cmpnt. 4 |
|---|---|---|---|---|---|---|---|---|---|---|
| 060A3C | 10 | OTH40 | 0.5 | — | — | OTH41 | 1.8 | 1.2 | 0.8:1 | — |
| 060B7R | 10 | OTH40 | 0.5 | — | — | OTH41 | 0.5 | 0.3 | 3.3:1 | OTH42 (0.2%) |
| 060C4T | 10 | OTH40 | 0.5 | — | — | OTH41 | 0.2 | 0.2 | 6.7:1 | — |
| 060D5V | 10 | CIS19 | 0.25 | NIS13 | 0.25 | OTH1 | 2.0 | 1.2 | 0.8:1 | — |
| 060E7B | 62 | CIS19 | 1.5 | NIS13 | 1.5 | OTH1 | 2.9 | 1.8 | 3.3:1 | — |
| 060F2Z | 62 | CIS19 | 1.5 | NIS13 | 1.5 | OTH1 | 1.4 | 0.9 | 6.7:1 | — |
| 060G9M | 10 | CIS19 | 0.5 | — | — | OTH1 | 2.0 | 1.2 | 0.8:1 | — |
| 060H1W | 62 | CIS19 | 3.0 | — | — | OTH1 | 2.9 | 1.8 | 3.3:1 | — |
| 060I0E | 62 | CIS19 | 3.0 | — | — | OTH1 | 1.4 | 0.9 | 6.7:1 | — |
| 060J4L | 10 | — | — | NIS29 | 0.5 | OTH1 | 2.0 | 1.2 | 0.8:1 | — |
| 060K3U | 62 | — | — | NIS29 | 3.0 | OTH1 | 2.9 | 1.8 | 3.3:1 | — |
| 060L2X | 62 | — | — | NIS29 | 3.0 | OTH1 | 1.4 | 0.9 | 6.7:1 | — |
| 060M9K | 62 | — | — | OTH40 | 3.0 | — | — | — | — | — |
| 060N6G | 62 | CIS19 | 1.5 | NIS13 | 1.5 | — | — | — | — | — |
| 060O1N | 62 | CIS19 | 3.0 | — | — | — | — | — | — | — |
| 060P8Y | 62 | — | — | NIS29 | 3.0 | — | — | — | — | — |

The compositions of Table 25A, and comparative compositions STD4, STD5 and STD12 were applied to TRZXV, ABUTH, ECHCF and SIDSP at various rates of application, reported in g a.e. glyphosate/ha. TRZVX and SIDSP were treated at application rates of 75, 100, 200 and 400 g a.e./ha with % inhibition results reported in Table 33B in that order. TRZVX was evaluated 13 DAT and SIDSP was evaluated 14 DAT. ABUTH and ECHCF were treated at application rates 75, 100, 200 and 300 g a.e./hectare with % inhibition results reported in Table 25B in that order.

TABLE 25B

| Comp. | TRZVX | ABUTH | ECHCF | SIDSP |
|---|---|---|---|---|
| 060A3C | 87, 96, 98, 99 | 50, 68, 83, 88[b] | 58, 63, 67, 75[b] | 58, 66, 78, 94 |
| 060B7R | 89, 91, 98, 100 | 38, 60, 75, 80[b] | 54, 60, 65, 68[b] | 57, 62, 73, 91 |
| 060C4T | 85, 91, 98, 97 | 22, 53, 65, 78[b] | 52, 61, 68, 68[b] | 46, 53, 67, 81 |
| 060D5V | 93, 97, 99, 99 | 77, 78, 88, 90[b] | 63, 66, 81, 91[b] | 63, 71, 79, 94 |
| 060E7B | 95, 95, 100, 100 | 74, 75, 86, 90[b] | 64, 66, 83, 86[b] | 64, 69, 78, 93 |
| 060F2Z | 92, 97, 98, 100 | 58, 70, 81, 89[b] | 62, 66, 86, 92[b] | 57, 65, 75, 91 |
| 060G9M | 95, 98, 100, 100 | 79, 83, 87, 95[a] | 60, 77, 86, 87[a] | — |
| 060H1W | 98, 98, 100, 100 | 75, 78, 80, 85[a] | 60, 67, 80, 84[a] | — |
| 060I0E | 98, 99, 99, 100 | 65, 75, 80, 88[a] | 60, 65, 75, 85[a] | — |
| 060J4L | 93, 96, 99, 100 | 75, 83, 87, 92[a] | 56, 64, 82, 86[a] | — |
| 060K3U | 86, 93, 99, 100 | 60, 78, 83, 91[a] | 53, 59, 73, 87[a] | — |
| 060L2X | 83, 90, 98, 99 | 52, 69, 86, 91[a] | 50, 56, 67, 75[a] | — |
| 060M9K | 76, 86, 96, 99 | 5, 10, 50, 60[b] | 45, 56, 65, 68[b] | 28, 33, 51, 63 |

TABLE 25B-continued

| Comp. | TRZVX | ABUTH | ECHCF | SIDSP |
|---|---|---|---|---|
| 060N6G | 91, 92, 100, 100 | 59, 66, 82, 91[b] | 63, 67, 78, 83[b] | 61, 68, 78, 93 |
| 060O1N | 87, 96, 98, 100 | 4, 30, 71, 84[a] | 60, 65, 73, 76[a] | — |
| 060P8Y | 76, 85, 94, 98 | 32, 43, 74, 82[a] | 48, 59, 66, 84[a] | — |
| STD4 | 82, 87, 95, 99 | 43, 53, 76, 84[a] 39, 50, 68, 80[b] | 60, 61, 67, 75[a] 53, 61, 65, 68[b] | 50, 57, 71, 86 |
| STD5 | 40, 52, 72, 82 | 0, 5, 64, 74[a] 0, 5, 62, 72[b] | 40, 51, 57, 65[a] 23, 53, 63, 66[b] | 25, 28, 37, 57 |
| STD12 | 88, 90, 95, 100 | 55, 78, 82, 93[a] 53, 72, 82, 88[b] | 59, 65, 70, 80[a] 61, 63, 77, 79[b] | 53, 58, 73, 93 |

[a] 13 DAT;
[b] 14 DAT

Overall, oxalate was effective for enhancing the performance of each surfactant system evaluated and the general order of effectiveness with oxalate was as follows: CIS=CIS+NIS> or =NIS> or =AIS. Generally the AIS+oxalate and NIS+oxalate formulations were the poorest performing formulations while CIS+oxalate or CIS+NIS+oxalate were the highest performing formulations.

Example 26

A trial was done to evaluate the efficacy of ammonium glyphosate formulations containing ammonium sulfate and oxalate on ABUTH, ECHCF and SIDSP. Compositions were prepared as indicated in Table 26A below wherein in each composition ammonium glyphosate was formulated at about 62 g a.e. per liter.

TABLE 26A

| Comp. | Cmpnt. 1 | wt % | Cmpnt. 2 | wt % | Cmpnt. 3 | wt % | Cmpnt. 4 | wt % |
|---|---|---|---|---|---|---|---|---|
| 847A2V | — | — | CIS28 | 1.2 | OTH1 | 1.0 | — | — |
| 847B9K | — | — | CIS28 | 1.2 | — | — | OTH20 | 1.0 |
| 847C5F | — | — | CIS28 | 1.2 | OTH1 | 0.5 | OTH20 | 0.5 |
| 847D3X | — | — | CIS28 | 1.2 | OTH1 | 0.3 | OTH20 | 0.7 |
| 847E2H | NIS12 | 0.8 | CIS28 | 0.4 | OTH1 | 1.0 | — | — |
| 847F1S | NIS12 | 0.8 | CIS28 | 0.4 | — | — | OTH20 | 1.0 |
| 847G6R | NIS12 | 0.8 | CIS28 | 0.4 | OTH1 | 0.5 | OTH20 | 0.5 |
| 847H7N | NIS12 | 0.8 | CIS28 | 0.4 | OTH1 | 0.5 | OTH20 | 0.7 |

TABLE 26B

The composition of Table 26A and compositions STD4, STD5 and STD6 were applied to ABUTH, ECHCF and SIDSP at rates of 75, 100, 200 and 400 g a.e. glyphosate per hectare with percent inhibition results reported for each plant species in Table 26B in that order. ABUTH and ECHCF were evaluated 15 days after treatment (DAT) and SIDSP was evaluated at 14 DAT.

| Comp. | ABUTH | ECHCF | SIDSP |
|---|---|---|---|
| 847A2V | 63, 83, 93, 100 | 59, 75, 92, 99 | 8, 41, 68, 73 |
| 847B9K | 48, 58, 84, 99 | 56, 73, 81, 98 | 5, 35, 60, 75 |
| 847C5F | 66, 80, 92, 99 | 68, 78, 85, 98 | 27, 43, 64, 78 |
| 847D3X | 81, 88, 99, 100 | 65, 77, 91, 100 | 32, 47, 70, 78 |
| 847E2H | 88, 92, 99, 100 | 53, 64, 90, 98 | 28, 53, 70, 80 |
| 847F1S | 85, 88, 93, 100 | 62, 65, 92, 100 | 23, 38, 63, 77 |
| 847G6R | 85, 87, 100, 100 | 62, 70, 88, 99 | 32, 49, 67, 84 |
| 847H7N | 81, 88, 98, 100 | 62, 75, 97, 99 | 27, 45, 62, 72 |
| STD6 | 14, 35, 81, 96 | 63, 68, 83, 96 | 14, 35, 62, 75 |
| STD4 | 22, 55, 81, 92 | 69, 75, 92, 99 | 14, 38, 69, 76 |
| STD5 | 2, 3, 78, 88 | 5, 41, 53, 78 | 0, 0, 40, 63 |

Formulations 847D3X, 847E2H, 847F1S, 847G6R and 847H$_7$N were superior to STD4 and STD5 for ABUTH control. Formulations 847C5F, 847D3X, 847G6R and 847H$_7$N were as effective as STD4 on ECHCF. All NIS+CIS formulations containing oxalate and/or ammonium sulfate were equally efficacious and superior to STD4 and STD5 on SIDSP.

Example 27

A study was done to evaluate the efficacy of glyphosate compositions containing tallowamine-oxalate ester surfactants with different EO chain lengths and varying tallowamine to oxalate mole ratios on TRZVX, ABUTH, ECHCF and SIDSP. Compositions were prepared as indicated in Table 27A below with each formulation containing about 62 g a.e. per liter of potassium glyphosate. Those compositions as well as STD2, STD4 and STD6 were applied to TRZVX, ABUTH (the results for two separate trials reported), ECHCF and SIDSP at rates of 75, 100, 200 and 400 g a.e. per hectare with % inhibition results reported in Table 27A in that order.

TABLE 27A

| Comp. | Cmpnt. 1 | wt % | TRZVX | ABUTH | ECHCF | SIDSP |
|---|---|---|---|---|---|---|
| 852A2B | CIS3 | 1.5 | 62, 85, 97, 100 | 28, 53, 81, 100 | 70, 75, 90, 99 | 60, 62, 75, 90 |
|  |  |  | — | 7, 12, 64, 90 | — | — |
| 852B7G | CIS29 | 1.5 | 64, 83, 98, 100 | 53, 56, 82, 98 | 70, 73, 92, 100 | 63, 68, 78, 86 |
|  |  |  | — | 28, 45, 78, 93 | — | — |
| 852C4D | NIS30 | 1.5 | 55, 83, 97, 100 | 62, 71, 85, 100 | 68, 72, 84, 98 | 68, 69, 80, 93 |
|  |  |  | — | 54, 62, 87, 93 | — | — |
| 852D3K | NIS31 | 1.5 | 61, 83, 98, 100 | 60, 76, 78, 100 | 70, 78, 91, 99 | 65, 74, 76, 93 |
|  |  |  | — | 28, 54, 76, 91 | — | — |
| 852E2N | NIS32 | 1.5 | 60, 85, 97, 99 | 66, 69, 89, 100 | 71, 80, 89, 99 | 66, 73, 74, 87 |
|  |  |  | — | 23, 37, 72, 94 | — | — |
| 852F9L | NIS33 | 1.5 | 65, 79, 96, 99 | 70, 76, 93, 99 | 70, 77, 88, 99 | 68, 73, 78, 87 |
|  |  |  | — | 35, 68, 88, 98 | — | — |
| 852G0P | NIS34 | 1.5 | 58, 79, 96, 99 | 83, 85, 89, 99 | 74, 82, 93, 99 | 67, 71, 73, 87 |
|  |  |  | — | 43, 54, 86, 94 | — | — |
| 852H8A | NIS35 | 1.5 | 55, 78, 97, 99 | 78, 84, 93, 100 | 73, 79, 95, 99 | 64, 70, 78, 89 |
|  |  |  | — | 54, 66, 83, 99 | — | — |
| STD2 | — | — | 5, 27, 35, 55 | 11, 21, 68, 82 | 8, 36, 58, 78 | 30, 50, 60, 73 |
|  |  |  | — | 0, 0, 6, 67 | — | — |
| STD6 | — | — | 68, 83, 97, 100 | 41, 57, 78, 94 | 63, 70, 88, 99 | 48, 63, 70, 86 |
|  |  |  | — | 0, 12, 43, 88 | — | — |
| STD4 | — | — | 60, 80, 96, 100 | 1, 27, 69, 85 | 28, 53, 74, 97 | 55, 60, 72, 88 |
|  |  |  | — | 8, 28, 74, 90 | — | — |

Formulations with amine to oxalate mole ratios exceeding about 1:1 outperformed the remaining formulations for control of ABUTH and provided superior results to non-oxalate ester surfactants as well as STD4 and STD6. On ECHCF compositions 852G0P and 852H8A provided the greatest control versus non-oxalate ester surfactants as well as STD4 and STD6. All tallowamine-oxalate ester formulations showed efficacy similar to that of STD4 and STD6. All tallowamine-oxalate ester formulations showed high levels of performance on SIDSP and were superior to STD4 and STD6 as well as non-ester surfactants.

Example 28

The efficacy of compositions containing oxalic acid, ammonium sulfate and potassium glyphosate were evaluated on ABUTH and ECHCG. Compositions were prepared as in Table 28A with the potassium glyphosate concentration in each being about 63 g a.e. per liter. Each composition as well as STD6 and STD2 were applied to ABUTH and ECHCF at rates of 75, 100, 200 and 400 g a.e. per hectare with % inhibition results reported in Table 28A in that order.

Ammonium iron III and ammonium oxalate hydrate had similar ABUTH efficacy. The more water soluble iron III oxalate did not appear to provide better efficacy versus the ammonium oxalate hydrate. The overall best efficacy results for all oxalate and ammonium sulfate additive formulations occurred when formulated with the etheramine surfactant, CIS23.

TABLE 28A

| Comp. | Cmpnt. 1 | wt % | Cmpnt. 2 | wt % | Cmpnt. 3 | wt % | Cmpnt. 4 | wt % | ABUTH | ECHCF |
|---|---|---|---|---|---|---|---|---|---|---|
| 854A3M | OTH5 | 2.0 | — | — | — | — | — | — | 17, 38, 82, 90 | 25, 64, 71, 88 |
| 854B7J | OTH25 | 2.0 | — | — | — | — | — | — | 4, 9, 53, 83 | 29, 48, 58, 67 |
| 854C0L | OTH24 | 2.0 | — | — | — | — | — | — | 0, 3, 39, 77 | 27, 42, 52, 65 |
| 854D6N | OTH25 | 1.0 | OTH5 | 1.0 | — | — | — | — | 18, 21, 69, 88 | 27, 41, 53, 66 |
| 854E2A | OTH24 | 1.0 | OTH5 | 1.0 | — | — | — | — | 1, 3, 50, 88 | 12, 40, 57, 64 |
| 854F0Q | CIS28 | 0.5 | NIS1 | 0.5 | OTH5 | 2.0 | — | — | 58, 64, 89, 97 | 53, 62, 68, 97 |
| 854G6Y | CIS28 | 0.5 | NIS1 | 0.5 | OTH5 | 1.2 | OTH25 | 0.8 | 52, 65, 90, 96 | 61, 66, 75, 97 |
| 854H8H | CIS28 | 0.5 | NIS1 | 0.5 | OTH5 | 0.7 | OTH24 | 1.3 | 63, 66, 89, 97 | 65, 68, 84, 99 |
| 854I4P | CIS28 | 0.5 | NIS1 | 0.5 | OTH5 | 1.0 | OTH20 | 1.0 | 70, 75, 89, 97 | 64, 70, 90, 99 |
| STD6 | — | — | — | — | — | — | — | — | 0, 1, 35, 75 | 45, 64, 71, 88 |
| STD2 | — | — | — | — | — | — | — | — | 0, 0, 5, 66 | 8, 34, 55, 68 |

The highest ABUTH efficacy compositions contained a cationic surfactant a nonionic surfactant and oxalate with or without added ammonium sulfate, urea or glucamine. Results for those compositions were similar on ECHCF but the addition of ammonium sulfate or glucamine provided some efficacy enhancement.

Example 29

The efficacy of dilute potassium glyphosate formulations containing ammonium iron oxalates on ABUTH and ECHCF was evaluated. Compositions were prepared as in Table 29A with each containing about 63 g a.e. per liter potassium glyphosate. Each composition as well as STD2 and STD6 were applied to ABUTH and ECHCF at rates of 75, 100, 200 and 400 g a.e. per hectare with % inhibition results reported in Table 29A in that order.

Example 30

The efficacy of dilute ammonium glyphosate formulations containing oxalate was evaluated on CYPES in duplicate, and on CYPRO. Compositions were prepared as in Table 30A with each containing about 62 g a.e. per liter ammonium glyphosate except for STD12 (68 wt % active) and 155X0M (Table 33A, with 60 wt % active). Each composition as well as STD4 were applied to CYPES and CYPRO at rates of 200, 400, 800 and 1200 g a.e. per hectare with % inhibition evaluated 14 DAT (CYPRO) and 18 DAT (CYPES) and results reported in Table 30A in that order. An additional application to CYPES at rates of 200, 400, 600 and 1000 g a.e. per hectare

TABLE 29A

| Comp. | Cmpnt. 1 | wt % | Cmpnt. 2 | wt % | ABUTH | ECHCF |
|---|---|---|---|---|---|---|
| 866A9K | — | — | OTH28 | 1.5 | 10, 20, 63, 81 | 50, 54, 66, 73 |
| 866B1C | — | — | OTH26 | 1.5 | 0, 5, 13, 63 | 38, 48, 57, 67 |
| 866C1W | — | — | OTH20 | 1.5 | 0, 14, 48, 73 | 48, 53, 70, 74 |
| 866D6H | — | — | OTH27 | 1.5 | 39, 42, 67, 75 | 38, 55, 59, 77 |
| 866E4N | CIS23 | 1.5 | OTH28 | 0.6 | 38, 70, 79, 83 | 65, 73, 93, 99 |
| 866F3L | CIS23 | 1.5 | OTH26 | 0.6 | 27, 70, 70, 79 | 63, 72, 78, 88 |
| 866G5V | CIS23 | 1.5 | OTH27 | 0.6 | 38, 47, 69, 85 | 63, 63, 82, 95 |
| 866H9R | CIS23 | 1.5 | OTH20 | 0.6 | 37, 42, 70, 78 | 72, 75, 93, 98 |
| STD2 | — | — | — | — | 0, 0, 19, 72 | 25, 45, 58, 71 |
| STD6 | — | — | — | — | 0, 11, 69, 80 | 60, 63, 75, 94 | was done with the results for each composition, evaluated at 25 DAT, reported in the second set of results in Table 30A.

TABLE 30A

| Comp. | Cmpnt. 1 | wt % | Cmpnt. 2 | wt % | Cmpnt. 3 | wt % | CYPES | CYPRO |
|---|---|---|---|---|---|---|---|---|
| 061C5H | CIS2 | 0.8 | NIS1 | 0.8 | — | — | 82, 88, 89, 97<br>31, 61, 85, 88 | 0, 0, 15, 66<br>— |
| 061D2P | CIS2 | 0.8 | NIS1 | 0.8 | OTH1 | 0.8 | 83, 87, 93, 98<br>57, 68, 82, 90 | 0, 0, 0, 77<br>— |
| 061E9M | CIS2 | 0.8 | NIS1 | 0.8 | OTH1 | 1.6 | 82, 93, 94, 97<br>26, 63, 81, 92 | 0, 2, 3, 60<br>— |
| 061F6B | STD4 | — | — | — | OTH1 | 0.8 | 83, 92, 93, 97<br>41, 70, 79, 89 | 0, 0, 12, 52<br>— |
| 061G7K | STD4 | — | — | — | — | — | 84, 88, 89, 95<br>— | 0, 13, 37, 77<br>— |
| STD12 | CIS19 | 5.7 | NIS13 | 7.9 | OTH1 | 8.3 | 80, 90, 93, 97<br>35, 66, 81, 88 | 0, 0, 15, 66<br>— |
| 155X0M | CIS19 | 8.0 | NIS13 | 8.0 | OTH1 | 15.0 | —<br>40, 73, 80, 88 | —<br>— |
| STD5 | — | — | — | — | — | — | —<br>1, 24, 40, 64 | —<br>— |
| STD4 | — | — | — | — | — | — | 80, 92, 95, 98<br>38, 68, 84, 88 | 0, 0, 18, 69<br>— |

Efficacy on CYPES was determined to be substantially equivalent for all glyphosate formulations evaluated in each trial. Efficacy on CYPRO was determined to be highly variable across replications for all glyphosate formulations evaluated in this trial.

Compositions 061C5H, 061E9M and 061F6B were applied to ERICG at rates of 1250, 2500 and 5000 g a.e. per hectare with % inhibition evaluated at 20 and 35 days after treatment (DAT). The results are reported in Table 30B.

TABLE 30B

| Comp. | ERICG (20 DAT) | ERICG (35 DAT) |
|---|---|---|
| 061C5H | 68, 84, 93 | 58, 79, 94 |
| 061E9M | 50, 89, 98 | 55, 89, 99 |
| 061F6B | 53, 75, 93 | 50, 73, 98 |
| STD12 | 45, 84, 99 | 48, 74, 100 |
| STD4 | 35, 78, 88 | 38, 75, 93 |

Each of formulations 061C5H, 061E9M and 061F6B gave significant efficacy enhancement on ERICG versus STD4.

Example 31

The efficacy of high load glyphosate formulations was evaluated on ABUTH, TRZVX, CYPES and GLXMV. Compositions were prepared as in Table 31A with [Gly] representing the glyphosate concentration in wt % a.e.

The compositions of Table 31A and STD2, STD4 and STD6 were applied to: ABUTH at g a.e. per hectare rates of 75, 100, 200 and 400 with % inhibition evaluated 17DAT; TRZVX at rates of 50, 75, 100 and 300 g a.e. per hectare with results evaluated 17 DAT; CYPES at rates of 300, 500, 800 and 1200 g a.e. per hectare with results evaluated 14 DAT; and GLXMV at rates of 150, 300, 450 and 600 g a.e. per hectare with results evaluated 14 DAT. Results are reported in Table 31B.

TABLE 31B

| Comp. | ABUTH | TRZVX | CYPES | GLXMV |
|---|---|---|---|---|
| 780J7X | 0, 0, 19, 71 | 27, 38, 55, 82 | 84, 88, 96, 100 | 52, 83, 88, 88 |
| 784W0P | 0, 5, 30, 79 | 27, 40, 52, 89 | 88, 87, 98, 99 | 77, 88, 88, 90 |
| 793Q2N | 7, 20, 65, 92 | 31, 32, 53, 89 | 76, 81, 94, 98 | 66, 84, 89, 93 |
| 794D6N | 17, 51, 75, 98 | 25, 34, 48, 83 | 67, 84, 96, 98 | 87, 88, 89, 91 |
| 795P0E | 8, 19, 63, 87 | 23, 34, 50, 85 | 79, 85, 95, 98 | 83, 86, 88, 93 |
| 796Y3M | 0, 0, 20, 60 | 15, 38, 48, 84 | 85, 96, 99, 99 | 71, 83, 85, 88 |
| 797A1N | 0, 0, 13, 70 | 22, 36, 50, 84 | 90, 92, 98, 98 | 74, 85, 87, 89 |
| STD2 | 0, 0, 1, 26 | 0, 0, 5, 37 | 58, 73, 88, 97 | 8, 11, 17, 27 |
| STD6 | 0, 0, 17, 65 | 25, 43, 56, 79 | 87, 91, 98, 100 | 62, 70, 87, 93 |
| STD4 | 0, 4, 38, 80 | 28, 33, 50, 86 | 87, 92, 94, 99 | 70, 85, 90, 91 |

TABLE 31A

| Comp. | Gly salt | [Gly] | Cmpnt. 1 | wt % | Cmpnt. 2 | wt % | Cmpnt. 3 | wt % | Cmpnt. 4 | wt % |
|---|---|---|---|---|---|---|---|---|---|---|
| 780J7X | K | 39.7 | CIS23 | 8.0 | NIS7 | 3.0 | OTH5 | 1.0 | — | — |
| 784W0P | K | 36.7 | CIS23 | 6.0 | NIS7 | 2.4 | OTH5 | 1.0 | NIS24 | 1.4 |
| 793Q2N | $NH_4$ | 72.1 | NIS26 | 9.0 | NIS1 | 9.0 | — | — | — | — |
| 794D6N | $NH_4$ | 68.0 | CIS21 | 9.0 | NIS1 | 4.5 | OTH1 | 3.0 | OTH20 | 6.0 |
| 795P0E | $NH_4$ | 68.1 | CIS21 | 7.0 | NIS1 | 6.5 | OTH20 | 9.0 | — | — |
| 796Y3M | K | 40.0 | CIS2 | 4.0 | NIS24 | 1.0 | CIS25 | 4.5 | OTH29 | 1.5 |
| 797A1N | K | 40.0 | NIS25 | 10.0 | — | — | — | — | — | — |

Formulations containing ammonium glyphosate, an NIS+CIS surfactant system and either oxalte/ammonium sulfate or a tallowamine-oxalic ester with NIS gave the highest efficacy against ABUTH. The high load potassium glyphosate formulations performed similarly to STD4 and STD6 on ABUTH. All formulations were equal to STD4 and STD6 on TRZVX. The potassium glyphosate formulations equal to or slightly superior to STD4 and STD6 on CYPES. Ammonium glyphosate formulations gave slightly greater overall efficacy versus STD4 and TRZVX on CYPES. All formulations gave equal or slightly superior GLXMV control than STD4 and STD6.

Example 32

The efficacy of ammonium glyphosate formulations containing oxalic acid and ammonium sulfate in a cationic+nonionic surfactant system was evaluated on ABUTH and ECHCF. Compositions were prepared as in Table 32A with each containing about 62 g a.e. per liter of ammonium glyphosate. The compositions as well as STD4, STD5 and STD6 were applied to ABUTH and ECHCF at rates of 75, 100, 200, and 400 g a.e. per hectare with results evaluated 14 days after treatment and reported in that order.

Example 33

The efficacy of ammonium glyphosate formulations containing diammonium oxalate in a cationic+nonionic surfactant system was evaluated on GLXMV, ABUTH, ECHCF, TRZVX and SIDSP. Compositions were prepared as in Table 33A with each containing about 600 g a.e. per kilogram of ammonium glyphosate.

TABLE 33A

| Comp. | Cmpnt. 1 | wt % | Cmpnt. 2 | wt % | Cmpnt. 3 | wt % |
|---|---|---|---|---|---|---|
| 063A8J | CIS21 | 8.0 | NIS1 | 8.0 | OTH1 | 15.0 |
| 063B4S | CIS21 | 9.6 | NIS1 | 6.4 | OTH1 | 15.0 |
| 063C0L | CIS21 | 6.4 | NIS1 | 9.6 | OTH1 | 15.0 |
| 063D8N | CIS21 | 8.0 | NIS27 | 8.0 | OTH1 | 15.0 |
| 063E3M | CIS21 | 9.6 | NIS27 | 6.4 | OTH1 | 15.0 |
| 063F7I | CIS21 | 6.4 | NIS27 | 9.6 | OTH1 | 15.0 |
| 155X0M | CIS19 | 8.0 | NIS13 | 8.0 | OTH1 | 15.0 |

The compositions as well as STD4 and STD5 were applied to: ABUTH and ECHCF at rates of 75, 100, 200 and 300 g a.e.

TABLE 32A

| Comp. | Cmpnt. 1 | wt % | Cmpnt. 2 | wt % | Cmpnt. 3 | wt % | Cmpnt. 4 | wt % | ABUTH | ECHCF |
|---|---|---|---|---|---|---|---|---|---|---|
| 870A2V | CIS21 | 0.6 | NIS1 | 0.6 | — | — | — | — | 19, 79, 92, 99 | 53, 63, 68, 80 |
| 870B8M | CIS21 | 0.6 | NIS1 | 0.6 | OTH5 | 0.9 | — | — | 87, 90, 99, 100 | 58, 62, 69, 82 |
| 870C9A | CIS21 | 0.6 | NIS1 | 0.6 | OTH5 | 0.3 | OTH20 | 0.6 | 90, 91, 100, 100 | 55, 62, 68, 83 |
| 870D4N | CIS21 | 0.6 | NIS1 | 0.6 | — | — | OTH20 | 0.9 | 88, 86, 97, 99 | 58, 60, 73, 87 |
| 870E3L | CIS21 | 0.9 | NIS1 | 0.3 | OTH5 | 0.9 | — | — | 86, 90, 95, 100 | 57, 62, 73, 95 |
| 870F4Q | CIS21 | 0.9 | NIS1 | 0.3 | OTH5 | 0.3 | OTH20 | 0.6 | 86, 88, 98, 100 | 60, 63, 73, 93 |
| 870G1P | CIS21 | 0.9 | NIS1 | 0.3 | — | — | OTH20 | 0.9 | 51, 83, 94, 97 | 58, 62, 68, 84 |
| STD5 | — | — | — | — | — | — | — | — | 7, 35, 75, 89 | 18, 20, 42, 63 |
| STD6 | — | — | — | — | — | — | — | — | 6, 53, 89, 98 | 50, 60, 68, 86 |
| STD4 | — | — | — | — | — | — | — | — | 26, 73, 88, 97 | 56, 62, 68, 85 |

On ABUTH: all NIS+CIS surfactant blend formulations containing oxalate and/or ammonium sulfate outperformed STD4, STD5 and STD6; Oxalate+ammonium sulfate blends had higher efficacy that either component formulated alone; and the ratio of NIS to CIS did not dramatically affect efficacy. All formulations at least equaled STD4, STD5 and STD6 performance on ECHCF with compositions 870F4Q and 870E3L being statistically superior.

per hectare (Rate A) with ABUTH results evaluated 14 and 15 DAT and ECHCF evaluated 15 DAT; TRZVX at 75, 100, 150 and 300 g a.e. per hectare (Rate B) and evaluated at 14 and 16 DAT; SIDSP at 75, 100, 200 and 400 g a.e. per hectare (Rate C) and evaluated at 16 DAT; and GLXMV at 176, 264, 352 and 400 g a.e. per hectare (Rate D) with results evaluated 16 DAT. Two additional evaluation were done at: 66, 88, 132 and 264 g a.e. per hectar (Rate E); and 200, 300, 400 and 500 g a.e. per hectare (Rate F). The results are reported in Table 33B.

TABLE 33B

| Comp. | TRZVX (Rate) | SIDSP | ABUTH | ECHCF | GLXMV |
|---|---|---|---|---|---|
| 063A8J | 59, 68, 83, 84 (E)$^a$ | 43, 50, 61, 86 (E)$^a$ | 73, 76, 88, 90 (E)$^c$ | 53, 59, 71, 78 (E)$^c$ | 68, 83, 87, 94 (D)$^a$ |
| | 48, 48, 61, 71 (E)$^b$ | — | 82, 88, 96, 99 (E)$^b$ | — | — |
| 063B4S | 61, 68, 73, 84 (E)$^a$ | 48, 52, 63, 91 (E)$^a$ | 70, 83, 83, 93 (E)$^c$ | 56, 59, 69, 70 (E)$^c$ | 88, 88, 90, 92 (D)$^a$ |
| | 50, 52, 61, 68 (E)$^b$ | — | 81, 87, 95, 99 (E)$^b$ | — | — |
| 063C0L | 60, 68, 74, 83 (E)$^a$ | 43, 53, 69, 87 (E)$^a$ | 52, 76, 83, 93 (E)$^c$ | 52, 59, 70, 86 (E)$^c$ | 82, 87, 90, 91 (D)$^a$ |
| | 50, 53, 61, 73 (E)$^b$ | — | 80, 85, 93, 98 (E)$^b$ | — | — |
| 063D8N | 57, 67, 73, 88 (E)$^a$ | 46, 48, 63, 83 (E)$^a$ | 70, 79, 83, 92 (E)$^c$ | 53, 59, 66, 78 (E)$^c$ | 84, 89, 91, 91 (D)$^a$ |
| | 53, 55, 60, 68 (E)$^b$ | — | 82, 88, 95, 98 (E)$^b$ | — | — |
| 063E3M | 58, 64, 78, 84 (E)$^a$ | 46, 47, 65, 87 (E)$^a$ | 69, 77, 85, 93 (E)$^c$ | 58, 63, 76, 93 (E)$^c$ | 79, 88, 91, 93 (D)$^a$ |
| | 50, 55, 63, 74 (E)$^b$ | — | 80, 87, 94, 98 (E)$^b$ | — | — |
| 063F7I | 53, 62, 73, 83 (E)$^a$ | 47, 50, 65, 87 (E)$^a$ | 63, 73, 85, 90 (E)$^c$ | 58, 59, 73, 77 (E)$^c$ | 74, 84, 90, 92 (D)$^a$ |
| | 53, 55, 62, 68 (E)$^b$ | — | 78, 86, 93, 96 (E)$^b$ | — | — |
| 155X0M | 61, 75, 78, 84 (B)$^a$ | 47, 52, 69, 88 (C)$^a$ | 50, 72, 85, 92 (A)$^c$ | 55, 60, 74, 79 (A)$^c$ | 81, 88, 90, 93 (F)$^a$ |
| | 55, 72, 73, 80 (E)$^a$ | 43, 50, 62, 88 (E)$^a$ | 43, 71, 82, 89 (E)$^c$ | 51, 60, 69, 79 (E)$^c$ | 73, 84, 88, 91 (D)$^a$ |
| | 50, 50, 62, 77 (B)$^b$ | — | 83, 90, 97, 99 (A)$^b$ | — | — |
| | 51, 52, 60, 72 (E)$^b$ | — | 79, 87, 95, 99 (E)$^b$ | — | — |

TABLE 33B-continued

| Comp. | TRZVX (Rate) | SIDSP | ABUTH | ECHCF | GLXMV |
|---|---|---|---|---|---|
| STD5 | 0, 0, 0, 37 (B)[a]<br>0, 5, 10, 40 (B)[b] | 0, 6, 25, 43 (C)[a]<br>— | 0, 8, 60, 70 (A)[c]<br>0, 0, 34, 77 (A)[b] | 12, 41, 49, 63 (A)[c]<br>— | 30, 43, 50, 58 (F)[a]<br>— |
| STD4 | 58, 70, 75, 85 (B)[a]<br>50, 50, 62, 70 (B)[b] | 36, 50, 58, 90 (C)[a]<br>— | 18, 29, 63, 83 (A)[c]<br>10, 59, 85, 90 (A)[b] | 53, 62, 67, 77 (A)[c]<br>— | 75, 83, 88, 93 (F)[a]<br>— |

[a] 16 DAT;
[b] 14 DAT;
[c] 15 DAT

As applied to TRZVX: 155X0M and STD5 provided similar efficacy; 063C0L and 063F7I were of lowest efficacy; hetoxol 15EO and 20EO gave similar efficacy; and 155X0M and 063A8J gave the highest efficacy of the formulations. As applied to SIDSP: Nearly all formulations were equal or slightly superior to STD5; 063D8N was statistically inferior; and no significant differences were found between hetoxol 15EO and 20EO. As applied to ABUTH: All formulations were found to be equally superior to STD5; the highest efficacy was achieved with 1:1 and 1.5:1 CIS:NIS ratios; and no significant differences were noted between hetoxol 15EO and 20EO. As applied to ECHCF: Some efficacy differences were noted at the highest application rate; and 063E3M, 155X0M and 063C0L gave the best efficacy and were superior to STD5 at high application rates. As applied to GLXMV: All formulations were substantially equivalent and of similar efficacy to STD5. In general, substitution of Surfonic T15 with Flomo 1407 results in substantially equivalent efficacies across weed species.

Example 34

A trial was done to evaluate the ABUTH, ECHCF, TRZVX and GLXMV efficacy effect of pH on compositions containing ammonium glyphosate, a cationic surfactant, a nonionic surfactant and oxalate. Compositions were prepared as indicated in Table 34A with each containing about 62 g a.e. per liter ammonium glyphosate.

TABLE 34A

| Comp. | Cmpnt. 1 | wt % | Cmpnt. 2 | wt % | Cmpnt. 3 | wt % | pH |
|---|---|---|---|---|---|---|---|
| 065A9M | CIS19 | 0.5 | NIS1 | 0.7 | OTH5 | 0.5 | 3.8 |
| 065B4S | CIS19 | 0.8 | NIS1 | 0.8 | OTH5 | 1.0 | 3.8 |
| 065C7H | CIS19 | 1.1 | NIS1 | 1.1 | OTH5 | 1.9 | 3.7 |
| 065D1R | STD12 | — | — | — | — | — | 4.5 |
| 065E8L | 155X0M | — | — | — | — | — | 4.6 |
| 065F2Q | 884R3C | — | — | — | — | — | 4.7 |
| 065G5B | STD4 | — | — | — | — | — | 4.1 |
| 065H7L | STD4 | — | — | — | — | — | 3.8 |

The compositions as well as STD4 and STD5 were applied to: ABUTH and ECHCF at rates of 75, 100, 200 and 400 g a.e. per hectare with results evaluated 15 DAT; TRZVX at 75, 100, 150 and 300 g a.e. per hectare and evaluated at 16 DAT; and GLXMV at 75, 100, 200 and 350 g a.e. per hectare and evaluated at 14 DAT. The results are reported in Table 34B.

TABLE 34B

| Comp. | ABUTH | ECHCF | TRZVX | GLXMV |
|---|---|---|---|---|
| 065A9M | 73, 91, 98, 100 | 47, 65, 87, 97 | 61, 68, 81, 93 | 67, 73, 90, 93 |
| 065B4S | 83, 88, 95, 99 | 50, 65, 90, 98 | 64, 69, 79, 89 | 68, 75, 87, 93 |

TABLE 34B-continued

| Comp. | ABUTH | ECHCF | TRZVX | GLXMV |
|---|---|---|---|---|
| 065C7H | 85, 87, 96, 100 | 58, 68, 89, 99 | 67, 73, 78, 95 | 50, 81, 90, 90 |
| 065D1R | 80, 89, 95, 100 | 48, 63, 80, 97 | 59, 68, 73, 91 | 63, 80, 88, 95 |
| 065E8L | 83, 85, 93, 98 | 54, 68, 84, 98 | 58, 59, 79, 91 | 62, 80, 88, 94 |
| 065F2Q | 84, 85, 97, 99 | 60, 65, 82, 98 | 63, 65, 73, 91 | 60, 78, 92, 92 |
| 065G5B | 42, 59, 86, 93 | 53, 63, 83, 95 | 57, 67, 82, 91 | 69, 83, 89, 91 |
| 065H7L | 39, 48, 81, 93 | 53, 61, 68, 90 | 60, 70, 78, 93 | 69, 80, 88, 88 |
| STD4 | 45, 59, 78, 94 | 46, 61, 77, 96 | 62, 71, 81, 93 | 60, 79, 86, 90 |
| STD5 | 20, 46, 70, 86 | 3, 28, 52, 73 | 0, 20, 39, 55 | 0, 0, 3, 17 |

Varying the pH levels within the range of 3.7 to 4.6 did not appear to significantly affect the efficacy on ABUTH, ECHCF, TRZVX or GLXMV. All formulations containing oxalate showed equal and superior ABUTH and ECHCF control versus STD4. Most formulations gave TRZXV efficacy performance similar to STD4 except 065D1R and 065F2Q which were slightly less efficacious. Most formulations gave GLXMV performance similar or slightly greater than STD4.

Example 35

A trial was done to evaluate formulations containing ammonium glyphosate, a cationic surfactant, an anionic surfactant, oxalate and citrate and/or ammonium sulfate on TRZVX, GLXMV and SIDSP. Compositions were prepared as indicated in Table 35A with each containing about 62 g a.e. per liter ammonium glyphosate.

TABLE 35A

| Comp. | Cmpnt. 1 | wt % | Cmpnt. 2 | wt % | Cmpnt. 3 | wt % | Cmpnt. 4 | wt % |
|---|---|---|---|---|---|---|---|---|
| 066A8N | CIS19 | 0.8 | NIS1 | 0.8 | OTH1 | 1.5 | — | — |
| 066B7D | CIS19 | 0.8 | NIS1 | 0.8 | OTH1 | 1.0 | OTH20 | 0.5 |
| 066C4H | CIS19 | 0.8 | NIS1 | 0.8 | OTH1 | 0.8 | OTH20 | 0.8 |
| 066D2J | CIS19 | 0.8 | NIS1 | 0.8 | OTH1 | 0.6 | OTH20 | 0.9 |
| 066E4K | CIS19 | 0.8 | NIS1 | 0.8 | OTH1 | 1.0 | OTH21 | 0.5 |
| 066F3S | CIS19 | 0.8 | NIS1 | 0.8 | OTH1 | 0.8 | OTH21 | 0.8 |
| 066G9K | CIS19 | 0.8 | NIS1 | 0.8 | OTH1 | 0.6 | OTH21 | 0.9 |

The compositions as well as STD4 and STD5 were applied to: TRZVX at rates of 75, 100, 150 and 300 g a.e. per hectare with results evaluated 15 DAT; GLXMV at 200, 300, 400 and 500 g a.e. per hectare and evaluated at 14 DAT; and SIDSP at 75, 100, 200 and 400 g a.e. per hectare and evaluated at 14 DAT. The results are reported in Table 35B.

TABLE 35B

| Comp. | TRZVX | GLXMV | SIDSP |
|---|---|---|---|
| 066A8N | 48, 50, 67, 88 | 87, 92, 93, 94 | 42, 52, 88, 95 |
| 066B7D | 52, 62, 68, 87 | 89, 90, 91, 93 | 45, 60, 88, 97 |
| 066C4H | 52, 62, 65, 87 | 88, 93, 94, 95 | 45, 53, 90, 93 |
| 066D2J | 55, 59, 69, 88 | 83, 86, 93, 94 | 48, 53, 89, 94 |
| 066E4K | 10, 53, 55, 90 | 87, 90, 92, 95 | 42, 50, 83, 96 |
| 066F3S | 42, 55, 65, 87 | 89, 89, 94, 95 | 42, 52, 84, 94 |
| 066G9K | 45, 53, 58, 88 | 88, 92, 94, 96 | 45, 48, 84, 94 |
| STD4 | 40, 53, 67, 86 | 85, 89, 92, 93 | 32, 42, 63, 95 |
| STD5 | 25, 37, 40, 50 | 10, 25, 37, 44 | 3, 37, 43, 52 |

As applied to TRZVX: The efficacy of all formulations and STD4 were determined to be equal; at low application rates formulations containing oxalate were statistically superior to formulations containing oxalate and citrate; and oxalate plus ammonium sulfate formulations gave higher efficacy than oxalate alone. As applied to GLXMV: 066D2J, containing the lowest level of oxalate and the highest ammonium sulfate load, was statistically weaker versus all remaining formulations; all remaining formulations and STD4 were of about similar efficacy. As applied to SIDSP: all formulations were determined to be of equal efficacy and superior to STD4.

Example 36

A trial was done to evaluate formulations containing potassium glyphosate, a cationic surfactant, oxalate and other additives on ABUTH, TRZVX and GLXMV. Compositions were prepared as indicated in Table 36A with each containing about 63 g a.e. per liter potassium glyphosate. The compositions as well as STD2 and STD6 were applied to: ABUTH at rates of 75, 150, 250 and 350 g a.e. per hectare with results evaluated 15 DAT; TRZVX at 75, 150, 250 and 350 g a.e. per hectare and evaluated at 15 DAT; and GLXMV at 100, 200, 300 and 500 g a.e. per hectare and evaluated at 15 DAT. The results are reported in Table 36A.

TABLE 36A

| Comp. | Cmpnt. 1 | wt % | Cmpnt. 2 | wt % | Cmpnt. 3 | wt % | ABUTH | TRZVX | GLXMV |
|---|---|---|---|---|---|---|---|---|---|
| 874A3N | NIS7 | 1.0 | — | — | — | — | 0, 40, 84, 89 | 35, 40, 50, 67 | 16, 53, 73, 85 |
| 874B7H | NIS7 | 1.0 | OTH30 | 0.8 | — | — | 13, 78, 88, 90 | 30, 38, 46, 65 | 35, 60, 80, 91 |
| 874C9K | NIS7 | 1.0 | OTH30 | 0.6 | — | — | 3, 68, 85, 91 | 28, 37, 48, 60 | 22, 78, 83, 95 |
| 874D2P | NIS7 | 1.0 | OTH30 | 0.6 | OTH25 | 0.3 | 13, 76, 88, 91 | 29, 36, 45, 55 | 33, 67, 77, 95 |
| 874E0M | NIS7 | 1.0 | OTH30 | 0.6 | OTH4 | 0.3 | 2, 67, 88, 90 | 28, 41, 50, 65 | 23, 65, 79, 91 |
| 874F1G | NIS7 | 1.0 | OTH30 | 0.6 | OTH15 | 0.3 | 14, 75, 88, 90 | 28, 38, 47, 69 | 27, 67, 83, 90 |
| 874G8J | NIS7 | 1.0 | OTH30 | 0.6 | OTH20 | 0.3 | 5, 82, 89, 90 | 32, 42, 57, 71 | 26, 67, 84, 95 |
| 874H6B | NIS7 | 1.0 | OTH30 | 0.6 | OTH31 | 0.3 | 0, 39, 75, 87 | 25, 35, 47, 65 | 18, 48, 72, 86 |
| STD2 | — | — | — | — | — | — | 0, 2, 38, 81 | 3, 25, 30, 38 | 0, 0, 3, 8 |
| STD6 | — | — | — | — | — | — | 2, 37, 86, 90 | 45, 50, 55, 67 | 48, 75, 88, 91 |

As applied to ABUTH: At 150 g a.e. per hectare, oxalate+ additives provided some efficacy improvement versus the cationic surfactant alone and STD6; at other application rates all formulations we of about equal efficacy to STD6. As applied to TRZVX: With the exception of lower efficacy for 874D2P, all formulations were about as efficacious as STD6; and the formulation additives did not increase efficacy. As applied to GLXMV: STD6 exhibited slightly higher efficacy versus the formulations; and the formulation additives did not increase efficacy.

Example 37

A trial was done to evaluate high load potassium glyphosate formulations containing a cationic surfactant, a nonionic surfactant and oxalate on ABUTH, TRZVX and SIDSP. Compositions were prepared as indicated in Table 37A with each containing about 40% a.e. potassium glyphosate. The compositions as well as STD2, STD6 and STD12 were applied to: ABUTH at rates of 100, 200, 300 and 400 g a.e. per hectare with results evaluated 16 DAT; TRZVX at 150, 250, 350 and 450 g a.e. per hectare and evaluated at 17 DAT; and SIDSP at 100, 200, 325 and 450 g a.e. per hectare and evaluated at 17 DAT. The results are reported in Table 37A.

TABLE 37A

| Comp. | Cmpnt. 1 | wt % | Cmpnt. 2 | wt % | Cmpnt. 3 | wt % | ABUTH | TRZVX | SIDSP |
|---|---|---|---|---|---|---|---|---|---|
| 880A2N[a] | NIS28 | 10.0 | — | — | — | — | 25, 70, 78, 83 | 33, 42, 51, 57 | 43, 56, 67, 75 |
| 880B9I[a] | NIS28 | 8.0 | CIS23 | 2.0 | — | — | 25, 52, 69, 83 | 33, 50, 68, 73 | 44, 60, 68, 76 |
| 880C2S[a] | NIS28 | 6.0 | CIS23 | 4.0 | — | — | 30, 65, 78, 84 | 42, 59, 73, 74 | 51, 58, 74, 83 |
| 880D0J[a] | NIS28 | 4.0 | CIS23 | 6.0 | — | — | 35, 76, 78, 88 | 41, 59, 71, 78 | 52, 61, 79, 83 |
| 880E4V[a] | NIS28 | 10.0 | — | — | OTH30 | 2.0 | 76, 83, 87, 89 | 35, 38, 62, 64 | 50, 60, 71, 77 |
| 880F9L[a] | NIS28 | 8.0 | CIS23 | 2.0 | OTH30 | 2.0 | 73, 83, 85, 88 | 38, 55, 81, 83 | 58, 64, 76, 82 |
| 880G1Z[a] | NIS28 | 6.0 | CIS23 | 4.0 | OTH30 | 2.0 | 80, 86, 88, 90 | 42, 67, 73, 81 | 58, 69, 83, 85 |
| STD2 | — | — | — | — | — | — | 0, 0, 20, 33 | 3, 14, 25, 32 | 0, 33, 46, 47 |
| STD6 | — | — | — | — | — | — | 15, 75, 79, 83 | 43, 53, 72, 79 | 54, 63, 83, 89 |
| STD12 | — | — | — | — | — | — | 85, 92, 95, 96 | 45, 56, 80, 89 | 59, 78, 88, 92 |

[a]Also contained about 1.5% Isopar L (OTH29)

As applied to ABUTH: Formulations containing oxalate gave the greatest efficacy; efficacy increased with increasing CIS to NIS ratios; the efficacy of formulations 880E4V, 880F9L and 880G1Z exceeded STD6; and STD12 provided the highest efficacy. As applied to TRZVX: The highest efficacy formulations contained a combination of cationic and nonionic surfactants; the efficacy of formulations 880A2N and 880E4V was lower than STD6, the efficacy of the other formulations was similar to STD6; and oxalate had little effect on efficacy. As applied to SIDSP: increasing the ratio of cationic surfactant to nonionic surfactant increased efficacy; STD12 was the highest performing composition; and 880G1Z was the next highest performing formulation with efficacy similar to STD6.

Example 38

A trial was done to evaluate potassium glyphosate formulations containing a nonionic surfactant and small carboxylic acids on ABUTH and SIDSP. Compositions were prepared as indicated in Table 38A with each containing about 63 g a.e. per liter potassium glyphosate. The compositions as well as STD2, STD4 and STD6 were applied to: ABUTH at rates of 100, 200, 300 and 400 g a.e. per hectare with results evaluated 14 DAT; and SIDSP at 100, 200, 400 and 500 g a.e. per hectare and evaluated at 16 DAT. The results are reported in Table 38A.

TABLE 38A

| Comp. | Cmpnt. 1 | wt % | Cmpnt. 2 | wt % | ABUTH | SIDSP |
|---|---|---|---|---|---|---|
| 882A0G | NIS7 | 1.0 | — | — | 0, 15, 46, 64 | 45, 51, 65, 74 |
| 882B6H | NIS7 | 1.0 | OTH5 | 0.5 | 5, 14, 35, 53 | 45, 54, 67, 73 |
| 882C9J | NIS7 | 1.0 | OTH32 | 0.5 | 5, 9, 24, 28 | 32, 49, 63, 67 |
| 882D2V | NIS7 | 1.0 | OTH33 | 0.5 | 18, 18, 23, 51 | 33, 53, 64, 70 |
| 882E5F | NIS7 | 1.0 | OTH34 | 0.5 | 17, 18, 42, 58 | 35, 50, 59, 67 |
| 882F4K | NIS7 | 1.0 | OTH35 | 0.5 | 17, 23, 51, 51 | 30, 48, 63, 68 |
| 882G5R | NIS7 | 1.0 | OTH36 | 0.5 | 39, 39, 40, 53 | 22, 50, 59, 65 |
| STD2 | — | — | — | — | 0, 1, 12, 23 | 20, 40, 58, 60 |
| STD4 | — | — | — | — | 1, 48, 69, 80 | 53, 67, 83, 90 |
| STD6 | — | — | — | — | 3, 12, 56, 69 | 55, 58, 73, 83 |

As applied to ABUTH: No formulation containing a small acid functional group was as efficacious as STD 4 and STD6; the small acids gave equal efficacy versus the alkylpolyglucoside surfactant alone (882A0G). As applied to SIDSP: No formulation containing a small acid functional group was as efficacious as STD 4 and STD6; the small acids used in this trial resulted in slightly lower efficacy versus the alkylpolyglucoside surfactant alone (882A0G) or alkylpolyglucoside+ oxalic acid (882B6H).

Example 39

A trial was done to evaluate (1) potassium glyphosate formulations and (2) ammonium glyphosate formulations, each containing a nonionic surfactant, dipotassium oxalate and other additives on ABUTH, TRZVX and SIDSP. Compositions were prepared as indicated in Table 39A with 884A8N, 884B5F, 884C1 J, 884D7J AND 884E4P containing about 63 g a.e. per liter potassium glyphosate and 884F9T containing about 63 g a.e. per liter ammonium glyphosate. The compositions as well as STD4, STD5, 155X0M (Table 33A) and STD12 were applied to: ABUTH at rates of 75, 150, 250 and 350 g a.e. per hectare with results evaluated 14 DAT; TRZVX at rates of 100, 200, 300 and 400 g a.e. per hecatre with results evaluated 15 DAT; and SIDSP at 75, 150, 300 and 400 g a.e. per hectare and evaluated at 14 DAT. The results are reported in Table 39A.

TABLE 39A

| Comp. | Cmpnt. 1 | wt % | Cmpnt. 2 | wt % | Cmpnt. 3 | wt % | ABUTH | TRZVX | SIDSP |
|---|---|---|---|---|---|---|---|---|---|
| 884A8N | NIS7 | 1.0 | — | — | — | — | 0, 0, 25, 40 | 55, 59, 65, 66 | 5, 15, 37, 50 |
| 884B5F | NIS7 | 1.0 | OTH30 | 0.8 | — | — | 18, 42, 47, 78 | 56, 60, 67, 71 | 9, 28, 48, 53 |
| 884C1J | NIS7 | 1.0 | OTH30 | 0.4 | OTH17 | 0.4 | 0, 13, 48, 68 | 47, 58, 68, 74 | 8, 23, 47, 51 |
| 844D7J | NIS7 | 1.0 | OTH30 | 0.4 | OTH20 | 0.4 | 3, 11, 57, 75 | 52, 58, 63, 75 | 8, 28, 48, 53 |
| 884E4P | NIS7 | 1.0 | OTH30 | 0.4 | OTH37 | 0.4 | 2, 8, 25, 63 | 48, 57, 68, 73 | 8, 24, 49, 53 |
| 884F9T | NIS7 | 1.0 | OTH30 | 0.4 | OTH38 | 0.4 | 0, 8, 14, 26 | 52, 62, 68, 74 | 8, 17, 45, 48 |
| STD4 | — | — | — | — | — | — | 4, 27, 77, 85 | 61, 67, 70, 76 | 27, 47, 52, 65 |
| STD5 | — | — | — | — | — | — | 0, 4, 7, 23 | 6, 17, 40, 54 | 4, 19, 32, 39 |
| 155X0M | — | — | — | — | — | — | 69, 84, 91, 93 | 60, 67, 74, 83 | 38, 52, 71, 73 |
| STD12 | — | — | — | — | — | — | 76, 85, 89, 94 | 65, 68, 72, 84 | 39, 54, 65, 74 |

As applied to ABUTH, TRZVX and SIDSP: The highest efficacy was provided by STD4, 155X0M and STD12; and the anionic derivatives gave no efficacy benefit over alkylpolyglucoside+oxalate (884B5F).

Example 40

A trial was done to evaluate potassium glyphosate concentrate formulations containing a nonionic surfactant, dipotassium oxalate and other additives on ABUTH. Compositions were prepared as indicated in Table 40A with potassium glyphosate concentration for each being about 39 wt % a.e. and ([Gly]) reported in g a.e. per liter. The compositions as well as STD2, STD4 and STD12 were applied to ABUTH at rates of 75, 150, 250 and 350 g a.e. per hectare with results evaluated 12 DAT. The efficacy results are reported in Table 40A.

TABLE 40A

| Comp. | [Gly] | Cmpnt. 1 | wt % | Cmpnt. 2 | wt % | Cmpnt. 3 | wt % | ABUTH |
|---|---|---|---|---|---|---|---|---|
| 891A5V | 552 | NIS7 | 10.0 | — | — | — | — | 13, 17, 34, 41 |
| 891B8S | 541 | NIS7 | 10.0 | OTH30 | 2.0 | — | — | 14, 19, 46, 58 |
| 891C6G | 539 | NIS7 | 10.0 | OTH30 | 2.0 | OTH24 | 2.0 | 13, 17, 43, 45 |
| 891D0I | 552 | NIS7 | 10.0 | OTH30 | 1.0 | OTH24 | 3.0 | 6, 12, 44, 54 |
| 891E7A | 539 | NIS7 | 10.0 | OTH30 | 2.0 | OTH25 | 2.0 | 14, 19, 40, 53 |
| 891F6M | 551 | NIS7 | 10.0 | OTH30 | 1.0 | OTH25 | 3.0 | 3, 10, 42, 48 |
| STD2 | — | — | — | — | — | — | — | 0, 5, 13, 33 |
| STD4 | — | — | — | — | — | — | — | 11, 37, 64, 85 |
| STD12 | — | — | — | — | — | — | — | 64, 83, 93, 97 |

All alkylpolyglucoside formulations with and without N-methyl glucamine or urea were less efficacious on ABUTH than STD4 and STD12.

Example 41

A trial was done to evaluate potassium glyphosate concentrate formulations containing a nonionic surfactant dipotassium oxalate and other additives on ABUTH. Compositions were prepared as indicated in Table 40A with potassium glyphosate concentration for each being about 39 wt % a.e. and ([Gly]) reported in g a.e. per liter. The compositions as well as STD2, STD4 and STD12 were applied to ABUTH at rates of 75, 150, 250 and 350 g a.e. per hectare with results evaluated 12 DAT. The efficacy results are reported in Table 41A.

TABLE 41A

| Comp. | [Gly] | Cmpnt. 1 | wt % | Cmpnt. 2 | wt % | Cmpnt. 2 | wt % | Cmpnt. 3 | wt % | ABUTH |
|---|---|---|---|---|---|---|---|---|---|---|
| 893A5J | 547 | NIS7 | 6.0 | CIS36 | 5.0 | — | — | — | — | 43, 28, 50, 64 |
| 893B7F | 537 | NIS7 | 6.0 | CIS36 | 5.0 | OTH30 | 2.0 | — | — | 28, 54, 72, 89 |
| 893C9K | 536 | NIS7 | 6.0 | CIS36 | 5.0 | OTH30 | 2.0 | OTH24 | 2.0 | 26, 44, 73, 85 |
| 893D2Y | 537 | NIS7 | 6.0 | CIS36 | 5.0 | OTH30 | 2.0 | OTH4 | 2.0 | 25, 51, 68, 79 |
| 893E3R | 536 | NIS7 | 6.0 | CIS36 | 5.0 | OTH30 | 2.0 | OTH15 | 2.0 | 35, 48, 60, 77 |
| 893F8L | 535 | NIS7 | 6.0 | CIS36 | 5.0 | OTH30 | 2.0 | OTH25 | 2.0 | 28, 56, 73, 85 |
| STD2 | — | — | — | — | — | — | — | — | — | 0, 2, 13, 30 |
| STD4 | — | — | — | — | — | — | — | — | — | 7, 46, 74, 84 |
| STD12 | — | — | — | — | — | — | — | — | — | 63, 83, 97, 98 |

Formulations 893B7F, 893C9K, 893D2Y, 893E3R and 893F8L gave efficacy equal to that of STD4. 893B7F at the highest application rate gave similar efficacy to that of STD12. N-methyl glucamine, urea, EDTA and citric acid did not give increased efficacy when combined with a cationic surfactant, nonionic surfactant and oxalic acid.

Example 42

A trial was done to evaluate ammonium glyphosate concentrate formulations containing a cationic surfactant, a nonionic surfactant, dipotassium and oxalate on CYPRO and CYPCP. Compositions STD4, STD5, 634Y7 (Table 48A), STD12 and 155X0M (Table 33A) were applied to: CYPRO at rates of 400, 800, 1200, 1600, 2000 and 2400 g a.e. per hectare with results evaluated 16 DAT; and CYPCP at rates of 300, 500, 700, 900, 1200 and 2000 g a.e. per hectare with results evaluated 22 DAT. The efficacy results are reported in Table 42A.

A trial was also done to evaluate the formulations for rainfast properties on ABUTH. Overhead irrigation (2 cm) was applied to selected treatments one hour after chemical applications at rates of 300 and 500 g a.e. per hectare to simulate rainfall with efficacy results evaluated 22 DAT.

TABLE 42A

| Comp. | CYPRO | CYPCP | ABUTH (no rain) | ABUTH (rain) |
|---|---|---|---|---|
| STD4 | 24, 56, 77, 88, 95, 98 | 6 26, 28, 39, 43, 53, 84 | 74, 97 | 27, 52 |
| STD5 | 18, 34, 43, 58, 74, 83 | 2, 12, 24, 27, 27, 36 | 10, 47 | 3, 14 |
| 634Y7 | 31, 55, 85, 96, 99, 99 | 18, 34, 41, 38, 63, 91 | 96, 100 | 78, 85 |
| STD12 | 19, 39, 58, 65, 78, 89 | 25, 33, 45, 50, 61, 81 | 98, 100 | 28, 48 |
| 155X0M | 18, 38, 59, 69, 84, 90 | 28, 44, 49, 51, 57, 79 | 98, 99 | 27, 51 |
| STD6 | — | — | 61, 88 | 27, 52 |

As applied to CYPRO: STD12 and 155X0M did not perform as well as STD4; and 634Y7 was equivalent to STD4. As applied to CYPCP: STD12, 155X0M and 634Y7 were equivalent to STD4.

As applied to ABUTH: The formulations did not improve the rainfast properties of glyphosate; STD12, 155X0M showed equal rainfast properties to STD4, all of which were superior to STD6; and 634Y7 showed commercially and statistically superior rainfast properties.

Example 43

A trial was done to evaluate oxalate and EDTA for chelation properties in high load potassium glyphosate concentrate formulations containing 1000 ppm hard water as applied to ABUTH and SIDSP. Compositions were prepared as indicated in Table 43A with potassium glyphosate concentration for each being about 39 wt % a.e. (542 g a.e. per liter). In a first series of evaluations the compositions as well as STD6 were diluted with deionized water to form a tank mixture and then applied to ABUTH and SIDSP at rates of 200, 300 and 400 g a.e. per hectare with results evaluated 14 DAT. A duplicate set of evaluations was done by adding 2% v/v ammonium sulfate to the tank mix. In a second series of evaluations the compositions as well as STD6 were diluted in 1000 ppm hard water to form a tank mixture and then applied to ABUTH and SIDSP at rates of 200, 300 and 400 g a.e. per hectare with results evaluated 14 DAT. A duplicate set of evaluations was done by adding 2% v/v ammonium sulfate to the tank mix. The efficacy results are reported in Table 43B.

TABLE 43A

| Comp. | Cmpnt. 1 | wt % | Cmpnt. 2 | wt % | Cmpnt. 3 | wt % | Cmpnt. 4 | wt % |
|---|---|---|---|---|---|---|---|---|
| 718A4N | CIS23 | 5.0 | NIS7 | 6.0 | OTH30 | 2.0 | — | — |
| 718B7H | CIS23 | 5.0 | NIS7 | 6.0 | OTH30 | 2.0 | OTH39 | 2.0 |
| 718C9L | CIS23 | 5.0 | NIS7 | 6.0 | OTH30 | 1.0 | OTH39 | 3.0 |

TABLE 43B

| Comp. | ABUTH[a] | ABUTH[b] | ABUTH[c] | ABUTH[d] | SIDSP[a] | SIDSP[b] | SIDSP[c] | SIDSP[d] |
|---|---|---|---|---|---|---|---|---|
| 718A4N | 33, 75, 92 | 77, 84, 97 | 6, 29, 75 | 78, 83, 94 | 38, 53, 63 | 58, 65, 71 | 27, 43, 54 | 30, 43, 58 |
| 718B7H | 53, 75, 86 | 77, 87, 91 | 6, 12, 59 | 75, 82, 94 | 44, 60, 63 | 47, 70, 80 | 8, 21, 41 | 38, 45, 53 |
| 718C9L | 49, 72, 86 | 76, 86, 93 | 3, 6, 58 | 75, 79, 92 | 44, 53, 65 | 50, 63, 83 | 4, 18, 38 | 32, 41, 46 |
| STD6 | 33, 71, 84 | 72, 81, 88 | 0, 9, 65 | 70, 79, 88 | 29, 35, 54 | 33, 48, 67 | 3, 23, 43 | 35, 40, 49 |

[a]Deionized water dilution.
[b]Deionized water dilution + 2% v/v ammonium sulfate.
[c]Hard water dilution.
[d]Hard water dilution + 2% v/v ammonium sulfate.

As applied to ABUTH and SIDSP: 718A4N, 718B7H and 718C9L each containing ammonium sulfate gave the greatest efficacy; in deionized water or hard water both ammonium sulfate and oxalate, either alone or blended together, provided efficacy improvements over STD6 alone; 718A4N, 718B7H and 718C9L, with or without ammonium sulfate, were more efficacious than STD6 with and without ammonium sulfate, respectively, in either deionized water or hard water (except for 718C9L which contains 1% oxalate); the addition of EDTA in formulations 718B7H and 718C9L appeared to be detrimental to glyphosate efficacy when diluted in hard water; substituting ammonium sulfate with oxalate to overcome hard water effects requires higher levels of oxalate; and glyphosate efficacy in deionized water was greater than for each corresponding formulation in hard water.

Example 44

A trial was done to evaluate the efficacy effects on ABUTH due to pH changes as a result of the addition of oxalic acid to ammonium glyphosate tank mix formulations. Compositions were prepared as indicated in Table 44A by diluting STD4 to achieve an ammonium glyphosate concentration of about 10 g a.e. per liter followed by addition of the other components. The compositions as well as STD5 were applied to ABUTH at rates of 75, 100, 200 and 300 g a.e. per hectare with results evaluated 20 DAT, and at rates of 100, 200, 300 and 400 g a.e. per hectare with results evaluated 14 DAT. Diammonium oxalate (OTH1) and oxalic acid (OTH5) were applied at rates of 2, 3, 4 and 5 g a.e. per hectare. The efficacy results are reported in Table 44A.

in a second process (denoted as$^b$), a blend of the cationic surfactant Surfonic T-15 and the nonionic surfactant Hunstman L68-20 were added. In all other compositions, the cationic and nonionic surfactants are added separately in the ammonium glyphosate composition formation process. Also evaluated was a comparison of two application rates, in g a.e. of ammonium glyphosate per hectare, applied at equal volumes. Compositions were prepared as in Table 45A.

TABLE 45A

| Comp. | [Gly] | Cmpnt. 1 | wt % | Cmpnt. 2 | wt % | Cmpnt. 3 | wt % |
|---|---|---|---|---|---|---|---|
| 518A2L | 68% | CIS19 | 5.7 | NIS13 | 7.9 | OTH1 | 8.3 |
| 518B5B | 68% | CIS19 | 7.5 | NIS13 | 6.1 | OTH1 | 8.3 |
| 518C2W$^a$ | 68% | CIS19 | 7.5 | NIS13 | 6.1 | OTH1 | 8.3 |
| 518D0J$^b$ | 68% | CIS19 | 7.5 | NIS13 | 6.1 | OTH1 | 8.3 |
| 518E4G | 68% | CIS21 | 13.6 | OTH1 | 8.3 | — | — |
| 518F5T | 60% | CIS19 | 8.0 | NIS13 | 8.0 | OTH1 | 15.0 |
| 518G5Y | 60% | CIS21 | 16.0 | OTH1 | 15.0 | — | — |
| 518H9R | 60% | CIS19 | 8.8 | NIS13 | 7.2 | OTH1 | 15.0 |
| 518I3S$^a$ | 60% | CIS19 | 8.8 | NIS13 | 7.2 | OTH1 | 15.0 |
| 518J9U$^b$ | 60% | CIS19 | 8.8 | NIS13 | 7.2 | OTH1 | 15.0 |

$^a$process 1
$^b$process 2

In test series 1, each of compositions: 518A2L, 518B5B, 518C2W, 518D0J and 518E4G, and STD4, STD5 and STD6 were applied to ABUTH at rates of 100, 200, 300 and 400 g

TABLE 44A

| Comp. | Cmpnt. 1 | Cmpnt. 2 | wt % | Cmpnt. 3 | wt % | pH | ABUTH (20 DAT) | ABUTH (14 DAT) |
|---|---|---|---|---|---|---|---|---|
| 510A3H | STD4 | CIS21 | 0.31 | — | — | 4.1 | 18, 52, 78, 94 | 38, 78, 92, 96 |
| 510B7K | STD4 | CIS21 | 0.31 | OTH5 | 1.1 | 1.8 | 78, 88, 99, 99 | 81, 93, 98, 99 |
| 510C0L | STD4 | CIS21 | 0.31 | OTH5 | 0.4 | 2.6 | 67, 85, 97, 99 | 88, 95, 97, 98 |
| 510D1N | STD4 | CIS21 | 0.31 | OTH5 | 0.2 | 2.9 | 58, 78, 99, 99 | 79, 95, 98, 99 |
| 510E4J | STD4 | CIS21 | 0.31 | OTH1 | 1.2 | 4.7 | 73, 87, 95, 99 | 89, 92, 99, 99 |
| 510F6L | STD4 | CIS21 | 0.31 | OTH1 | 0.4 | 4.5 | 65, 86, 99, 99 | 81, 96, 98, 100 |
| 510G2C | STD4 | CIS21 | 0.31 | OTH1 | 0.2 | 4.4 | 65, 81, 98, 99 | 81, 95, 98, 99 |
| OTH1 | — | — | — | OTH1 | 63.0 | — | 0, 0, 0, 0 | 0, 0, 0, 0 |
| OTH5 | — | — | — | OTH5 | 100 | — | 0, 0, 0, 0 | 0, 0, 0, 0 |
| STD5 | — | — | — | — | — | — | 4, 28, 59, 72 | 1, 28, 63, 71 |

510A3H was the lowest performing composition, and the remaining test formulations, representing various pH levels were superior for ABUTH control. Composition 510B7K, containing the highest level of acid and lowest pH, was superior to 510C0L and 510D1 N which contain lesser amounts of acid and higher pH. Thus addition of oxalic acid or oxalate to ammonium glyphosate formulations could provide for efficacy increase compared to standard ammonium glyphosate formulations and the resulting lower pH should not affect performance.

Example 45

A trial was done to evaluate the efficacy effect of surfactant changes in ammonium glyphosate compositions due to processing conditions. In particular in a first process (denoted as$^a$), a blend of the cationic surfactant Surfonic T-15 and the nonionic surfactant Hunstman L68-20 were added in the ammonium glyphosate composition formation process, and a.e. per hectare; 518F5T, 518G5Y, 518H9R, 518I3S and 518J9U were applied to ABUTH at rates of 88, 176, 264 and 352 g a.e. per hectare; and the efficacy results were evaluated 14 DAT. In test series 2, each of compositions: 518A2L, 518B5B, 518C2W, 518D0J and 518E4G, and STD4, STD5 and STD6 were applied to ABUTH at rates of 75, 100, 200 and 400 g a.e. per hectare; 518F5T, 518G5Y, 518H9R, 518I3S and 518J9U were applied to ABUTH at rates of 66, 88, 176 and 352 g a.e. per hectare; and the efficacy results were evaluated 15 or 16 DAT. In test series 3, each of compositions: 518A2L, 518B5B, 518C2W, 518D0J and 518E4G, and STD4, STD5 and STD6 were applied to ABUTH at rates of 25, 50, 75 and 100 g a.e. per hectare; 518F5T, 518G5Y, 518H9R, 518I3S and 518J9U were applied to ABUTH at rates of 22, 44, 66 and 88 g a.e. per hectare; and the efficacy results were evaluated 15 DAT. The results are reported in Table 45B.

TABLE 45B

| Comp. | ABUTH[1] | ABUTH[1] | ABUTH[2c] | ABUTH[2d] | ABUTH[3] | ABUTH[3] |
|---|---|---|---|---|---|---|
| 518A2L | 76, 94, 98, 99 | 79, 95, 98, 98 | 73, 88, 99, 99 | 83, 93, 99, 100 | 8, 52, 63, 88 | 8, 53, 77, 87 |
| 518B5B | 80, 96, 97, 99 | 83, 92, 97, 97 | 64, 87, 99, 99 | 78, 88, 98, 100 | 5, 43, 64, 85 | 3, 51, 79, 84 |
| 518C2W[a] | 82, 95, 97, 98 | — | 69, 93, 97, 100 | — | 3, 33, 71, 85 | — |
| 518D0J[b] | 69, 93, 97, 97 | — | 64, 90, 98, 99 | — | 7, 51, 69, 83 | — |
| 518E4G | 66, 88, 96, 96 | 75, 95, 95, 98 | 60, 79, 96, 96 | 79, 84, 99, 100 | 5, 33, 63, 77 | 3, 28, 72, 83 |
| 518F5T | 74, 88, 94, 98 | 86, 96, 96, 99 | 64, 92, 99, 99 | 73, 85, 98, 100 | 3, 43, 65, 79 | 8, 60, 77, 83 |
| 518G5Y | 65, 88, 93, 97 | 74, 94, 96, 97 | 63, 88, 98, 97 | 72, 89, 97, 100 | 2, 43, 63, 69 | 5, 28, 60, 76 |
| 518H9R | — | 84, 94, 96, 98 | — | 73, 90, 97, 100 | — | 8, 67, 79, 83 |
| 518I3S[a] | — | 83, 95, 96, 98 | — | 78, 86, 96, 100 | — | 12, 57, 73, 83 |
| 518J9U[b] | — | 83, 95, 97, 97 | — | 80, 85, 95, 100 | — | 18, 48, 73, 83 |
| STD4 | 26, 70, 80, 88 | 20, 76, 86, 93 | 20, 59, 87, 96 | 18, 64, 83, 99 | 3, 15, 22, 43 | 1, 5, 22, 37 |
| STD5 | 0, 8, 25, 38 | 0, 20, 45, 58 | 3, 18, 65, 84 | 4, 33, 66, 80 | 0, 4, 6, 19 | 0, 2, 2, 8 |
| STD6 | 7, 63, 78, 88 | — | 28, 40, 86, 94 | — | 4, 10, 16, 32 | — |

[a]process 1
[b]process 2
[c]15 DAT
[d]16 DAT
[1]Test series 1.
[2]Test series 2.
[3]Test series 3.

Each of compositions: 518A2L, 518B5B, 518C2W, 518D0J and 518E4G, and STD4, STD5 and STD6 were applied to SIDSP at rates of 200, 300, 500 and 700 g a.e. per hectare; 518F5T, 518G5Y, 518H9R, 518I3S and 518J9U were applied to SIDSP at rates of 176, 264, 440 and 616 g a.e. per hectare; and the efficacy results were evaluated 14 or 18 DAT. The results are reported in Table 45C.

TABLE 45C

| Comp. | SIDSP[c] | SIDSP[d] |
|---|---|---|
| 518A2L | 72, 83, 90, 97 | 78, 83, 91, 93 |
| 518B5B | 69, 80, 92, 92 | 78, 86, 91, 96 |
| 518C2W[a] | 69, 78, 90, 90 | — |
| 518D0J[b] | 70, 78, 92, 94 | — |
| 518E4G | 64, 70, 89, 89 | 73, 85, 90, 94 |
| 518F5T | 67, 76, 89, 89 | 73, 83, 88, 94 |
| 518G5Y | 57, 68, 77, 85 | 63, 78, 86, 92 |
| 518H9R | — | 73, 80, 91, 94 |
| 518I3S[a] | — | 68, 83, 90, 92 |
| 518J9U[b] | — | 68, 78, 83, 91 |
| STD4 | 63, 70, 84, 91 | 64, 75, 90, 93 |
| STD5 | 22, 48, 67, 68 | 33, 48, 61, 66 |
| STD6 | 63, 65, 83, 86 | — |

[a]process 1
[b]process 2
[c]18 DAT
[d]14 DAT

Formulations 518A2L, 518B5B, 518C2W and 518D0J gave the highest efficacy on both ABUTH and SIDSP and were superior to STD4 and STD6. Process conditions 1 and 2 produced no significant efficacy differences between ABUTH and SIDSP. For SIDSP, comparing the 68% a.e. loaded formulations to their respective reduced 60% a.e. loaded formulations showed equivalent efficacy for 518A2L (68%) versus 518F5T (60%), however, comparison of 518B5B (68%) versus 518H9R (60%) and 518E4G (68%) versus 518G5Y (60%) show efficacy advantages for the higher loaded formulations.

For ABUTH, a comparison of the 68% a.e. standard load formulations versus their respective 60% reduced loaded formulations showed all to be generally equivalent or to have only a slight advantage in efficacy in spite of 12% lower application rates for the 60% a.e. formulations. All eight oxalate containing formulations were superior to STD4 and STD6 for ABUTH control.

Example 46

A trial was also done to evaluate formulations for rainfast properties on ABUTH. Overhead irrigation (2 cm; 0.25 inch) was applied to selected treatments one hour after chemical application at rates of 300 and 500 g a.e. per hectare, and at reduced rates of 285 and 475 g a.e. per hectare, to simulate rainfall with efficacy results evaluated 14 DAT. Compositions were prepared as indicated in Table 46A with each containing about 65% w/w a.e. ammonium glyphosate.

TABLE 46A

| Comp. | Cmpnt. 1 | wt % | Cmpnt. 2 | wt % | Cmpnt. 3 | wt % |
|---|---|---|---|---|---|---|
| 544A3M | CIS19 | 10.5 | NIS13 | 8.5 | OTH5 | 6.8 |
| 544B7U | CIS19 | 8.0 | NIS13 | 11.0 | OTH5 | 6.8 |
| 544C1R | CIS21 | 19.0 | OTH5 | 6.8 | — | — |

The compositions of Table 46A and 155X0M (Table 33A), STD4, STD6, STD10 and 634Y7 (Table 48A) were applied to ABUTH with the results reported in Table 46B.

TABLE 46B

| Comp. | ABUTH (no rain) | ABUTH (no rain) | ABUTH (no rain) | ABUTH (rain) |
|---|---|---|---|---|
| 544A3M | 99, 100[1] | 40, 49[1] | 95, 99[2] | 20, 39[2] |
| 544B7U | 99, 100[1] | 20, 43[1] | 97, 99[2] | 23, 33[2] |
| 544C1R | 99, 100[1] | 10, 36[1] | 98, 99[2] | 6, 13[2] |
| STD4 | 81, 97[1] | 20, 39[1] | 83, 95[1] | 5, 13[1] |
| STD6 | 83, 96[1] | 18, 36[1] | 81, 96[1] | 8, 18[1] |
| STD10 | 88, 99[1] | 66, 77[1] | 93, 95[1] | 61, 76[1] |
| 155X0M | 98, 99[1] | 23, 51[1] | 97, 98[2] | 10, 30[2] |
| 634Y7 | 93, 99[1] | 74, 81[1] | 93, 98[1] | 62, 86[1] |

[1]300 and 500 g a.e. per hectare
[2]285 and 475 g a.e. per hectare.

Compositions 544A3M, 544B7U and 155X0M showed improved rainfast properties versus lower rainfast performance for 544C1R at the high application rate, and were superior to STD4 and STD6. The rainfast properties for 544A3M, 544B7U and 544C1R applied at lower application rates but equal volumes were still more efficacious than STD4 and STD6 applied at full rates (rain or no rain). Thus the high cationic surfactant+nonionic surfactant loading provided for increased rainfast properties.

Example 47

A trial was done to evaluate ammonium glyphosate formulations containing a reduced loading of a cationic surfactant and a nonionic surfactant on SIDSP. Also evaluated was the efficacy of similar volume applications to reduced rate applications (68% a.e. versus 60% a.e.). In application rate series 1, the compositions, STD4, STD5 and 634Y7 (Table 48A) were applied at rates of 200, 300, 500 and 700 g a.e. per hectare; in rate series 2 the reduced application rate of 194, 291, 485 and 679 g a.e. per hectare was used. In each composition, ammonium glyphosate was formulated at 68% a.e. by mass as contained the components as indicated in Table 47A. The efficacy results are reported in Table 47A.

TABLE 47A

| Comp. | Cmpnt. 1 | wt % | Cmpnt. 2 | wt % | Cmpnt. 3 | wt % | App. Rate | TRZVX |
|---|---|---|---|---|---|---|---|---|
| 572B6H | CIS19 | 10.0 | NIS13 | 10.0 | OTH1 | 4.5 | 200, 300, 500, 700 | 60, 71, 88, 87 |
|  |  |  |  |  |  |  | 194, 291, 485, 679 | 76, 78, 90, 91 |
| 572C9M | CIS19 | 10.0 | NIS13 | 10.0 | OTH20 | 4.5 | 200, 300, 500, 700 | 67, 83, 87, 91 |
|  |  |  |  |  |  |  | 194, 291, 485, 679 | 78, 82, 89, 92 |
| 572D1X | CIS19 | 9.0 | NIS13 | 9.0 | OTH1 | 6.5 | 200, 300, 500, 700 | 77, 77, 89, 90 |
|  |  |  |  |  |  |  | 194, 291, 485, 679 | 75, 83, 88, 90 |
| 572E4Z | CIS19 | 9.0 | NIS13 | 9.0 | OTH20 | 6.5 | 200, 300, 500, 700 | 73, 78, 88, 89 |
|  |  |  |  |  |  |  | 194, 291, 485, 679 | 75, 82, 86, 88 |
| STD4 | — | — | — | — | — | — | 200, 300, 500, 700 | 48, 67, 87, 88 |
| STD5 | — | — | — | — | — | — | 200, 300, 500, 700 | 11, 20, 44, 54 |
| 634Y7 | — | — | — | — | — | — | 200, 300, 500, 700 | 63, 76, 89, 90 |

The results indicate a slightly higher activity ranking for the reduced application rate samples 572F5G, 572G7R, 572H6N and 572I6F. All formulations were equal, or superior, to STD4 and 634Y7.

A trial was also done to evaluate the formulations for rainfast properties on ABUTH. Overhead irrigation (0.64 cm; 0.25 inch) was applied to selected treatments one hour after chemical applications at rates of 300 and 500 g a.e. per hectare, and at reduced rates of 291 and 582 g a.e. per hectare, to simulate rainfall with efficacy results evaluated 14 DAT and reported in Table 47B.

TABLE 47B

| Comp. | ABUTH (no rain) | ABUTH (rain) | ABUTH (no rain) | ABUTH (rain) |
|---|---|---|---|---|
| 572B6H | 94, 100 | 26, 40 | 93, 99[1] | 36, 44[1] |
| 572C9M | 91, 99 | 40, 60 | 89, 96[1] | 52, 73[1] |
| 572D1X | 95, 100 | 29, 48 | 93, 97[1] | 38, 44[1] |
| 572E4Z | 94, 98 | 37, 55 | 91, 95[1] | 49, 70[1] |
| STD4 | 78, 99 | 16, 41 | 84, 97 | 38, 57 |
| STD6 | 83, 99 | 22, 45 | 78, 97 | 39, 58 |
| 634Y7 | 95, 100 | 46, 75 | 94, 99 | 47, 75 |

[1]291 and 582 g a.e. per hectare application rates.

The results for the two application rates were similar although activity for the reduced application rate was generally higher. At the higher application rate, 634Y7 gave near commercial rainfast properties, and 572C9M and 572E4Z showed slightly greater rainfastedness over 572B6H and 572D1X. At the lower application rate, 572C9M and 572E4Z showed near commercial rainfast properties, and were essentially equivalent to 634Y7 and significantly greater than 572B6H and 572D1X. Across both application rates, ammonium sulfate was more effective than diammonium oxalate for maintaining rainfast properties.

Field Tests

Field studies were conducted to the compositions of the present invention. Glyphosate formulations were applied postemergence to all weed targets, generally when they were between about 8 cm and about 30 cm tall, depending on the species and the environmental conditions. Treated plot size was generally 2 meters wide and 4.6 meters long. Treatments were applied with spray booms/spray rigs. Carrier volume ranged between 93 l/ha and 112 l/ha. Tee-Jet brand tapered flat fan spray tips were used, at an appropriate spray pressure, with spacing and height from the weed canopy as recommended in the Tee-Jet technical manual. Experimental design in every study was a split plot arrangement with four replications. Each formulation was generally applied at four or five rates of application in each test, and rates are reported as grams acid equivalence per hectare (g a.e./ha).

Traditional weed control ratings were made at the time of maximum control with glyphosate formulations (14 to 35 days after treatment, or DAT). Ratings were based on quantitative visual estimates (0=no control, 100=completely dead, 85% threshold for commercial control). The effect of glyphosate on the species in the treated plot was compared to the health and vigor of the species growing in the untreated buffer area immediately surrounding the plot.

Example 48

The field efficacy of dry formulations containing a cationic:nonionic surfactant system and inerts was evaluated. Compositions were prepared containing ammonium glyphosate salt, reported in % wt a.e. and excipient ingredients as shown in Table 48A. Comparative composition 420Q2 was prepared from STD4 with the additional indicated added components.

TABLE 48A

| Comp. | [GLY] | Cmpnt. 1 | wt % | Cmpnt. 2 | wt % | Cmpnt. 3 | wt % | Cmpnt. 4 | wt % |
|---|---|---|---|---|---|---|---|---|---|
| 633A4 | 68.0 | CIS19 | 9.5 | NIS13 | 11.6 | OTH17 | 0.4 | OTH18 | 0.1 |
| 634Y7 | 65.0 | CIS9 | 11.0 | NIS14 | 13.4 | OTH17 | 0.4 | OTH18 | 0.1 |
| 636N8 | 72.0 | CIS15 | 17.2 | — | — | OTH17 | 0.4 | OTH18 | 0.1 |
| 637B4 | 72.0 | CIS16 | 12.0 | NIS1 | 5.2 | OTH17 | 0.4 | OTH18 | 0.1 |
| 768R0 | 65.0 | CIS10 | 8.0 | NIS15 | 8.0 | OTH20 | 10.0 | — | — |
| 769L7 | 71.0 | CIS11 | 10.0 | NIS16 | 2.0 | OTH5 | 8.0 | — | — |
| 483S2 | 68.0 | CIS16 | 5.7 | NIS1 | 7.9 | OTH1 | 8.3 | — | — |
| 420Q2 | 68.0 | CIS21 | 21.0 | — | — | OTH17 | 0.4 | — | — |

The compositions of Table 48A, including comparative composition 420Q2, were applied to AMAQU, CYNDA, MEUSS and POLAV plants at various rates of application. These studies were completed in and around Pergamino, Argentina. Results, averaged for all replicates of each treatment for each weed, are shown in Tables 48B to 48F. Results are also averaged across two or more species, where appropriate, to determine an "overall" mean.

TABLE 48B

| | % Weed Control | | |
|---|---|---|---|
| Composition | CYNDA | MEUSS | Overall |
| 633A4 | 50 | 54 | 52 |
| 634Y7 | 58 | 49 | 53 |
| 636N8 | 58 | 50 | 54 |
| 637B4 | 53 | 48 | 51 |
| 768R0 | 58 | 49 | 53 |
| 769L7 | 58 | 43 | 51 |
| 483S2 | 60 | 58 | 59 |
| 420Q2 | 47 | 51 | 49 |

Separate studies were conducted on CYNDA and MEUSS in Argentina. All compositions outperformed the 420Q2 standard for control of CYNDA and the formulation containing oxalic acid, 483S2, was the most efficacious formulation in the study. Against MEUSS, only two glyphosate formulations, 633A4 and 483S2, were more efficacious than the standard. Averaged across both weed species, the formulation containing oxalic acid (483S2) was the most efficacious composition evaluated.

Example 48C

The compositions of Table 25A were applied to an indigenous stand of AMAQU at rates of 748, 960 and 1156 g a.e./ha in a field trial near Pergamino, Argentina. Results, averaged for all replicates for each treatment across all rates of application are shown in Table 48C.

TABLE 48C

| | % Weed Control |
|---|---|
| Composition | AMAQU |
| 633A4 | 58 |
| 634Y7 | 62 |
| 636N8 | 61 |
| 637B4 | 60 |
| 768R0 | 67 |
| 769L7 | 49 |
| 483S2 | 65 |
| 420Q2 | 59 |

All but two of the formulations provided better control of AMAQU than the 420Q2 standard, with the two weakest being 769L7 and 633A4.

Example 48D

Solid ammonium glyphosate compositions 632I8 and 431C5 were formulated as follows wherein the glyphosate concentration is given in % w/w a.e.

| Comp. | [GLY] | Cmpnt. 1 | wt % | Cmpnt. 2 | wt % | Cmpnt. 3 | wt % | Cmpnt. 4 | wt % |
|---|---|---|---|---|---|---|---|---|---|
| 632I8 | 68.0 | CIS19 | 9.5 | NIS13* | 11.6 | OTH17 | 0.4 | OTH18 | 0.1 |
| 431C5 | 72.0 | CIS22 | 17.0 | OTH17 | 0.4 | OTH18 | 0.2 | OTH20 | 0.2 |

*Solid $C_{16-18}$ alcohol ethoxylate (20EO)

Composition 632I8 above, and compositions 420Q2, 483S2 and 633A4 were applied to a field infested with COMSS at various application rates near Pergamino, Argentina. Results, averaged for all replicates for each treatment across all rates of application are shown in Table 48D.

TABLE 48D

| | % Weed Control |
|---|---|
| Composition | COMSS |
| 483S2 | 85 |
| 632I8 | 85 |
| 633A4 | 85 |
| 420Q2 | 82 |

All compositions in Table 48D outperformed the 420Q2 standard for control of COMSS.

Example 48E

Compositions from Table 48A and composition 431C5 from Example 48D were compared to the standard formulation 420Q2 for control of POROL at various rates of application in a test near Pergamino, Argentina. Results, averaged for all replicates for each treatment across all rates of application are shown in Table 48E.

TABLE 48E

| Composition | % Weed Control POROL |
|---|---|
| 431C5 | 94 |
| 483S2 | 93 |
| 633A4 | 92 |
| 636N8 | 93 |
| 637B4 | 92 |
| 768R0 | 94 |
| 769L7 | 91 |
| 420Q2 | 92 |

All compositions evaluated in this field trial performed favorably compared to the standard for control of POROL. Only formulation 769L7 was less efficacious than 420Q2, but high levels of control were still achieved. 431C5 and 768R0 were the most efficacious formulations evaluated in the trial.

Example 48F

Compositions 483S2 and 633A4 from Table 48A were compared to the standard formulation 420Q2 for control of CYNDA at various rates of application in a field test in Pergamino, Argentina. Results, averaged for all replicates for each treatment across all rates of application are shown in Table 48F.

TABLE 48F

| Composition | % Weed Control CYNDA |
|---|---|
| 483S2 | 71 |
| 633A4 | 68 |
| 420Q2 | 61 |

Compositions 483S2 and 633A4 each controlled CYNDA more effectively than the 420Q2 standard in this trial. 483S2 was the most efficacious formulation evaluated.

Example 49

The field efficacy of ammonium glyphosate dry formulations containing a cationic:nonionic surfactant system and inerts was evaluated in this example. Compositions were prepared containing ammonium, potassium or IPA glyphosate salt, reported in % wt a.e., and excipient ingredients, reported a w/w % unless otherwise indicated, as shown in Table 49A.

TABLE 49A

| Comp. | gly salt | [gly] | Cmpnt 1 | wt % | Cmpnt 2 | wt % |
|---|---|---|---|---|---|---|
| 942A2W | Amm | 68 | CIS16 | 5.7 | NIS13 | 7.9 |
| 943E4B | Amm | 68 | CIS16 | 5.7 | NIS13 | 7.9 |
| 944U7M | Amm | 68 | CIS19 | 5.7 | NIS13 | 7.9 |
| 946L3J | K | 36.4 | CIS14 | 5.0 | NIS19 | 2.0 |
| 947A0P | K | 36.4 | CIS14 | 4.0 | NIS7 | 4.0 |
| 948V5N | IPA | 31 | CIS14 | 1.8 | NIS7 | 5.0 |
| 632M7A | Amm | 68 | CIS9 | 9.4 | NIS14 | 11.6 |

| Comp. | Cmpnt 3 | wt % | Cmpnt 4 | wt % | Cmpnt 5 | wt % |
|---|---|---|---|---|---|---|
| 942A2W | OTH1 | 8.3 | OTH17 | 0.4 | OTH18 | 0.1 |
| 943E4B | OTH20 | 8.3 | OTH17 | 0.4 | OTH18 | 0.1 |
| 944U7M | OTH1 | 8.3 | OTH17 | 0.4 | OTH18 | 0.1 |
| 946L3J | CIS8 | 6.0 | OTH2 | 0.5 | OTH3 | 2.0 |
| 947A0P | CIS8 | 6.0 | OTH2 | 0.5 | OTH3 | 2.0 |
| 948V5N | OTH1 | 3.0 | OTH2 | 0.1 | OTH3 | 2.0 |
| 632M7A | OTH20 | 0.4 | OTH18 | 0.1 | — | — |

The compositions of Table 49A were applied to LAMAM plants in three separate trials conducted in Texas at rates of 315, 473, 631, 788 and 946 g a.e./ha. Results, averaged for all replicates of each treatment and across all rates of application for each plant species (reported as the sixth value), as well as an overall average across all plant species, are shown Table 49B.

TABLE 49B

| | | % Weed Control | | | |
|---|---|---|---|---|---|
| Composition | Rate (g/ha) | LAMAM | LAMAM | LAMAM | Overall Ave. |
| App. Date | — | January, 2002 | January, 2002 | February, 2002 | — |
| 942A2W | 315, 473, 631, 788, 946, average | 61, 72, 73, 70, 76, 71 | 70, 79, 77, 80, 88, 79 | 73, 82, 79, 84, 86, 80 | 77 |
| 943E4B | 315, 473, 631, 788, 946, average | 64, 63, 78, 77, 71, 71 | 83, 72, 79, 80, 92, 81 | 68, 77, 80, 85, 87, 80 | 77 |
| 944U7M | 315, 473, 631, 788, 946, average | 67, 73, 71, 75, 75, 72 | 76, 76, 73, 84, 88, 79 | 73, 78, 82, 84, 91, 81 | 78 |
| 946L3J | 315, 473, 631, 788, 946, average | 68, 63, 64, 66, 75, 67 | 80, 73, 73, 84, 88, 80 | 66, 78, 83, 82, 86, 79 | 75 |
| 947A0P | 315, 473, 631, 788, 946, average | 64, 69, 75, 69, 74, 70 | 68, 71, 74, 84, 89, 77 | 70, 78, 79, 82, 87, 79 | 75 |
| 948V5N | 315, 473, 631, 788, 946, average | 68, 63, 67, 74, 80, 70 | 73, 78, 78, 85, 92, 81 | 73, 72, 76, 84, 84, 78 | 76 |
| STD6 | 315, 473, 631, 788, 946, average | 66, 62, 73, 70, 74, 69 | 70, 74, 73, 84, 89, 78 | 67, 77, 81, 85, 87, 79 | 75 |
| 632M7A | 315, 473, 631, 788, 946, average | 68, 65, 67, 75, 72, 69 | 79, 74, 76, 87, 93, 82 | 70, 82, 83, 86, 89, 82 | 78 |

In general, formulations containing diammonium oxalate were slightly more efficacious than the liquid standard (STD6) in the three aforementioned field studies. This included three dry formulations 942A2W, 943E4B and 944U7M, plus one liquid formulation, 948V5N. One dry formulation constructed with diammonium oxalate, 944U7M, stood out as being as efficacious as an internal efficacy standard, 632M7A.

The compositions of Table 49A were applied to LAMAM, LOLMG and LOLPE plants in a field trial at rates of 210, 368, 526, 684 and 840 g a.e./ha done in Baldwin County, Alabama. Results, averaged for all replicates of each treatment and across all rates of application for each plant species (reported as the sixth value), as well as an overall average across all plant species, are shown in Table 49C.

TABLE 49C

| | | % Weed Control | | | |
|---|---|---|---|---|---|
| Composition | Rate (g/ha) | LAMAM | LOLMG | LOLPE | Overall Ave. |
| 942A2W | 210, 368, 526, 683, 840, average | 75, 81, 86, 86, 97, 85 | 66, 78, 85, 87, 96, 82 | 59, 70, 80, 84, 96, 78 | 82 |
| 943E4B | 210, 368, 526, 683, 840, average | 75, 83, 89, 91, 95, 87 | 67, 76, 83, 89, 96, 82 | 59, 75, 79, 87, 95, 79 | 83 |
| 944U7M | 210, 368, 526, 683, 840, average | 79, 84, 86, 89, 94, 86 | 68, 79, 84, 86, 90, 81 | 59, 72, 81, 83, 92, 77 | 82 |
| 946L3J | 210, 368, 526, 683, 840, average | 74, 84, 86, 92, 91, 85 | 72, 85, 88, 93, 94, 86 | 61, 80, 88, 92, 95, 83 | 85 |
| 947A0P | 210, 368, 526, 683, 840, average | 78, 83, 89, 91, 95, 87 | 72, 81, 86, 88, 95, 84 | 63, 78, 84, 86, 95, 81 | 84 |
| 948V5N | 210, 368, 526, 683, 840, average | 75, 81, 88, 89, 94, 85 | 74, 82, 86, 87, 93, 84 | 64, 76, 83, 86, 91, 80 | 83 |
| STD6 | 210, 368, 526, 683, 840, average | 76, 85, 86, 91, 95, 87 | 71, 80, 85, 88, 94, 84 | 59, 76, 82, 85, 94, 79 | 83 |
| 632M7A | 210, 368, 526, 683, 840, average | 78, 84, 87, 96, 98, 89 | 66, 81, 86, 90, 93, 83 | 61, 78, 85, 89, 92, 81 | 84 |
| STD10 | 210, 368, 526, 683, 840, average | 76, 85, 88, 90, 94, 87 | 73, 81, 85, 88, 90, 83 | 60, 76, 83, 85, 90, 79 | 83 |

Two economically important grass weeds, LOLMG and LOLPE, were present in this experiment. Two dry formulations containing diammonium oxalate, 942A2W and 944U7M, were slightly less efficacious compared to the liquid standard STD6 and a commercial dry standard (STD10) against these grasses. Those standards were also equal to or slightly better than 942A2W AND 944U7M in this experiment.

The compositions of Table 49A were applied to TRZAV, AVESA, annual LOLMG and LOLPE plants in a field trial at rates of 200, 300 and 400 g a.e./ha done in Washington County, Mississippi. Results, averaged for all replicates of each treatment and across all rates of application for each plant species (reported as the fourth value), as well as an overall average across all plant species, are shown in Table 49D.

TABLE 49D

| | | % Weed Control | | | | |
|---|---|---|---|---|---|---|
| Composition | Rate (g/ha) | TRZAV | AVESA | LOLMG | LOLPE | Overall Ave. |
| 942A2W | 200, 300, 400, average | 34, 53, 55, 47 | 35, 55, 56, 49 | 36, 54, 55, 48 | 24, 33, 40, 32 | 44 |
| 943E4B | 200, 300, 400, average | 50, 60, 68, 59 | 46, 58, 73, 59 | 44, 53, 65, 54 | 24, 34, 49, 35 | 52 |
| 944U7M | 200, 300, 400, average | 36, 50, 59, 48 | 39, 50, 58, 49 | 41, 48, 58, 49 | 23, 35, 41, 33 | 45 |
| 946L3J | 200, 300, 400, average | 56, 60, 74, 63 | 54, 59, 74, 62 | 53, 59, 73, 61 | 28, 41, 50, 40 | 57 |
| 947A0P | 200, 300, 400, average | 56, 66, 80, 68 | 53, 63, 78, 64 | 54, 63, 78, 64 | 29, 43, 50, 40 | 59 |
| 948V5N | 200, 300, 400, average | 43, 63, 63, 56 | 36, 56, 60, 51 | 44, 59, 69, 57 | 21, 39, 47, 36 | 50 |
| STD6 | 200, 300, 400, average | 55, 71, 71, 66 | 51, 68, 70, 63 | 45, 61, 69, 58 | 23, 41, 41, 35 | 56 |
| 632M7A | 200, 300, 400, average | 49, 64, 70, 61 | 49, 63, 66, 59 | 45, 61, 63, 56 | 25, 39, 45, 36 | 53 |
| STD10 | 200, 300, 400, average | 45, 65, 75, 62 | 45, 61, 79, 62 | 45, 60, 70, 58 | 25, 40, 49, 38 | 55 |

In this particular test an enhancement in efficacy was not derived from the addition of diammonium oxalate to the given formulations.

The compositions of Table 49A were applied to TRZVX, AVESS, LOLMG and LOLPE plants at rates of 150, 250, 350, 450 and 550 g a.e./ha in a field trial done in Washington County, Mississippi. Results, averaged for all replicates of each treatment and across all rates of application for each plant species (reported as the sixth value), as well as an overall average across all plant species, are shown in Table 49E.

TABLE 49E

| | | % Weed Control | | | | |
|---|---|---|---|---|---|---|
| Comp. | Rate (g/ha) | TRZVX | AVESS | LOLMG | LOLPE | Overall Ave. |
| 942A2W | 150, 250, 350, 450, 550, average | 51, 58, 80, 83, 89, 72 | 56, 70, 84, 91, 95, 79 | 50, 53, 66, 79, 84, 66 | 34, 39, 58, 70, 73, 55 | 68 |
| 943E4B | 150, 250, 350, 450, 550, average | 51, 59, 76, 83, 89, 72 | 58, 76, 83, 94, 96, 81 | 53, 59, 75, 84, 84, 71 | 39, 43, 60, 68, 74, 57 | 70 |
| 944U7M | 150, 250, 350, 450, 550, average | 54, 65, 74, 81, 85, 72 | 59, 76, 85, 92, 94, 81 | 51, 59, 94, 79, 81, 67 | 31, 43, 59, 70, 69, 54 | 69 |
| 946L3J | 150, 250, 350, 450, 550, average | 54, 61, 76, 85, 82, 72 | 59, 81, 88, 96, 96, 84 | 56, 63, 75, 84, 86, 73 | 35, 50, 66, 79, 84, 63 | 73 |
| 947A0P | 150, 250, 350, 450, 550, average | 55, 64, 72, 78, 84, 71 | 61, 80, 84, 93, 96, 83 | 53, 63, 74, 80, 85, 71 | 45, 54, 68, 74, 81, 64 | 72 |
| 948V5N | 150, 250, 350, 450, 550, average | 55, 65, 69, 78, 86, 71 | 60, 78, 79, 91, 95, 81 | 50, 61, 68, 80, 86, 69 | 36, 44, 64, 71, 74, 58 | 69 |
| STD6 | 150, 250, 350, 450, 550, average | 53, 63, 78, 81, 86, 72 | 60, 80, 84, 93, 95, 82 | 54, 60, 68, 80, 80, 68 | 39, 46, 56, 68, 73, 57 | 70 |
| 632M7A | 150, 250, 350, 450, 550, average | 58, 63, 78, 84, 89, 74 | 60, 80, 89, 94, 96, 84 | 51, 64, 78, 80, 86, 72 | 35, 45, 64, 69, 75, 58 | 72 |
| STD10 | 150, 250, 350, 450, 550, average | 55, 664, 71, 78, 88, 71 | 61, 78, 88, 91, 98, 83 | 53, 60, 71, 84, 85, 71 | 34, 46, 63, 68, 75, 57 | 70 |

Four grassy species were included in this field test completed in Mississippi. In this particular test an enhancement in efficacy was not derived from the addition of diammonium oxalate to the given formulations.

The compositions of Table 49A were applied to CRUNU and TRZVX plants at rates of 150, 390, 650, and 910 g a.e./ha in a field trial done in Gillespie County, Texas. Results, averaged for all replicates of each treatment and across all rates of application for each plant species (reported as the fifth value), as well as an overall average across all plant species, are shown in Table 49F.

TABLE 49F

| | | % Weed Control | | |
|---|---|---|---|---|
| Composition | Rate (g/ha) | CRUNU | TRZVX | Overall Ave. |
| 942A2W | 150, 390, 650, 910, average | 23, 47, 76, 91, 60 | 44, 95, 100, 97, 84 | 72 |
| 943E4B | 150, 390, 650, 910, average | 23, 50, 79, 84, 59 | 44, 88, 99, 99, 82 | 71 |
| 944U7M | 150, 390, 650, 910, average | 20, 60, 72, 94, 62 | 40, 96, 94, 100, 82 | 73 |
| 946L3J | 150, 390, 650, 910, average | 22, 48, 79, 87, 59 | 43, 92, 99, 100, 83 | 72 |
| 947A0P | 150, 390, 650, 910, average | 20, 58, 78, 91, 59 | 37, 91, 99, 100, 82 | 72 |
| 948V5N | 150, 390, 650, 910, average | 23, 65, 70, 91, 64 | 41, 92, 95, 100, 82 | 74 |
| STD6 | 150, 390, 650, 910, average | 22, 41, 73, 90, 57 | 40, 92, 98, 100, 83 | 70 |
| 632M7A | 150, 390, 650, 910, average | 23, 51, 79, 92, 63 | 39, 90, 96, 99, 81 | 74 |

In this study completed in Texas, all formulations provided at least 85% control of TRZVX at the second lowest rate of application, 390 g a.e./ha. Control of CRUNU, a tough biennial weed, required higher rates of application for commercial control; every formulation controlled this weed at 910 g a.e./ha, except for formulation 943E4B, constructed with ammonium sulfate, rather than diammonium oxalate.

The compositions of Table 49A were applied to SECCW plants at rates of 131, 158, 184, and 210 g a.e./ha in a field trial done in Baldwin county Alabama. Results, averaged for all replicates of each treatment for each plant species, as well as an overall average for all of the plant species, are shown in Table 49G.

TABLE 49G

| Composition | % Weed Control SECCW |
|---|---|
| 942A2W | 38, 56, 68, 71, 58 |
| 943E4B | 36, 56, 63, 71, 56 |
| 944U7M | 37, 56, 68, 71, 58 |
| 946L3J | 43, 57, 72, 75, 62 |
| 947A0P | 43, 58, 71, 78, 62 |
| 948V5N | 38, 57, 71, 76, 61 |
| STD6 | 41, 59, 70, 73, 60 |
| 632M7A | 42, 57, 67, 73, 59 |
| STD10 | 41, 55, 65, 76, 59 |

Another over-wintered cereal, SECCW was targeted in this field test in Alabama. The lowest performing formulation, 943E4B, was constructed with ammonium sulfate and did not contain diammonium oxalate.

Data from the experiments conducted for Example 49 were pooled and analyzed with the pared t-test to examine overall effects of these formulations compared to the STD6 liquid formulation.

All three formulations containing diammonium oxalate (942A2W, 944U7M and 948V5N) were significantly less efficacious than STD6 against narrow leaf species. (44U7M was significantly more efficacious than STD6 on broadleaf species. 942A2W and 948V5N could not be distinguished from this standard on the broadleaf species in this experiment.

Example 50

The field efficacy of ammonium glyphosate dry formulations containing a cationic:nonionic surfactant system and inerts was evaluated. Compositions were prepared containing ammonium, potassium or IPA glyphosate salt, reported in % wt a.e., and excipient ingredients, reported a w/w % unless otherwise indicated, as shown in Table 50A. Another composition, 944U7M (Table 49A) was also evaluated in this example.

TABLE 50A

| Comp. | gly salt | [gly] | Cmpnt 1 | wt % | Cmpnt 2 | wt % |
|---|---|---|---|---|---|---|
| 148Y5V | Amm | 68.0 | CIS16 | 5.7 | NIS7 | 7.9 |
| 149P8M | Amm | 68.0 | CIS19 | 5.7 | NIS7 | 7.9 |
| 483Q1D | Amm | 68.0 | CIS16 | 5.7 | NIS1 | 7.9 |
| 150P4B | Amm | 65.0 | CIS16 | 8.0 | NIS1 | 8.0 |
| 151O8W | Amm | 65.0 | CIS19 | 8.0 | NIS13 | 8.0 |
| 152K3N | Amm | 62.0 | CIS16 | 8.0 | NIS1 | 8.0 |
| 153C6E | Amm | 62.0 | CIS19 | 8.0 | NIS13 | 8.0 |
| 154T6B | Amm | 60.0 | CIS16 | 8.0 | NIS1 | 8.0 |
| 155L1J | Amm | 60.0 | CIS19 | 8.0 | NIS13 | 8.0 |
| STD4 | Amm | 68.0 | CIS21 | 21.0 | — | — |
| STD9 | Amm | 72.0 | CIS2 | 21.0 | — | — |

TABLE 50A-continued

| Comp. | Cmpnt 3 | wt % | Cmpnt 4 | wt % | Cmpnt 5 | wt % |
|---|---|---|---|---|---|---|
| 148Y5V | OTH1 | 8.3 | OTH17 | 0.4 | OTH18 | 0.1 |
| 149P8M | OTH1 | 8.3 | OTH17 | 0.4 | OTH18 | 0.1 |
| 483Q1D | OTH1 | 8.3 | OTH17 | 0.4 | OTH18 | 0.1 |
| 150P4B | OTH1 | 9.0 | OTH17 | 0.4 | OTH18 | 0.1 |
| 151O8W | OTH1 | 9.0 | OTH17 | 0.4 | OTH18 | 0.1 |
| 152K3N | OTH1 | 12.5 | OTH17 | 0.4 | OTH18 | 0.1 |
| 153C6E | OTH1 | 12.5 | OTH17 | 0.4 | OTH18 | 0.1 |
| 154T6B | OTH1 | 15.0 | OTH17 | 0.4 | OTH18 | 0.1 |
| 155L1J | OTH1 | 15.0 | OTH17 | 0.4 | OTH18 | 0.1 |
| STD4 | — | — | OTH17 | 0.4 | — | — |
| STD9 | — | — | OTH17 | 0.4 | — | — |

The compositions of Table 50A were applied to IPOLA and ABUTH plants at rates of 350, 475, 600 and 725 g a.e./ha in a field trial done in Washington county Mississippi. Results, averaged for all replicates of each treatment and across all rates of application for each plant species (reported as the fifth value), as well as an overall average across all plant species, are shown in Table 50B.

TABLE 50B

| | % Weed Control | | |
|---|---|---|---|
| Comp. | IPOLA | ABUTH | Overall Ave. |
| 148Y5V | 84, 88, 93, 96, 90 | 94, 95, 99, 100, 97 | 93 |
| 149P8M | 84, 86, 91, 94, 89 | 95, 98, 99, 100, 98 | 93 |
| 483Q1D | 86, 88, 93, 99, 91 | 94, 99, 100, 100, 98 | 95 |
| 944U7M | 84, 88, 95, 95, 90 | 94, 98, 100, 100, 98 | 94 |
| 150P4B | 84, 88, 91, 93, 89 | 93, 100, 100, 99, 98 | 93 |
| 151O8W | 84, 88, 95, 96, 91 | 94, 96, 99, 100, 97 | 94 |
| 152K3N | 83, 86, 94, 94, 89 | 93, 99, 99, 100, 98 | 93 |
| 153C6E | 83, 88, 93, 93, 89 | 93, 99, 99, 100, 98 | 93 |
| 154T6B | 84, 85, 94, 95, 89 | 95, 96, 100, 100, 98 | 94 |
| 155L1J | 85, 90, 93, 94, 90 | 94, 96, 100, 100, 98 | 94 |
| STD4 | 84, 88, 94, 95, 90 | 90, 93, 100, 99, 95 | 93 |
| STD9 | 88, 91, 95, 94, 92 | 93, 95, 96, 100, 96 | 93 |

Two difficult to control annual broadleaf weeds, ABUTH and IPOLA, were targeted in this test. Formulations were similarly effective against ABUTH, as all of them controlled this weed at 350 g a.e./ha. In general, most of the formulations provided commercially acceptable IPOLA control at 475 g a.e./ha. However, three formulations provided a slight efficacy advantage against IPOLA, providing control at 350 g a.e./ha, including the commercial formulation STD9, 483QID and 155LIJ. 483QID is comprised of 68% glyphosate acid, with 8.2% diammonium oxalate, and only 13.6% total surfactant load. With formulation 155LIJ the glyphosate content was decreased to 60%, while the diammonium oxalate content was increased to 15%, and an additional 16% total surfactant load was included. STD9 contains 72% glyphosate with 16.5% TAM 20EO surfactant.

The compositions of Table 50A were applied to IPOLA, ABUTH and ECHCG plants at rates of 350, 475, 600 and 725 g a.e./ha in a field trial done in Washington County, Mississippi. Results, averaged for all replicates of each treatment and across all rates of application for each plant species (reported as the fifth value), as well as an overall average across all plant species, are shown in Table 50C.

TABLE 50C

| Composition | % Weed Control | | | |
|---|---|---|---|---|
| | IPOLA | ABUTH | ECHCG | Overall Ave. |
| 148Y5V | 76, 85, 86, 88, 84 | 86, 94, 91, 95, 92 | 100, 100, 100, 100, 100 | 92 |
| 149P8M | 81, 86, 86, 88, 85 | 78, 89, 91, 93, 88 | 100, 100, 100, 100, 100 | 91 |
| 483Q1D | 74, 83, 86, 86, 82 | 78, 93, 94, 94, 89 | 100, 100, 100, 100, 100 | 91 |
| 944U7M | 74, 88, 88, 88, 84 | 79, 90, 91, 93, 88 | 100, 100, 100, 100, 100 | 91 |
| 150P4B | 78, 84, 85, 91, 84 | 79, 90, 91, 94, 88 | 100, 100, 100, 100, 100 | 91 |
| 151O8W | 78, 84, 85, 89, 84 | 83, 94, 94, 95, 91 | 100, 100, 100, 100, 100 | 92 |
| 152K3N | 74, 81, 86, 89, 83 | 75, 85, 90, 95, 86 | 100, 100, 100, 100, 100 | 90 |
| 153C6E | 81, 84, 84, 85, 83 | 78, 91, 90, 94, 88 | 100, 100, 100, 100, 100 | 91 |
| 154T6B | 78, 84, 85, 85, 83 | 78, 85, 94, 96, 88 | 100, 100, 100, 100, 100 | 90 |
| 155L1J | 69, 80, 85, 89, 81 | 81, 89, 93, 94, 89 | 100, 100, 100, 100, 100 | 90 |
| STD4 | 78, 84, 85, 89, 84 | 83, 90, 91, 91, 89 | 100, 100, 100, 100, 100 | 91 |
| STD9 | 80, 84, 85, 90, 85 | 81, 88, 93, 94, 89 | 100, 100, 100, 100, 100 | 91 |

Tough broadleaf weeds, IPOLA and ABUTH were targeted in this test completed in Mississippi. In addition, ECHCG was also included as a common narrowleaf weed. All formulations provided perfect control (100%) of ECHCG, at the lowest rate of application, 350 g a.e./ha. Both of the commercial standard formulations, STD4 and STD9 controlled ABUTH at 475 g a.e./ha and IPOLA at 600 g a.e./ha. All of the experimental formulations containing diammonium oxalate were equivalent to the standards against ABUTH, despite lower glyphosate loadings.

Three formulations controlled IPOLA at 475 g a.e./ha and were thus superior to the standards: 148Y5V, 149P8M, and 944U7M. All three of the aforementioned formulations contained 68% glyphosate, but efficacy benefitted from the addition of diammonium oxalate.

The compositions of Table 50A were applied to IPOLA, ABUTH and ECHCG plants at rates of 400, 525, 650 and 755 g a.e./ha in a field trial done in Washington County, Mississippi. Results, averaged for all replicates of each treatment and across all rates of application for each plant species (reported as the fifth value), as well as an overall average across all plant species, are shown in Table 50D.

Difficult-to-control broadleaf weeds, IPOLA and ABUTH, were targeted in this test. In addition, ECHCG was also included as a common narrowleaf weed. All formulations provided perfect control (100%) of ECHCG at the lowest rate of application, 350 g a.e./ha.

Commercial standards STD4 and STD9 required 725 g a.e./ha to provide commercial control of ABUTH. Only one of the ten experimental formulations failed to provide superior ABUTH control compared to the standards, and that was 154T6B. Eight of the formulations controlled ABUTH at 600 g a.e./ha: 149P8M, 483Q1D, 944U7M, 150P4B, 151O8W, 152K3N, 153C6E and 155L1J. Formulation 148Y5V controlled ABUTH at 475 g a.e./ha, which is 50% of the rate required by STD4 and STD9 for control of the same weed.

STD4 was more efficacious than STD9 against IPOLA in this field trial, with control achieved at 475 and 600 g a.e./ha, respectively. Relative to STD4, which controlled IPOLA at 475 g a.e./ha, six of the ten experimental formulations were similarly efficacious, being 148Y5V, 483Q1D, 944U7M, 150P4B, 151O8W and 155L1J. It is notable that formulation 155L1J, with only 60% glyphosate, was capable of providing excellent IPOLA control, despite lower glyphosate rates.

TABLE 50D

| Composition | % Weed Control | | | |
|---|---|---|---|---|
| | IPOLA | ABUTH | ECHCG | Overall Ave. |
| 148Y5V | 81, 86, 89, 90, 87 | 73, 85, 85, 93, 84 | 100, 100, 100, 100, 100 | 90 |
| 149P8M | 79, 84, 89, 90, 85 | 65, 81, 85, 89, 80 | 100, 100, 100, 100, 100 | 88 |
| 483Q1D | 83, 86, 89, 90, 87 | 75, 81, 89, 93, 84 | 100, 100, 100, 100, 100 | 90 |
| 944U7M | 83, 89, 91, 91, 88 | 74, 83, 86, 94, 84 | 100, 100, 100, 100, 100 | 91 |
| 150P4B | 80, 86, 89, 94, 87 | 71, 81, 90, 96, 85 | 100, 100, 100, 100, 100 | 91 |
| 151O8W | 84, 88, 90, 94, 89 | 73, 80, 88, 95, 84 | 100, 100, 100, 100, 100 | 91 |
| 152K3N | 80, 84, 91, 93, 87 | 70, 84, 88, 89, 83 | 100, 100, 100, 100, 100 | 90 |
| 153C6E | 79, 84, 93, 93, 87 | 69, 83, 86, 94, 83 | 100, 100, 100, 100, 100 | 90 |
| 154T6B | 79, 84, 90, 95, 87 | 69, 78, 83, 94, 81 | 100, 100, 100, 100, 100 | 89 |
| 155L1J | 83, 88, 91, 93, 88 | 70, 81, 85, 91, 82 | 100, 100, 100, 100, 100 | 90 |
| STD4 | 78, 85, 89, 91, 86 | 66, 81, 84, 90, 80 | 100, 100, 100, 100, 100 | 89 |
| STD9 | 81, 84, 86, 89, 85 | 70, 78, 84, 91, 81 | 100, 100, 100, 100, 100 | 89 |

The compositions of Table 50A were applied to TRZVX, AVESX, LOLMG and LOLPE plants at rates of 250, 350, 450 and 550 g a.e./ha in a field trial done in Washington County, Mississippi. Results, averaged for all replicates of each treatment and across all rates of application for each plant species (reported as the fifth value), as well as an overall average across all plant species, are shown in Table 50E.

TABLE 50E

| | % Weed Control | | | | |
|---|---|---|---|---|---|
| Composition | TRZVX | AVESX | LOLMG | LOLPE | Overall ave. |
| 148Y5V | 63, 60, 73, 81, 60 | 63, 80, 88, 94, 81 | 45, 51, 63, 63, 55 | 40, 45, 59, 59, 51 | 64 |
| 149P8M | 61, 71, 76, 85, 73 | 71, 79, 90, 95, 84 | 55, 61, 74, 78, 67 | 41, 51, 60, 69, 55 | 70 |
| 483Q1D | 59, 58, 71, 76, 66 | 70, 75, 90, 93, 82 | 45, 54, 63, 68, 57 | 43, 49, 60, 60, 53 | 65 |
| 944U7M | 60, 61, 74, 79, 68 | 66, 78, 91, 93, 82 | 43, 49, 65, 66, 56 | 40, 45, 54, 59, 49 | 64 |
| 150P4B | 54, 56, 75, 79, 66 | 66, 74, 91, 95, 82 | 46, 50, 64, 65, 56 | 41, 43, 56, 58, 49 | 63 |
| 151O8W | 60, 68, 76, 81, 71 | 73, 84, 88, 94, 84 | 48, 58, 66, 69, 60 | 43, 48, 56, 60, 52 | 67 |
| 152K3N | 59, 61, 80, 80, 70 | 66, 74, 93, 91, 81 | 41, 46, 63, 65, 54 | 40, 44, 54, 59, 49 | 63 |
| 153C6E | 58, 60, 75, 84, 69 | 65, 80, 93, 95, 83 | 44, 51, 65, 69, 57 | 36, 48, 55, 64, 51 | 65 |
| 154T6B | 56, 58, 78, 80, 68 | 69, 74, 91, 93, 82 | 44, 49, 69, 69, 58 | 39, 45, 59, 61, 51 | 65 |
| 155L1J | 60, 63, 78, 83, 71 | 71, 79, 91, 95, 84 | 46, 50, 69, 71, 59 | 46, 49, 58, 63, 54 | 67 |
| STD4 | 58, 64, 71, 81, 68 | 64, 79, 88, 94, 81 | 49, 60, 70, 76, 64 | 38, 48, 53, 61, 50 | 66 |
| STD9 | 54, 61, 74, 76, 66 | 65, 79, 88, 93, 81 | 50, 64, 74, 74, 65 | 39, 49, 55, 58, 50 | 66 |

Four grass species were targeted in this test in Mississippi. Few differences were detected among formulations in this trial. No formulation proved capable of controlling either LOLMG or LOLPE at the rates applied. All formulations provided control of AVESX at 450 g a.e./ha. Only one formulation provided control of TRZVX at 550 g a.e./ha, 149P8M. When grand means were compared in this study, 155L1J, 149P8M and 151O8W were superior to STD4 and STD9.

The compositions of Table 50A were applied to CAPSS plants at rates of 275, 400, 525 and 650 g a.e./ha in a field trial done in Washington County, Mississippi. Results, averaged for all replicates of each treatment for each plant species, as well as an overall average for all of the plant species, are shown in Table 50F.

TABLE 50F

| | % Weed Control |
|---|---|
| Composition | CAPSS |
| 148Y5V | 75, 74, 83, 89, 80 |
| 149P8M | 74, 74, 81, 89, 79 |
| 483Q1D | 74, 79, 80, 86, 80 |
| 944U7M | 69, 84, 85, 86, 81 |
| 150P4B | 74, 78, 81, 86, 80 |
| 151O8W | 69, 74, 81, 84, 77 |
| 152K3N | 73, 75, 76, 86, 78 |
| 153C6E | 76, 79, 80, 89, 81 |
| 154T6B | 71, 78, 81, 86, 79 |

TABLE 50F-continued

| | % Weed Control |
|---|---|
| Composition | CAPSS |
| 155L1J | 73, 78, 85, 88, 81 |
| STD4 | 73, 78, 80, 84, 78 |
| STD9 | 69, 76, 78, 85, 77 |

CAPSS, a winter annual broadleaf weed species, was targeted for control in this field test in Mississippi. STD9 provided commercial control of this weed at 650 g a.e./ha and STD4 failed to achieve commercial control at the same rate. Excellent results were achieved with experimental formulations containing diammonium oxalate. Nine of the ten formulations provided commercial control of CAPSS at 650 g a.e./ha. Furthermore, two experimental formulations provided commercial control of this weed at a lower rate of application, 525 g a.e./ha, specifically 944U7M and 155L1J.

The compositions of Table 50A were applied to SIDSP, ABUTH, IPOLA, CASOB and SEBEX plants at rates of 473, 631, 788 and 946 g a.e./ha in a field trial done in Baldwin County, Alabama. The fifth result reported for each plant species represents the average % weed control of the four application rates. Results, averaged for all replicates of each treatment and across all rates of application for each plant species (reported as the fifth value), as well as an overall average across all plant species, are shown in Table 50G.

TABLE 50G

| | % Weed Control | | | | | |
|---|---|---|---|---|---|---|
| Comp. | SIDSP | ABUTH | IPOLA | CASOB | SEBEX | Overall ave. |
| 148Y5V | 94, 97, 96, 99, 97 | 61, 77, 91, 94, 81 | 59, 72, 71, 76, 69 | 61, 68, 74, 75, 69 | 57, 57, 65, 63, 61 | 75 |
| 149P8M | 94, 96, 99, 99, 97 | 65, 73, 78, 86, 75 | 64, 74, 65, 76, 70 | 64, 73, 69, 75, 70 | 57, 61, 66, 65, 62 | 75 |
| 483Q1D | 93, 96, 98, 99, 97 | 69, 72, 86, 91, 79 | 68, 69, 75, 76, 72 | 63, 65, 71, 72, 68 | 58, 59, 64, 66, 61 | 75 |
| 944U7M | 97, 96, 97, 97, 97 | 69, 80, 85, 93, 82 | 64, 70, 70, 74, 70 | 63, 66, 73, 73, 69 | 56, 60, 61, 59, 59 | 75 |
| 150P4B | 94, 97, 98, 99, 97 | 65, 70, 85, 94, 79 | 72, 67, 72, 79, 72 | 65, 68, 70, 75, 69 | 62, 58, 60, 64, 61 | 76 |
| 151O8W | 100, 97, 97, 99, 97 | 62, 76, 85, 89, 78 | 68, 73, 70, 80, 73 | 65, 70, 68, 76, 70 | 56, 60, 62, 66, 61 | 76 |

TABLE 50G-continued

| | % Weed Control | | | | | |
|---|---|---|---|---|---|---|
| Comp. | SIDSP | ABUTH | IPOLA | CASOB | SEBEX | Overall ave. |
| 152K3N | 90, 98, 99, 98, 76 | 65, 74, 82, 94, 79 | 67, 68, 72, 79, 71 | 64, 67, 70, 74, 69 | 56, 56, 63, 66, 60 | 75 |
| 153C6E | 90, 98, 99, 99, 96 | 64, 78, 87, 94, 80 | 66, 71, 70, 74, 70 | 62, 66, 72, 72, 68 | 54, 60, 62, 63, 59 | 75 |
| 154T6B | 93, 91, 99, 99, 95 | 65, 69, 85, 89, 77 | 71, 71, 68, 76, 71 | 62, 68, 71, 73, 68 | 58, 60, 60, 63, 60 | 74 |
| 155L1J | 89, 89, 96, 99, 93 | 72, 76, 90, 89, 81 | 66, 72, 75, 78, 73 | 63, 67, 74, 74, 69 | 56, 58, 62, 61, 59 | 75 |
| STD4 | 89, 96, 96, 99, 95 | 60, 71, 78, 85, 73 | 62, 70, 71, 80, 71 | 63, 69, 70, 72, 68 | 58, 58, 59, 70, 61 | 74 |
| STD9 | 91, 95, 99, 99, 96 | 65, 68, 75, 87, 74 | 68, 73, 70, 76, 71 | 64, 67, 70, 74, 69 | 60, 58, 61, 63, 60 | 74 |

Five difficult-to-control annual broadleaf weeds were included in this field test completed in Alabama. Nine of ten experimental formulations provided higher levels of efficacy than both STD4 and STD9, based upon overall averages. Each of these weeds shows varying susceptibility to glyphosate, but the weed that was targeted for control in this particular field experiment was ABUTH. As such, none of the formulations provided commercial control of IPOLA, CASOB or SEBEX as the rates were too low. All formulations evaluated, including both commercial standards, gave excellent control of SIDSP at all rates of application.

Both standards (STD4 and STD9) controlled ABUTH at the highest rate of application in this study, 946 g a.e./ha. Furthermore, the following six formulations containing diammonium oxalate were superior to the standards in that they controlled ABUTH at an even lower rate of application, 788 g a.e./ha: 148Y5V, 483Q1D, 944U7M, 151O8W, 153C6E and 155 µl J.

The compositions of Table 50A were applied to SIDSP, ABUTH, IPOLA, CASOB and SEBEX plants at rates of 473, 631, 788 and 946 g a.e./ha in a field trial done in Baldwin County, Alabama. The fifth result reported for each plant species represents the average % weed control of the four application rates. Results, averaged for all replicates of each treatment and across all rates of application for each plant species (reported as the fifth value), as well as an overall average across all plant species, are shown in Table 50H.

Five difficult-to-control annual broadleaf weeds were included in this field test completed in Alabama. All ten experimental formulations provided higher levels of efficacy than both STD4 and STD9, based upon overall averages and superior control of ABUTH. Each of these weeds shows varying susceptibility to glyphosate, but the weed that was targeted for control in this particular field experiment was ABUTH. As such, none of the formulations provided commercial control of IPOLA, CASOB or SEBEX. The commercial formulations controlled SIDSP at 631 g a.e./ha, and they failed to control ABUTH, the targeted species.

All ten of the experimental formulations containing diammonium oxalate provided a commercial level of control of ABUTH at 946 g a.e./ha. Three of the experimental formulations stood as being superior for control of ABUTH, with control achieved at 788 g a.e./ha: 483Q1D, 944U7M and 153C6E. Seven of ten experimental formulations were equal to the standards for control of SIDSP, providing control at 631 g a.e./ha. Superior control of SIDSP relative to STD4 and STD9 (control at 473 g a.e./ah) was obtained with two of ten formulations prepared with diammonium oxalate: 483Q1D and 154T6B.

The compositions of Table 50A were applied to LOLMG, LAMAM, LOLPE and ABUTH plants at rates of 473, 631, 788 and 946 g a.e./ha in a field trial done in Baldwin County, Alabama. The fifth result reported for each plant species represents the average % weed control of the four application

TABLE 50H

| | % Weed Control | | | | | |
|---|---|---|---|---|---|---|
| Comp. | SIDSP | ABUTH | IPOLA | CASOB | SEBEX | Overall ave. |
| 148Y5V | 83, 88, 92, 96, 90 | 66, 79, 83, 96, 81 | 67, 69, 71, 74, 70 | 63, 70, 66, 75, 68 | 57, 60, 60, 62, 59 | 74 |
| 149P8M | 82, 86, 93, 98, 90 | 62, 72, 75, 88, 74 | 63, 67, 73, 70, 68 | 58, 65, 70, 77, 67 | 55, 60, 64, 65, 61 | 72 |
| 483Q1D | 87, 88, 95, 98, 92 | 66, 76, 85, 98, 81 | 65, 68, 74, 74, 70 | 63, 68, 69, 79, 69 | 59, 58, 63, 69, 62 | 75 |
| 944U7M | 81, 92, 97, 98, 92 | 66, 78, 85, 99, 82 | 69, 69, 73, 74, 71 | 64, 69, 65, 75, 68 | 54, 56, 63, 65, 59 | 75 |
| 150P4B | 80, 94, 95, 95, 91 | 64, 80, 78, 97, 80 | 65, 71, 72, 74, 70 | 61, 68, 67, 74, 67 | 55, 61, 61, 63, 60 | 74 |
| 151O8W | 80, 95, 99, 93, 92 | 57, 78, 84, 96, 79 | 59, 70, 72, 72, 68 | 55, 70, 66, 75, 66 | 48, 59, 59, 66, 58 | 73 |
| 152K3N | 83, 94, 96, 98, 93 | 64, 77, 79, 95, 79 | 62, 70, 74, 73, 70 | 61, 65, 67, 72, 66 | 55, 60, 59, 65, 60 | 73 |
| 153C6E | 84, 89, 94, 98, 91 | 64, 78, 85, 97, 81 | 62, 72, 73, 75, 70 | 62, 69, 69, 72, 68 | 55, 60, 63, 66, 61 | 74 |
| 154T6B | 85, 90, 92, 96, 91 | 63, 81, 83, 94, 80 | 62, 69, 72, 76, 70 | 59, 64, 68, 73, 66 | 53, 60, 64, 64, 60 | 73 |
| 155L1J | 82, 88, 99, 99, 92 | 62, 77, 84, 91, 78 | 61, 71, 73, 71, 69 | 60, 69, 67, 73, 67 | 53, 63, 61, 66, 61 | 73 |
| STD4 | 83, 87, 96, 90, 89 | 64, 69, 72, 80, 71 | 64, 65, 73, 73, 69 | 62, 64, 66, 73, 66 | 57, 59, 60, 65, 59 | 71 |
| STD9 | 85, 87, 90, 96, 89 | 62, 70, 72, 82, 71 | 62, 67, 70, 73, 68 | 63, 67, 66, 74, 67 | 58, 59, 59, 64, 60 | 71 | rates. Results, averaged for all replicates of each treatment and across all rates of application for each plant species (reported as the fifth value), as well as an overall average across all plant species, are shown in Table 50I.

controlled this weed at 520 g a.e./ha. No benefit was observed with the formulations containing diammonium oxalate in this field study compared to both commercial formulations, STD4 and STD9.

TABLE 50I

% Weed Control

| Comp. | LOLMG | LAMAM | LOLPE | ABUTH | Overall ave. |
|---|---|---|---|---|---|
| 148Y5V | 100, 100, 100, 100, 100, | 100, 100, 100, 100, 100 | 100, 100,100, 100, 100 | 67, 73, 78, 90, 77 | 94 |
| 149P8M | 100, 100, 100, 100, 100 | 100, 100, 100, 100, 100 | 100, 100, 100, 100, 100 | 54, 73, 72, 83, 70 | 93 |
| 483Q1D | 100, 100, 100, 100, 100 | 100, 100, 100, 100, 100 | 100, 100, 100, 100, 100 | 65, 73, 84, 92, 79 | 95 |
| 944U7M | 100, 100, 100, 100, 100 | 100, 100, 100, 100, 100 | 100, 100, 100, 100, 100 | 63, 75, 87, 91, 79 | 95 |
| 150P4B | 100, 100, 100, 100, 100 | 100, 100, 100, 100, 100 | 100, 100, 100, 100, 100 | 66, 79, 84, 96, 81 | 95 |
| 151O8W | 100, 100, 100, 100, 100 | 100, 100, 100, 100, 100 | 100, 100, 100, 100, 100 | 58, 70, 85, 92, 76 | 94 |
| 152K3N | 100, 100, 100, 100, 100 | 100, 100, 100, 100, 100 | 100, 100, 100, 100, 100 | 69, 73, 88, 92, 80 | 95 |
| 153C6E | 100, 100, 100, 100, 100 | 100, 100, 100, 100, 100 | 100, 100, 100, 100, 100 | 60, 75, 86, 95, 79 | 95 |
| 154T6B | 100, 100, 100, 100, 100 | 100, 100, 100, 100, 100 | 100, 100, 100, 100, 100 | 56, 71, 82, 95, 76 | 94 |
| 155L1J | 100, 100, 100, 100, 100 | 100, 100, 100, 100, 100 | 100, 100, 100, 100, 100 | 66, 72, 89, 95, 80 | 95 |
| STD4 | 100, 100, 100, 100, 100 | 100, 100, 100, 100, 100 | 100, 100, 100, 100, 100 | 55, 65, 69, 84, 68 | 92 |
| STD9 | 100, 100, 100, 100, 100 | 100, 100, 100, 100, 100 | 100, 100, 100, 100, 100 | 57, 70, 68, 78, 68 | 92 |

Two grass weeds (LOLMG and LOLPE) were present in this field test completed in Alabama where the difficult-to-control annual broadleaf weed, ABUTH, was targeted. Another broadleaf weed, LAMAM, was also present in the test. Because rates of application were targeted for ABUTH, perfect control of LAMAM, LOLMG and LOLPE (all more susceptible to glyphosate) was achieved with all formulations at the lowest rate of application, 473 g a.e./ha. All ten experimental formulations provided higher levels of efficacy than both STD4 and STD9, based upon overall averages and superior control of ABUTH. STD4 and STD9 failed to provided commercial control of ABUTH at 946 g a.e./ha, the highest rate of application in this particular. Nine of ten experimental formulations containing diammonium oxalate controlled ABUTH at 946 g a.e./ha. Furthermore, five formulations stood out as being superior to the remaining set by providing control of ABUTH at 788 g a.e./ha: 944U7M, 151O8W, 152K3N, 153C6E and 155L1J.

The compositions of Table 50A were applied to TRZVX plants at rates of 260, 390, 520 and 715 g a.e./ha in a field trial done in Gillespie County, Texas. Results, averaged for all replicates of each treatment and across all rates of application for each plant species (reported as the fifth value) are shown in Table 50J.

TABLE 50J

% Weed Control

| Composition | TRZVX |
|---|---|
| 148Y5V | 58, 73, 84, 93, 77 |
| 149P8M | 57, 74, 83, 93, 77 |
| 483Q1D | 56, 72, 82, 92, 75 |
| 944U7M | 58, 73, 84, 94, 77 |
| 150P4B | 60, 77, 84, 94, 79 |
| 151O8W | 60, 74, 84, 94, 78 |
| 152K3N | 58, 72, 84, 93, 77 |
| 153C6E | 58, 73, 84, 91, 77 |
| 154T6B | 57, 72, 83, 92, 77 |
| 155L1J | 57, 72, 84, 93, 76 |
| STD4 | 60, 76, 86, 95, 79 |
| STD9 | 60, 74, 84, 92, 77 |

TRZVX was the target species in this test completed in Texas. All twelve formulations evaluated controlled TRZVX at 715 g a.e./ha, but STD4 was the only formulation that The compositions of Table 50A were applied to OEOLA plants at rates of 780, 1170, 1689 and 2209 g a.e./ha in a field trial done in Gillespie County, Texas. Results, averaged for all replicates of each treatment and across all rates of application for each plant species (reported as the fifth value) are shown in Table 50K.

TABLE 50K

% Weed Control

| Composition | OEOLA |
|---|---|
| 148Y5V | 65, 79, 85, 88, 79 |
| 149P8M | 64, 74, 88, 88, 79 |
| 483Q1D | 67, 73, 82, 88, 77 |
| 944U7M | 64, 76, 81, 90, 78 |
| 150P4B | 66, 77, 83, 85, 78 |
| 151O8W | 68, 75, 84, 90, 79 |
| 152K3N | 64, 76, 87, 91, 80 |
| 153C6E | 64, 73, 84, 91, 78 |
| 154T6B | 66, 79, 82, 89, 79 |
| 155L1J | 64, 73, 80, 88, 76 |
| STD4 | 67, 74, 83, 86, 77 |
| STD9 | 65, 75, 82, 92, 78 |

OEOLA, a difficult-to-control broadleaf perennial species, was targeted in this field test in Texas. STD4 and STD9 provided commercial control of this weed at 2209 g a.e./ha, and all ten of the experimental formulations containing diammonium oxalate matched the standards in efficacy. However, three of the formulations were superior to the standards in that they controlled OEOLA at 1689 g a.e./ha: 148Y5V, 149P8M and 152K3N.

The compositions of Table 50A were applied to CRUNU plants in at rates of 390, 652, 975 and 1170 g a.e./ha in a field trial done in Gillespie County, Texas. Results, averaged for all replicates of each treatment and across all rates of application for each plant species (reported as the fifth value) are shown in Table 50L.

TABLE 50L

| Composition | % Weed Control CRUNU |
|---|---|
| 148Y5V | 53, 57, 76, 78, 66 |
| 149P8M | 33, 59, 67, 78, 59 |
| 483Q1D | 43, 64, 69, 82, 64 |
| 944U7M | 43, 72, 70, 81, 66 |
| 150P4B | 36, 53, 72, 78, 60 |
| 151O8W | 37, 58, 65, 86, 61 |
| 152K3N | 41, 52, 71, 80, 61 |
| 153C6E | 38, 50, 69, 80, 59 |
| 154T6B | 45, 55, 62, 80, 61 |
| 155L1J | 38, 63, 74, 82, 64 |
| STD4 | 35, 50, 78, 76, 60 |
| STD9 | 42, 57, 71, 90, 65 |

CRUNU, a broadleaf perennial species, was targeted in this field test in Texas. STD9 provided control of this weed at 1170 g a.e./ha, while STD4 failed to reach the 85% control threshold. Only one of the experimental diammonium formulations, 151O8W, matched STD9 for control of this weed (at 1170 g a.e./ha).

Data for all experiments conducted with the experimental formulations contained in Example 50 were pooled and analyzed. Results of the analysis revealed that nine of ten experimental formulations were significantly more efficacious than both standards. Formulation 154T6B could not be distinguished from the standards.

Example 51

The field efficacy effect of ammonium glyphosate dry formulations containing a cationic:nonionic surfactant system and inerts was evaluated. Compositions were prepared containing ammonium, potassium or IPA glyphosate salt, reported in % wt a.e., and excipient ingredients, reported a w/w % unless otherwise indicated, as shown in Table 51A. Compositions 483Q1D, 944U7M, 151O8W and 155L1J were prepared as indicated in Table 50A above.

TABLE 51A

| Comp. | gly salt | [gly] | Cmpnt 1 | wt % | Cmpnt 2 | wt % | Cmpnt 3 | wt % |
|---|---|---|---|---|---|---|---|---|
| 874G8W | Amm | 57.0 | CIS19 | 9.0 | NIS13 | 9.0 | OTH1 | 16.5 |
| 875W1I | Amm | 57.0 | CIS19 | 9.0 | NIS13 | 9.0 | OTH1 | 8.5 |
| 876L0S | Amm | 54.0 | CIS19 | 8.5 | NIS18 | 8.5 | OTH1 | 11.0 |
| 877K7A | Amm | 50.0 | CIS19 | 8.0 | NIS13 | 8.0 | OTH1 | 13.0 |
| 878L6H | Amm | 57.0 | CIS19 | 9.0 | NIS13 | 9.0 | OTH1 | 8.5 |
| 879K7T | Amm | 50.0 | CIS19 | 8.0 | NIS13 | 8.0 | OTH1 | 13.0 |
| STD4 | Amm | 68.0 | CIS21 | 21.0 | — | — | — | — |
| STD9 | Amm | 72.0 | CIS21 | 16.5 | — | — | — | — |

| Comp. | Cmpnt 4 | wt % | Cmpnt 5 | wt % | Cmpnt 6 | wt % |
|---|---|---|---|---|---|---|
| 874G8W | OTH17 | 0.4 | OTH18 | 0.1 | — | — |
| 875W1I | OTH17 | 0.4 | OTH18 | 0.1 | OTH21 | 0.9 |
| 876L0S | OTH17 | 0.4 | OTH18 | 0.1 | OTH21 | 10.9 |
| 877K7A | OTH17 | 0.4 | OTH18 | 0.1 | OTH21 | 13.5 |
| 878L6H | OTH17 | 0.4 | OTH18 | 0.1 | OTH21 | 8.0 |
| 879K7T | OTH17 | 0.4 | OTH18 | 0.1 | OTH21 | 13.5 |
| STD4 | OTH17 | 0.4 | — | — | — | — |
| STD9 | OTH17 | 0.4 | — | — | — | — |

The compositions of Table 51A were applied to LACSE plants at rates of 260, 390, 585 and 780 g a.e./ha in a field trial done in Warren County, Illinois. Results, averaged for all replicates of each treatment and across all rates of application for each plant species (reported as the fifth value) are shown in Table 51B.

TABLE 51B

| Composition | % Weed Control LACSE |
|---|---|
| 483Q1D | 68, 73, 80, 92, 78 |
| 944U7M | 63, 70, 85, 94, 78 |
| 151O8W | 65, 77, 90, 86, 79 |
| 155L1J | 66, 73, 79, 96, 79 |
| 874G8W | 65, 67, 77, 83, 73 |
| 875W1I | 65, 72, 85, 89, 78 |
| 876L0S | 66, 73, 75, 78, 73 |
| 877K7A | 58, 71, 76, 83, 72 |
| 878L6H | 65, 74, 86, 86, 78 |
| 879K7T | 66, 73, 84, 93, 79 |
| STD4 | 72, 76, 80, 91, 80 |
| STD9 | 65, 73, 89, 87, 79 |

LACSE, a difficult-to-control broadleaf biennial species, was targeted in this field test in Illinois. STD4 controlled LACSE at 780 g a.e./ha and STD9 was more efficacious, providing control at 585 g a.e./ha. Four of the experimental formulations containing diammonium oxalate were as efficacious as STD9: 944U7M, 151O8W, 875W1I and 878L6H. Three of the experimental formulations containing diammonium oxalate were as efficacious as STD4 for control of LACSE: 483Q1D, 875W1I and 879K7T.

The compositions of Table 51A were applied to AMBTR plants in at rates of 260, 455, 650 and 845 g a.e./ha in a field trial done in Warren County, Illinois. Results, averaged for all replicates of each treatment and across all rates of application for each plant species (reported as the fifth value) are shown in Table 51C.

TABLE 51C

| Composition | % Weed Control AMBTR |
|---|---|
| 483Q1D | 46, 75, 76, 83, 70 |
| 944U7M | 51, 63, 78, 81, 68 |
| 151O8W | 55, 69, 76, 83, 71 |
| 155L1J | 57, 68, 82, 79, 71 |
| 874G8W | 51, 73, 65, 82, 67 |
| 875W1I | 57, 62, 73, 80, 68 |
| 876L0S | 47, 66, 74, 78, 66 |
| 877K7A | 51, 59, 85, 82, 69 |
| 878L6H | 59, 70, 80, 84, 73 |
| 879K7T | 55, 71, 73, 81, 70 |
| STD4 | 49, 57, 67, 81, 65 |
| STD9 | 43, 61, 73, 76, 64 |

AMBTR was targeted in this study completed in Illinois. At the highest rate of application in this field study, 845 g a.e./ha, none of the formulations reached the 85% control threshold. However, when weed efficacy values were averaged across all rates of application, all ten of the experimental formulations containing diammonium oxalate were more efficacious than both STD4 and STD9.

The compositions of Table 51A were applied to TRZVX plants at rates of 325, 585, 845 and 1040 g a.e./ha in a field trial done in Warren County, Illinois. Results, averaged for all replicates of each treatment and across all rates of application for each plant species (reported as the fifth value) are shown in Table 51D.

TABLE 51D

| Composition | % Weed Control TRZVX |
|---|---|
| 483Q1D | 44, 59, 79, 76, 65 |
| 944U7M | 45, 67, 71, 81, 66 |
| 151O8W | 47, 68, 82, 81, 69 |
| 155L1J | 44, 64, 80, 85, 68 |
| 874G8W | 46, 66, 75, 83, 67 |
| 875W1I | 46, 58, 76, 81, 65 |
| 876L0S | 45, 56, 74, 79, 63 |
| 877K7A | 40, 59, 68, 74, 60 |
| 878L6H | 48, 58, 78, 82, 66 |
| 879K7T | 55, 59, 79, 88, 70 |
| STD4 | 48, 72, 78, 82, 70 |
| STD9 | 47, 68, 71, 85, 68 |

TRZVX was the target species in this test completed in Illinois. Neither standard controlled this weed at the highest rate of application, 1040 g a.e./ha. Two of the ten experimental formulations containing diammonium oxalate, 155L1J and 879K7T, reached the 85% commercial control threshold at 1040 g a.e./ha.

The compositions of Table 51A were applied to POLCO plants in at rates of 535, 780, 975 and 1235 g a.e./ha in a field trial done in Warren County, Illinois. Results, averaged for all replicates of each treatment and across all rates of application for each plant species (reported as the fifth value) are shown in Table 51E.

TABLE 51E

| Composition | % Weed Control POLCO |
|---|---|
| 483Q1D | 56, 56, 72, 79, 66 |
| 944U7M | 67, 64, 68, 77, 69 |
| 151O8W | 53, 64, 70, 83, 68 |
| 155L1J | 57, 61, 73, 80, 68 |
| 874G8W | 37, 64, 67, 79, 62 |
| 875W1I | 42, 54, 62, 75, 58 |
| 876L0S | 51, 62, 71, 73, 64 |
| 877K7A | 51, 63, 65, 73, 63 |
| 878L6H | 58, 58, 83, 89, 72 |
| 879K7T | 58, 72, 77, 86, 73 |
| STD4 | 49, 67, 70, 73, 64 |
| STD9 | 43, 51, 62, 71, 57 |

POLCO, a difficult-to-control annual broadleaf weed was targeted in this test in Illinois. Neither standard STD4 nor STD9 provided commercial control of this species at 1235 g a.e./ha, the highest rate applied in this study. Two of the experimental formulations containing diammonium oxalate, 878L6H and 879K7T, were superior to all other formulations, being the only ones to reach the 85% threshold (commercial control) at 1235 g a.e./ha.

The compositions of Table 51A were applied to IPOLA and ABUTH plants at rates of 500, 650, 800 and 950 g a.e./ha in a field trial done in Washington County, Mississippi. Results, averaged for all replicates of each treatment and across all rates of application for each plant species (reported as the fifth value), as well as an overall average across all plant species, are shown in Table 51F.

TABLE 51F

| | % Weed Control | | |
|---|---|---|---|
| Composition | IPOLA | ABUTH | overall ave. |
| 483Q1D | 79, 85, 95, 97, 89 | 99, 100, 100, 100, 100 | 94 |
| 944U7M | 78, 86, 96, 97, 89 | 98, 100, 100, 100, 99 | 94 |
| 151O8W | 78, 89, 90, 99, 89 | 100, 100, 100, 100, 100 | 94 |
| 155L1J | 74, 85, 86, 95, 85 | 95, 100, 100, 100, 99 | 92 |
| 874G8W | 75, 88, 89, 91, 86 | 98, 100, 100, 100, 99 | 93 |
| 875W1I | 78, 91, 95, 95, 89 | 94, 100, 100, 100, 98 | 94 |
| 876L0S | 79, 88, 92, 94, 88 | 93, 100, 100, 100, 98 | 93 |
| 877K7A | 79, 84, 88, 89, 85 | 91, 100, 100, 100, 98 | 91 |
| 878L6H | 79, 89, 93, 98, 90 | 96, 100, 99, 100, 99 | 94 |
| 879K7T | 79, 93, 99, 100, 92 | 95, 100, 100, 100, 999 | 96 |
| STD4 | 81, 91, 95, 96, 91 | 93, 100, 100, 100, 98 | 94 |
| STD9 | 84, 89, 91, 96, 90 | 98, 100, 100, 100, 99 | 95 |

Difficult-to-control broadleaf weeds, IPOLA and ABUTH, were targeted in this test completed in Mississippi. All formulations, including STD4, STD9 and all the experimental formulations, demonstrated excellent control of ABUTH at the lowest rate of application, 500 g a.e./ha. Both standards provided commercial control of IPOLA at 650 g a.e./ha, and their efficacy was matched by nine of the ten experimental formulations containing diammonium oxalate, with only 877K7A failing to reach the threshold.

The compositions of Table 51A were applied to IPOLA, ABUTH and SEBEX plants at rates of 450, 600, 750 and 900 g a.e./ha in a trial done in Washington County, Mississippi. Results, averaged for all replicates of each treatment and across all rates of application for each plant species (reported as the fifth value), as well as an overall average across all plant species, are shown in Table 51G.

TABLE 51G

| | % Weed Control | | | |
|---|---|---|---|---|
| Comp. | IPOLA | ABUTH | SEBEX | overall ave. |
| 483Q1D | 68, 85, 88, 93, 83 | 96, 100, 100, 100, 99 | 100, 100, 100, 100, 100 | 94 |
| 944U7M | 70, 84, 85, 94, 83 | 89, 100, 100, 100, 97 | 100, 100, 100, 100, 100 | 93 |
| 151O8W | 70, 78, 90, 92, 82 | 93, 98, 100, 100, 98 | 100, 100, 100, 100, 100 | 93 |
| 155L1J | 75, 76, 79, 90, 80 | 98, 100, 100, 100, 99 | 98, 100, 99, 100, 99 | 93 |
| 874G8W | 70, 76, 81, 89, 79 | 98, 99, 99, 100, 99 | 100, 100, 99, 100, 100 | 93 |
| 875W1I | 75, 79, 81, 90, 81 | 94, 100, 100, 100, 98 | 99, 100, 100, 100, 100 | 93 |
| 876L0S | 68, 76, 81, 88, 78 | 94, 100, 100, 100, 98 | 95, 100, 100, 100, 99 | 92 |
| 877K7A | 64, 76, 84, 88, 78 | 89, 96, 100, 100, 96 | 98, 100, 100, 100, 99 | 91 |
| 878L6H | 69, 75, 86, 94, 81 | 93, 95, 99, 100, 97 | 100, 100, 100, 100, 100 | 93 |
| 879K7T | 78, 85, 90, 93, 86 | 98, 99, 100, 100, 99 | 100, 100, 100, 100, 100 | 95 |
| STD4 | 58, 69, 74, 91, 73 | 58, 86, 94, 100, 84 | 73, 96, 100, 100, 92 | 83 |
| STD9 | 74, 81, 84, 89, 82 | 79, 98, 98, 99, 93 | 100, 100, 99, 100, 100 | 92 |

Three difficult-to-control annual broadleaf weeds were included in this field test completed in Mississippi. Each of these weeds shows varying susceptibility to glyphosate, but the weed that was targeted for control in this particular field experiment was IPOLA. As such, excellent control of ABUTH and nearly perfect control of SEBEX was observed with all ten experimental formulations containing diammonium oxalate. STD4 was less performant in this field study compared to STD9. STD9 provided commercial control of ABUTH at 600 g a.e./ha and IPOLA at 900 g a.e./ha. Every experimental formulation containing diammonium oxalate was superior to STD9 for control of ABUTH, providing at least 85% control of this weed at 450 g a.e./ha. Based on the overall average, all ten experimental formulations were superior to STD4. Eight of ten formulations containing diammonium oxalate were superior to STD9, based upon overall averages.

The compositions of Table 51A were applied to IPOLA, ABUTH, CASOB and SEBEX plants at rates of 350, 475, 600 and 725 g a.e./ha in a field testing trial done in Washington County, Mississippi. Results, averaged for all replicates of each treatment and across all rates of application for each plant species, (reported as the fifth value), as well as an overall average across all plant species, are shown in Table 51H.

TABLE 51H

| Comp. | IPOLA | ABUTH | CASOB | SEBEX | overall ave. |
|---|---|---|---|---|---|
| 483Q1D | 68, 88, 93, 96, 86 | 71, 85, 93, 98, 87 | 83, 88, 95, 98, 91 | 66, 71, 91, 94, 81 | 86 |
| 944U7M | 75, 86, 95, 98, 88 | 75, 89, 93, 98, 88 | 83, 86, 91, 99, 90 | 69, 79, 84, 88, 80 | 87 |
| 151O8W | 70, 86, 89, 95, 85 | 76, 86, 93, 99, 88 | 83, 85, 93, 96, 89 | 71, 78, 86, 88, 81 | 86 |
| 155L1J | 65, 83, 92, 94, 83 | 70, 84, 85, 98, 84 | 81, 88, 89, 96, 88 | 66, 80, 83, 90, 80 | 84 |
| 874G8W | 69, 86, 91, 93, 85 | 70, 85, 90, 96, 85 | 80, 89, 91, 94, 88 | 66, 85, 88, 89, 82 | 85 |
| 875W1I | 71, 82, 91, 93, 84 | 66, 85, 96, 96, 86 | 79, 89, 93, 94, 88 | 70, 84, 86, 81, 81 | 85 |
| 876L0S | 65, 84, 85, 95, 82 | 65, 88, 89, 96, 84 | 80, 83, 88, 98, 87 | 69, 79, 80, 91, 80 | 83 |
| 877K7A | 58, 83, 86, 94, 80 | 68, 80, 84, 99, 83 | 80, 85, 86, 95, 87 | 63, 73, 76, 88, 75 | 81 |
| 878L6H | 79, 89, 93, 96, 89 | 76, 89, 94, 100, 90 | 85, 88, 95, 100, 90 | 70, 82, 80, 95, 82 | 88 |
| 879K7T | 75, 93, 95, 96, 90 | 78, 93, 99, 100, 92 | 85, 89, 96, 98, 92 | 70, 84, 91, 94, 85 | 90 |
| STD4 | 70, 79, 89, 94, 83 | 66, 80, 91, 96, 83 | 84, 88, 91, 98, 90 | 70, 81, 89, 96, 84 | 85 |
| STD9 | 70, 78, 86, 95, 82 | 68, 84, 90, 96, 84 | 85, 89, 94, 95, 91 | 71, 80, 89, 90, 83 | 85 |

Four difficult-to-control annual broadleaf weeds were included in this field test completed in Mississippi. All species were controlled effectively in this field study. Both STD4 and STD9 controlled IPOLA, ABUTH and SEBEX at 600 g a.e./ha. STD9 controlled CASOB at 350 g a.e./ha, while STD4 required 475 g a.e./ha to reach the commercial threshold of control for this weed.

Efficacy across the four species with the ten experimental formulations containing diammonium oxalate varied widely. Six of the experimental formulations provided commercial control of IPOLA and ABUTH one rate lower (475 g a.e./ha) than both of the standard formulations, including 483Q1D, 944U7M, 151O8W, 874G8W, 878L6H and 879K7T. Only two formulations matched the efficacy of STD9 for control of CASOB, those being 878L6H and 879K7T. Among the formulations, control of SEBEX with best with 874G8W, which controlled this weed at only 475 g a.e./ha.

The compositions of Table 51A were applied to IPOLA, ABUTH, CASOB and SEBEX plants at rates of 500, 650, 800 and 950 g a.e./ha in a field trial done in Washington County, Mississippi. Results, averaged for all replicates of each treatment and across all rates of application for each plant species (reported as the fifth value), as well as an overall average across all plant species, are shown in Table 51I.

TABLE 51I

| Comp. | IPOLA | ABUTH | CASOB | SEBEX | overall ave. |
|---|---|---|---|---|---|
| 483Q1D | 83, 90, 90, 94, 89 | 94, 99, 99, 100, 98 | 94, 100, 100, 100, 98 | 85, 93, 98, 98, 93 | 95 |
| 944U7M | 83, 85, 93, 96, 89 | 90, 96, 100, 100, 97 | 95, 96, 100, 100, 98 | 90, 91, 100, 100, 95 | 95 |
| 151O8W | 83, 88, 95, 97, 90 | 95, 99, 100, 100, 98 | 96, 98, 100, 100, 98 | 86, 96, 100, 100, 96 | 96 |
| 155L1J | 80, 86, 94, 94, 88 | 93, 98, 100, 99, 97 | 90, 98, 98, 100, 96 | 85, 95, 99, 99, 94 | 94 |
| 874G8W | 81, 86, 90, 95, 88 | 93, 95, 95, 100, 96 | 90, 91, 98, 100, 95 | 85, 93, 94, 96, 92 | 93 |
| 875W1I | 76, 88, 93, 94, 88 | 94, 96, 99, 99, 97 | 88, 96, 98, 99, 95 | 84, 95, 100, 99, 94 | 93 |

TABLE 51I-continued

| | % Weed Control | | | | |
|---|---|---|---|---|---|
| Comp. | IPOLA | ABUTH | CASOB | SEBEX | overall ave. |
| 876L0S | 79, 83, 89, 92, 86 | 88, 94, 100, 99, 95 | 89, 94, 95, 95, 93 | 89, 93, 96, 99, 94 | 92 |
| 877K7A | 75, 84, 89, 94, 85 | 95, 96, 99, 100, 98 | 86, 95, 95, 99, 94 | 84, 96, 96, 96, 93 | 92 |
| 878L6H | 84, 93, 94, 96, 92 | 93, 99, 98, 100, 97 | 94, 98, 99, 100, 98 | 91, 98, 98, 98, 96 | 96 |
| 879K7T | 86, 93, 91, 95, 91 | 95, 99, 98, 100, 98 | 95, 100, 98, 99, 98 | 98, 98, 98, 100, 98 | 96 |
| STD4 | 80, 88, 94, 96, 89 | 93, 96, 99, 100, 97 | 94, 100, 100, 100, 98 | 88, 94, 98, 100, 95 | 95 |
| STD9 | 78, 88, 92, 94, 88 | 90, 95, 100, 99, 96 | 91, 98, 100, 100, 97 | 91, 95, 96, 100, 96 | 94 |

Four difficult-to-control annual broadleaf weeds were included in this field test completed in Mississippi. All species were controlled effectively in this field study. Both STD4 and STD9 provided commercial control of ABUTH, CASOB and SEBEX at the lowest rate of application, 500 g a.e./ha. IPOLA control was achieved with these standards at 650 g a.e./ha.

Efficacy of the two standard formulations was matched by seven of the ten experimental formulations containing diammonium oxalate. The only differences in control between the commercial standards and the experimental formulations were obtained on IPOLA. Two of the experimental formulations, 876LOS and 877K7A, were slightly less efficacious than the standards on this weed. Formulation 879K7T was superior to the standard formulations, providing commercial control of IPOLA at 500 g a.e./ha.

Data from the field experiments detailed in Example 51 were pooled and analyzed. Results showed that four formulations were significantly more efficacious than the standards: 878L6H, 879K7T, 944U7M and 151O8W. The analysis showed the diammonium oxalate enhanced glyphosate formulations were significantly more efficacious against the broadleaf weeds in this experiment as compared to the grass weeds. However, 879K7T was significantly better than the standards for controlling grass weeds. Three formulations, 874G8W, 876LOS and 877K7A, were significantly less efficacious than the standards.

Example 52

The field efficacy effect of high load glyphosate formulations containing a cationic:nonionic surfactant system and inerts was evaluated. Compositions were prepared containing potassium or IPA glyphosate salt, reported in % wt a.e., and excipient ingredients, reported a w/w % unless otherwise indicated, as shown in Table 52A.

TABLE 52A

| Comp. | gly salt | [gly] | Cmpnt 1 | wt % | Cmpnt 2 | wt % |
|---|---|---|---|---|---|---|
| 043A1J | K | 36.5 | CIS6 | 160 g/l | — | — |
| 948I9W | IPA | 31.0 | CIS13 | 1.8 | NIS7 | 5.0 |
| 780L3V | K | 40.0 | CIS23 | 8.0 | NIS7 | 3.0 |
| 781U0M | K | 40.0 | CIS23 | 8.0 | NIS7 | 3.0 |
| 782S6Y | K | 40.0 | CIS23 | 6.0 | NIS7 | 5.0 |
| 783P1D | K | 40.0 | CIS23 | 4.0 | NIS7 | 8.0 |
| 784K6C | K | 36.7 | CIS23 | 6.0 | NIS7 | 2.4 |
| STD6 | K | 39.7 | — | — | — | — |

| Comp. | Cmpnt 3 | wt % | Cmpnt 4 | wt % | Cmpnt 5 | wt % |
|---|---|---|---|---|---|---|
| 043A1J | — | — | — | — | — | — |
| 948I9W | OTH1 | 3.0 | OTH2 | 0.12 | OTH3 | 2.0 |
| 780L3V | OTH5 | 1.0 | OTH3 | 1.0 | — | — |
| 781U0M | — | — | — | — | — | — |
| 782S6Y | OTH5 | 1.0 | OTH3 | 1.0 | — | — |
| 783P1D | OTH5 | 1.0 | OTH3 | 1.0 | OTH16 | 2.0 |
| 784K6C | NIS23 | 1.4 | OTH5 | 1.0 | OTH3 | 1.0 |
| STD6 | OTH4 | 7.3 g/l | — | — | — | — |

The compositions of Table 52A were applied to TAROF plants at rates of 650, 975, 1299 and 1689 g a.e./ha in a field trial done in Warren County, Illinois. Results, averaged for all replicates of each treatment and across all rates of application for each plant species (reported as the fifth value) are shown in Table 52B.

TABLE 52B

| | % Weed Control |
|---|---|
| Composition | TAROF |
| 043A1J | 83, 94, 93, 99, 91 |
| 948I9W | 79, 92, 92, 96, 90 |
| 780L3V | 86, 97, 96, 100, 95 |
| 781U0M | 80, 92, 91, 100, 91 |
| 782S6Y | 83, 92, 97, 100, 93 |
| 783P1D | 83, 87, 91, 95, 88 |
| 784K6C | 86, 85, 92, 100, 91 |
| STD6 | 77, 91, 92, 100, 90 |

When results were averaged across all rates of application in this field test, five experimental formulations were more efficacious against TAROF than the standard (STD6). Three of these five formulations contained oxalic acid (780L3V, 782S6Y and 784K6C). At the lowest rate of application, 650 g a.e./ha, 780L3V and 784K6C were the only formulations that provided commercial control (85%) of TAROF. 043A1J did not contain oxalic acid, but the higher surfactant load (3:1) in this formulation contributed to improved efficacy compared to the standard.

The compositions of Table 52A were applied to TRZVX and SECSS plants at rates of 325, 585, 845, 1040 and 1299 g a.e./ha in a field trial done in Warren County, Illinois. Results, averaged for all replicates of each treatment and across all rates of application for each plant species (reported as the sixth value), as well as an overall average across all plant species, are shown in Table 52C.

TABLE 52C

| | % Weed Control | | |
|---|---|---|---|
| Composition | TRZVX | SECSS | overall ave. |
| 043A1J | 80, 90, 99, 100, 100, 94 | 58, 61, 65, 68, 77, 66 | 80 |
| 948I9W | 81, 92, 98, 100, 100, 94 | 54, 56, 62, 67, 68, 61 | 78 |

TABLE 52C-continued

| | % Weed Control | | |
|---|---|---|---|
| Composition | TRZVX | SECSS | overall ave. |
| 780L3V | 83, 88, 98, 100, 100, 94 | 56, 59, 63, 71, 73, 64 | 79 |
| 781U0M | 79, 92, 98, 100, 100, 94 | 51, 58, 67, 66, 75, 63 | 79 |
| 782S6Y | 81, 85, 95, 100, 100, 92 | 57, 60, 63, 72, 78, 66 | 79 |
| 783P1D | 80, 95, 97, 100, 100, 94 | 52, 67, 65, 64, 75, 65 | 79 |
| 784K6C | 81, 86, 97, 100, 100, 93 | 56, 57, 62, 70, 80, 65 | 79 |
| STD6 | 81, 88, 99, 100, 100, 93 | 53, 57, 61, 69, 79, 64 | 79 |

Commercial control of TRZVX was achieved in this test at 585 g a.e./ha for all formulations, but SECSS proved more difficult to control, with suppression attained at 1299 g a.e./ha, the highest rate of application in this field trial. The top performing formulation, based upon the (across both species) was 043A1J. On grassy weeds, glyphosate efficacy is generally correlated to surfactant levels, and the additional surfactant load (3:1) helped this formulation outperform the standard, STD6. Four of the experimental formulations containing oxalic acid (783P1D, 780L3V, 782S6Y and 784K6C) were as efficacious as the standard.

The compositions of Table 52A were applied to AMBTR plants at rates of 260, 455, 650 and 845 g a.e./ha in a field trial done in Warren County, Illinois. Results, averaged for all replicates of each treatment and across all rates of application for each plant species (reported as the fifth value) are shown in Table 52D.

TABLE 52D

| | % Weed Control |
|---|---|
| Composition | AMBTR |
| 043A1J | 49, 66, 66, 69, 62 |
| 948I9W | 50, 71, 68, 76, 66 |
| 780L3V | 50, 66, 67, 72, 64 |
| 781U0M | 52, 66, 75, 72, 66 |
| 782S6Y | 48, 65, 71, 77, 65 |
| 783P1D | 47, 64, 66, 76, 63 |
| 784K6C | 51, 64, 73, 73, 65 |
| STD6 | 54, 69, 71, 76, 68 |

None of the formulations in this test provided a commercial level of control of AMBTR. The standard, STD6, was the most efficacious formulation when data were averaged across all rates of application.

The compositions of Table 52A were applied to OEOLA plants at rates of 650, 1040, 1429, 1819 and 2209 g a.e./ha in a field trial done in Gillespie County, Texas. Results, averaged for all replicates of each treatment and across all rates of application for each plant species (reported as the sixth value) are shown in Table 52E.

TABLE 52E

| | % Weed Control |
|---|---|
| Comp | OEOLA |
| 043A1J | 69, 80, 81, 88, 92, 82 |
| 948I9W | 67, 73, 84, 86, 91, 80 |
| 780L3V | 67, 72, 84, 89, 88, 80 |
| 781U0M | 65, 72, 86, 85, 91, 80 |
| 782S6Y | 69, 75, 81, 87, 91, 81 |
| 783P1D | 66, 77, 83, 87, 90, 80 |

TABLE 52E-continued

| | % Weed Control |
|---|---|
| Comp | OEOLA |
| 784K6C | 66, 74, 82, 87, 87, 79 |
| STD6 | 69, 78, 83, 90, 93, 83 |

All formulations compared in this field trial in Texas provided commercial control (85%) of OEOLA at an application rate of 1819 g a.e./ha. When data were averaged across all rates of application STD6, the standard, was the most efficacious formulation evaluated.

The compositions of Table 52A were applied to TRZVX plants at rates of 195, 325, 455, 585 and 715 g a.e./ha in a field trial done in Gillespie County, Texas. Results, averaged for all replicates of each treatment and across all rates of application for each plant species (reported as the sixth value) are shown in Table 52F.

TABLE 52F

| | % Weed Control |
|---|---|
| Composition | TRZVX |
| 043A1J | 41, 65, 78, 82, 90, 71 |
| 948I9W | 37, 62, 72, 77, 83, 66 |
| 780L3V | 40, 64, 80, 85, 89, 72 |
| 781U0M | 40, 63, 74, 87, 85, 70 |
| 782S6Y | 43, 63, 76, 81, 89, 70 |
| 783P1D | 37, 62, 75, 80, 83, 67 |
| 784K6C | 41, 66, 80, 82, 92, 72 |
| STD6 | 41, 62, 79, 81, 90, 70 |

Two of the experimental formulations, 780L3V and 781U0M, controlled TRZVX at 585 g a.e./ha in this field study. At 715 g a.e./ha, STD6 all formulations except 783P1D and 948I9W provided commercial control of TRZVX. When data were averaged for each formulation across all rates of application two experimental formulations containing oxalic acid were more efficacious against TRZVX than the standard (STD6), specifically 784K6C and 780L3V. 043A1J, with a higher surfactant concentration than all other formulations, was also slightly more efficacious than the standard.

The compositions of Table 52A were applied to CENME and CRUNU plants at rates of 230, 520, 780, 1040 and 1299 g a.e./ha in a field trial done in Gillespie County, Texas. Results, averaged for all replicates of each treatment for each plant species (reported as the sixth value), as well as an overall average for all of the plant species, are shown in Table 52G.

TABLE 52G

| | % Weed Control | | |
|---|---|---|---|
| Composition | CENME | CRUNU | overall ave. |
| 043A1J | 67, 85, 94, 100, 100, 89 | 60, 79, 72, 75, 90, 76 | 83 |
| 948I9W | 68, 80, 95, 100, 100, 89 | 47, 63, 81, 75, 90, 71 | 80 |
| 780L3V | 67, 79, 90, 100, 100, 87 | 57, 64, 65, 80, 83, 70 | 78 |
| 781U0M | 68, 80, 93, 100, 100, 89 | 52, 69, 68, 74, 85, 70 | 80 |
| 782S6Y | 72, 79, 95, 100, 100, 89 | 57, 73, 69, 82, 83, 73 | 81 |
| 783P1D | 66, 80, 92, 100, 100, 87 | 53, 72, 70, 78, 90, 72 | 80 |
| 784K6C | 67, 80, 94, 100, 100, 88 | 47, 70, 65, 76, 91, 70 | 79 |
| STD6 | 71, 84, 95, 100, 100, 90 | 50, 71, 69, 77, 90, 72 | 81 |

All formulations evaluated controlled CENME at a commercial level (85%) at 780 g a.e./ha. CRUNU proved more difficult to control, and all but two of the formulations (780L3V and 782S6Y) controlled this weed at 1299 g a.e./ha. When data were averaged across both weeds and all rates of application, the top performing formulation was 043A1J, a K-salt with a higher surfactant load (3:1 glyphosate: surfactant) relative to the standard, STD6 (4:1 glyphosate:surfactant). The best performing liquid formulation containing oxalic acid was 782S6Y, was equal to the standard, STD6.

The compositions of Table 52A were applied to ABUTH plants at rates of 390, 585, 780, and 910 g a.e./ha in a field trial done in Gillespie County, Texas. Results, averaged for all replicates of each treatment and across all rates of application for each plant species (reported as the sixth value) are shown in Table 52H.

TABLE 52H

| Composition | % Weed Control ABUTH |
|---|---|
| 043A1J | 29, 48, 60, 66, 75, 56 |
| 948I9W | 20, 43, 63, 71, 74, 54 |
| 780L3V | 18, 48, 69, 79, 75, 58 |
| 781U0M | 18, 42, 58, 60, 65, 49 |
| 782S6Y | 21, 48, 57, 70, 68, 53 |
| 783P1D | 19, 40, 58, 60, 62, 48 |

TABLE 52H-continued

| Composition | % Weed Control ABUTH |
|---|---|
| 784K6C | 26, 45, 68, 71, 87, 59 |
| STD6 | 21, 43, 61, 78, 83, 57 |

The only formulation that provided a commercial level of control of ABUTH in this field test in Texas was 784K6C at 910 g a.e./ha, the highest rate of application in this field test. In comparison, STD6 only provided 83% ABUTH control at this rate. When data were averaged across all rates of application in this study, two of the experimental formulations containing oxalic acid were more efficacious than the standard (STD6), specifically 780L3V and 784K6C.

The compositions of Table 52A were applied to LOLMG, LAMAM, LOLPE, COPDI, ABUTH and SPRAR plants at rates of 315, 473, 631, 788 and 946 g a.e./ha in a field trial done in Baldwin County, Alabama. Results, averaged for all replicates of each treatment and across all rates of application for each plant species (reported as the sixth value), as well as an overall average across all plant species, are shown in Table 52I.

TABLE 52I

| | | % Weed Control | | | | | | |
|---|---|---|---|---|---|---|---|---|
| Comp. | Rate (g/ha) | LOLMG | LAMAM | LOLPE | COPDI | ABUTH | SPRAR | overall ave. |
| 043A1J | 315, 473, 631, | 88, 96, 100, | 100, 100, 100, | 93, 100, 100, | 100, 100, 100, | 35, 57, 66, | 100, 100, 100, | 93 |
| | 788, 946, ave. | 98, 100, 96 | 100, 100, 100 | 100, 100, 99 | 100, 100, 100 | 69, 81, 62 | 100, 100, 100 | |
| 948I9W | 315, 473, 631, | 87, 96, 100, | 100, 100, 100, | 100, 100, 100, | 100, 100, 100, | 40, 65, 63, | 100, 100, 100, | 94 |
| | 788, 946, ave. | 97, 99, 96 | 100, 100, 100 | 100, 100, 100 | 100, 100, 100 | 78, 83, 66 | 100, 100, 100 | |
| 780L3V | 315, 473, 631, | 92, 98, 100, | 100, 100, 100, | 95, 99, 100, | 100, 100, 100, | 38, 56, 63, | 100, 100, 100, | 93 |
| | 788, 946, ave. | 98, 100, 97 | 100, 100, 100 | 100, 100, 99 | 100, 100, 100 | 71, 85, 62 | 100, 100, 100 | |
| 781U0M | 315, 473, 631, | 94, 99, 99, | 100, 100, 100, | 92, 100, 100, | 100, 100, 100, | 35, 51, 57, | 100, 100, 100, | 93 |
| | 788, 946, ave. | 97, 100, 98 | 100, 100, 100 | 100, 100, 99 | 100, 100, 100 | 72, 80, 59 | 100, 100, 100 | |
| 782S6Y | 315, 473, 631, | 90, 99, 97, | 100, 100, 100, | 95, 100, 100, | 100, 100, 100, | 31, 48, 65, | 100, 100, 100, | 93 |
| | 788, 946, ave. | 98, 100, 97 | 100, 100, 100 | 100, 100, 100 | 100, 100, 100 | 77, 84, 61 | 100, 100, 100 | |
| 783P1D | 315, 473, 631, | 92, 96, 100, | 100, 100, 100, | 87, 99, 100, | 100, 100, 100, | 39, 51, 59, | 100, 100, 100, | 93 |
| | 788, 946, ave. | 100, 100, 98 | 100, 100, 100 | 100, 100, 97 | 100, 100, 100 | 75, 83, 61 | 100, 100, 100 | |
| 784K6C | 315, 473, 631, | 91, 100, 100, | 100, 100, 100, | 93, 100, 100, | 100, 100, 100, | 30, 56, 58, | 100, 100, 100, | 93 |
| | 788, 946, ave. | 100, 100, 98 | 100, 100, 100 | 100, 100, 99 | 100, 100, 100 | 77, 80, 60 | 100, 100, 100 | |
| STD3 | 315, 473, 631, | 93, 100, 100, | 100, 100, 100, | 95, 100, 100, | 100, 100, 100, | 30, 59, 65, | 100, 100, 100, | 93 |
| | 788, 946, ave. | 100, 100, 99 | 100, 100, 100 | 100, 100, 99 | 100, 100, 100 | 80, 81, 63 | 100, 100, 100 | |
| STD6 | 315, 473, 631, | 91, 90, 98, | 100, 100, 100, | 100, 100, 100, | 100, 100, 100, | 41, 53, 61, | 100, 100, 100, | 93 |
| | 788, 946, ave. | 100, 100, 96 | 100, 100, 100 | 100, 100, 100 | 100, 100, 100 | 71, 76, 60 | 100, 100, 100 | |

Application rates in this Alabama field test were selected to provide control of ABUTH, the most difficult weed to control with glyphosate. As such, susceptible species such as LAMAM, SPRAR and COPDI were controlled at the 100% level at the lowest rate of application, 315 g a.e./ha. Furthermore, all nine formulations provided at least 85% control of LOLMG and LOLPE at 315 g a.e./ha. At 946 g a.e./ha, the highest application rate in the study, only 780L3V, an experimental formulation containing oxalic acid, provided commercial control (85%) of ABUTH. All other formulations, except the STD6 standard, provided greater than 80% ABUTH control at this rate. When data were averaged across all six weed species and all rates of application, all formulations were equal.

The compositions of Table 52A were applied to ABUTH, IPOLA, CASOB and COPDI plants at rates of 315, 473, 631, 788 and 946 g a.e./ha in a field trial done in Baldwin County, Alabama. Results, averaged for all replicates of each treatment and across all rates of application for each plant species (reported as the sixth value), as well as an overall average across all plant species, are shown in Table 52J.

TABLE 52J

| | | % Weed Control | | | | |
|---|---|---|---|---|---|---|
| Comp. | Rate (g/ha) | ABUTH | IPOLA | CASOB | COPDI | overall ave. |
| 043A1J | 315, 473, 631, 788, 946, ave. | 48, 53, 66, 70, 76, 62 | 54, 60, 68, 64, 70, 63 | 50, 57, 64, 65, 70, 61 | 100, 100, 100, 100, 100, 100 | 72 |
| 948I9W | 315, 473, 631, 788, 946, ave. | 48, 55, 56, 58, 70, 57 | 55, 60, 56, 57, 67, 59 | 51, 54, 60, 55, 62, 56 | 100, 100, 100, 100, 100, 100 | 68 |
| 780L3V | 315, 473, 631, 788, 946, ave. | 53, 51, 65, 70, 72, 62 | 54, 60, 65, 64, 68, 62 | 58, 59, 61, 65, 64, 61 | 100, 100, 100, 100, 100, 100 | 71 |
| 781U0M | 315, 473, 631, 788, 946, ave. | 48, 59, 58, 63, 71, 60 | 48, 62, 58, 61, 64, 58 | 48, 61, 57, 58, 64, 57 | 100, 100, 100, 100, 100, 100 | 69 |
| 782S6Y | 315, 473, 631, 788, 946, ave. | 41, 53, 59, 70, 69, 59 | 49, 63, 61, 66, 66, 61 | 46, 59, 58, 62, 65, 58 | 100, 100, 100, 100, 100, 100 | 70 |
| 783P1D | 315, 473, 631, 788, 946, ave. | 43, 49, 60, 66, 71, 58 | 48, 58, 63, 64, 64, 59 | 49, 55, 57, 66, 68, 59 | 100, 100, 100, 100, 100, 100 | 69 |
| 784K6C | 315, 473, 631, 788, 946, ave. | 43, 48, 58, 60, 76, 57 | 46, 57, 58, 59, 66, 57 | 49, 53, 60, 63, 70, 59 | 100, 100, 100, 100, 100, 100 | 68 |
| STD3 | 315, 473, 631, 788, 946, ave. | 44, 50, 56, 66, 79, 59 | 48, 55, 59, 58, 66, 57 | 47, 53, 60, 56, 60, 55 | 100, 100, 100, 100, 100, 100 | 67 |
| STD6 | 315, 473, 631, 788, 946, ave. | 41, 56, 60, 62, 76, 59 | 45, 58, 61, 61, 72, 59 | 45, 59, 57, 61, 64, 57 | 100, 100, 100, 100, 100, 100 | 69 |

All formulations provided perfect control (100%) of COPDI at 315 g a.e./ha, the lowest rate of application in this field test. Rates of application were too low to provide a commercial level of control for tough annual broadleaf weeds such as ABUTH, CASOB and IPOLA. At the highest rate of application in this study, 946 g a.e./ha, control values were typically 60% to 75% across formulations and species. When data were averaged across all four species and all rates of application, the STD3 standard was the least efficacious formulation evaluated. The top formulation in this study, based upon the highest overall average, was 043A1J, the formulation which contained the most surfactant (3:1 ratio). 780L3V, 782S6Y and 783P1D were all experimental high load formulations containing oxalic acid, and all were as good or more efficacious than the STD6 standard.

The compositions of Table 52A were applied to SIDSP, ABUTH, IPOLA, CASOB and SEBEX plants at rates of 315, 473, 631, 788 and 946 g a.e./ha in a field trial done in Baldwin County, Alabama. Results, averaged for all replicates of each treatment and across all rates of application for each plant species (reported as the sixth value), as well as an overall average across all plant species, are shown in Table 52K.

TABLE 52K

| | | % Weed Control | | | | | |
|---|---|---|---|---|---|---|---|
| Comp. | Rate (g/ha) | SIDSP | ABUTH | IPOLA | CASOB | SEBEX | overall ave. |
| 043A1J | 315, 473, 631, 788, 946, ave. | 59, 79, 88, 96, 98, 84 | 42, 51, 60, 68, 75, 59 | 51, 62, 59, 66, 71, 62 | 55, 62, 73, 79, 80, 70 | 49, 53, 58, 64, 71, 59 | 67 |
| 948I9W | 315, 473, 631, 788, 946, ave. | 64, 82, 90, 94, 95, 85 | 45, 53, 62, 67, 76, 61 | 55, 60, 56, 63, 78, 63 | 57, 65, 71, 75, 80, 70 | 46, 52, 59, 65, 69, 58 | 67 |
| 780L3V | 315, 473, 631, 788, 946, ave. | 58, 81, 91, 97, 99, 85 | 42, 56, 61, 70, 75, 61 | 45, 63, 61, 67, 74, 62 | 55, 65, 71, 77, 81, 70 | 45, 51, 58, 64, 69, 57 | 67 |
| 781U0M | 315, 473, 631, 788, 946, ave. | 64, 85, 88, 96, 97, 86 | 50, 54, 60, 72, 74, 62 | 58, 63, 63, 65, 73, 65 | 57, 64, 74, 81, 80, 71 | 53, 53, 54, 66, 70, 59 | 68 |
| 782S6Y | 315, 473, 631, 788, 946, ave. | 58, 80, 87, 93, 99, 83 | 50, 50, 63, 71, 78, 62 | 59, 55, 56, 67, 73, 62 | 60, 60, 67, 79, 82, 70 | 51, 53, 56, 64, 68, 58 | 67 |

TABLE 52K-continued

| | | % Weed Control | | | | | |
|---|---|---|---|---|---|---|---|
| Comp. | Rate (g/ha) | SIDSP | ABUTH | IPOLA | CASOB | SEBEX | overall ave. |
| 783P1D | 315, 473, 631, 788, 946, ave. | 62, 79, 87, 94, 99, 84 | 47, 60, 60, 73, 76, 63 | 50, 66, 65, 67, 68, 63 | 53, 67, 72, 81, 79, 70 | 49, 60, 62, 64, 71, 61 | 68 |
| 784K6C | 315, 473, 631, 788, 946, ave. | 65, 78, 94, 92, 96, 85 | 46, 57, 66, 68, 76, 62 | 52, 64, 65, 64, 68, 62 | 55, 65, 73, 79, 82, 71 | 46, 57, 57, 63, 71, 59 | 68 |
| STD3 | 315, 473, 631, 788, 946, ave. | 64, 85, 92, 96, 96, 87 | 47, 60, 61, 73, 73, 63 | 56, 68, 59, 67, 69, 64 | 53, 65, 70, 79, 73, 68 | 48, 61, 55, 61, 62, 57 | 68 |
| STD6 | 315, 473, 631, 788, 946, ave. | 63, 82, 89, 92, 99, 85 | 48, 57, 59, 70, 74, 61 | 55, 62, 56, 64, 70, 61 | 56, 64, 70, 78, 81, 70 | 48, 53, 53, 65, 69, 58 | 67 |

The only weed that was controlled at a commercial level (85%) in this field test was SIDSP. All formulations provided a grand mean of 67% to 68%.

The compositions of Table 52A were applied to TRZVX, AVESX, LOLMG and LOLPE plants at rates of 250, 350, 450, 550 and 650 g a.e./ha in a field trial done in Washington County, Mississippi. Results, averaged for all replicates of each treatment and across all rates of application for each plant species (reported as the sixth value), as well as an overall average across all plant species, are shown in Table 52L.

effective than the second standard, STD6. 043A1J, with a higher surfactant concentration than all other formulations evaluated, was also less efficacious than STD3 but more efficacious than STD6. At the highest rate of application in this test, 650 g a.e./ha, all of the high load (480 g/L and 540 g/L glyphosate) experimental formulations that contained oxalic acid provided commercial control of AVESX, along with STD3 and the high surfactant loaded material, 043A1J.

The compositions of Table 52A were applied to TRZVX, AVESX, LOLMG and LOLPE plants at rates of 250, 350,

TABLE 52L

| | | % Weed Control | | | | |
|---|---|---|---|---|---|---|
| Comp. | Rate (g/ha) | TRZVX | AVESX | LOLMG | LOLPE | overall ave. |
| 043A1J | 250, 350, 450, 550, 650, ave. | 48, 61, 66, 73, 76, 65 | 51, 66, 75, 73, 86, 72 | 45, 54, 59, 69, 76, 61 | 35, 43, 48, 59, 60, 49 | 62 |
| 948I9W | 250, 350, 450, 550, 650, ave. | 43, 50, 61, 65, 66, 57 | 46, 56, 74, 78, 79, 67 | 40, 46, 64, 65, 71, 57 | 31, 38, 49, 51, 56, 45 | 56 |
| 780L3V | 250, 350, 450, 550, 650, ave. | 50, 59, 66, 73, 76, 65 | 54, 71, 79, 88, 88, 76 | 40, 50, 64, 75, 80, 62 | 36, 44, 54, 65, 66, 53 | 64 |
| 781U0M | 250, 350, 450, 550, 650, ave. | 41, 56, 61, 71, 73, 61 | 45, 68, 79, 84, 84, 72 | 38, 49, 59, 69, 71, 57 | 33, 40, 51, 61, 65, 50 | 60 |
| 782S6Y | 250, 350, 450, 550, 650, ave. | 45, 56, 64, 68, 74, 61 | 53, 71, 76, 88, 85, 75 | 44, 49, 61, 69, 79, 60 | 38, 45, 50, 58, 65, 51 | 62 |
| 783P1D | 250, 350, 450, 550, 650, ave. | 41, 59, 64, 69, 74, 61 | 46, 69, 78, 86, 89, 74 | 39, 51, 65, 68, 73, 59 | 28, 44, 54, 61, 63, 50 | 61 |
| 784K6C | 250, 350, 450, 550, 650, ave. | 48, 68, 64, 78, 81, 68 | 55, 78, 83, 90, 90, 79 | 44, 59, 71, 78, 84, 67 | 43, 51, 63, 76, 75, 62 | 69 |
| STD3 | 250, 350, 450, 550, 650, ave. | 46, 58, 66, 73, 78, 64 | 53, 65, 78, 88, 89, 74 | 40, 48, 60, 70, 78, 59 | 36, 41, 54, 61, 71, 53 | 63 |
| STD6 | 250, 350, 450, 550, 650, ave. | 49, 61, 64, 68, 79, 64 | 49, 65, 75, 81, 84, 71 | 39, 54, 59, 68, 79, 60 | 30, 46, 48, 50, 61, 47 | 60 |

Commercial control (85%) was reached only on AVESX. Two of the experimental formulations containing oxalic acid, 784K6C and 780L3V, were more efficacious than STD3 when the data were averaged across all four grass species. 782S6Y and 783P1D, experimental formulations containing oxalic acid, were slightly less efficacious than STD3 but more 450, 550 and 650 g a.e./ha in a field trial done in Washington County, Mississippi. Results, averaged for all replicates of each treatment and across all rates of application for each plant species (reported as the sixth value), as well as an overall average across all plant species, are shown in Table 52M.

TABLE 52M

| | | % Weed Control | | | | |
|---|---|---|---|---|---|---|
| Comp. | Rate (g/ha) | TRZVX | AVESX | LOLMG | LOLPE | overall ave. |
| 043A1J | 250, 350, 450, 550, 650, ave. | 70, 83, 83, 85, 89, 82 | 80, 95, 94, 99, 98, 93 | 55, 71, 76, 80, 84, 73 | 40, 43, 51, 59, 69, 52 | 75 |
| 948I9W | 250, 350, 450, 550, 650, ave. | 70, 76, 81, 85, 90, 81 | 83, 93, 95, 96, 100, 93 | 60, 70, 79, 81, 90, 76 | 40, 43, 60, 61, 73, 55 | 76 |
| 780L3V | 250, 350, 450, 550, 650, ave. | 74, 76, 78, 85, 90, 81 | 84, 93, 95, 98, 98, 93 | 50, 65, 75, 84, 85, 72 | 35, 43, 50, 61, 76, 53 | 75 |

TABLE 52M-continued

| | | % Weed Control | | | | |
|---|---|---|---|---|---|---|
| Comp. | Rate (g/ha) | TRZVX | AVESX | LOLMG | LOLPE | overall ave. |
| 781U0M | 250, 350, 450, 550, 650, ave. | 63, 80, 78, 81, 85, 77 | 81, 94, 95, 98, 98, 93 | 51, 70, 76, 80, 88, 73 | 33, 41, 53, 53, 70, 50 | 73 |
| 782S6Y | 250, 350, 450, 550, 650, ave. | 76, 75, 81, 85, 91, 82 | 90, 90, 95, 96, 99, 94 | 53, 65, 75, 83, 89, 73 | 40, 44, 49, 59, 68, 52 | 75 |
| 783P1D | 250, 350, 450, 550, 650, ave. | 60, 76, 81, 86, 89, 79 | 75, 93, 95, 99, 100, 92 | 48, 71, 74, 88, 88, 74 | 30, 44, 50, 61, 74, 52 | 74 |
| 784K6C | 250, 350, 450, 550, 650, ave. | 75, 85, 85, 85, 90, 84 | 90, 96, 98, 99, 100, 97 | 60, 74, 81, 86, 88, 78 | 44, 49, 55, 66, 80, 59 | 79 |
| STD3 | 250, 350, 450, 550, 650, ave. | 65, 79, 80, 81, 88, 79 | 75, 89, 95, 98, 99, 91 | 51, 61, 69, 81, 89, 70 | 34, 40, 53, 58, 73, 51 | 73 |
| STD6 | 250, 350, 450, 550, 650, ave. | 68, 79, 78, 84, 88, 79 | 85, 93, 93, 99, 98, 93 | 55, 69, 71, 81, 88, 73 | 30, 39, 46, 58, 66, 48 | 73 |

When data were averaged across all four species and all rates of application, all of the experimental formulations, except 782S6Y, outperformed both standards, STD6 and STD3. 782S6Y was equal to the standards. All formulations controlled TRZVX at 650 g a.e./ha, but every experimental formulation containing oxalic acid provided at least 85% control of this weed at 550 g a.e./ha. AVESX was the most susceptible grass species in this study; 784K6C and 782S6Y were the most efficacious formulation against AVESX based upon averages across all rates of application. No formulation provided commercial control (85%) of LOLPE, but 784K6C had the highest overall average (across rates) against this weed.

The compositions of Table 52A were applied to OEOLA plants at rates of 1300, 1500, 1700, 1900 and 2100 g a.e./ha in a field trial done in Washington County, Mississippi. Results, averaged for all replicates of each treatment and across all rates of application for each plant species (reported as the fifth value) are shown in Table 52N.

TABLE 52N

| | % Weed Control |
|---|---|
| Comp. | OEOLA |
| 043A1J | 61, 71, 70, 76, 75, 71 |
| 948I9W | 68, 66, 70, 74, 76, 71 |
| 780L3V | 65, 68, 70, 75, 78, 71 |
| 781U0M | 60, 71, 68, 73, 75, 69 |
| 782S6Y | 63, 66, 68, 74, 76, 69 |
| 783P1D | 65, 74, 74, 80, 81, 75 |
| 784K6C | 61, 69, 68, 74, 79, 70 |
| STD3 | 58, 69, 65, 70, 79, 68 |
| STD6 | 65, 68, 69, 76, 78, 71 |

None of the formulations compared in this study reached the 85% threshold for commercial control. When data were averaged across all rates of application, the least efficacious formulation was the STD3 formulation. 783P1D, an experimental formulation containing oxalic acid, was the most efficacious formulation and was the only formulation to provide 80% control, achieved at 1900 g a.e./ha.

The compositions of Table 52A were applied to ABUTH, IPOLA and ECHCG plants at rates of 300, 400, 500, 600 and 700 g a.e./ha in a field trial done in Washington County, Mississippi. Results, averaged for all replicates of each treatment and across all rates of application for each plant species (reported as the sixth value), as well as an overall average across all plant species, are shown in Table 52O.

TABLE 52O

| | | % Weed Control | | | |
|---|---|---|---|---|---|
| Comp. | Rate (g/ha) | ABUTH | IPOLA | ECHCG | overall ave. |
| 043A1J | 300, 400, 500, 600, 700, ave. | 74, 86, 88, 91, 93, 86 | 71, 85, 88, 88, 89, 84 | 100, 100, 100, 100, 100, 100 | 90 |
| 948I9W | 300, 400, 500, 600, 700, ave. | 79, 73, 84, 94, 91, 84 | 79, 81, 85, 89, 93, 85 | 100, 100, 100, 100, 100, 100 | 90 |
| 780L3V | 300, 400, 500, 600, 700, ave. | 71, 81, 88, 91, 93, 85 | 74, 80, 86, 89, 89, 84 | 100, 100, 100, 100, 100, 100 | 89 |
| 781U0M | 300, 400, 500, 600, 700, ave. | 66, 83, 86, 95, 93, 85 | 71, 81, 85, 86, 88, 82 | 100, 100, 100, 100, 100, 100 | 89 |
| 782S6Y | 300, 400, 500, 600, 700, ave. | 69, 80, 88, 86, 89, 82 | 73, 76, 86, 88, 90, 83 | 100, 100, 100, 100, 100, 100 | 88 |
| 783P1D | 300, 400, 500, 600, 700, ave. | 73, 74, 90, 91, 91, 84 | 74, 76, 89, 89, 90, 84 | 100, 100, 100, 100, 100, 100 | 89 |
| 784K6C | 300, 400, 500, 600, 700, ave. | 69, 83, 84, 86, 95, 83 | 76, 79, 84, 89, 90, 84 | 100, 100, 100, 100, 100, 100 | 89 |
| STD3 | 300, 400, 500, 600, 700, ave. | 71, 71, 81, 85, 91, 80 | 74, 80, 84, 88, 89, 83 | 100, 100, 100, 100, 100, 100 | 88 |
| STD6 | 300, 400, 500, 600, 700, ave. | 64, 84, 84, 91, 94, 83 | 70, 81, 88, 86, 90, 83 | 100, 100, 100, 100, 100, 100 | 89 |

All formulations provided perfect control (100%) of ECHCG in this field test at 300 g a.e./ha, the lowest rate of application. The higher surfactant load in 043A1J (3:1) resulted in this formulation being the only formulation to reach the 85% control threshold for IPOLA at 400 g a.e./ha. The best performing high load experimental formulations containing oxalic acid were 780L3V, 782S6Y and 783P1D, as they controlled both ABUTH and IPOLA at 500 g a.e./ha. In comparison, the STD3 standard failed to provide 85% control of these weeds at the same rate. STD6 gave commercial control of IPOLA, but not ABUTH, at 500 g a.e./ha.

The compositions of Table 52A were applied to IPOLA, ABUTH, CASOB and SEBEX plants at rates of 300, 400, 500, 600 and 700 g a.e./ha in a field trial done in Washington County, Mississippi. Results, averaged for all replicates of each treatment and across all rates of application for each plant species (reported as the sixth value), as well as an overall average across all plant species, are shown in Table 52P.

TABLE 52P

| | | % Weed Control | | | | |
|---|---|---|---|---|---|---|
| Comp. | Rate (g/ha) | IPOLA | ABUTH | CASOB | SEBEX | overall ave. |
| 043A1J | 300, 400, 500, 600, 700, ave. | 76, 85, 93, 93, 96, 89 | 74, 89, 95, 100, 100, 92 | 100, 100, 100, 100, 100, 100 | 70, 81, 85, 91, 95, 85 | 91 |
| 948I9W | 300, 400, 500, 600, 700, ave. | 83, 88, 91, 98, 96, 91 | 84, 96, 100, 100, 100, 96 | 100, 100, 100, 100, 100, 100 | 75, 79, 86, 91, 95, 85 | 93 |
| 780L3V | 300, 400, 500, 600, 700, ave. | 76, 89, 90, 93, 96, 89 | 79, 80, 99, 96, 99, 91 | 100, 100, 100, 100, 100, 100 | 71, 78, 88, 94, 94, 85 | 91 |
| 781U0M | 300, 400, 500, 600, 700, ave. | 78, 85, 86, 93, 93, 87 | 78, 86, 94, 99, 99, 91 | 100, 100, 100, 100, 100, 100 | 69, 81, 85, 93, 100, 86 | 91 |
| 782S6Y | 300, 400, 500, 600, 700, ave. | 75, 86, 85, 95, 94, 87 | 76, 89, 94, 99, 100, 92 | 100, 100, 100, 100, 100, 100 | 70, 81, 88, 90, 91, 84 | 91 |
| 783P1D | 300, 400, 500, 600, 700, ave. | 74, 83, 90, 91, 91, 86 | 75, 76, 95, 94, 99, 88 | 100, 100, 100, 100, 100, 100 | 73, 80, 85, 93, 96, 85 | 90 |
| 784K6C | 300, 400, 500, 600, 700, ave. | 79, 84, 91, 95, 96, 89 | 81, 85, 98, 98, 100, 92 | 100, 100, 100, 100, 100, 100 | 74, 80, 85, 98, 96, 87 | 92 |
| STD3 | 300, 400, 500, 600, 700, ave. | 76, 85, 95, 95, 95, 89 | 80, 86, 99, 100, 100, 93 | 100, 100, 100, 100, 100, 100 | 75, 78, 85, 89, 94, 84 | 92 |
| STD6 | 300, 400, 500, 600, 700, ave. | 78, 84, 90, 91, 95, 88 | 75, 84, 94, 99, 98, 90 | 100, 100, 100, 100, 100, 100 | 69, 74, 85, 90, 95, 83 | 90 |

All formulations provided perfect control (100%) of CASOB at 300 g a.e./ha, the lowest rate of application. All formulations provided commercial control (85%) of ABUTH, IPOLA and SEBEX at 500 g a.e./ha. Differences among formulations were discerned on ABUTH and IPOLA at the 400 g a.e./ha application rate. Only four of nine formulations controlled both of these weeds at 400 g a.e./ha, which included the STD3 standard, 043A1J, 948I9W, 781U0M and 782S6Y. Of the aforementioned formulations, only 948I9W and 782S6Y contained oxalic acid. When data were averaged across all weed species and all rates of application 948I9W was the most efficacious formulation, followed by 784K6C and the STD3 standard.

The compositions of Table 52A were applied to ABUTH, IPOLA, and ECHCG plants at rates of 350, 450, 550, 650 and 750 g a.e./ha in a field trial done in Washington County, Mississippi. Results, averaged for all replicates of each treatment and across all rates of application for each plant species (reported as the sixth value), as well as an overall average across all plant species, are shown in Table 52Q.

All formulations provided perfect control (100%) of ECHCG in this field test in Mississippi at 350 g a.e./ha, the lowest rate of application. Consistent with the results from test Table 52O, 043A1J, with the highest surfactant load of all formulations in this trial, was the most efficacious formulation, when overall averages (across all three weed species and all rates of application) were compared. 948I9W, an IPA-based glyphosate containing oxalic acid, was the next best formulation in this field study. All formulations except 782S6Y controlled IPOLA at 550 g a.e./ha. ABUTH was more difficult to control than IPOLA in this test, evidenced by the observation that only four formulations reached the 85% control threshold at 750 g a.e./ha, both standards, 043A1J and 948I9W.

The compositions of Table 52A were applied to IPOLA, ABUTH, CASOB and SEBEX plants at rates of 400, 525, 650, 775 and 900 g a.e./ha in a field trial done in Washington County, Mississippi. Results, averaged for all replicates of each treatment and across all rates of application for each plant species (reported as the sixth value), as well as an overall average across all plant species, are shown in Table 52R.

TABLE 52Q

| | % Weed Control | | | |
|---|---|---|---|---|
| Comp. | ABUTH | IPOLA | ECHCG | overall ave. |
| 043A1J | 65, 71, 80, 89, 90, 79 | 83, 88, 88, 93, 93, 89 | 100, 100, 100, 100, 100, 100 | 89 |
| 948I9W | 65, 71, 79, 80, 93, 78 | 80, 81, 85, 91, 90, 86 | 100, 100, 100, 100, 100, 100 | 88 |
| 780L3V | 60, 70, 81, 83, 83, 75 | 79, 85, 86, 88, 90, 86 | 100, 100, 100, 100, 100, 100 | 87 |
| 781U0M | 60, 68, 79, 81, 83, 74 | 79, 81, 88, 88, 90, 85 | 100, 100, 100, 100, 100, 100 | 86 |
| 782S6Y | 58, 75, 81, 84, 84, 76 | 76, 81, 83, 89, 90, 84 | 100, 100, 100, 100, 100, 100 | 87 |
| 783P1D | 56, 69, 79, 81, 83, 74 | 76, 81, 85, 86, 89, 84 | 100, 100, 100, 100, 100, 100 | 86 |
| 784K6C | 61, 70, 81, 84, 84, 76 | 81, 83, 85, 90, 90, 86 | 100, 100, 100, 100, 100, 100 | 87 |
| STD3 | 59, 75, 80, 83, 85, 76 | 79, 81, 86, 89, 91, 85 | 100, 100, 100, 100, 100, 100 | 87 |
| STD6 | 59, 75, 80, 83, 85, 76 | 81, 84, 88, 89, 89, 86 | 100, 100, 100, 100, 100, 100 | 87 |

TABLE 52R

| | | % Weed Control | | | | |
|---|---|---|---|---|---|---|
| Comp. | Rate (g/ha) | IPOLA | ABUTH | SEBEX | CASOB | overall ave. |
| 043A1J | 400, 525, 650, 775, 900, ave. | 53, 60, 66, 71, 83, 67 | 69, 78, 81, 86, 98, 82 | 100, 100, 100, 100, 100, 100 | 100, 100, 100, 100, 100, 100 | 87 |
| 948I9W | 400, 525, 650, 775, 900, ave. | 56, 60, 65, 69, 80, 66 | 71, 73, 84, 85, 91, 81 | 100, 100, 100, 100, 100, 100 | 100, 100, 100, 100, 100, 100 | 87 |
| 780L3V | 400, 525, 650, 775, 900, ave. | 51, 55, 66, 76, 81, 66 | 65, 73, 83, 91, 93, 81 | 100, 100, 100, 100, 100, 100 | 100, 100, 100, 100, 100, 100 | 87 |
| 781U0M | 400, 525, 650, 775, 900, ave. | 53, 54, 63, 70, 80, 64 | 64, 70, 78, 83, 93, 77 | 100, 100, 100, 100, 100, 100 | 100, 100, 100, 100, 100, 100 | 85 |
| 782S6Y | 400, 525, 650, 775, 900, ave. | 48, 61, 63, 73, 84, 66 | 65, 76, 83, 86, 93, 81 | 100, 100, 100, 100, 100, 100 | 100, 100, 100, 100, 100, 100 | 86 |
| 783P1D | 400, 525, 650, 775, 900, ave. | 49, 55, 60, 68, 79, 62 | 65, 69, 75, 86, 95, 78 | 100, 100, 100, 100, 100, 100 | 100, 100, 100, 100, 100, 100 | 85 |
| 784K6C | 400, 525, 650, 775, 900, ave. | 51, 63, 64, 76, 84, 68 | 64, 78, 80, 85, 94, 80 | 100, 100, 100, 100, 100, 100 | 100, 100, 100, 100, 100, 100 | 87 |
| STD3 | 400, 525, 650, 775, 900, ave. | 55, 60, 74, 73, 83, 69 | 69, 74, 80, 88, 93, 81 | 100, 100, 100, 100, 100, 100 | 100, 100, 100, 100, 100, 100 | 88 |
| STD6 | 400, 525, 650, 775, 900, ave. | 53, 60, 69, 70, 83, 67 | 70, 76, 80, 88, 91, 81 | 100, 100, 100, 100, 100, 100 | 100, 100, 100, 100, 100, 100 | 87 |

All formulations provided perfect control (100%) of CASOB and SEBEX at 400 g a.e./ha, the lowest rate of application in this field study. None of the formulations provided a commercial level of control (85%) of IPOLA at 900 g a.e./ha, but when data were averaged across all rates of application, the STD3 standard was the most effective formulation against this weed. 784K6C, an experimental formulation containing oxalic acid, was less efficacious than STD3, but equal to STD6 standard on this weed. All nine formulations provided commercial control of ABUTH at 900 g a.e./ha. Furthermore, the only formulation that failed to provide at least 85% control of ABUTH at 775 g a.e./ha was 781U0M, an experimental formulation lacking oxalic acid. When data were averaged across all rates for ABUTH, 043A1J was the most efficacious formulation, followed by the STD6 standard.

The data from the field experiments conducted under Example 52 were pooled and analyzed with the paired t-test and compared to STD6. Formulations 784K6C, 043A1J and 780L3V were significantly more efficacious than STD6. 780L3V and 784K6C were formulated with diammonium oxalate. The remaining formulations and STD3 could not be distinguished from STD6.

Example 53

The field efficacy effect of high load glyphosate formulations containing a cationic:nonionic surfactant system and inerts was evaluated. Compositions 780L3V, 781U0M, 782S6Y and 783P1D as indicated in Table 52A, above, were prepared. Additional compositions were prepared containing potassium or IPA glyphosate salt, reported in % wt a.e., and excipient ingredients, reported as w/w % unless otherwise indicated, as shown in Table 53.

TABLE 53A

| Comp. | gly salt | [gly] | Cmpnt 1 | wt % | Cmpnt 2 | wt % |
|---|---|---|---|---|---|---|
| 787X8N | K | 39.7 | CIS23 | 9.0 | — | — |
| 788P3A | K | 39.7 | CIS25 | 4.0 | NIS21 | 3.0 |
| 792L7D | K | 36.7 | CIS23 | 6.0 | NIS7 | 2.4 |

TABLE 53A-continued

| Comp. | Cmpnt 3 | wt % | Cmpnt 4 | wt % | Cmpnt 5 | wt % |
|---|---|---|---|---|---|---|
| 787X8N | — | — | OTH5 | 1.0 | — | — |
| 788P3A | NIS22 | 3.0 | OTH23 | 2.5 | — | — |
| 792L7D | NIS23 | 1.4 | OTH5 | 1.0 | OTH3 | 1.0 |

The indicated compositions of Table 52A, the compositions of Table 53A and standards STD3 and STD6 were applied to ABUTH and AMATA plants at rates of 130, 260, 455, 650 and 845 g a.e./ha in a field trial done in Warren County, Illinois. Results, averaged for all replicates of each treatment and across all rates of application for each plant species (reported as the sixth value), as well as an overall average across all plant species, are shown in Table 53B.

TABLE 53B

| | % Weed Control | | |
|---|---|---|---|
| Comp. | ABUTH | AMATA | overall ave. |
| 780L3V | 33, 43, 63, 77, 84, 60 | 82, 84, 92, 85, 99, 88 | 74 |
| 781U0M | 33, 40, 63, 72, 82, 58 | 79, 79, 87, 94, 95, 87 | 72 |
| 782S6Y | 32, 43, 62, 73, 82, 58 | 80, 78, 88, 89, 96, 86 | 72 |
| 783P1D | 33, 42, 61, 70, 86, 58 | 74, 79, 86, 98, 99, 87 | 73 |
| 787X8N | 30, 45, 62, 75, 79, 58 | 84, 80, 86, 90, 99, 88 | 73 |
| 788P3A | 36, 43, 57, 71, 87, 59 | 79, 82, 92, 88, 99, 88 | 73 |
| 792L7D | 34, 41, 58, 75, 80, 58 | 78, 81, 86, 87, 96, 85 | 72 |
| STD3 | 30, 42, 64, 73, 77, 57 | 80, 83, 87, 87, 97, 87 | 72 |
| STD6 | 23, 42, 56, 71, 84, 55 | 81, 84, 88, 90, 97, 88 | 71 |

780L3V and 788P3A provided the greatest ABUTH efficacy. 792L7D was loaded at 480 g a.e./L but was applied as if it were loaded at 540 g a.e./L, hence it was applied at approximately 12% less glyphosate versus the remaining formulations. It demonstrated comparable efficacy at the reduced application rate. Based upon overall averages, all seven of the experimental formulations outperformed STD6.

The indicated compositions of Table 52A, the compositions of Table 53A and standards STD3 and STD6 were applied to ABUTH and AMATA plants at rates of 260, 455, 650, 845 and 1040 g a.e./ha in a field trial done in Warren County, Illinois. Results, averaged for all replicates of each treatment and across all rates of application for each plant species (reported as the sixth value), as well as an overall average across all plant species, are shown in Table 53C.

TABLE 53C

| | % Weed Control | | |
|---|---|---|---|
| Comp. | ABUTH | AMATA | overall ave. |
| 780L3V | 35, 45, 63, 67, 73, 57 | 74, 78, 88, 87, 98, 85 | 71 |
| 781U0M | 36, 48, 56, 72, 80, 58 | 65, 79, 90, 90, 95, 85 | 71 |
| 782S6Y | 37, 52, 55, 66, 81, 58 | 70, 84, 89, 91, 98, 87 | 72 |
| 783P1D | 42, 50, 62, 66, 81, 60 | 78, 83, 89, 89, 96, 87 | 74 |
| 787X8N | 36, 53, 63, 70, 83, 61 | 73, 87, 90, 92, 98, 88 | 74 |
| 788P3A | 38, 52, 50, 63, 71, 55 | 71, 80, 87, 89, 93, 84 | 69 |
| 792L7D | 35, 43, 60, 66, 74, 56 | 75, 80, 90, 86, 95, 85 | 70 |
| STD3 | 42, 51, 68, 72, 80, 63 | 75, 80, 88, 92, 96, 86 | 74 |
| STD6 | 40, 48, 58, 68, 76, 58 | 76, 78, 91, 88, 98, 86 | 72 |

STD3 was the top performing composition for control of ABUTH in this field test, while 787X8N was the next most efficacious composition, and it was best of the formulations containing oxalic acid. For AMATA control, compositions 787X8N, 782S6Y and 783P1D were more efficacious than standards STD3 and STD6. Overall, composition 787X8N, 783P1D and STD3 were the most efficacious formulations in this trial.

The indicated compositions of Table 52A, the compositions of Table 53A and standards STD3 and STD6 were applied to IPOSS and ABUTH plants at rates of 455, 715, 975 and 1235 g a.e./ha in a field trial done in Warren County, Illinois. Results, averaged for all replicates of each treatment and across all rates of application for each plant species (reported as the fifth value), as well as an overall average across all plant species, are shown in Table 53D.

TABLE 53D

| | % Weed Control | | |
|---|---|---|---|
| Comp. | IPOSS | ABUTH | overall ave. |
| 780L3V | 60, 66, 71, 72, 67 | 80, 94, 100, 100, 93 | 80 |
| 781U0M | 57, 66, 69, 75, 67 | 80, 92, 97, 100, 92 | 79 |
| 782S6Y | 57, 66, 69, 71, 66 | 81, 93, 97, 100, 93 | 79 |
| 783P1D | 60, 64, 70, 71, 66 | 76, 95, 100, 100, 93 | 80 |
| 787X8N | 56, 68, 68, 76, 67 | 80, 97, 98, 100, 93 | 80 |
| 788P3A | 57, 65, 67, 71, 65 | 79, 87, 100, 100, 91 | 78 |
| 792L7D | 58, 65, 70, 72, 66 | 80, 93, 100, 100, 93 | 80 |
| STD3 | 56, 69, 68, 74, 67 | 78, 94, 92, 100, 91 | 79 |
| STD6 | 53, 64, 69, 74, 65 | 81, 92, 98, 100, 93 | 79 |

Compositions 780L3V and 787X8N, both containing oxalic acid, and STD3 were the most efficacious against IPOSS. Against ABUTH, all formulations containing oxalic acid were more efficacious than STD3. Based upon the overall averages, compositions 787X8N, 780L3V, 782S6Y and 783P1D outperformed STD6.

The indicated compositions of Table 52A, the compositions of Table 53A and standards STD3 and STD6 were applied to IPOSS and ABUTH plants at rates of 325, 585, 845 and 1105 g a.e./ha in a field trial done in Warren County, Illinois. Results, averaged for all replicates of each treatment and across all rates of application for each plant species (reported as the fifth value), as well as an overall average across all plant species, are shown in Table 53E.

TABLE 53E

| | % Weed Control | | |
|---|---|---|---|
| Comp. | IPOSS | ABUTH | overall ave. |
| 780L3V | 60, 75, 84, 86, 76 | 80, 93, 99, 100, 93 | 85 |
| 781U0M | 62, 70, 85, 88, 76 | 82, 94, 96, 99, 93 | 84 |
| 782S6Y | 60, 73, 82, 91, 76 | 84, 95, 99, 100, 94 | 85 |
| 783P1D | 57, 75, 81, 87, 75 | 86, 96, 93, 100, 94 | 84 |
| 787X8N | 61, 73, 82, 86, 75 | 77, 97, 100, 98, 93 | 84 |
| 788P3A | 60, 74, 82, 82, 74 | 78, 89, 94, 100, 90 | 82 |
| 792L7D | 61, 73, 81, 86, 75 | 79, 91, 96, 100, 91 | 83 |
| STD3 | 59, 71, 84, 87, 75 | 80, 98, 99, 100, 94 | 85 |
| STD6 | 59, 78, 82, 88, 76 | 83, 91, 97, 100, 92 | 84 |

782S6Y and 783P1D were was the only formulations that matched standard STD3 for control of ABUTH. Three of the experimental formulations containing oxalic acid, 780L3V, 781U0M and 787X8N ranked lower than standard STD3 on ABUTH, but were better than standard STD6. Standard STD6 and three formulations, 782S6Y, 780L3V and 781U0M were the most efficacious formulations for IPOSS control. 780L3V and 782S6Y were the most efficacious formulations averaged across both broadleaf weed species and all rates of application, equaling the efficacy of standard STD3.

The indicated compositions of Table 52A, the compositions of Table 53A and standards STD3 and STD6 were applied to SEBEX, CASOB, ABUTH, IPOLA, SIDSP and ECHCG plants at rates of 210, 420, 630 and 840 g a.e./ha in a field trial done in Baldwin County, Alabama. Results, averaged for all replicates of each treatment and across all rates of application for each plant species (reported as the fifth value), as well as an overall average across all plant species, are shown in Table 53F.

TABLE 53F

| | % Weed Control | | | | | | |
|---|---|---|---|---|---|---|---|
| Comp. | SEBEX | CASOB | IPOLA | SIDSP | ABUTH | ECHCG | overall ave. |
| 780L3V | 48, 75, 77, 86, 71 | 69, 81, 80, 87, 79 | 39, 51, 68, 76, 59 | 41, 68, 74, 91, 69 | 44, 56, 73, 76, 62 | 56, 71, 79, 88, 74 | 69 |
| 781U0M | 45, 75, 78, 83, 60 | 58, 85, 87, 85, 78 | 38, 51, 64, 69, 55 | 43, 67, 82, 91, 70 | 42, 52, 63, 87, 61 | 53, 71, 75, 82, 70 | 68 |
| 782S6Y | 47, 76, 78, 81, 70 | 69, 77, 87, 85, 80 | 38, 50, 61, 71, 55 | 41, 71, 78, 90, 70 | 36, 57, 70, 81, 61 | 54, 72, 75, 75, 69 | 67 |
| 783P1D | 40, 75, 78, 86, 70 | 71, 82, 85, 86, 81 | 39, 51, 65, 73, 57 | 45, 74, 82, 89, 72 | 41, 54, 79, 80, 63 | 52, 68, 80, 82, 70 | 69 |
| 787X8N | 59, 72, 76, 87, 74 | 75, 76, 83, 83, 79 | 41, 49, 63, 72, 56 | 40, 69, 77, 87, 68 | 44, 50, 69, 89, 63 | 61, 66, 71, 77, 69 | 68 |
| 788P3A | 44, 65, 76, 82, 67 | 70, 83, 75, 85, 78 | 38, 49, 63, 64, 53 | 41, 57, 85, 91, 68 | 41, 51, 65, 69, 56 | 46, 70, 80, 76, 68 | 65 |
| 792L7D | 38, 75, 82, 79, 69 | 66, 80, 88, 88, 81 | 37, 50, 64, 68, 55 | 45, 58, 78, 94, 69 | 42, 50, 71, 75, 59 | 50, 73, 79, 81, 70 | 67 |

TABLE 53F-continued

% Weed Control

| Comp. | SEBEX | CASOB | IPOLA | SIDSP | ABUTH | ECHCG | overall ave. |
|---|---|---|---|---|---|---|---|
| STD3 | 42, 68, 76, 81, 67 | 65, 83, 84, 82, 78 | 39, 53, 62, 70, 57 | 43, 75, 87, 93, 74 | 45, 57, 79, 89, 68 | 58, 71, 81, 82, 73 | 69 |
| STD6 | 50, 73, 78, 84, 71 | 69, 84, 85, 83, 80 | 40, 53, 61, 71, 56 | 43, 71, 83, 91, 72 | 41, 57, 82, 79, 65 | 56, 66, 77, 81, 70 | 69 |

Standards STD3 and STD6, and experimental formulations 780L3V and 783P1D, were the most efficacious compositions across all weed species in this trial. The compositions containing oxalic acid generally outperformed STD3 against CASOB and SEBEX. STD3 showed greater efficacy against ABUTH and SIDSP than the experimental compositions.

The indicated compositions of Table 52A, the compositions of Table 53A and standards STD3 and STD6 were applied to SEBEX, CASOB, ABUTH, IPOLA, SIDSP and ECHCG plants at rates of 400, 600, 800 and 1000 g a.e./ha in a field trial done in Baldwin Conty, Ala. Results, averaged for all replicates of tion for each plant species (reported as the fifth value), as well as an overall average across all plant species, are shown in Table 53G.

TABLE 53G

% Weed Control

| Comp. | SEBEX | CASOB | ABUTH | IPOLA | SIDSP | ECHCG | overall ave. |
|---|---|---|---|---|---|---|---|
| 780L3V | 43, 55, 58, 60, 54 | 68, 85, 85, 87, 81 | 56, 69, 85, 87, 74 | 48, 59, 64, 68, 60 | 78, 84, 84, 91, 84 | 62, 77, 81, 83, 76 | 71 |
| 781U0M | 38, 55, 56, 63, 53 | 69, 83, 84, 89, 81 | 50, 64, 74, 87, 69 | 45, 55, 56, 63, 55 | 65, 72, 85, 93, 79 | 60, 73, 76, 86, 74 | 68 |
| 782S6Y | 49, 55, 57, 60, 55 | 75, 85, 88, 87, 84 | 59, 67, 81, 78, 71 | 48, 59, 64, 67, 60 | 79, 82, 89, 94, 86 | 61, 77, 78, 85, 75 | 72 |
| 783P1D | 45, 56, 54, 65, 55 | 67, 83, 85, 87, 80 | 50, 61, 69, 80, 65 | 51, 55, 56, 68, 57 | 68, 74, 73, 89, 76 | 60, 76, 70, 86, 73 | 68 |
| 787X8N | 42, 55, 55, 58, 52 | 63, 80, 83, 89, 79 | 56, 69, 71, 84, 70 | 45, 58, 62, 71, 59 | 71, 77, 78, 93, 80 | 60, 73, 79, 83, 74 | 69 |
| 788P3A | 38, 49, 52, 60, 50 | 65, 76, 85, 89, 78 | 50, 62, 75, 78, 66 | 45, 54, 63, 71, 58 | 60, 77, 82, 88, 77 | 58, 73, 78, 81, 73 | 67 |
| 792L7D | 33, 50, 57, 62, 50 | 68, 78, 87, 85, 80 | 48, 70, 72, 76, 68 | 45, 53, 66, 66, 57 | 67, 79, 83, 90, 80 | 56, 79, 79, 80, 73 | 68 |
| STD3 | 37, 50, 55, 58, 50 | 75, 83, 84, 81, 81 | 56, 71, 76, 80, 71 | 50, 62, 72, 72, 64 | 74, 77, 77, 87, 79 | 67, 73, 80, 76, 74 | 70 |
| STD6 | 41, 53, 57, 63, 53 | 74, 87, 86, 90, 84 | 56, 61, 75, 83, 69 | 46, 53, 63, 70, 58 | 64, 71, 85, 94, 78 | 64, 69, 81, 82, 74 | 69 |

When the data were averaged across all six weed species present in this test, 780L3V and 782S6Y demonstrated greater overall efficacy than standards STD3 and STD6.

The indicated compositions of Table 52A, the compositions of Table 53A and standards STD3 and STD6 were applied to IPOLA, CASOB and SEBEX plants at rates of 260, 390, 520 and 650 g a.e./ha in a field trial done in Washington County, Miss. Results, averaged for all replicates of each treatment and across all rates of application for each plant species (reported as the fifth value), as well as an overall average across all plant species, are shown in Table 53H.

TABLE 53H

% Weed Control

| Comp. | IPOLA | CASOB | SEBEX | overall ave. |
|---|---|---|---|---|
| 780L3V | 50, 65, 74, 81, 68 | 73, 83, 86, 88, 82 | 46, 60, 66, 70, 61 | 70 |
| 781U0M | 54, 64, 79, 84, 70 | 75, 84, 86, 88, 83 | 51, 61, 65, 76, 63 | 72 |
| 782S6Y | 53, 65, 75, 78, 68 | 75, 84, 85, 86, 83 | 45, 60, 63, 73, 60 | 70 |
| 783P1D | 54, 64, 76, 84, 69 | 74, 83, 85, 88, 82 | 51, 61, 71, 75, 65 | 72 |
| 787X8N | 58, 63, 71, 78, 67 | 78, 83, 88, 88, 84 | 49, 56, 68, 71, 61 | 71 |
| 788P3A | 50, 56, 68, 75, 62 | 71, 80, 81, 84, 79 | 45, 59, 61, 66, 58 | 66 |
| 792L7D | 53, 63, 69, 75, 65 | 74, 78, 83, 86, 80 | 49, 53, 65, 73, 60 | 68 |
| STD3 | 54, 61, 79, 84, 69 | 74, 81, 85, 88, 82 | 49, 60, 63, 76, 62 | 71 |
| STD6 | 55, 66, 79, 84, 71 | 75, 83, 84, 89, 83 | 48, 63, 66, 73, 62 | 72 |

Experimental compositions 781U0M and 783P1D, both containing oxalic acid, outperformed standard STD3 and were equal to STD6, based upon the overall average across all three weed species.

The indicated compositions of Table 52A, the compositions of Table 53A and standards STD3 and STD6 were applied to IPOLA, ABUTH, CASOB and SEBEX plants at rates of 250, 375, 500 and 625 g a.e./ha in a field trial done in Washington County, Miss. Results, averaged for all replicates of each treatment and across all rates of application for each plant species (reported as the fifth value), as well as an overall average across all plant species, are shown in Table 53I.

TABLE 53I

% Weed Control

| Comp. | IPOLA | ABUTH | CASOB | SEBEX | overall ave. |
|---|---|---|---|---|---|
| 780L3V | 56, 78, 79, 80, 73 | 64, 75, 89, 90, 79 | 75, 90, 91, 96, 88 | 56, 75, 79, 81, 73 | 78 |
| 781U0M | 51, 65, 71, 79, 67 | 70, 73, 81, 88, 78 | 83, 84, 88, 95, 87 | 69, 71, 80, 85, 76 | 77 |
| 782S6Y | 51, 65, 80, 84, 70 | 64, 75, 89, 91, 80 | 80, 83, 88, 94, 86 | 54, 69, 84, 85, 73 | 78 |
| 783P1D | 55, 66, 75, 79, 69 | 65, 74, 81, 84, 76 | 80, 83, 88, 95, 86 | 53, 68, 78, 81, 70 | 75 |
| 787X8N | 53, 68, 71, 88, 70 | 64, 76, 85, 89, 78 | 79, 86, 90, 93, 87 | 59, 65, 75, 79, 69 | 76 |
| 788P3A | 50, 70, 74, 84, 69 | 64, 79, 81, 88, 78 | 74, 86, 86, 93, 85 | 49, 64, 76, 79, 67 | 75 |
| 792L7D | 56, 63, 70, 84, 68 | 69, 74, 80, 89, 78 | 80, 84, 89, 98, 88 | 61, 69, 79, 85, 73 | 77 |
| STD3 | 59, 70, 74, 81, 71 | 69, 81, 84, 88, 80 | 78, 83, 88, 93, 85 | 58, 70, 73, 83, 71 | 77 |
| STD6 | 53, 65, 74, 78, 67 | 70, 80, 85, 88, 81 | 79, 83, 88, 91, 85 | 55, 63, 78, 79, 68 | 75 |

All of the experimental compositions containing oxalic acid, except 788P3M and 783P1D, were more efficacious across all weed species than standards STD3 and STD6.

The indicated compositions of Table 52A, the compositions of Table 53A and standards STD3 and STD 6 were applied to IPOLA, ABUTH, CASOB and SEBEX plants at rates of 250, 375, 500 and 625 g a.e./ha in a field trial done in Washington County, Miss. Results, averaged for all replicates of each treatment and across all rates of application for each plant species (reported as the fifth value), as well as an overall average across all plant species, are shown in Table 53J.

TABLE 53J

% Weed Control

| Comp. | IPOLA | ABUTH | CASOB | SEBEX | overall ave. |
|---|---|---|---|---|---|
| 780L3V | 53, 60, 69, 88, 67 | 64, 73, 75, 86, 74 | 80, 89, 90, 96, 89 | 54, 70, 70, 86, 70 | 75 |
| 781U0M | 51, 61, 71, 90, 68 | 58, 76, 76, 84, 73 | 83, 88, 89, 93, 88 | 59, 70, 74, 81, 71 | 75 |
| 782S6Y | 54, 64, 75, 93, 71 | 58, 66, 83, 90, 74 | 79, 88, 91, 91, 87 | 54, 60, 66, 81, 65 | 75 |
| 783P1D | 56, 64, 75, 85, 70 | 61, 70, 78, 85, 73 | 75, 89, 91, 93, 87 | 53, 75, 78, 84, 72 | 76 |
| 787X8N | 49, 64, 74, 84, 68 | 53, 65, 70, 86, 68 | 68, 89, 88, 94, 84 | 55, 69, 70, 84, 69 | 72 |
| 788P3A | 51, 58, 73, 81, 66 | 56, 66, 71, 81, 69 | 80, 88, 90, 93, 88 | 53, 71, 73, 84, 70 | 73 |
| 792L7D | 51, 60, 76, 86, 68 | 66, 68, 75, 90, 75 | 75, 88, 91, 94, 87 | 55, 75, 78, 84, 73 | 76 |
| STD3 | 54, 63, 81, 86, 71 | 55, 78, 85, 93, 78 | 79, 86, 93, 95, 88 | 59, 70, 69, 80, 69 | 77 |
| STD6 | 53, 56, 80, 84, 68 | 58, 66, 78, 83, 71 | 81, 88, 91, 91, 88 | 54, 76, 79, 83, 73 | 75 |

Standard STD3 was the most efficacious formulation across the four broadleaf weed species ABUTH, CASOB, IPOLA and SEBEX. Experimental compositions 780L3V, 781U0M, 782S6Y, 783P1D and 792L7D, each containing oxalic acid, were equal to standard STD6.

Data from the experiments presented for Example 53 were pooled and analyzed using the paired t-test method of analysis. Results from the analysis revealed that only one formulation, 780L3V, was significantly more efficacious than STD6. Two experimental formulations, 788P3A and 792L7D, proved to be significantly less efficacious than STD6. The remaining five formulations could not be distinguished from this commercial standard.

Example 54

The field efficacy effect of high load potassium glyphosate formulations containing a cationic:nonionic surfactant system and inerts was evaluated. Composition 784K6C was prepared as indicated in Table 52A above and composition 791P9N was prepared containing 480 g a.e./kg (36.7 wt %) potassium glyphosate salt and excipient ingredients, reported as w/w %, as shown in Table 54A. The efficacy of the two experimental compositions were compared to STD6 and STD11 for their ability to control broadleaf weeds. Nine separate field trials were conducted, and each experiment contained between two and five different broadleaf weed species. Each test included four rates of application, but the rates in each study varied depending upon the target weed species and its stage of growth at the time of treatment.

TABLE 54A

| Comp. | Cmpnt 1 | wt % | Cmpnt 2 | wt % | Cmpnt 3 | wt % |
|---|---|---|---|---|---|---|
| 791P9N | CIS26 | 3.0 | NIS25 | 6.0 | — | — |

Compositions 784K6C and 791P9N, and standards STD6 and STD11 were applied to IPOLA, ABUTH, CASOB and SEBEX plants at three rate schedules, expressed in g a.e./ha of: Rate1 at 260, 390, 520 and 650; Rate 2 at 250, 325, 500 and 625; and Rate 3 at 260, 390, 520 and 650 in a field trial done in Stoneville, Miss. Results, averaged for all replicates of each treatment and across all rates of application for each plant species (reported as the fifth value), as well as an overall average across all plant species, are shown in Table 54B.

TABLE 54B

% Weed Control

| Comp. | Rate | IPOLA | ABUTH | CASOB | SEBEX | overall ave. |
|---|---|---|---|---|---|---|
| 784K6C | 1 | 53, 60, 73, 78, 66 | — | 75, 81, 89, 91, 84 | 45, 58, 73, 78, 63 | 71 |
| 791P9N | 1 | 56, 61, 74, 88, 70 | — | 74, 83, 89, 95, 85 | 41, 53, 69, 74, 59 | 71 |
| STD6 | 1 | 54, 56, 66, 80, 64 | — | 76, 78, 91, 93, 84 | 50, 51, 68, 66, 59 | 69 |
| STD11 | 1 | 50, 55, 68, 75, 62 | — | 68, 81, 86, 91, 82 | 36, 55, 63, 70, 56 | 67 |
| 784K6C | 2 | 41, 74, 75, 85, 69 | — | 71, 84, 86, 90, 83 | 40, 54, 61, 68, 56 | 69 |
| 791P9N | 2 | 53, 65, 74, 93, 71 | — | 73, 83, 90, 98, 86 | 45, 48, 63, 71, 57 | 71 |
| STD6 | 2 | 46, 64, 69, 85, 66 | — | 65, 81, 88, 98, 83 | 43, 50, 59, 71, 56 | 68 |
| STD11 | 2 | 48, 65, 76, 88, 69 | — | 64, 83, 88, 98, 83 | 36, 48, 59, 73, 54 | 69 |
| 784K6C | 3 | 56, 71, 74, 76, 69 | 66, 74, 85, 88, 78 | 86, 95, 95, 100, 94 | 75, 89, 93, 94, 88 | 82 |
| 791P9N | 3 | 53, 66, 74, 81, 68 | 68, 81, 84, 94, 82 | 84, 94, 96, 100, 93 | 76, 88, 94, 98, 89 | 83 |
| STD11 | 3 | 53, 59, 79, 79, 67 | 70, 78, 81, 90, 80 | 86, 93, 94, 100, 93 | 83, 86, 89, 98, 89 | 82 |
| 784K6C | 3 | — | 56, 73, 80, 84, 76 | 68, 78, 88, 91, 86 | 55, 63, 71, 76, 75 | 79 |
| 791P9N | 3 | — | 63, 71, 81, 84, 75 | 73, 83, 88, 89, 83 | 63, 66, 69, 78, 69 | 75 |
| STD11 | 3 | — | 66, 75, 81, 83, 73 | 80, 86, 89, 90, 81 | 65, 73, 79, 84, 66 | 73 |

Data from the four field experiments presented for Table 54B were pooled and analyzed. The results of the analysis showed that 791P9N was significantly more efficacious than STD6. The remaining formulations could not be distinguished from STD6.

Compositions 784K6C and 791P9N, and standards STD6 and STD11 were applied to SEBEX, CASOB, IPOLA, SIDSP and ABUTH plants at three rate schedules, expressed in g a.e./ha: Rate 1 at 189, 378, 567 and 756; Rate 2 at 426, 615, 804 and 993; and Rate 3 at 350, 550, 750 and 950 in a field trial done in Loxley, Ala. Results, averaged for all replicates of each treatment and across all rates of application for each plant species (reported as the fifth value), as well as an overall average across all plant species, are shown in Table 54C.

TABLE 54C

% Weed Control

| Comp. | Rate | SEBEX | CASOB | IPOLA | SIDSP | ABUTH | overall ave. |
|---|---|---|---|---|---|---|---|
| 784K6C | 1 | 18, 54, 67, 73, 53 | 35, 63, 79, 87, 66 | 28, 48, 54, 71, 50 | 31, 55, 87, 87, 65 | 36, 69, 86, 91, 70 | 60.7 |
| 791P9N | 1 | 18, 53, 66, 75, 53 | 40, 65, 82, 87, 68 | 35, 46, 58, 65, 51 | 39, 68, 88, 88, 71 | 39, 73, 87, 95, 73 | 63.3 |
| STD6 | 1 | 16, 53, 63, 72, 51 | 35, 62, 74, 82, 63 | 33, 51, 54, 66, 51 | 36, 75, 92, 90, 73 | 40, 68, 85, 93, 72 | 61.9 |
| STD11 | 1 | 16, 55, 70, 73, 53 | 31, 67, 78, 85, 65 | 31, 48, 57, 65, 50 | 36, 77, 91, 88, 73 | 38, 72, 81, 84, 69 | 62.1 |
| 784K6C | 2 | 45, 52, 70, 70, 60 | 57, 74, 87, 88, 77 | 48, 53, 67, 68, 59 | 53, 77, 85, 83, 74 | 46, 62, 71, 73, 63 | 66.5 |
| 791P9N | 2 | 31, 51, 57, 65, 51 | 45, 75, 76, 85, 70 | 48, 61, 71, 70, 62 | 53, 81, 81, 84, 74 | 54, 66, 72, 83, 68 | 65.1 |
| STD11 | 2 | 43, 44, 65, 73, 56 | 58, 68, 84, 84, 73 | 50, 55, 64, 70, 59 | 53, 72, 86, 82, 73 | 54, 57, 66, 83, 65 | 65.3 |
| 784K6C | 3 | 46, 53, 61, 63, 56 | 60, 72, 85, 90, 77 | 54, 64, 69, 73, 65 | 56, 82, 92, 95, 81 | 53, 74, 83, 86, 74 | 70.3 |
| 791P9N | 3 | 43, 43, 59, 63, 52 | 63, 72, 84, 90, 77 | 49, 55, 64, 76, 61 | 53, 72, 93, 94, 78 | 49, 69, 81, 85, 71 | 67.7 |
| STD11 | 3 | 47, 52, 58, 62, 55 | 61, 76, 82, 89, 77 | 50, 57, 63, 73, 61 | 57, 81, 92, 97, 82 | 57, 82, 87, 86, 78 | 70.4 |

Data from the three studies in Loxley, Ala. were pooled and analyzed using the paired t-test method of analysis. Results showed that all formulations were essentially equal to STD6.

Compositions 784K6C and 791P9N, and standards STD6 and STD11 were applied to IPOSS, ABUTH and AMATA plants at three rate schedules, in g a.e./ha: Rate 1 at 325, 585, 845 and 1105; Rate 2 at 390, 650, 910 and 1235; and Rate 3 at 195, 390, 650 and 910 in a field trial done in Monmouth and Warren Counties in Illinois. Results, averaged for all replicates of each treatment and across all rates of application for each plant species (reported as the fifth value), as well as an overall average across all plant species, are shown in Table 54D.

TABLE 54D

% Weed Control

| Comp. | IPOSS | ABUTH | AMATA | overall ave. |
|---|---|---|---|---|
| 784K6C[1] | 49, 62, 68, 74, 63 | 67, 85, 88, 92, 83 | — | 73 |
| 791P9N[1] | 50, 61, 68, 72, 63 | 63, 80, 93, 89, 81 | — | 72 |
| STD6[1] | 50, 61, 67, 73, 63 | 61, 82, 84, 94, 80 | — | 71 |
| STD11[1] | 48, 59, 67, 74, 62 | 68, 77, 84, 91, 80 | — | 71 |
| 784K6C[2] | 56, 63, 65, 76, 65 | 64, 82, 81, 92, 80 | — | 72 |
| 791P9N[2] | 54, 57, 68, 71, 62 | 61, 80, 83, 90, 78 | — | 70 |
| STD6[2] | 53, 58, 66, 71, 62 | 60, 77, 84, 92, 78 | — | 70 |
| STD11[2] | 55, 59, 72, 66, 63 | 59, 79, 83, 87, 77 | — | 70 |

TABLE 54D-continued

% Weed Control

| Comp. | IPOSS | ABUTH | AMATA | overall ave. |
|---|---|---|---|---|
| 784K6C[3] | — | 37, 52, 72, 90, 63 | 83, 97, 100, 100, 95 | 79 |
| 791P9N[3] | — | 31, 53, 75, 84, 60 | 80, 95, 100, 100, 94 | 77 |
| STD11[3] | — | 34, 46, 69, 80, 57 | 82, 95, 99, 100, 94 | 76 |
| 784K6C[1] | 53, 75, 78, 83, 72 | 83, 100, 100, 100, 96 | — | 84 |

TABLE 54D-continued

% Weed Control

| Comp. | IPOSS | ABUTH | AMATA | overall ave. |
|---|---|---|---|---|
| 791P9N[1] | 50, 65, 77, 85, 70 | 88, 100, 100, 100, 97 | — | 83 |
| STD11[1] | 47, 62, 79, 83, 68 | 85, 96, 100, 100, 95 | — | 81 |

[1]Rate 1;
[2]Rate 2; and
[3]Rate 3

The data for the four experiments were pooled and analyzed using the paired t-test method of analysis. Results showed that 784K6C was significantly more efficacious than STD6.

The data from example 54 is summarized in Tables 54E through 54H. Efficacy comparisons with STD11 are shown in Tables 54E and 54F. Efficacy comparisons with STD6 are shown in Tables 54G and 54H. Results for compositions 784K6C and 791P9N are reported in Tables 54E and 54F, respectively. In those tables the data are reported for each weed, averaged across all tests and rates of application for each of the individual species. The overall average, or the grand means, are also shown.

TABLE 54E

Efficacy of 784K6C compared to STD11

| Weed Target | # of Field Tests | STD11 | 784K6C |
|---|---|---|---|
| ABUTH | 9 | 75 | 76 |
| AMATA | 1 | 94 | 95 |
| CASOB | 7 | 79 | 81 |
| IPOLA | 6 | 61 | 63 |
| IPOSS | 3 | 64 | 67 |
| SEBEX | 7 | 62 | 64 |
| SIDSP | 3 | 77 | 73 |
| overall ave. | — | 71 | 72 |

TABLE 54F

Efficacy of 791P9N compared to STD11

| Weed Target | # of Field Tests | STD11 | 791P9N |
|---|---|---|---|
| ABUTH | 9 | 75 | 76 |
| AMATA | 1 | 94 | 94 |
| CASOB | 7 | 79 | 80 |
| IPOLA | 6 | 61 | 64 |
| IPOSS | 3 | 64 | 65 |
| SEBEX | 7 | 61 | 61 |
| SIDSP | 3 | 76 | 74 |
| overall ave. | — | 70 | 71 |

The data of Tables 54E and 54F were analyzed. 784K6C was significantly more efficacious than STD11 on an overall basis. 784K6C outperformed STD11 on IPOSS, CASOB and SEBEX but was less efficacious than the standard on SIDSP. 791P9N was found to be more efficacious than STD11 and outperformed it on ABUTH and IPOLA.

Results for compositions 784K6C and 791P9N as compared to STD6 are reported in Tables 54G and 54H, respectively. In those tables the data are reported for each weed, averaged across all tests and rates of application for each of the individual species. The overall averages, or the grand means, are also shown.

TABLE 54G

Efficacy of 784K6C compared to STD6

| Weed Target | # of Field Tests | STD6 | 784K6C |
|---|---|---|---|
| ABUTH | 3 | 77 | 78 |
| CASOB | 3 | 77 | 78 |
| IPOLA | 3 | 60 | 61 |
| IPOSS | 2 | 62 | 64 |
| SEBEX | 3 | 55 | 57 |
| SIDSP | 1 | 73 | 65 |
| overall ave. | — | 67 | 68 |

TABLE 54H

Efficacy of 791P9N compared to STD6

| Weed Target | # of Field Tests | STD6 | 791P9N |
|---|---|---|---|
| ABUTH | 3 | 77 | 78 |
| CASOB | 3 | 77 | 80 |
| IPOLA | 3 | 60 | 64 |
| IPOSS | 2 | 62 | 63 |
| SEBEX | 3 | 55 | 56 |
| SIDSP | 1 | 73 | 71 |
| overall ave. | — | 67 | 69 |

Data for the experiments conducted for 784K6C and 791P9N compared to STD6 were pooled and analyzed with the paired t-test method of analysis. 784K9C could not be distinguished from STD6 when all of the data were considered. However, control of SIDSP in the one test where these formulations were compared, 784K9C was significantly less efficacious than the standard. 791P9N was significantly more efficacious than STD6 and outperformed STD6 on SEBEX and CASOB.

Example 55

The efficacy effect of oxalic acid and diammonium oxalate was evaluated on TOUCHDOWN IQ® (TDIQ), a glyphosate diammonium salt formulation and compared to standards STD3, a glyphosate IPA salt formulation, and STD6, a glyphosate potassium salt formulation. Results are reported in Tables 55A-55G. The superscript letters in each table represent:

[a] Ammonium sulfate added; 2.0% w/w

[b] Diammonium oxalate added at 10:1 TD-IQ:DA a.e.:a.e. ratio;

[c] Diammonium oxalate added at 25:1 TD-IQ:DA ratio;

[d] Oxalic acid added at 10:1 TD-IQ:OA ratio; and

[e] Oxalic acid added at 25:1 TD-IQ:OA ratio.

The compositions were applied to TRZAX, AVESS, LOLMG and LOLPE plants at 100, 200, 300, 400 and 500 g a.e. per hectare in a field trial done in Washington County, Miss. Results, averaged for all replicates of each treatment and across all rates of application for each plant species (reported as the sixth value), as well as an overall average across all plant species, are shown in Table 55A.

TABLE 55A

| Comp. | TRZAX | AVESS | LOLMG | LOLPE | overall ave. |
|---|---|---|---|---|---|
| STD6 | 59, 84, 88, 94, 99, 85 | 64, 94, 98, 99, 100, 91 | 63, 75, 84, 90, 95, 81 | 43, 58, 74, 79, 86, 68 | 81 |
| STD6$^a$ | 61, 86, 90, 95, 99, 86 | 65, 91, 98, 100, 100, 91 | 65, 83, 88, 93, 98, 85 | 50, 65, 78, 85, 89, 73 | 84 |
| STD3 | 58, 83, 90, 96, 99, 85 | 63, 93, 99, 100, 100, 91 | 59, 83, 85, 91, 94, 82 | 43, 65, 80, 85, 90, 73 | 83 |
| TD-IQ | 55, 81, 86, 96, 99, 84 | 59, 93, 96, 100, 100, 90 | 56, 85, 88, 93, 96, 84 | 44, 71, 81, 91, 93, 76 | 83 |
| TD-IQ$^b$ | 59, 83, 86, 98, 100, 85 | 64, 90, 95, 100, 100, 90 | 61, 81, 91, 95, 100, 86 | 48, 75, 84, 91, 94, 78 | 85 |
| TD-IQ$^c$ | 58, 81, 85, 98, 100, 84 | 60, 91, 96, 100, 100, 90 | 59, 83, 88, 96, 100, 85 | 49, 76, 86, 91, 93, 79 | 84 |
| TD-IQ$^d$ | 59, 80, 86, 95, 99, 84 | 68, 90, 95, 100, 100, 91 | 66, 79, 91, 95, 99, 86 | 50, 75, 85, 90, 94, 79 | 85 |
| TD-IQ$^e$ | 58, 83, 88, 99, 100, 85 | 61, 90, 98, 100, 100, 90 | 68, 84, 86, 95, 98, 86 | 49, 73, 81, 93, 94, 78 | 85 |

The compositions were applied to TRZAX, AVESS, LOLMG and LOLPE plants at 100, 200, 300, 400 and 500 g a.e. per hectare in a field trial done in Washington County, Miss. Results, averaged for all replicates of each treatment and across all rates of application for each plant species (reported as the sixth value), as well as an overall average across all plant species, are shown in Table 55B.

TABLE 55B

| Comp. | TRZAX | AVESS | LOLMG | LOLPE | overall ave. |
|---|---|---|---|---|---|
| STD6 | 50, 75, 84, 88, 91, 78 | 49, 75, 85, 88, 90, 77 | 44, 58, 75, 74, 85, 67 | 33, 48, 55, 63, 79, 55 | 69 |
| STD6$^a$ | 68, 83, 90, 95, 98, 87 | 64, 76, 86, 94, 94, 83 | 55, 73, 81, 86, 91, 77 | 39, 53, 64, 69, 81, 61 | 77 |
| STD3 | 43, 74, 84, 88, 91, 76 | 41, 71, 83, 89, 94, 76 | 43, 61, 70, 80, 86, 68 | 24, 50, 56, 65, 79, 55 | 69 |
| TD-IQ | 53, 73, 80, 85, 86, 75 | 54, 69, 76, 81, 89, 74 | 46, 64, 71, 78, 88, 69 | 29, 51, 60, 73, 83, 59 | 69 |
| TD-IQ$^b$ | 59, 80, 84, 89, 94, 81 | 56, 76, 86, 93, 95, 81 | 50, 70, 75, 84, 90, 74 | 36, 55, 73, 83, 90, 67 | 76 |
| TD-IQ$^c$ | 61, 78, 86, 93, 96, 83 | 55, 75, 84, 94, 96, 81 | 49, 61, 76, 85, 93, 73 | 34, 53, 66, 79, 86, 64 | 75 |
| TD-IQ$^d$ | 60, 78, 85, 91, 91, 81 | 55, 75, 85, 95, 93, 81 | 49, 64, 78, 88, 85, 73 | 31, 56, 73, 85, 84, 66 | 75 |
| TD-IQ$^e$ | 56, 78, 84, 92, 94, 81 | 53, 75, 84, 95, 96, 81 | 50, 63, 75, 88, 90, 73 | 35, 54, 74, 85, 85, 67 | 75 |

The compositions were applied to LOLMG, EROCI, LOLPE and OEOLA plants at 100, 200, 300, 400 and 500 g a.e. per hectare in a field trial done in Baldwin County, Ala. Results, averaged for all replicates of each treatment and across all rates of application for each plant species (reported as the sixth value), as well as an overall average across all plant species, are shown in Table 55C.

TABLE 55C

| Comp. | LOLMG | EROCI | LOLPE | OEOLA | overall ave. |
|---|---|---|---|---|---|
| STD6 | 71, 79, 81, 83, 92, 81 | 83, 89, 94, 96, 97, 92 | 75, 86, 85, 92, 92, 86 | 44, 54, 59, 64, 70, 58 | 79 |
| STD6$^a$ | 74, 82, 80, 88, 93, 83 | 85, 89, 92, 96, 98, 92 | 84, 90, 91, 95, 96, 91 | 46, 55, 65, 66, 69, 60 | 82 |
| STD3 | 70, 77, 79, 84, 88, 80 | 82, 90, 93, 95, 95, 91 | 81, 88, 86, 95, 93, 89 | 43, 53, 60, 70, 71, 59 | 80 |
| TD-IQ | 75, 81, 85, 86, 89, 83 | 84, 88, 93, 95, 97, 91 | 80, 90, 90, 96, 92, 90 | 44, 51, 64, 63, 64, 57 | 80 |
| TD-IQ$^b$ | 72, 79, 85, 87, 91, 83 | 85, 88, 93, 96, 97, 92 | 81, 89, 89, 97, 93, 90 | 44, 51, 59, 66, 76, 59 | 81 |
| TD-IQ$^c$ | 76, 78, 81, 85, 92, 82 | 85, 86, 93, 96, 98, 92 | 82, 86, 89, 93, 98, 90 | 45, 51, 63, 66, 70, 59 | 81 |
| TD-IQ$^d$ | 75, 81, 80, 86, 96, 84 | 82, 90, 90, 93, 98, 91 | 79, 87, 86, 93, 98, 88 | 44, 55, 59, 64, 74, 59 | 80 |
| TD-IQ$^e$ | 70, 79, 84, 88, 97, 84 | 80, 86, 93, 96, 98, 90 | 76, 88, 84, 96, 98, 89 | 45, 54, 59, 68, 70, 59 | 80 |

The compositions were applied to ABUTH plants at the indicated application rates in a field trial done in Gillespie County, Tex. Results, averaged for all replicates of each treatment and across all rates of application for each plant species (reported as the sixth value) are shown in Table 55D.

TABLE 55D

| Comp. | % Weed Control ABUTH |
|---|---|
| STD6 | 39, 53, 64, 75, 89, 64 |
| STD6[a] | 60, 81, 86, 90, —, 79 |
| STD3 | 31, 49, 70, 76, 92, 64 |
| TD-IQ | 36, 48, 67, 74, 80, 61 |
| TD-IQ[b] | 26, 57, 78, 76, 89, 65 |
| TD-IQ[c] | 25, 56, 80, 79, 90, 66 |
| TD-IQ[d] | 35, 58, 69, 78, 90, 66 |
| TD-IQ[e] | 26, 58, 76, 66, 86, 63 |

The compositions were applied to TRZVX plants at the indicated application rates in a field trial done in Gillespie County, Tex. Results, averaged for all replicates of each treatment and across all rates of application for each plant species (reported as the sixth value) are shown in Table 55E.

TABLE 55E

| Comp. | % Weed Control TRZVX |
|---|---|
| STD6 | 56, 74, 80, 87, 88, 77 |
| STD6[a] | —, 76, 82, 87, 91, 84 |
| STD3 | 52, 73, 80, 83, 85, 75 |
| TD-IQ | 49, 62, 74, 78, 82, 69 |
| TD-IQ[b] | 50, 69, 74, 82, 84, 72 |
| TD-IQ[c] | 51, 70, 75, 82, 85, 71 |
| TD-IQ[d] | 51, 71, 74, 83, 84, 73 |
| TD-IQ[e] | 50, 69, 75, 79, 85, 71 |

The compositions were applied to OEOLA plants at 650, 1040, 1429, 1819 and 2209 g a.e. per hectare in a field trial done at Gillespie County, Tex. Data set OEOLA(1) represents application of the compositions to plants under moderate drought stress, induced by withholding supplemental irrigation. Data set OEOLA(2) represents application of the compositions to primrose plants not subjected to drought stress, which was relieved by irrigating the field block several times before the glyphosate treatments were applied. Results, averaged for all replicates of each treatment and across all rates of application for each plant species (reported as the sixth value), as well as an overall average across all plant species, are shown in Table 55F.

TABLE 55F

| Comp. | OEOLA(1) | OEOLA(2) | overall ave |
|---|---|---|---|
| STD6 | 67, 75, 77, 82, 83, 77 | 73, 78, 84, 84, 89, 81 | 79 |
| STD6[a] | 68, 75, 76, 86, 86, 78 | 75, 79, 81, 83, 87, 81 | 80 |
| STD3 | 68, 78, 76, 82, 89, 78 | 74, 77, 78, 86, 88, 81 | 80 |
| TD-IQ | 66, 74, 74, 80, 84, 76 | 71, 79, 81, 84, 89, 81 | 78 |
| TD-IQ[b] | 69, 80, 79, 86, 84, 79 | 75, 78, 82, 84, 86, 81 | 80 |
| TD-IQ[c] | 68, 75, 79, 83, 89, 79 | 74, 80, 83, 86, 90, 82 | 81 |
| TD-IQ[d] | 69, 75, 80, 79, 89, 78 | 75, 80, 84, 84, 88, 82 | 80 |
| TD-IQ[e] | 70, 80, 76, 84, 84, 79 | 72, 79, 79, 84, 87, 80 | 80 |

The compositions were applied to LAMAM plants at the indicated application rates in a field trial done in Gillespie County, Tex. Results, averaged for all replicates of each treatment and across all rates of application for each plant species (reported as the sixth value) are shown in Table 55G.

TABLE 55G

| Comp. | % Weed Control LAMAM |
|---|---|
| STD6 | 71, 76, 84, 81, 95, 81 |
| STD6[a] | 73, 76, 80, 82, 85, 79 |
| STD3 | 76, 72, 84, 89, 90, 82 |
| TD-IQ | 78, 77, 79, 86, 88, 81 |
| TD-IQ[b] | 71, 76, 75, 83, 89, 79 |
| TD-IQ[c] | 73, 73, 83, 82, 85, 79 |
| TD-IQ[d] | 74, 74, 83, 83, 88, 80 |
| TD-IQ[e] | 78, 74, 80, 91, 90, 82 |

Overall the data collected from the eight field studies of this example indicate that oxalic acid and diammonium oxalate significantly improve efficacy of TDIQ at both 10:1 and 25:1 ratios. The enhancement of oxalic acid and diammonium oxalate on TDIQ was noted primarily against the monocot species, compared to the dicot species. Moreover, LOLMG and LOLPE were responsible for the overall enhancement. Neither TRZVX nor AVESS responded to the oxalic acid+diammonium oxalate tank mixtures like the Lolium species.

Ammonium sulfate (AMS) also enhances STD6 in a similar fashion, but the efficacy gain was observed on all four of the grass species, not just the two Lolium species. Finally, AMS significantly improved the efficacy of STD6 on ABUTH. AMS did not enhance the efficacy of STD6 against the three remaining broadleaf species in this project (EROCI, LAMAM and OEOLA).

Example 56

The field efficacy effect of high load ammonium glyphosate formulations containing a cationic:nonionic surfactant system and inerts was evaluated. Compositions 884E5P and 886Y7N were prepared containing 500 g a.e./kg (50 wt %) ammonium glyphosate salt and compositions 885R9K and 904T5B were prepared containing 600 g a.e./kg (60 wt %) and 680 g a.e./kg (68 wt %), respectively, ammonium glyphosate salt; each formulation additionally contained excipient ingredients, reported as w/w %, as shown in Table 56A. The efficacy of those compositions, as well as compositions 634Y7, 944U7M (Table 49A), 151O8W (Table 50A) and 155L1J (Table 50A), were compared to STD4 and STD9 for their ability to control weeds. Each test included four titers of application, but the titers in each study varied depending upon the target weed species and its stage of growth at the time of treatment.

TABLE 56A

| Comp. | Cmpnt 1 | wt % | Cmpnt 2 | wt % | Cmpnt 3 | wt % |
|---|---|---|---|---|---|---|
| 884E5P | CIS19 | 9.0 | NIS13 | 9.0 | OTH1 | 24.5 |
| 885R9K | CIS19 | 8.0 | NIS13 | 8.0 | OTH1 | 15.0 |
| 886Y7N | OTH43 | 24.8 | OTH41 | 22.2 | — | — |
| 904T5B | CIS19 | 9.0 | NIS13 | 7.0 | OTH5 | 8.0 |

| Comp. | Cmpnt 4 | wt % | Cmpnt 5 | wt % |
|---|---|---|---|---|
| 884E5P | OTH17 | 0.4 | OTH18 | 0.1 |
| 885R9K | OTH17 | 0.4 | OTH18 | 0.1 |
| 886Y7N | — | — | — | — |
| 904T5B | OTH17 | 0.4 | — | — |

Compositions 884E5P, 885R9K, 886Y7N, 904T5B, 634Y7, 944U7M, 151O8W, 155L1J, STD4 and STD9 were applied to the following plants at the indicated titers, expressed in g a.e. per hectare: CYNDA at 1540, 1740, 1940 and 2140 (two separate trials); STDSS at 680, 900, 1130 and 1360; POROL at 900, 1130, 1360 and 1600; RUMEX at 960, 1100, 1300 and 1440; ELEIN at 360, 500, 650 and 790; A mixed stand of CYPRO and CYNDA at 1200, 1400, 1600 and 1800; mixed stand of grass and broadleaf weeds (ZZZZZ) at 1300, 1500, 1700 and 1900; ERIBO at 240, 480, 720 and 960; ABUTH at 390, 650, 910 and 1170; XANSI at 340, 410, 480 and 580; and GERDI at 720, 860, 1000 and 1150 in field trials done in Pergamino and Salto, Argentina. Results, averaged for all replicates of each treatment and across all titers of application for each plant species (reported as the fifth value) are shown in Table 56B.

TABLE 56B

| Comp. | CYNDA | STDSS | POROL |
|---|---|---|---|
| 634Y7 | 78, 81, 80, 100, 85 73, 77, 85, 96, 83 | 58, 60, 69, 73, 65 — | — — |
| 884E5P | — | 56, 59, 69, 70, 63 | — |
| 885R9K | 76, 81, 79, 100, 84 74, 74, 82, 96, 81 | 56, 61, 69, 75, 65 — | 58, 61, 69, 75, 66 — |
| 886Y7N | 78, 88, 87, 100, 88 74, 77, 77, 97, 82 | 58, 60, 70, 74, 65 — | 59, 63, 66, 79, 67 — |
| 904T5B | 78, 81, 83, 100, 86 — | — | 59, 63, 69, 76, 67 |
| 944U7M | 80, 83, 80, 100, 86 73, 76, 85, 96, 82 | 58, 59, 70, 75, 65 — | 56, 63, 69, 76, 66 — |
| 15l08W | 77, 82, 81, 100, 85 — | 53, 61, 66, 71, 63 | 59, 61, 68, 75, 66 |
| 155L1J | 78, 84, 81, 100, 86 | 59, 60, 70, 73, 65 | 56, 62, 68, 74, 65 |
| STD4 | 78, 85, 83, 100, 87 70, 73, 78, 97, 80 | 55, 60, 69, 70, 63 — | 59, 61, 69, 79, 67 — |
| STD9 | — | — | 56, 63, 66, 74, 65 |

| Comp. | RUMEX | ELEIN | CYPRO CYNDA |
|---|---|---|---|
| 634Y7 | — | — | — |
| 884E5P | — | — | — |
| 885R9K | 64, 66, 72, 84, 71 — | 64, 73, 78, 88, 75 — | 50, 62, 67, 73, 63 53, 69, 79, 84, 71 |
| 886Y7N | 58, 61, 71, 81, 68 — | 68, 74, 75, 88, 76 — | 51, 60, 65, 78, 63 58, 68, 78, 87, 72 |
| 904T5B | 61, 65, 73, 83, 70 — | 68, 69, 79, 86, 75 — | 53, 62, 70, 75, 65 56, 70, 78, 83, 71 |
| 944U7M | 60, 66, 72, 83, 71 — | 66, 70, 78, 85, 75 — | 55, 66, 66, 77, 66 55, 74, 76, 87, 73 |
| 15l08W | 56, 66, 71, 84, 69 — | 65, 71, 76, 85, 74 — | 53, 59, 71, 78, 65 56, 70, 77, 87, 71 |
| 155L1J | 59, 65, 73, 83, 70 — | 66, 74, 76, 85, 75 — | 55, 59, 69, 78, 66 57, 65, 83, 86, 74 |
| STD4 | 60, 60, 72, 83, 68 — | 68, 70, 77, 88, 76 — | 48, 61, 68, 70, 62 51, 66, 81, 81, 70 |
| STD9 | 58, 67, 70, 85, 70 — | 65, 73, 75, 86, 75 — | 53, 63, 70, 79, 65 53, 70, 80, 87, 71 |

| Comp. | ZZZZZ | ERIBO | ABUTH |
|---|---|---|---|
| 634Y7 | — | 44, 59, 78, 89, 67 | — |
| 884E5P | — | — | — |
| 885R9K | 66, 70, 75, 82, 73 | 44, 60, 78, 90, 68 | — |
| 886Y7N | 66, 68, 76, 81, 73 | 44, 58, 77, 90, 67 | — |
| 904T5B | 65, 67, 75, 80, 72 | — | 50, 63, 77, 90, 71 |
| 944U7M | 66, 70, 75, 81, 73 | 45, 58, 75, 88, 68 | 50, 61, 76, 90, 69 |
| 15l08W | 65, 69, 77, 81, 75 | — | 48, 63, 76, 89, 69 |
| 155L1J | 67, 70, 74, 81, 73 | — | 45, 60, 80, 89, 68 |
| STD4 | 66, 68, 74, 82, 72 | 43, 53, 75, 88, 66 | 46, 61, 75, 86, 67 |
| STD9 | 66, 68, 74, 80, 72 | — | — |

| Comp. | XANSI | GERDI |
|---|---|---|
| 634Y7 | — | — |
| 884E5P | — | — |
| 885R9K | 55, 73, 78, 88, 73 | 44, 50, 71, 80, 62 |
| 886Y7N | 59, 75, 77, 86, 74 | 48, 60, 70, 79, 64 |
| 904T5B | 60, 77, 80, 86, 76 | 50, 59, 71, 81, 66 |
| 944U7M | 63, 75, 78, 83, 75 | 55, 60, 70, 79, 67 |
| 15l08W | — | — |
| 155L1J | — | — |
| STD4 | 60, 76, 79, 86, 75 | 46, 61, 73, 80, 65 |
| STD9 | 60, 74, 74, 86, 73 | 51, 60, 71, 75, 65 |

In the first CYNDA trial all formulations gave perfect control at 2140 g a.e. per hectare with each formulation providing similar control as STD4. In the second CYNDA trial all experimental formulations gave higher control than did STD4, with each formulation giving at least 95% control at an application titer of 2140 g a.e. per hecatre.

STDSS control for all treatments across the titers ranged from 53% at the lowest titer to 75% at the highest titer. 885R9K, 886Y7N, 155L1J, 944U7M and 634Y7 each gave greater average control than STD4.

POROL control for all treatments across the titers ranged from 55% at the lowest titer to 80% at the highest titer. STD4 and STD9 were the highest and lowest performing compositions, respectively. 886Y7N and 904T5B were equal to STD4.

RUMEX control for all treatments across the titers ranged from 56% at the lowest titer to 85% at the highest titer. All formulations performed similarly to STD4 and STD9.

ELEIN control for all treatments across the titers ranged from 64% at the lowest titer to 88% at the highest titer. All formulations performed similarly to STD4 and STD9.

In the mixed CYPRO/CYNDA trial CYPRO control for all treatments across the titers ranged from 48% at the lowest titer to 79% at the highest titer and CYNDA control for all treatments across the titers ranged from 51% at the lowest titer to 87% at the highest titer. The best performing formulations were 944U7M and 155L1J.

Control for the mixed plant trial (ZZZZZ) control for all treatments across the titers ranged from 65% at the lowest titer to 82% at the highest titer. None of the formulations achieved 85% control at the highest titer of application. The best performing formulation was 15lO8W, while 904T5B, STD4 and STD9 were the lowest performing formulations.

ERIBO control for all treatments across the titers ranged from 41% at the lowest titer to 91% at the highest titer. All formulations provided commercial level control of 85% at 960 g a.e. per hectare application titer. STD4 was the least efficacious formulation, while 904T5B was the most effective.

ABUTH control for the experimental formulations exceeded STD4.

XANSI control for all treatments across the titers ranged from 55% at the lowest titer to 88% at the highest titer. All formulations and STD4 and STD9 provided similar control.

GERDI control for all treatments across the titers ranged from 44% at the lowest titer to 81% at the highest titer. No formulation provided greater than 85% control. 904T5B and 944U7M were the most efficacious and 885R9K and 886Y7N were the least efficacious.

Table 56C

Compositions 884E5P, 885R9K, 886Y7N, 634Y7, 944U7M, 15lO8W, 155L1J, STD4 and STD9 were applied to the following plants at the indicated titer schedules expressed in g a.e. per hectare: Titer 1 at 540, 720, 900 and 1080; Titer 2 at 360, 540, 720 and 900; Titer 3 at 1080, 1440, 1800 and 2160; Titer 4 at 720, 900, 1080 and 1260; Titer 5 at 720, 900, 1080 and 1440; Titer 6 at 900, 1080, 1260 and 1440; and Titer 7 at 180, 360, 540 and 720.

Applications were done to various plant species in field trials done in Santa Cruz Das Palmeira, Prodopolis, Santa Helena de Goias, Rolandia and Ponta Grossa, all of Brazil, as follows: IPOAO at Titer 1 (one trial) and Titer 2 (three trials); COMBE at Titer 1 (three trials), Titer 2 (three trials) and Titer 3 (one trial); AMAVI at Titer 2 (two trials); EPHHL at Titer 2 (two trials), Titer 1 (one trial) and Titer 4 (one trial); DIGIN at Titer 1 (one trial); CYPRO at Titer 5 (one trial); BLARH at Titer 1 (one trial); ALRTE at Titer 1 (one trial); BRADC at Titer 1 (one trial); EPHHT at Titer 1 (one trial); IPOAC at Titer 1 (one trial) and Titer 6 (two trials); BIDPI at Titer 1 (one trial); ECHCF at Titer 1 (one trial); IPOPD at Titer 6 (one trial); DIGHO at Titer 7 (one trial); and BOILF at Titer 4 (one trial).

Results, averaged for all replicates of each treatment and across all titers of application for each plant species (reported as the fifth value) are shown in Table 56C.

TABLE 56C

| | | | | | | | | | |
|---|---|---|---|---|---|---|---|---|---|
| % Weed Control | | | | | | | | | |
| Comp. | Titer | IPOAO | Titer | COMBE | Titer | AMAVI | Titer | EPHHL | |
| 634Y7 | 1 | 85, 88, 91, 94, 89 | 1 | 75, 81, 81, 84, 80 | 2 | 90, 93, 94, 91, 92 | 1 | 74, 83, 90, 96, 86 | |
| | 2 | 71, 85, 86, 95, 84 | 1 | 59, 73, 75, 81, 72 | 2 | 96, 95, 96, 96, 96 | 2 | 59, 55, 69, 71, 63 | |
| | 2 | 74, 76, 98, 96, 86 | 1 | 74, 73, 85, 84, 79 | | | 2 | 63, 78, 70, 78, 72 | |
| | 2 | 54, 71, 74, 78, 69 | 2 | 79, 80, 80, 83, 80 | | | 4 | 93, 98, 100, 100, 98 | |
| | | | 2 | 79, 79, 85, 84, 82 | | | | | |
| | | | 2 | 64, 70, 68, 69, 68 | | | | | |
| | | | 3 | 45, 50, 71, 79, 61 | | | | | |
| 884E5P | 1 | 60, 79, 85, 91, 76 | 1 | 60, 68, 70, 74, 68 | 2 | 93, 91, 95, 90, 92 | 1 | 68, 73, 79, 86, 76 | |
| | 2 | 70, 83, 84, 93, 82 | 1 | 51, 58, 63, 73, 61 | 2 | 94, 94, 93, 94, 93 | 2 | 58, 48, 75, 75, 64 | |
| | 2 | 68, 68, 86, 93, 78 | 1 | 48, 54, 83, 85, 67 | | | 2 | 59, 73, 65, 75, 68 | |
| | 2 | 53, 65, 74, 76, 67 | 2 | 80, 78, 81, 78, 79 | | | 4 | 88, 97, 100, 100, 96 | |
| | | | 2 | 79, 76, 76, 83, 78 | | | | | |
| | | | 2 | 63, 65, 64, 64, 64 | | | | | |
| | | | 3 | 43, 48, 65, 71, 57 | | | | | |
| 885R9K | 1 | 58, 89, 88, 83, 79 | 1 | 66, 78, 79, 74, 74 | 2 | 86, 94, 98, 90, 92 | 1 | 75, 83, 84, 94, 84 | |
| | 2 | 76, 84, 94, 90, 86 | 1 | 58, 69, 69, 84, 70 | 2 | 93, 95, 95, 100, 96 | 2 | 71, 56, 76, 73, 69 | |
| | 2 | 69, 76, 89, 96, 83 | 1 | 59, 70, 76, 79, 71 | | | 2 | 60, 74, 74, 83, 73 | |
| | 2 | 53, 74, 75, 74, 69 | 2 | 79, 79, 83, 83, 81 | | | 4 | 86, 98, 100, 100, 96 | |
| | | | 2 | 78, 75, 76, 85, 78 | | | | | |
| | | | 2 | 65, 74, 69, 66, 68 | | | | | |
| | | | 3 | 50, 50, 68, 76, 61 | | | | | |
| 886Y7N | 1 | 71, 84, 81, 90, 82 | 1 | 65, 70, 76, 80, 73 | 2 | 93, 91, 93, 96, 93 | 1 | 73, 81, 83, 94, 83 | |
| | 2 | 70, 84, 89, 94, 84 | 1 | 54, 70, 76, 84, 71 | 2 | 90, 94, 89, 100, 93 | 2 | 55, 60, 69, 73, 64 | |
| | 2 | 70, 70, 89, 96, 81 | 1 | 74, 93, 93, 98, 89 | | | 2 | 70, 66, 69, 78, 71 | |
| | 2 | 58, 55, 75, 79, 67 | 2 | 83, 79, 84, 84, 82 | | | 4 | 92, 94, 100, 100, 97 | |
| | | | 2 | 78, 75, 78, 83, 78 | | | | | |
| | | | 2 | 63, 63, 69, 66, 65 | | | | | |
| | | | 3 | 48, 54, 71, 74, 62 | | | | | |
| 944U7M | 1 | 75, 84, 89, 89, 84 | 1 | 68, 73, 83, 80, 76 | 2 | 93, 93, 94, 94, 93 | 1 | 71, 83, 85, 90, 82 | |
| | 2 | 71, 85, 93, 95, 86 | 1 | 60, 71, 74, 85, 73 | 2 | 95, 94, 93, 98, 95 | 2 | 60, 64, 76, 70, 68 | |
| | 2 | 76, 74, 95, 99, 86 | 1 | 65, 58, 77, 78, 69 | | | 2 | 64, 70, 75, 79, 72 | |
| | 2 | 63, 73, 73, 74, 70 | 2 | 79, 81, 84, 81, 81 | | | 4 | 92, 100, 100, 100, 98 | |
| | | | 2 | 79, 79, 81, 86, 81 | | | | | |
| | | | 2 | 63, 68, 66, 69, 66 | | | | | |
| | | | 3 | 43, 53, 71, 75, 60 | | | | | |
| 151O8W | 1 | 74, 89, 89, 91, 86 | 1 | 68, 76, 81, 80, 76 | 2 | 84, 91, 96, 95, 92 | 1 | 76, 86, 90, 96, 87 | |
| | 2 | 70, 89, 93, 90, 85 | 1 | 59, 75, 79, 86, 75 | 2 | 95, 94, 94, 99, 95 | 2 | 54, 64, 75, 70, 66 | |
| | 2 | 76, 79, 91, 96, 86 | 1 | 64, 53, 84, 83, 71 | | | 2 | 63, 69, 75, 76, 71 | |
| | 2 | 49, 58, 74, 74, 63 | 2 | 71, 78, 84, 81, 78 | | | 4 | 94, 96, 100, 100, 98 | |
| | | | 2 | 78, 74, 78, 88, 79 | | | | | |
| | | | 2 | 63, 65, 66, 68, 65 | | | | | |
| | | | 3 | 48, 54, 75, 80, 64 | | | | | |
| 155L1J | 1 | 73, 89, 84, 88, 83 | 1 | 70, 80, 76, 73, 75 | 2 | 91, 91, 95, 94, 93 | 1 | 69, 80, 85, 88, 80 | |
| | 2 | 74, 81, 89, 91, 84 | 1 | 51, 63, 66, 75, 64 | 2 | 95, 94, 91, 98, 94 | 2 | 55, 55, 70, 71, 63 | |
| | 2 | 75, 81, 89, 95, 85 | 1 | 61, 61, 72, 69, 66 | | | 2 | 65, 73, 68, 81, 72 | |
| | 2 | 50, 70, 73, 78, 68 | 2 | 73, 76, 83, 80, 78 | | | 4 | 88, 99, 100, 100, 97 | |
| | | | 2 | 76, 73, 80, 85, 78 | | | | | |
| | | | 2 | 61, 68, 68, 68, 66 | | | | | |
| | | | 3 | 40, 45, 69, 66, 55 | | | | | |
| STD4 | 1 | 89, 90, 88, 89, 89 | 1 | 81, 73, 78, 78, 77 | 2 | 79, 95, 94, 93, 90 | 1 | 56, 70, 70, 79, 83 | |
| | 2 | 68, 83, 90, 90, 83 | 1 | 56, 70, 70, 79, 69 | 2 | 93, 94, 93, 96, 94 | 2 | 58, 55, 61, 71, 61 | |
| | 2 | 71, 85, 91, 94, 85 | 1 | 68, 78, 86, 90, 80 | | | 2 | 65, 76, 73, 76, 73 | |
| | 2 | 60, 66, 73, 78, 69 | 2 | 76, 78, 86, 79, 80 | | | 4 | 85, 100, 100, 100, 96 | |
| | | | 2 | 78, 74, 80, 84, 79 | | | | | |
| | | | 2 | 63, 65, 63, 64, 63 | | | | | |
| | | | 3 | 40, 49, 68, 76, 58 | | | | | |
| STD9 | 1 | 80, 90, 94, 94, 89 | 1 | 80, 81, 76, 80, 79 | 2 | 80, 90, 91, 91, 88 | 1 | 53, 65, 68, 76, 84 | |
| | 2 | 58, 78, 89, 90, 78 | 1 | 53, 65, 68, 76, 65 | 2 | 94, 95, 90, 96, 94 | 2 | 49, 65, 69, 70, 63 | |
| | 2 | 71, 88, 94, 95, 87 | 1 | 58, 50, 87, 79, 68 | | | 2 | 60, 69, 71, 76, 69 | |
| | 2 | 61, 71, 71, 80, 71 | 2 | 71, 78, 84, 83, 79 | | | 4 | 89, 99, 100, 100, 97 | |

TABLE 56C-continued

% Weed Control

|   |   |
|---|---|
| 2 | 76, 75, 80, 83, 78 |
| 2 | 64, 73, 70, 66, 68 |
| 3 | 43, 48, 74, 76, 60 |

| Comp. | Titer | DIGIN | Titer | CYPRO | Titer | BLARH | Titer | ALRTE |
|---|---|---|---|---|---|---|---|---|
| 634Y7  | 1 | 54, 63, 65, 78, 65 | 5 | 65, 65, 74, 96, 75 | 1 | 76, 90, 100, 100, 92 | 1 | 86, 94, 100, 100, 95 |
| 884E5P | 1 | 41, 60, 58, 75, 58 | 5 | 59, 69, 70, 98, 74 | 1 | 70, 86, 96, 100, 88 | 1 | 80, 93, 100, 100, 93 |
| 885R9K | 1 | 64, 55, 64, 79, 65 | 5 | 65, 68, 71, 95, 75 | 1 | 74, 90, 100, 100, 91 | 1 | 84, 94, 99, 100, 94 |
| 886Y7N | 1 | 66, 60, 73, 74, 68 | 5 | 61, 74, 69, 96, 75 | 1 | 75, 91, 100, 100, 92 | 1 | 83, 91, 100, 100, 93 |
| 944U7M | 1 | 55, 59, 75, 84, 68 | 5 | 59, 66, 73, 96, 73 | 1 | 73, 91, 99, 100, 91 | 1 | 84, 95, 100, 100, 95 |
| 151O8W | 1 | 60, 58, 68, 75, 64 | 5 | 61, 69, 69, 90, 72 | 1 | 75, 95, 100, 100, 93 | 1 | 85, 93, 99, 100, 94 |
| 155L1J | 1 | 47, 63, 63, 81, 64 | 5 | 65, 63, 70, 95, 73 | 1 | 69, 89, 98, 100, 89 | 1 | 84, 91, 100, 100, 94 |
| STD4   | 1 | 44, 63, 71, 79, 64 | 5 | 60, 71, 73, 97, 75 | 1 | 71, 88, 100, 100, 90 | 1 | 81, 90, 98, 100, 92 |
| STD9   | 1 | 48, 61, 69, 81, 66 | 5 | 64, 66, 75, 95, 75 | 1 | 74, 89, 100, 100, 91 | 1 | 83, 91, 99, 100, 93 |

| Comp. | Titer | BRADC | Titer | EPHHT | Titer | IPOAC | Titer | BIDPI |
|---|---|---|---|---|---|---|---|---|
| 634Y7  | 1 | 76, 83, 96, 98, 88 | 1 | 84, 81, 94, 95, 88 | 1 | 94, 97, 100, 100, 98 | 1 | 83, 93, 100, 100, 94 |
|        |   |                    |   |                    | 6 | 54, 66, 80, 88, 72   |   |                     |
|        |   |                    |   |                    | 6 | 30, 40, 66, 81, 54   |   |                     |
| 884E5P | 1 | 78, 79, 97, 98, 88 | 1 | 85, 80, 94, 93, 88 | 1 | 76, 76, 95, 100, 87  | 1 | 78, 74, 95, 100, 87 |
|        |   |                    |   |                    | 6 | 30, 41, 61, 65, 49   |   |                     |
|        |   |                    |   |                    | 6 | 28, 31, 60, 70, 47   |   |                     |
| 885R9K | 1 | 76, 84, 96, 99, 89 | 1 | 73, 86, 90, 91, 85 | 1 | 88, 94, 100, 100, 95 | 1 | 79, 97, 100, 100, 94 |
|        |   |                    |   |                    | 6 | 50, 59, 63, 70, 60   |   |                     |
|        |   |                    |   |                    | 6 | 30, 45, 71, 76, 56   |   |                     |
| 886Y7N | 1 | 81, 83, 96, 98, 89 | 1 | 86, 83, 91, 90, 87 | 1 | 96, 98, 100, 100, 98 | 1 | 79, 86, 93, 98, 89  |
|        |   |                    |   |                    | 6 | 33, 41, 83, 93, 62   |   |                     |
|        |   |                    |   |                    | 6 | 35, 48, 75, 80, 58   |   |                     |
| 944U7M | 1 | 73, 83, 96, 97, 87 | 1 | 82, 78, 91, 90, 85 | 1 | 91, 91, 99, 100, 95  | 1 | 76, 91, 97, 98, 90  |
|        |   |                    |   |                    | 6 | 43, 70, 74, 86, 68   |   |                     |
|        |   |                    |   |                    | 6 | 26, 43, 63, 78, 52   |   |                     |
| 151O8W | 1 | 76, 84, 96, 99, 89 | 1 | 74, 75, 89, 97, 84 | 1 | 91, 90, 100, 100, 95 | 1 | 73, 90, 99, 100, 90 |
|        |   |                    |   |                    | 6 | 43, 65, 66, 88, 65   |   |                     |
|        |   |                    |   |                    | 6 | 30, 40, 68, 71, 52   |   |                     |
| 155L1J | 1 | 71, 80, 96, 98, 86 | 1 | 86, 84, 89, 98, 89 | 1 | 83, 88, 93, 100, 91  | 1 | 86, 71, 88, 98, 86  |
|        |   |                    |   |                    | 6 | 56, 61, 63, 75, 64   |   |                     |
|        |   |                    |   |                    | 6 | 25, 41, 65, 69, 50   |   |                     |
| STD4   | 1 | 75, 84, 94, 97, 87 | 1 | 85, 80, 94, 100, 90 | 1 | 89, 90, 98, 100, 94  | 1 | 82, 80, 100, 100, 91 |
|        |   |                    |   |                    | 6 | —                    |   |                     |
|        |   |                    |   |                    | 6 | 25, 39, 61, 78, 51   |   |                     |
| STD9   | 1 | 73, 85, 94, 98, 87 | 1 | 81, 84, 93, 91, 87 | 1 | 86, 92, 100, 100, 95 | 1 | 76, 91, 100, 100, 92 |
|        |   |                    |   |                    | 6 | 38, 59, 78, 93, 67   |   |                     |
|        |   |                    |   |                    | 6 | 24, 39, 61, 71, 49   |   |                     |

| Comp. | Titer | ECHCF | Titer | IPOPD | Titer | DIGHO | Titer | BOILF |
|---|---|---|---|---|---|---|---|---|
| 634Y7  | 1 | 48, 64, 63, 79, 63 | 6 | 33, 41, 64, 66, 51 | 7 | 27, 46, 49, 71, 48 | 4 | 79, 95, 100, 100, 93 |
| 884E5P | 1 | 40, 51, 52, 70, 53 | 6 | 30, 30, 44, 46, 38 | 7 | 30, 33, 36, 51, 38 | 4 | 78, 87, 100, 100, 91 |
| 885R9K | 1 | 46, 57, 59, 74, 59 | 6 | 31, 43, 49, 51, 43 | 7 | 28, 34, 37, 60, 40 | 4 | 73, 94, 100, 100, 92 |
| 886Y7N | 1 | 44, 51, 57, 76, 57 | 6 | 30, 30, 63, 68, 48 | 7 | 26, 35, 39, 65, 40 | 4 | 86, 91, 100, 100, 94 |
| 944U7M | 1 | 42, 51, 59, 77, 57 | 6 | 30, 53, 56, 66, 51 | 7 | 21, 35, 37, 54, 37 | 4 | 83, 97, 100, 100, 96 |
| 151O8W | 1 | 44, 53, 65, 76, 59 | 6 | 30, 49, 51, 69, 50 | 7 | 23, 28, 31, 66, 37 | 4 | 89, 92, 100, 100, 96 |
| 155L1J | 1 | 43, 56, 61, 76, 59 | 6 | 35, 46, 48, 59, 47 | 7 | 23, 29, 33, 60, 36 | 4 | 79, 96, 100, 100, 94 |
| STD4   | 1 | 45, 55, 48, 73, 55 | 6 | —                  | 7 | 26, 45, 53, 69, 48 | 4 | 74, 97, 100, 100, 93 |
| STD9   | 1 | 44, 59, 57, 79, 60 | 6 | 30, 41, 58, 69, 49 | 7 | 23, 40, 46, 63, 43 | 4 | 79, 94, 100, 100, 93 |

As applied to DIGIN, the grand means for 886Y7N and 944U7M ranked higher than STD9.

As applied to CYPRO, 634Y7, 885R9K, 886Y7N, STD4 and STD9 each gave equal control.

As applied to BLARH all formulations provided a commercial level of control at 720 g a.e./hectare with 151O8W being the most efficacious by a significant amount. 944U7M and 886Y7N were significantly more efficacious than STD4.

As applied to ALTRE, only 151O8W and 634Y7 provided at least 85% control at the 720 g a.e./hectare titer of application. When averaged across BLARH and ALTRE weed species, 151O8W and 634Y7 were the most efficacious.

As applied to BRADC, 886Y7N, 885R9K and 151O8W were the most efficacious while 155L1J was the least efficacious. At 540 g a.e./hectare 886Y7N was the only formulation to give at least 80% control. At 720 g a.e./hectare STD9 was the only formulation to give at least 85% control; but six other formulations were statistically equivalent. At 900 g a.e./hectare 884E5P was significantly more efficacious than STD4 and STD9.

As applied to EPHHT, STD4 was the most efficacious formulation and 151O8W was the least efficacious. At 540 g a.e./hectare STD4, 884E5P, 886Y7N and 155L1J each gave at least 85% control. At 720 g a.e./hectare STD9, 885R9K and 155L1J showed the highest efficacy.

As applied to IPOAC, 884E5P was the least efficacious formulation. 634Y7, 886Y7N and 944U7M were consistently the most efficacious formulations.

As applied to BIDPI, 885R9K and 634Y7 were the highest efficacy formulations and significantly more active than STD4 and STD9 at 720 g a.e./hectare.

As applied to ECHCF, 634Y7 was the highest efficacy formulation followed by STD9. No formulation provided commercial control.

As applied to IPOPD, no formulation provided commercial control but formulations 944U7M and 634Y7 were the most efficacious and outperformed STD9.

As applied to DIGHO, no formulation gave commercial control because the titers of application were too low. 634Y7 was the most active formulation and gave greater control than STD9.

As applied to BOILF, all formulations provided commercial control at 900 g a.e./hectare. At 720 g a.e./hectare only 886Y7N and 151O8W gave commercial control. 944U7M, 886Y7N, 155L1J and 151O8W were the highest overall ranking formulations.

As applied to IPOAO, the overall average results indicate that STD4, STD9, 634Y7 and 944U7M are the highest efficacy formulations.

As applied to COMBE, the overall average results indicate that 634Y7 and 886Y79 were the highest efficacy formulations followed by 944U7M, 151O8W and STD4.

As applied to AMAVI, all formulations except STD4 and 151O8W provided at least 85% control at the lowest titer and each formulation performed similarly.

As applied to EPHHL, the overall average results indicate that 885R9K, 151O8W, 944U7M and 634Y7 were the highest efficacy formulations.

Example 57

Compositions 944U7M (Table 49A); 151O8W (Table 50A); 155L1J (Table 50A); 874G8W, 875W1I, 876LOS, 877K7A, 878L6H and 879K7T each of Table 51A; and STD1, STD4 and STD9 were applied to: FESAR at 900, 1600 and 2500 g a.e./hectare; and to AGRRR at 1559, 1949 and 2339 g a.e./hectare in field trials done in Monmouth, Ill., USA. Results, averaged for all replicates of each treatment and across all titers of application for each plant species (reported as the fourth value) are shown in Table 57A.

TABLE 57A

% Weed Control (2002395028 and 029)

| Comp. | FESAR | AGRRR |
|---|---|---|
| 944U7M | 79, 89, 96, 88 | 85, 91, 93, 89 |
| 151O8W | 81, 89, 99, 90 | 78, 88, 93, 86 |
| 155L1J | 82, 89, 98, 90 | 83, 83, 89, 85 |
| 874G8W | 80, 90, 98, 89 | 88, 81, 93, 87 |
| 875W1I | 84, 86, 98, 89 | 85, 84, 90, 86 |
| 876L0S | 77, 85, 94, 85 | 80, 87, 91, 86 |
| 877K7A | 76, 89, 98, 88 | 85, 77, 95, 86 |
| 878L6H | 80, 91, 94, 88 | 82, 85, 95, 87 |
| 879K7T | 82, 88, 98, 89 | 90, 87, 91, 89 |

TABLE 57A-continued

% Weed Control (2002395028 and 029)

| Comp. | FESAR | AGRRR |
|---|---|---|
| STD1 | 81, 94, 98, 91 | 87, 82, 91, 87 |
| STD4 | 79, 92, 95, 87 | 82, 83, 91, 85 |
| STD9 | 81, 88, 94, 88 | 82, 86, 91, 87 |

Each composition provided commercial control of FESAR and AGRRR. STD1 was the most efficacious composition against FESAR and 876L0S was the least efficacious. 879K7T and 944U7M were the most efficacious compositions against AGRRR.

Example 58

The field efficacy effect of high load ammonium glyphosate formulations containing a cationic:nonionic surfactant system and inerts was evaluated. The glyphosate concentration in wt % a.e. is reported Table 58A below for each composition as [gly]. The efficacy of those compositions, as well as compositions 634Y7 (Table 48A), 944U7M (Table 49A) and 155L1J (Table 50A) were compared to STD4 and STD9 for their ability to control ABUTH, IPOSS, DACGL, TAROF and AGRRR in field studies done in Monmouth, Ill., USA with % control results reported in Table 58B. Application, in g a.e. per hectare, was done to the plants as follows: ABUTH and IPOSS at 455, 715, 975 and 1235; DACGL and TAROF at 520, 910, 1299 and 1819; and AGRRR at 1559, 1949 and 2339. Results, averaged for all replicates of each treatment and across all titers of application for each plant species (reported as the fifth value, except for AGRRR (fourth value)) are shown in Table 58B.

TABLE 58A

| Comp. | [gly] | Cmpnt. 1 | wt % | Cmpnt. 2 | wt % | Cmpnt. 3 | wt % |
|---|---|---|---|---|---|---|---|
| 880R5B | 50 | CIS19 | 8.0 | NIS13 | 8.0 | OTH1 | 26.5 |
| 819P0N | 40 | CIS19 | 8.0 | NIS13 | 8.0 | OTH1 | 37.8 |
| 820Y5V | 34 | CIS19 | 8.0 | NIS13 | 8.0 | OTH1 | 34.0 |
| 821Q3X | 40 | CIS19 | 10.0 | NIS13 | 10.0 | OTH1 | 33.8 |
| 822E7C | 40 | CIS19 | 10.0 | NIS13 | 10.0 | OTH1 | 20.0 |
| 823K8S | 34 | CIS19 | 8.0 | NIS13 | 8.0 | OTH17 | 0.4 |
| 824P9J | 34 | CIS19 | 8.0 | NIS13 | 8.0 | OTH1 | 44.7 |

| Comp. | Cmpnt. 4 | wt % | Cmpnt. 5 | wt % | Cmpnt. 6 | wt % |
|---|---|---|---|---|---|---|
| 880R5B | OTH17 | 0.4 | OTH18 | 0.1 | OTH20 | 10.7 |
| 819P0N | OTH17 | 0.4 | OTH18 | 0.1 | — | — |
| 820Y5V | OTH17 | 0.4 | OTH18 | 0.1 | — | — |
| 821Q3X | OTH17 | 0.4 | OTH18 | 0.1 | — | — |
| 822E7C | OTH17 | 0.4 | OTH18 | 0.1 | OTH20 | 13.8 |
| 823K8S | OTH18 | 0.1 | OTH20 | 44.7 | — | — |
| 824P9J | OTH17 | 0.4 | OTH18 | 0.1 | — | — |

TABLE 58B

% Weed Control

| Comp. | ABUTH | IPOSS | DACGL | TAROF | AGRRR |
|---|---|---|---|---|---|
| 634Y7 | 92, 100, 100, 100, 98 | 70, 88, 93, 95, 86 | 69, 81, 85, 95, 82 | 79, 82, 86, 90, 84 | 91, 88, 98, 92 |
| 944U7M | 89, 100, 99, 100, 97 | 76, 87, 91, 95, 87 | 67, 75, 83, 92, 79 | 73, 81, 86, 91, 83 | 89, 96, 96, 94 |
| 155L1J | 89, 98, 100, 100, 97 | 67, 86, 88, 93, 84 | 67, 79, 85, 96, 82 | 68, 79, 86, 94, 82 | 92, 90, 93, 92 |
| 880R5B | 87, 98, 100, 100, 96 | 67, 84, 86, 90, 82 | 63, 76, 89, 91, 80 | 62, 78, 85, 88, 78 | 88, 90, 91, 89 |

TABLE 58B-continued

| | % Weed Control | | | | |
|---|---|---|---|---|---|
| Comp. | ABUTH | IPOSS | DACGL | TAROF | AGRRR |
| 819P0N | 82, 99, 99, 100, 95 | 60, 73, 88, 89, 77 | 59, 65, 79, 89, 73 | 66, 72, 82, 84, 76 | 82, 85, 86, 84 |
| 820Y5V | 80, 98, 100, 100, 94 | 55, 74, 81, 85, 74 | 56, 70, 77, 88, 73 | 52, 75, 80, 79, 71 | 81, 85, 94, 87 |
| 821Q3X | 86, 99, 96, 100, 95 | 63, 83, 85, 89, 80 | 60, 73, 81, 91, 76 | 65, 71, 79, 87, 75 | 83, 88, 95, 88 |
| 822E7C | 87, 98, 100, 100, 96 | 56, 78, 84, 91, 77 | 62, 75, 83, 87, 77 | 72, 78, 83, 82, 79 | 82, 85, 94, 87 |
| 823K8S | 77, 92, 100, 100, 92 | 55, 74, 83, 88, 75 | 55, 67, 76, 85, 71 | 56, 67, 77, 86, 72 | 83, 83, 94, 87 |
| 824P9J | 82, 97, 100, 100, 95 | 56, 72, 83, 86, 74 | 56, 69, 80, 88, 73 | 60, 71, 81, 83, 74 | 83, 91, 89, 87 |
| STD4 | 87, 100, 93, 100, 95 | 73, 90, 90, 95, 87 | 66, 73, 81, 93, 78 | 74, 83, 84, 94, 84 | 86, 93, 99, 93 |
| STD9 | 86, 98, 100, 100, 96 | 74, 79, 91, 93, 84 | 64, 74, 83, 88, 77 | 72, 82, 91, 93, 84 | 87, 87, 95, 90 |

As applied to ABUTH, all compositions gave overall commercial control with 823K8S being least efficacious, followed by 820Y5V, 819P0N, 821 Q3X and 824P9J. All other formulations gave similar control.

As applied to IPOSS, 944U7M, STD4, 634Y7, 155L1J and STD9 gave the greatest control.

As applied to DACGL, commercial control was achieved at 1819 g a.e. per hectare. 880R5B, 155L1J, 634Y7 and 944U7M each gave higher efficacy that STD4 and STD9.

As applied to TAROF, commercial control was generally achieved at 1819 g a.e. per hecatre. 634Y7, STD4 and STD9 gave the highest efficacy.

As applied to AGRRR, commercial control was generally achieved at all titers of application. Each of formulations 634Y7, 880R5B, 944U7M, 155L1J, STD4 and STD9 provided the greatest, and similar, efficacy.

Example 59

The field efficacy effect of high load ammonium glyphosate formulations containing a cationic:nonionic surfactant system and inerts was evaluated. Composition 853F4J, containing 45 wt % a.e. ammonium glyphosate, 10 wt % CIS19, 10 wt % NIS13, 28 wt % OTH1, 0.4 wt % OTH17 and 0.1 wt % OTH18 was prepared. That composition, as well as compositions 634Y7 (Table 48A), 944U7M (Table 49A), 793Q2N (Table 31A), 794D6N (Table 31A), 795P0E (Table 31A), 884E5P (Table 56A), 821Q3X (Table 58A) and 822E7C (Table 58A) were compared to STD4 and STD9 for their ability to control IPOAO, COMBE, AMAVI, EPHHL, IPOAC, IPOPD, and DIGHO in field studies done in Santa Cruz Das Palmeira and Ponta Grassa, Brazil with % control results reported in Table 59A. Application, in g a.e. per hectare, was done at four titer schedules: Titer 1 at 540, 720, 900 and 1080; Titer 2 at 360, 540, 720 and 900; Titer 3 at 900, 1080, 1260 and 1440; and Titer 4 at 180, 360, 540 and 720. IPOAO was tested at Titer 1 (one trial) and Titer 2 (two trials). COMBE was evaluated at Titer 1 (one trial) and Titer 2 (two trials). AMAVI was evaluated at Titer 2 (two trials). EPHHL was evaluated at Titer 2 (two trials). IPOAC was evaluated at Titer 1 (one trial) and Titer 3 (one trial). IPOPD was evaluated at Titer 3 (one trial). DIGHO was evaluated at Titer 4 (one trial). Results, averaged for all replicated of each treatment and across all titers of application for each plant species (reported as the fifth value) are shown in Table 59A.

TABLE 59A

| | | % Weed Control | | | |
|---|---|---|---|---|---|
| Comp. | Titer | IPOAO | COMBE | AMAVI | EPHHL |
| 634Y7 | 1 | 81, 88, 90, 94, 88 | 76, 83, 88, 89, 84 | — | — |
| | 2 | 76, 88, 91, 94, 87 | 74, 78, 80, 81, 78 | 94, 81, 99, 90, 91 | 61, 66, 78, 75, 70 |
| | 2 | 71, 74, 85, 93, 81 | 69, 71, 75, 76, 73 | 90, 94, 95, 89, 92 | 64, 70, 79, 80, 73 |
| 821Q3X | 1 | 74, 78, 79, 79, 77 | 64, 65, 81, 83, 73 | — | — |
| | 2 | 64, 90, 88, 94, 84 | 71, 76, 81, 80, 77 | 86, 91, 89, 90, 89 | 48, 71, 70, 74, 66 |
| | 2 | 65, 69, 79, 83, 74 | 74, 66, 76, 81, 74 | 86, 95, 88, 95, 91 | 58, 71, 74, 74, 69 |
| 822E7C | 1 | 65, 79, 81, 86, 78 | 66, 73, 81, 85, 76 | — | — |
| | 2 | 66, 85, 80, 85, 79 | 70, 73, 78, 78, 74 | 86, 91, 86, 91, 89 | 50, 58, 75, 73, 64 |
| | 2 | 53, 69, 84, 86, 73 | 76, 73, 71, 75, 74 | 91, 94, 89, 89, 91 | 63, 64, 75, 75, 69 |
| 853F4J | 1 | 74, 78, 81, 83, 79 | 70, 73, 81, 78, 75 | — | — |
| | 2 | 74, 84, 84, 90, 83 | 76, 73, 81, 80, 78 | 91, 88, 94, 95, 92 | 50, 69, 75, 71, 66 |
| | 2 | 69, 74, 76, 84, 76 | 70, 71, 71, 78, 73 | 89, 93, 89, 90, 90 | 64, 69, 75, 73, 70 |
| 884E5P | 1 | 73, 79, 88, 86, 81 | 70, 74, 85, 85, 78 | — | — |
| | 2 | 75, 86, 90, 94, 86 | 78, 71, 83, 80, 78 | 89, 85, 91, 90, 89 | 60, 66, 73, 78, 69 |
| | 2 | 63, 81, 78, 88, 77 | 73, 70, 75, 79, 74 | 95, 96, 91, 94, 94 | 64, 70, 73, 76, 71 |
| 944U7M | 1 | 75, 88, 88, 90, 85 | 71, 80, 84, 83, 79 | — | — |
| | 2 | 76, 91, 93, 96, 89 | 75, 75, 83, 81, 78 | 81, 94, 93, 95, 91 | 58, 74, 68, 76, 69 |
| | 2 | 68, 76, 86, 89, 80 | 75, 74, 81, 81, 78 | 90, 99, 95, 90, 93 | 60, 71, 78, 79, 72 |
| 793Q2N | 1 | 76, 85, 86, 93, 85 | 75, 76, 80, 85, 79 | — | — |
| | 2 | 75, 91, 86, 95, 87 | 71, 73, 79, 83, 76 | 85, 93, 90, 94, 90 | 53, 74, 76, 76, 70 |
| | 2 | 69, 74, 89, 85, 79 | 73, 73, 76, 76, 74 | 94, 93, 95, 91, 93 | 70, 70, 76, 71, 72 |
| 794D6N | 1 | 80, 83, 88, 90, 85 | 75, 75, 84, 88, 80 | — | — |
| | 2 | 78, 89, 88, 94, 87 | 76, 73, 84, 83, 79 | 89, 84, 94, 93, 90 | 55, 74, 76, 76, 70 |
| | 2 | 73, 79, 86, 91, 82 | 71, 69, 73, 83, 74 | 93, 95, 91, 90, 92 | 66, 69, 75, 74, 71 |
| 795P0E | 1 | 76, 84, 88, 90, 84 | 73, 80, 84, 85, 80 | — | — |
| | 2 | 76, 84, 93, 96, 87 | 75, 74, 83, 80, 78 | 85, 86, 95, 93, 90 | 63, 73, 74, 73, 70 |
| | 2 | 71, 84, 83, 90, 82 | 68, 69, 74, 84, 73 | 84, 96, 93, 90, 91 | 71, 74, 78, 81, 76 |

TABLE 59A-continued

| | | % Weed Control | | | | |
|---|---|---|---|---|---|---|
| STD4 | 1 | 78, 81, 84, 89, 83 | 73, 76, 81, 85, 79 | — | — | |
| | 2 | 74, 91, 90, 91, 87 | 74, 73, 81, 83, 78 | 84, 90, 94, 91, 90 | 63, 78, 75, 71, 72 | |
| | 2 | 61, 75, 85, 95, 79 | 69, 73, 73, 80, 73 | 94, 94, 89, 93, 92 | 64, 70, 70, 83, 72 | |
| STD9 | 1 | 76, 85, 86, 88, 84 | 70, 73, 85, 84, 78 | — | — | |
| | 2 | 74, 90, 89, 95, 87 | 75, 71, 83, 81, 78 | 83, 86, 91, 90, 88 | 55, 65, 73, 71, 66 | |
| | 2 | 66, 81, 89, 94, 83 | 74, 79, 79, 76, 77 | 88, 98, 90, 86, 90 | 68, 75, 75, 78, 74 | |

| Comp. | Titer | IPOAC | IPOPD | DIGHO |
|---|---|---|---|---|
| 634Y7 | 1 | 12, 31, 50, 81, 44 | — | — |
| | 3 | 44, 55, 71, 90, 65 | 26, 30, 38, 46, 35 | — |
| | 4 | — | — | 26, 60, 75, 81, 61 |
| 821Q3X | 1 | 12, 15, 34, 61, 30 | — | — |
| | 3 | 35, 30, 44, 74, 46 | 23, 20, 29, 39, 28 | — |
| | 4 | — | — | 23, 41, 56, 64, 46 |
| 822E7C | 1 | 20, 24, 41, 63, 37 | — | — |
| | 3 | 21, 36, 45, 54, 39 | 15, 21, 25, 31, 23 | — |
| | 4 | — | — | 16, 40, 53, 65, 43 |
| 853F4J | 1 | 10, 18, 39, 64, 33 | — | — |
| | 3 | 34, 37, 43, 64, 45 | 23, 27, 30, 39, 30 | — |
| | 4 | — | — | 18, 48, 63, 70, 49 |
| 884E5P | 1 | 18, 15, 31, 63, 32 | — | — |
| | 3 | 34, 38, 56, 59, 47 | 19, 20, 31, 34, 26 | — |
| | 4 | — | — | 24, 40, 63, 74, 50 |
| 944U7M | 1 | 24, 25, 55, 74, 44 | — | — |
| | 3 | 36, 55, 64, 83, 59 | 20, 30, 36, 48, 33 | — |
| | 4 | — | — | 32, 53, 73, 76, 60 |
| 793Q2N | 1 | 18, 15, 50, 74, 39 | — | — |
| | 3 | 40, 44, 75, 84, 61 | 29, 29, 41, 45, 36 | — |
| | 4 | — | — | 29, 51, 69, 74, 56 |
| 794D6N | 1 | 17, 17, 53, 68, 38 | — | — |
| | 3 | 44, 55, 66, 83, 62 | 28, 31, 36, 45, 35 | — |
| | 4 | — | — | 28, 50, 70, 71, 57 |
| 795P0E | 1 | 16, 18, 49, 63, 36 | — | — |
| | 3 | 40, 46, 70, 74, 58 | 25, 25, 34, 39, 31 | — |
| | 4 | — | — | 26, 46, 71, 74, 54 |
| STD4 | 1 | 20, 16, 58, 71, 41 | — | — |
| | 3 | — | — | — |
| | 4 | — | — | 26, 51, 69, 75, 55 |
| STD9 | 1 | 20, 27, 54, 71, 43 | — | — |
| | 3 | 43, 55, 70, 92, 65 | 26, 28, 36, 49, 35 | — |
| | 4 | — | — | 24, 56, 65, 73, 54 |

As applied to IPOAO: at Titer 1 634Y7, 794D6N, 795P0E, 944U7M and 793Q2N were the most efficacious compositions with 634Y7, 944U7M and 793Q2N each providing commercial control; in the first Titer 2 trial 944U7M gave higher efficacy than STD9 and STD4, and most formulations gave 85% control at 540 g a.e. per hectare application titer; and in the second Titer 2 trial 634Y7, 794D6N, 944U7M and 795P0E were not as efficacious as STD9 but were more efficacious than STD4.

As applied to COMBE: at Titer 1 634Y7, 794D6N, 795P0E, 944U7M, 793Q2N and STD4 were the most efficacious compositions; at Titer 2 trial 1, 634Y7, 794D6N, 795P0E, 944U7M, 884E5P, STD4 and STD9 were the most efficacious compositions, with no formulation providing commercial control at the highest application titer; and at Titer 2 trial 2, 944U7M was the most efficacious formulation followed by STD9.

As applied to AMAVI: in the first Titer 2 trial, 634Y7, 944U7M and 853F4J outperformed STD4, and 794D6N, 795P0E and 793Q2N gave similar efficacy as that of STD4, STD9 gave the lowest efficacy and each formulation gave commercial control; in the second Titer 2 trial, compositions 944U7M, 793Q2N and 884E5P each outperformed STD4, while STD9 and 853F4J gave the lowest efficacy, and each formulation gave commercial control.

As applied to EPHHL: in the first Titer 2 trial, no formulation gave commercial control at 900 g a.e. per hectare application titer. STD4 was the most efficacious followed closely by 634Y7, 944U7M, 793Q2N, 794D6N, 795P0E and 884E5P; and in the second Titer 2 trial 795P0E gave the highest efficacy followed by STD9 and 634Y7.

As applied to IPOAC, in one trial, at Titer 1, 944U7M and 634Y7 were more efficacious than STD4 and STD9. In another trial, at Titer 2, 634Y7 and STD9 provided at least 85% control at the highest application titer. 944U7M, 793Q2N and 794D6N were nearly as efficacious as 634Y7.

As applied to IPOPD, the formulations provided between 30% and 50% control at the 1440 g a.e. per hectare application titer.

As applied to DIGHO, None of the formulations gave commercial control at the tested titers of application. 634Y7, 794D6N, 793Q2N and 944U7M each gave greater control than STD4 and STD9.

Example 60

The field efficacy effect of high load ammonium glyphosate formulations was evaluated. Compositions were prepared as indicated in Table 60A with 914S2P and 924M1R each containing 68 wt % a.e. ammonium glyphosate, and compositions 934X4D, 905T9B and 264D7F each containing 65 wt % a.e. ammonium glyphosate. Those compositions, as well as compositions and 944U7M (Table 49A) and 151O8W (Table 50A) were compared to STD4 for their ability to control PYHCA, LOLMG, SORHR, CMIRA, ERICA, OEOLA, TRZVX, AVESX AND VERPG in field studies done in Thrall, Tex., Loxley, Ala. and Stoneville, Miss., all of the USA with % control results, averaged for all replicates of each treatment for each plant species and across titers shown as the sixth value, reported in Table 60B. Application, in g a.e. per hectare, was done according to six titer schedules: Titer 1 at 390, 585, 780, 1040 and 1299; Titer 2 at 260, 520, 780, 1040 and 1299; Titer 3 at 210, 420, 631, 840 and 1051; Titer 4 at 420, 631, 840, 1261 and 1682; Titer 5 at 600, 800, 1000, 1200 and 1400; and Titer 6 at 200, 325, 450, 575 and 700, with average efficacy reported as the last result. Titers of application to the plants species evaluated was as follows: PHYCA at Titer 1; LOLMG at Titer 2; SORHR at Titer 2; CMIRA at Titer 2; Erica at Titer 3 and Titer 4; OEOLA at Titer 3, Titer 4 and Titer 5; TRZVX at Titer 3; TRZAW at Titer 6; AVESX at Titer 6; and LOLMU at Titer 6.

TABLE 60A

| Comp. | Cmpnt. 1 | wt % | Cmpnt. 2 | wt % | Cmpnt. 3 | wt % |
|---|---|---|---|---|---|---|
| 914S2P | OTH45 | 14.0 | OTH17 | 0.5 | OTH5 | 8.0 |
| 924M1R | CIS21 | 14.0 | OTH17 | 0.5 | OTH5 | 8.0 |
| 934X4D | OTH45 | 15.5 | OTH17 | 0.5 | OTH5 | 9.5 |
| 905T9B | CIS21 | 16.0 | OTH17 | 0.5 | OTH5 | 9.0 |
| 264D7F | OTH45 | 15.5 | OTH17 | 0.5 | OTH5 | 9.5 |

TABLE 60B

| Comp. | Titer | PYHCA | LOLMG | SORHR | CMIRA |
|---|---|---|---|---|---|
| 905T9B | 1 | 75, 89, 95, 99, 97, 91 | — | — | — |
|  | 2 | — | 54, 86, 86, 97, 99, 84 | 50, 53, 60, 70, 66, 61 | 25, 48, 53, 52, 46, 45 |
| 914S2P | 1 | 76, 91, 89, 97, 100, 90 | — | — | — |
|  | 2 | — | 61, 86, 93, 96, 100, 87 | 60, 57, 61, 64, 67, 62 | 42, 51, 45, 46, 48, 47 |
| 924M1R | 1 | 75, 84, 87, 96, 98, 88 | — | — | — |
|  | 2 | — | 58, 86, 89, 94, 100, 85 | 60, 57, 58, 67, 67, 62 | 33, 44, 52, 54, 52, 47 |
| 934X4D | 1 | 72, 84, 94, 95, 100, 89 | — | — | — |
|  | 2 | — | 54, 84, 89, 95, 98, 84 | 50, 54, 58, 65, 65, 59 | 20, 50, 48, 56, 48, 46 |
| 944U7M | 1 | 84, 88, 92, 100, 100, 93 | — | — | — |
|  | 2 | — | 56, 88, 89, 95, 98, 85 | 58, 52, 58, 64, 68, 60 | 47, 54, 43, 55, 52, 50 |
| 151O8W | 1 | 81, 91, 95, 95, 99, 92 | — | — | — |
|  | 2 | — | 60, 90, 94, 95, 98, 88 | 63, 42, 59, 68, 67, 61 | 42, 50, 52, 48, 53, 49 |
| 264D7F | 1 | 77, 88, 92, 99, 99, 91 | — | — | — |
|  | 2 | — | 55, 87, 90, 95, 99, 85 | 60, 53, 63, 68, 66, 63 | 37, 40, 54, 49, 59, 47 |
| STD4 | 1 | 75, 84, 90, 95, 98, 88 | — | — | — |
|  | 2 | — | 53, 80, 89, 96, 98, 83 | 40, 50, 61, 63, 60, 57 | 30, 54, 52, 57, 51, 48 |

| Comp. | Titer | ERICA | OEOLA | TRZVX |
|---|---|---|---|---|
| 905T9B | 3 | 50, 70, 84, 92, 99, 79 | 56, 63, 73, 83, 86, 72 | 80, 89, 97, 98, 99, 93 |
|  | 4 | 72, 79, 88, 99, 100, 88 | 61, 71, 84, 96, 100, 83 | — |
|  | 5 | — | 73, 73, 83, 84, 91, 81 | — |
| 914S2P | 3 | 53, 71, 85, 98, 96, 80 | 54, 70, 78, 85, 84, 74 | 80, 88, 94, 99, 99, 92 |
|  | 4 | 73, 80, 89, 100, 100, 89 | 69, 78, 85, 97, 100, 86 | — |
|  | 5 | — | 70, 81, 83, 84, 93, 82 | — |
| 924M1R | 3 | 53, 67, 85, 99, 99, 80 | 56, 65, 74, 85, 85, 74 | 78, 89, 98, 99, 99, 93 |
|  | 4 | 76, 81, 89, 100, 100, 89 | 62, 77, 89, 97, 98, 85 | — |
|  | 5 | — | 68, 75, 81, 85, 88, 79 | — |
| 934X4D | 3 | 51, 70, 87, 96, 98, 80 | 50, 67, 76, 85, 85, 73 | 80, 88, 97, 99, 99, 92 |
|  | 4 | 72, 82, 93, 98, 100, 89 | 66, 76, 88, 97, 99, 85 | — |
|  | 5 | — | 70, 74, 81, 83, 89, 79 | — |
| 944U7M | 3 | 52, 74, 85, 98, 99, 81 | 53, 74, 70, 84, 85, 74 | 79, 90, 98, 99, 99, 93 |
|  | 4 | 77, 81, 90, 100, 100, 90 | 64, 80, 88, 95, 97, 85 | — |
|  | 5 | — | 65, 78, 81, 85, 88, 79 | — |
| 151O8W | 3 | 50, 74, 87, 97, 99, 81 | 55, 72, 71, 84, 84, 73 | 78, 90, 96, 99, 99, 93 |
|  | 4 | 70, 80, 89, 100, 100, 88 | 64, 77, 89, 100, 99, 86 | — |
|  | 5 | — | 74, 80, 83, 85, 93, 83 | — |
| 264D7F | 3 | 54, 70, 87, 96, 99, 81 | 55, 70, 75, 84, 86, 75 | 81, 90, 98, 99, 99, 93 |
|  | 4 | 68, 78, 90, 100, 100, 87 | 66, 74, 89, 94, 98, 84 | — |
|  | 5 | — | 73, 76, 81, 85, 91, 81 | — |
| STD4 | 3 | 53, 76, 84, 94, 98, 81 | 56, 72, 73, 85, 86, 74 | 79, 88, 97, 99, 99, 93 |
|  | 4 | 70, 80, 91, 98, 100, 88 | 66, 79, 88, 98, 99, 86 | — |
|  | 5 | — | 71, 75, 79, 80, 89, 79 | — |

| Comp. | Titer | TRZAW | AVESX | LOLMU |
|---|---|---|---|---|
| 905T9B | 6 | 78, 98, 100, 100, 100, 95 | 66, 90, 99, 99, 99, 91 | 71, 83, 96, 96, 98, 89 |
| 914S2P | 6 | 76, 95, 100, 100, 100, 94 | 65, 85, 98, 100, 100, 90 | 73, 83, 96, 98, 99, 90 |
| 924M1R | 6 | 70, 99, 100, 100, 100, 94 | 59, 89, 95, 100, 100, 89 | 66, 85, 91, 95, 98, 87 |
| 934X4D | 6 | 76, 91, 100, 100, 100, 94 | 69, 86, 100, 99, 100, 91 | 59, 79, 93, 95, 96, 84 |
| 944U7M | 6 | 79, 93, 100, 100, 100, 94 | 64, 90, 99, 100, 100, 91 | 71, 81, 94, 95, 95, 87 |
| 151O8W | 6 | 76, 99, 100, 100, 100, 95 | 65, 93, 99, 100, 100, 91 | 60, 90, 95, 96, 96, 88 |
| 264D7F | 6 | 80, 93, 100, 100, 100, 95 | 71, 84, 96, 100, 99, 90 | 64, 75, 94, 96, 98, 85 |
| STD4 | 6 | 76, 96, 100, 100, 100, 95 | 61, 86, 95, 96, 100, 88 | 69, 85, 88, 95, 96, 87 |

As applied to PYHCA, 944U7M and 151O8W gave the highest overall efficacy and each of the remaining compositions gave acceptable commercial control at 780 g a.e. per hectare application titer.

As applied to LOLMG, each formulation tested had higher efficacy than STD4 with each formulation, except for STD4 and 934X4D, providing commercial control at 520 g a.e. per hectare.

As applied to SORHR, each formulation tested had higher efficacy than STD4. No formulation gave commercial control at 1299 g a.e. per hectare.

As applied to CMIRA, compositions 944U7M and 151O8W each had higher efficacy than STD4. No formulation gave commercial control at 1299 g a.e. per hectare.

As applied to ERICA: at Titer 3, 944U7M, 151O8W and 264D7F each exhibited efficacy equivalent to STD4, with near commercial control for each formulation at 631 g a.e. per hecatare; and at Titer 4, 944U7M, 924M1R, 934X4D and 914S2P each exhibited greater efficacy than STD4 with each formulation providing commercial control at 840 g a.e. per hectare.

As applied to OEOLA: at Titer 3, 264D7F, 914S2P, 924M1R and 944U7M each showed greater or equal efficacy as STD4, with each formulation giving near commercial control at 840 g a.e. per hecatare; at Titer 4, STD4, 914S2P and 151O8W had the highest efficacy, with each formulation, except 905T9B, giving commercial control at 840 g a.e. per hectare; at Titer 5, 905T9B, 914S2P, 151O8W and 264D7F gave greater control than STD4, with commercial control shown for each composition at 1400 g a.e. per hectare.

As applied to TRZVX, at Titer 3 924M1R, 905T9B, 264D7F and 151O8W each gave equal control to STD4 and each formulation gave commercial control at 420 g a.e./ha.

As applied to TRZAW, at Titer 6 905T9B, 264D7F and 151O8W each showed equal control to STD4, with each formulation giving commercial control at 325 g a.e. per hectare.

As applied to AVESX, at Titer 6 each formulation gave greater control than STD4, with commercial control exhibited at 325 g a.e. per hectare by all formulations except 264D7F.

As applied to LOLMU, at Titer 6 914S2P, 924M1R, 905T9B, 944U7M and 151O8W each gave greater or equal control as STD4, with commercial control for all compositions shown at 450 g a.e. per hectare.

Example 61

The field efficacy effect of high load ammonium glyphosate formulations was evaluated. Compositions were prepared as indicated in Table 61A with 265T5O and 266R9T each containing 60 wt % a.e. ammonium glyphosate, and compositions 267Q3N, 268L4R and 269E8E each containing 62 wt % a.e. ammonium glyphosate. Those compositions, as well as composition 151O8W (Table 50A) were compared to STD9 and STD12 for their ability to control LOLMG, SORHR, AMBTR, OEOLA, ERICA, TRZVX AND AVESX in field studies done in College Station, Tex., Loxley, Ala. and Stoneville, Miss., all of the USA with % control results reported in Table 61B. Application, in g a.e. per hectare, was done according to six titer schedules: Titer 1 at 260, 520, 780, 1040 and 1299; Titer 2 at 260, 455, 650, 845 and 1040; Titer 3 at 210, 420, 631, 840 and 1051; Titer 4 at 420, 631, 840, 1261 and 1682; Titer 5 at 600, 800, 1000, 1200 and 1400; and Titer 6 at 200, 325, 450, 575 and 700, with average efficacy for each titer reported as the last result. Titers of application to the plants species evaluated is as follows: LOLMG at Titer 1 and Titer 6; SORHR at Titer 1; AMBTR at Titer 2; OEOLA at Titer 4 and Titer 5; ERICA at Titer 3 and Titer 4; TRZVX at Titer 3 and Titer 6; and AVESX at Titer 6.

TABLE 61A

| Comp. | Cmpnt. 1 | wt % | Cmpnt. 2 | wt % |
|---|---|---|---|---|
| 265T5O | OTH45 | 15.0 | OTH1 | 16.6 |
| 266R9T | CIS21 | 16.0 | OTH1 | 15.8 |
| 267Q3N | CIS21 | 15.0 | OTH1 | 14.2 |
| 268L4R | OTH45 | 15.0 | OTH1 | 14.2 |
| 269E8E | CIS21 | 14.0 | OTH1 | 15.3 |

TABLE 61B

% Weed Control

| Comp. | Titer | LOLMG | SORHR | AMBTR |
|---|---|---|---|---|
| 155L1J | 1 | 67, 93, 99, 100, 100, 92 | 58, 61, 68, 68, 67, 65 | — |
|  | 2 | — | — | 53, 61, 69, 83, 94, 72 |
|  | 6 | 58, 71, 85, 88, 89, 78 | — | — |
| 265T5O | 1 | 72, 90, 100, 100, 100, 92 | 60, 59, 67, 63, 69, 65 | — |
|  | 2 | — | — | 53, 61, 75, 79, 88, 71 |
|  | 6 | 55, 69, 78, 86, 86, 75 | — | — |
| 266R9T | 1 | 64, 89, 99, 99, 100, 90 | 45, 53, 69, 67, 74, 64 | — |
|  | 2 | — | — | 51, 68, 71, 84, 89, 73 |
|  | 6 | 53, 64, 78, 85, 88, 73 | — | — |
| 267Q3N | 1 | 66, 92, 97, 100, 100, 91 | 54, 54, 68, 68, 76, 65 | — |
|  | 2 | — | — | 58, 62, 75, 82, 91, 74 |
|  | 6 | 53, 71, 79, 85, 85, 75 | — | — |
| 268L4R | 1 | 60, 87, 98, 100, 100, 89 | 52, 57, 73, 84, 72, 66 | — |
|  | 2 | — | — | 46, 70, 70, 83, 89, 71 |
|  | 6 | 54, 71, 80, 88, 88, 73 | — | — |
| 269E8E | 1 | 61, 86, 99, 100, 100, 89 | 53, 58, 75, 67, 70, 64 | — |
|  | 2 | — | — | 43, 66, 73, 84, 91, 71 |
|  | 6 | 58, 70, 81, 88, 89, 77 | — | — |
| STD9 | 1 | 58, 87, 90, 100, 100, 87 | 68, 53, 67, 68, 73, 66 | — |
|  | 2 | — | — | 49, 62, 69, 83, 87, 70 |
|  | 6 | 58, 73, 79, 88, 90, 77 | — | — |
| STD12 | 1 | 66, 92, 98, 100, 100, 91 | 52, 57, 71, 65, 73, 64 | — |
|  | 2 | — | — | 50, 72, 80, 85, 90, 75 |

TABLE 61B-continued

% Weed Control

| Comp. | Titer | OEOLA | ERICA | TRZVX | AVESX |
|---|---|---|---|---|---|
|  | 6 | 56, 71, 81, 88, 88, 77 | — | — | |
| 155L1J | 3 | 51, 60, 83, 85, 97, 75 | 55, 65, 77, 89, 97, 77 | 86, 95, 99, 99, 99, 96 | — |
|  | 4 | 66, 75, 84, 95, 100, 84 | 66, 80, 88, 100, 99, 87 | — | — |
|  | 5 | 54, 60, 65, 73, 81, 67 | — | — | — |
|  | 6 | — | — | 60, 94, 100, 100, 100, 91 | 55, 84, 93, 100, 100, 86 |
| 265T5O | 3 | 52, 61, 81, 86, 95, 75 | 54, 67, 78, 91, 95, 77 | 85, 94, 98, 99, 99, 95 | — |
|  | 4 | 57, 72, 80, 95, 100, 81 | 64, 80, 84, 99, 100, 85 | — | — |
|  | 5 | 51, 61, 66, 70, 76, 65 | — | — | — |
|  | 6 | — | — | 59, 91, 100, 100, 100, 90 | 59, 81, 94, 100, 98, 86 |
| 266R9T | 3 | 63, 66, 74, 86, 95, 75 | 56, 62, 72, 90, 92, 74 | 85, 95, 99, 99, 99, 95 | — |
|  | 4 | 58, 74, 86, 95, 97, 82 | 64, 78, 87, 98, 99, 85 | — | — |
|  | 5 | 54, 61, 66, 71, 73, 65 | — | — | — |
|  | 6 | — | — | 60, 90, 100, 100, 100, 90 | 56, 79, 91, 100, 100, 85 |
| 267Q3N | 3 | 50, 61, 75, 79, 97, 72 | 54, 66, 83, 85, 97, 77 | 85, 95, 99, 99, 99, 95 | — |
|  | 4 | 58, 74, 80, 96, 96, 81 | 65, 79, 84, 99, 100, 85 | — | — |
|  | 5 | 54, 56, 69, 70, 76, 65 | — | — | — |
|  | 6 | — | — | 63, 91, 100, 100, 100, 91 | 56, 73, 93, 98, 99, 84 |
| 268L4R | 3 | 49, 60, 75, 92, 98, 75 | 50, 65, 78, 89, 93, 75 | 93, 95, 99, 99, 99, 95 | — |
|  | 4 | 62, 66, 83, 97, 97, 81 | 65, 75, 88, 100, 100, 86 | — | — |
|  | 5 | 56, 59, 63, 75, 75, 66 | — | — | — |
|  | 6 | — | — | 68, 89, 100, 100, 100, 90 | 64, 85, 89, 96, 100, 87 |
| 269E8E | 3 | 51, 66, 84, 89, 93, 77 | 54, 63, 76, 86, 99, 75 | 85, 95, 99, 99, 99, 95 | — |
|  | 4 | 64, 67, 84, 95, 97, 81 | 67, 76, 86, 99, 99, 85 | — | — |
|  | 5 | 51, 58, 64, 70, 76, 64 | — | — | — |
|  | 6 | — | — | 73, 90, 100, 100, 100, 93 | 61, 83, 85, 99, 100, 86 |
| STD9 | 3 | 49, 58, 84, 93, 97, 75 | 52, 62, 79, 86, 99, 75 | 84, 95, 99, 99, 99, 95 | — |
|  | 4 | 58, 75, 88, 99, 100, 84 | 67, 81, 91, 99, 100, 87 | — | — |
|  | 5 | 54, 59, 68, 71, 75, 65 | — | — | — |
|  | 6 | — | — | 58, 90, 100, 100, 100, 90 | 55, 75, 85, 94, 100, 82 |
| STD12 | 3 | 48, 70, 88, 95, 95, 79 | 52, 67, 83, 92, 98, 78 | 85, 95, 99, 99, 99, 95 | — |
|  | 4 | 72, 75, 89, 95, 97, 86 | 72, 84, 92, 99, 100, 89 | — | — |
|  | 5 | 54, 59, 69, 73, 78, 66 | — | — | — |
|  | 6 | — | — | 69, 90, 100, 100, 100, 92 | 60, 85, 90, 94, 100, 86 |

As applied to SORHR, 268L4R and STD9 gave the highest efficacy followed by 155L1J, 267Q3N and 265T5O. Commercial control was not established at any titer of application.

As applied to AMBTR, STD12 gave the highest efficacy and STD9 the lowest efficacy. Experimental formulations shown in Table 61B fell between the two standards. Commercial control for each composition was obtained at 1040 g a.e. per hectare.

As applied to ERICA: At Titer 3, STD12 gave the highest efficacy followed by 265T5O, 267Q3N and 155L1J with STD9 and 269E8E and 268L4R each giving essentially equal efficacy, and commercial control was established for each formulation at 840 g a.e. per hectare; and at Titer 4 STD12 and STD9 gave the highest efficacy with commercial control for each formulation, except 265T5O and 267Q3N, at 840 g a.e. per hectare.

As applied to LOLMG: at Titer1 265T5O and 155L1J gave the highest efficacy followed by STD12 while STD9 gave the lowest efficacy, and commercial control was established at 520 g a.e. per hectare for each composition; at Titer 6 155L1J gave the highest control followed by STD9, 269E8E and STD12, and commercial control was established at 575 g a.e. per hectare.

As applied to TRZVX: at Titer 3 all formulations were extremely efficacious and similar, with commercial control for all compositions established at 540 g a.e. per hectare; at Titer 6 269E8E gave the highest efficacy followed by STD12, with STD9 giving the lowest efficacy, and commercial control was established at 325 g a.e. per hectare.

As applied to OEOLA: at Titer 3 STD12 gave the greatest efficacy followed by 269E8E, 155L1J, 266R9T, 268L4R and 265T5O with commercial control for all formulations except 267Q3N established at 840 g a.e. per hectare; at Titer 4 STD12 was the most efficacious followed by STD9 and 155L1J which were the same, and commercial control was established for STD12, STD9 and 266R9T at 840 g a.e. per hectare; and at Titer 4 155L1J gave the greatest control followed by STD12 and 268L4R, and commercial control was not established at any titer of application in this test.

As applied to AVESX, at Titer 6 268L4R exhibited the greatest control followed by 155L1J, 265T5O, 269E8E and STD12. Commercial control was established at 450 g a.e. per hectare for all formulations. Only 268L4R and STD12 gave commercial control at 325 g a.e./ha.

Example 62

The field efficacy effect of high load ammonium glyphosate formulations was evaluated. Compositions were prepared as indicated in Table 62A with ammonium glyphosate concentration in wt % a.e. reported as [gly]. The compositions of Table 62A as well as composition 944U7M (Table 49A) were compared to STD12 for their ability to control SECCX, TRZVX, TAROF, LOLPE, LOLMG, GERCA, OEOLA, ERICA, AVESX, IPOLA, ABUTH and ECHCG in field studies done in Monmouth, Ill., Loxley, Ala. and Stoneville, Miss. all of the USA with % control results reported in Table 62B. Application, in g a.e. per hectare, was done according to six titer schedules: Titer 1 at 325, 585, 845, 1040 and 1299; Titer 2 at 433, 679, 926, 1172 and 1419; Titer 3 at 325, 585, 845, 1170 and 1559; Titer 4 at 210, 420, 631, 840 and 1051; Titer 5 at 250, 375, 500, 625 and 750; and Titer 6 at 375, 500, 625, 750 and 875, with average efficacy for each titer reported as the last result. Titers of application to the plants species evaluated is as follows: SECCX at Titer 1; TRZVX at Titer 1 and Titer 5; TAROF at Titer 2; LOLPE at Titer 3; LOLMG at Titer 3 and Titer 5; GERCA at Titer 3; OEOLA at Titer 3 and Titer 4; ERICA at Titer 4; AVESX at Titer 5; and IPOLA, ABUTH and ECHCG at Titer 6.

TABLE 62A

| Comp. | [gly] | Cmpnt. 1 | wt % | Cmpnt. 2 | wt % | Cmpnt. 3 | wt % |
|---|---|---|---|---|---|---|---|
| 271G7P | 68 | NIS37 | 8.0 | CIS21 | 6.0 | OTH1 | 8.3 |
| 272K2U | 65 | NIS37 | 8.5 | CIS21 | 8.5 | OTH1 | 8.0 |

TABLE 62A-continued

| Comp. | [gly] | Cmpnt. 1 | wt % | Cmpnt. 2 | wt % | Cmpnt. 3 | wt % |
|---|---|---|---|---|---|---|---|
| 273B9D | 62 | NIS37 | 8.0 | CIS21 | 8.0 | OTH1 | 12.5 |
| 274D5X | 60 | NIS37 | 8.0 | CIS21 | 8.0 | OTH1 | 15.0 |
| 237A6P | 60 | NIS37 | 9.5 | CIS21 | 9.5 | OTH1 | 12.0 |
| 238T3S | 72 | NIS37 | 6.0 | CIS21 | 5.0 | OTH1 | 5.5 |

TABLE 62B

| | | % Weed Control | | | |
|---|---|---|---|---|---|
| Comp. | Titer | SECCX | TRZVX | TAROF | LOLPE |
| 944U7M | 1 | 61, 88, 90, 95, 99, 87 | 58, 87, 86, 90, 93, 83 | — | — |
| | 2 | — | — | 57, 60, 74, 71, 80, 68 | — |
| | 3 | — | — | — | 58, 84, 92, 99, 100, 87 |
| | 5 | — | 69, 83, 90, 93, 94, 86 | — | — |
| 237A6P | 1 | 72, 88, 91, 89, 88, 86 | 59, 84, 84, 88, 91, 81 | — | — |
| | 2 | — | — | 61, 62, 61, 64, 79, 65 | — |
| | 3 | — | — | — | 55, 85, 96, 99, 100, 87 |
| | 5 | — | 70, 78, 93, 93, 98, 86 | — | — |
| 238T3S | 1 | 80, 87, 94, 85, 96, 88 | 61, 84, 82, 84, 90, 80 | — | — |
| | 2 | — | — | 58, 58, 72, 75, 75, 68 | — |
| | 3 | — | — | — | 59, 85, 95, 98, 100, 87 |
| | 5 | — | 78, 80, 90, 94, 94, 87 | — | — |
| 271G7P | 1 | 74, 88, 90, 90, 88, 86 | 62, 82, 83, 83, 86, 79 | — | — |
| | 2 | — | — | 56, 47, 59, 76, 77, 63 | — |
| | 3 | — | — | — | 56, 84, 92, 99, 100, 86 |
| | 5 | — | 68, 81, 89, 93, 94, 85 | — | — |
| 272K2U | 1 | 77, 83, 87, 91, 88, 85 | 67, 80, 83, 89, 91, 82 | — | — |
| | 2 | — | — | 57, 56, 68, 68, 71, 64 | — |
| | 3 | — | — | — | 59, 84, 91, 99, 100, 87 |
| | 5 | — | 68, 84, 91, 90, 96, 86 | — | — |
| 273B9D | 1 | 73, 86, 92, 94, 96, 88 | 57, 84, 85, 93, 98, 83 | — | — |
| | 2 | — | — | 61, 54, 77, 74, 72, 68 | — |
| | 3 | — | — | — | 54, 85, 91, 99, 100, 86 |
| | 5 | — | 79, 80, 86, 91, 96, 87 | — | — |
| 274D5X | 1 | 71, 86, 88, 92, 95, 87 | 63, 84, 86, 86, 91, 83 | — | — |
| | 2 | — | — | 51, 53, 56, 65, 82, 61 | — |
| | 3 | — | — | — | 58, 82, 93, 99, 100, 86 |
| | 5 | — | 69, 76, 88, 93, 95, 84 | — | — |
| STD12 | 1 | 85, 93, 99, 99, 100, 95 | 75, 84, 88, 93, 96, 87 | — | — |
| | 2 | — | — | 64, 59, 68, 70, 82, 68 | — |
| | 3 | — | — | — | 55, 81, 95, 99, 100, 86 |
| | 5 | — | 70, 86, 89, 95, 95, 87 | — | — |

| Comp. | Titer | LOLMG | GERCA | OEOLA | ERICA |
|---|---|---|---|---|---|
| 944U7M | 3 | 61, 77, 90, 99, 100, 85 | 65, 89, 93, 99, 100, 89 | 54, 68, 83, 97, 100, 80 | — |
| | 4 | — | — | 49, 68, 74, 87, 90, 74 | 46, 75, 81, 88, 92, 77 |
| | 5 | 51, 60, 66, 68, 78, 65 | — | — | — |
| 237A6P | 3 | 53, 72, 97, 99, 100, 84 | 59, 89, 94, 98, 100, 88 | 46, 66, 83, 88, 98, 76 | — |
| | 4 | — | — | 51, 64, 72, 79, 88, 71 | 44, 70, 69, 82, 87, 70 |
| | 5 | 50, 58, 68, 69, 70, 63 | — | — | — |
| 238T3S | 3 | 49, 74, 97, 99, 100, 84 | 61, 88, 94, 99, 100, 88 | 49, 67, 83, 91, 100, 78 | — |
| | 4 | — | — | 51, 65, 72, 84, 92, 73 | 46, 72, 77, 91, 96, 77 |
| | 5 | 51, 55, 66, 66, 73, 62 | — | — | — |
| 271G7P | 3 | 55, 79, 93, 99, 100, 85 | 58, 86, 91, 99, 100, 87 | 48, 72, 87, 91, 98, 79 | — |
| | 4 | — | — | 49, 67, 73, 85, 90, 73 | 48, 67, 74, 88, 90, 73 |
| | 5 | 53, 59, 65, 66, 75, 64 | — | — | — |
| 272K2U | 3 | 50, 76, 91, 99, 100, 83 | 61, 88, 88, 99, 100, 87 | 56, 62, 84, 97, 100, 80 | — |
| | 4 | — | — | 48, 63, 68, 85, 92, 71 | 43, 69, 75, 87, 97, 74 |
| | 5 | 50, 59, 65, 68, 71, 63 | — | — | — |
| 273B9D | 3 | 48, 72, 86, 99, 100, 81 | 55, 86, 90, 96, 100, 85 | 45, 68, 81, 88, 93, 75 | — |
| | 4 | — | — | 51, 62, 71, 82, 83, 70 | 45, 68, 76, 85, 91, 73 |
| | 5 | 56, 58, 65, 66, 73, 64 | — | — | — |
| 274D5X | 3 | 51, 78, 89, 95, 100, 83 | 57, 81, 90, 98, 100, 87 | 51, 65, 83, 93, 96, 78 | — |
| | 4 | — | — | 45, 61, 68, 79, 85, 68 | 45, 64, 74, 86, 88, 72 |
| | 5 | 51, 59, 66, 68, 75, 64 | — | — | — |
| STD12 | 3 | 53, 82, 89, 99, 100, 84 | 54, 89, 91, 99, 100, 87 | 50, 69, 79, 91, 99, 78 | — |
| | 4 | — | — | 48, 66, 75, 84, 89, 72 | 46, 69, 82, 90, 90, 76 |
| | 5 | 51, 64, 64, 71, 75, 65 | — | — | — |

TABLE 62B-continued

| Comp. | Titer | AVESX | IPOLA | ABUTH | ECHCG |
|---|---|---|---|---|---|
| 944U7M | 5 | 56, 63, 71, 71, 79, 68 | — | — | — |
|  | 6 | — | 70, 78, 83, 86, 88, 81 | 69, 76, 78, 83, 90, 79 | 88, 91, 94, 96, 96, 93 |
| 237A6P | 5 | 64, 64, 66, 66, 75, 67 | — | — | — |
|  | 6 | — | 70, 79, 80, 84, 86, 80 | 66, 73, 74, 81, 86, 76 | 85, 89, 91, 98, 98, 92 |
| 238T3S | 5 | 61, 63, 68, 68, 71, 66 | — | — | — |
|  | 6 | — | 70, 75, 81, 81, 85, 79 | 69, 75, 76, 83, 90, 79 | 83, 93, 94, 94, 96, 92 |
| 271G7P | 5 | 64, 64, 65, 69, 74, 67 | — | — | — |
|  | 6 | — | 74, 81, 83, 85, 86, 82 | 69, 74, 75, 83, 85, 77 | 83, 91, 94, 98, 96, 92 |
| 272K2U | 5 | 58, 61, 64, 70, 76, 66 | — | — | — |
|  | 6 | — | 68, 83, 84, 84, 85, 81 | 64, 75, 75, 79, 91, 77 | 83, 93, 93, 94, 96, 92 |
| 273B9D | 5 | 61, 61, 65, 66, 73, 65 | — | — | — |
|  | 6 | — | 69, 78, 80, 80, 85, 78 | 65, 78, 79, 79, 85, 77 | 84, 88, 93, 96, 98, 92 |
| 274D5X | 5 | 60, 60, 66, 68, 74, 66 | — | — | — |
|  | 6 | — | 75, 76, 79, 79, 83, 78 | 68, 70, 78, 79, 84, 76 | 88, 87, 96, 94, 98, 93 |
| STD12 | 5 | 58, 66, 68, 69, 76, 67 | — | — | — |
|  | 6 | — | 75, 80, 80, 83, 84, 80 | 73, 78, 78, 85, 86, 80 | 86, 90, 96, 99, 99, 94 |

As applied to SECCX, STD12 gave the greatest efficacy with commercial control, except for 272K2U, established at 585 g a.e. per hectare.

As applied to TRZVX: at Titer 1 STD12 gave the greatest efficacy with commercial control for each formulation, except 238T3S and 271G7P, established at 1040 g a.e. per hectare; and at Titer 5 STD12, 273B9D 238T3S were the most efficacious compositions with commercial control for each formulation established at 500 g a.e. per hectare.

As applied to TAROF, STD12 gave the greatest efficacy with no commercial control at any titer of application.

As applied to LOLPE, each formulation, except 273B9D and 271G7P, gave greater control than STD12 with commercial control for each formulation established at 845 g a.e. per hectare.

As applied to LOLMG: at Titer 3 compositions 944U7M and 271G7P each was of higher efficacy than STD12 with commercial control for each formulation established at 845 g a.e. per hectare; and at Titer 5 STD12 and 944U7M were the most efficacious formulations with no commercial control established at any titer of application in the trial.

As applied to GERCA, each composition, except for 273B9D gave greater control than STD12. Commercial control for each formulation, except for 274D5X was established at 585 g a.e. per hectare.

As applied to OEOLA: at Titer 3 each of compositions 944U7M, 272K2U and 271G7P outperformed STD12, 238T3S and 274D5X, which were of similar efficacy, while commercial control for all formulations was established at 1170 g a.e. per hectare; and at Titer 4 each of compositions 944U7M, 238T3S and 271G7P gave greater efficacy than STD12 with commercial control for each formulation except 273B9D established at 840 g a.e. per hectare.

As applied to ERICA, 944U7M and 238T3S were the most effective formulations and with exception of 237A6P providing commercial control at 840 g a.e. per hectare.

As applied to AVESX, 944U7M was the most efficacious composition with commercial control not achieved at any titer of application in this trial.

As applied to IPOLA, 271G7P, 944U7M and 272K2U gave the greatest control with commercial control established for all formulations, except for STD12 and 274D5X at 875 g a.e. per hectare.

As applied to ABUTH, STD12 was the most efficacious formulation, and commercial control was established for all formulations except 274D5X at 875 g a.e. per hectare.

As applied to ECHCG, STD12 was the most efficacious formulation, and commercial control was established for all formulations 500 g a.e. per hectare.

Example 63

The field efficacy effect of high load ammonium glyphosate formulations was evaluated. Compositions were prepared as indicated in Table 63A with ammonium glyphosate concentration in wt % a.e. reported as [gly]. The compositions of Table 63A as well as composition 634Y7 (Table 48A), 155L1J (Table 50A) and 273B9D (Table 62A) were compared to STD4, STD5 and STD9 for their ability to control AMBTR, CASOB, ABUTH, IPOLA, SEBEX, SIDSP, ECHCG, CHEAL, AMATA and ABUTH in field studies done in Monmouth, Ill., Loxley, Ala. and Stoneville, Miss., all of the USA with % control results reported in Table 63B. Application, in g a.e. per hectare, was done according to eight titer schedules: Titer 1 at 630, 867, 1064 and 1261; Titer 2 at 200, 400, 600 and 800; Titer 3 at 300, 500, 700 and 900; Titer 4 at 350, 500, 650 and 800; Titer 5 at 400, 600, 800 and 1000; and Titer 6 at 395, 552, 710 and 808; Titer 7 at 350, 550, 750 and 950; and Titer 8 at 868, 1026, 1105 and 1263, with average efficacy for each titer reported as the last result. Titers of application to the plants species evaluated is as follows: AMBTR at Titer 1; CASOB, IPOLA, SEBEX and SIDSAP at Titers 2-5 and 7; ABUTH at Titers 2-8; ECHCG at Titers 4, 5 and 7; and AMATA at Titer 8.

TABLE 63A

| Comp. | [gly] | Cmpnt. 1 | wt % | Cmpnt. 2 | wt % | Cmpnt. 3 | wt % | Cmpnt. 4 | wt % | Cmpnt. 5 | wt % |
|---|---|---|---|---|---|---|---|---|---|---|---|
| 631H2P | 68 | CIS21 | 14.6 | NIS37 | 5.9 | OTH47 | 0.6 | — | | — | |
| 212R7J | 68 | CIS21 | 7.0 | NIS38 | 11.7 | OTH25 | 2.4 | — | | — | |
| 362T3F | 68 | CIS21 | 5.3 | NIS39 | 5.3 | CIS29 | 5.3 | OTH47 | 5.3 | — | |

TABLE 63A-continued

| Comp. | [gly] | Cmpnt. 1 | wt % | Cmpnt. 2 | wt % | Cmpnt. 3 | wt % | Cmpnt. 4 | wt % | Cmpnt. 5 | wt % |
|---|---|---|---|---|---|---|---|---|---|---|---|
| 363K9L | 68 | CIS21 | 12.3 | NIS40 | 12.3 | CIS29 | 1.4 | OTH48 | 2.1 | — | — |
| 364S0N | 68 | CIS21 | 10.5 | | 10.5 | CIS29 | 3.5 | OTH47 | 3.5 | OTH49 | 3.5 |
| 365Q1L | 68 | CIS21 | 9.5 | NIS39 | 9.5 | CIS29 | 1.0 | OTH47 | 5.3 | — | — |
| 915Z4B | 68 | CIS21 | 10.5 | NIS39 | 10.5 | — | — | — | — | — | — |
| 940V5L | 71.6 | CIS21 | 16.2 | — | — | — | — | — | — | — | — |

TABLE 63B

| | | % Weed Control | | | |
|---|---|---|---|---|---|
| Comp. | Titer | AMBTR | CASOB | ABUTH | IPOLA |
| 634Y7 | 1 | 72, 86, 86, 90, 83 | — | — | — |
| | 2 | — | 45, 55, 69, 82, 63 | 46, 67, 87, 88, 72 | 44, 56, 66, 71, 59 |
| | 3 | — | 60, 68, 73, 81, 70 | 62, 84, 92, 94, 83 | 54, 67, 74, 75, 67 |
| | 4 | — | 84, 94, 100, 100, 94 | 66, 84, 85, 91, 82 | 68, 84, 89, 93, 83 |
| | 5 | — | 63, 71, 78, 89, 75 | 53, 76, 83, 94, 76 | 64, 70, 75, 85, 92 |
| | 6 | — | — | 97, 99, 100, 100, 99 | — |
| | 7 | — | 68, 83, 98, 96, 86 | 55, 83, 93, 99, 82 | 45, 65, 81, 93, 71 |
| | 8 | — | — | 80, 83, 87, 96, 86 | — |
| 915Z4B | 1 | 77, 76, 77, 91, 80 | — | — | — |
| | 2 | — | 46, 54, 66, 77, 61 | 43, 54, 69, 84, 63 | 42, 52, 65, 70, 57 |
| | 3 | — | 53, 63, 77, 86, 70 | 55, 82, 91, 94, 80 | 44, 66, 74, 69, 63 |
| | 4 | — | 85, 95, 96, 99, 94 | 59, 78, 78, 89, 76 | 70, 79, 86, 89, 81 |
| | 5 | — | 59, 70, 75, 83, 72 | 55, 66, 81, 85, 72 | 59, 74, 75, 88, 94 |
| | 6 | — | — | 91, 96, 100, 99, 96 | — |
| | 7 | — | 68, 80, 85, 95, 82 | 60, 73, 89, 91, 78 | 45, 59, 71, 79, 63 |
| | 8 | — | — | 75, 79, 86, 92, 83 | — |
| 940V5L | 1 | 59, 81, 84, 83, 77 | — | — | — |
| | 2 | — | 43, 59, 66, 76, 61 | 43, 63, 78, 88, 68 | 44, 61, 64, 69, 59 |
| | 3 | — | 56, 65, 74, 90, 71 | 65, 76, 90, 95, 81 | 53, 64, 72, 75, 66 |
| | 4 | — | 80, 100, 96, 99, 94 | 61, 78, 78, 89, 76 | 59, 75, 81, 89, 76 |
| | 5 | — | 60, 68, 75, 86, 72 | 55, 59, 81, 90, 71 | 58, 64, 75, 85, 91 |
| | 6 | — | — | 92, 97, 100, 100, 97 | — |
| | 7 | — | 71, 81, 93, 95, 85 | 49, 70, 84, 89, 73 | 45, 63, 73, 86, 67 |
| | 8 | — | — | 78, 84, 92, 94, 87 | — |
| 155L1J | 1 | 74, 84, 84, 91, 83 | — | — | — |
| | 2 | — | 46, 55, 68, 79, 62 | 46, 64, 90, 92, 73 | 44, 61, 65, 66, 59 |
| | 3 | — | 54, 62, 76, 81, 68 | 61, 88, 93, 97, 85 | 50, 68, 73, 78, 67 |
| | 4 | — | 84, 88, 99, 100, 93 | 54, 79, 79, 94, 76 | 59, 76, 80, 86, 75 |
| | 5 | — | 61, 63, 75, 83, 70 | 60, 74, 84, 90, 77 | 61, 66, 74, 86, 89 |
| | 6 | — | — | 99, 100, 99, 99, 99 | — |
| | 7 | — | 69, 86, 90, 93, 84 | 58, 76, 93, 96, 81 | 48, 70, 80, 90, 72 |
| | 8 | — | — | 77, 81, 88, 95, 85 | — |
| 212R7J | 1 | 70, 84, 86, 86, 81 | — | — | — |
| | 2 | — | 46, 58, 70, 79, 63 | 43, 62, 78, 88, 68 | 43, 53, 63, 64, 56 |
| | 3 | — | 52, 64, 74, 85, 69 | 62, 87, 93, 99, 85 | 48, 62, 78, 81, 67 |
| | 4 | — | 88, 89, 98, 100, 93 | 60, 76, 81, 88, 76 | 68, 70, 86, 88, 78 |
| | 5 | — | 61, 66, 74, 86, 72 | 60, 68, 70, 88, 71 | 55, 73, 73, 88, 91 |
| | 6 | — | — | 92, 97, 99, 100, 97 | — |
| | 7 | — | 68, 81, 85, 94, 82 | 58, 73, 81, 86, 74 | 45, 54, 73, 83, 63 |
| | 8 | — | — | 79, 81, 95, 95, 87 | — |
| 273B9D | 1 | 66, 81, 83, 82, 78 | — | — | — |
| | 2 | — | 52, 58, 68, 76, 64 | 51, 63, 81, 88, 71 | 51, 58, 66, 66, 60 |
| | 3 | — | 52, 67, 70, 86, 69 | 54, 80, 92, 94, 80 | 47, 66, 68, 75, 64 |
| | 4 | — | 83, 98, 96, 99, 94 | 60, 79, 76, 88, 76 | 58, 75, 81, 89, 76 |
| | 5 | — | 61, 64, 73, 84, 70 | 58, 65, 74, 84, 70 | 59, 73, 74, 85, 92 |
| | 6 | — | — | 97, 99, 99, 99, 99 | — |
| | 7 | — | 68, 84, 88, 89, 82 | 58, 75, 88, 89, 77 | 48, 68, 73, 81, 67 |
| | 8 | — | — | 75, 84, 92, 99, 88 | — |
| 361H2P | 1 | 63, 74, 89, 87, 78 | — | — | — |
| | 2 | — | 45, 56, 74, 70, 61 | 46, 58, 84, 86, 69 | 43, 56, 70, 67, 59 |
| | 3 | — | 54, 69, 80, 83, 71 | 53, 86, 96, 97, 83 | 50, 69, 73, 77, 67 |
| | 4 | — | 81, 96, 96, 99, 93 | 65, 75, 75, 83, 74 | 66, 73, 85, 86, 78 |
| | 5 | — | 60, 68, 75, 78, 70 | 56, 68, 76, 80, 70 | 63, 71, 78, 84, 92 |
| | 6 | — | — | 91, 96, 100, 99, 96 | — |
| | 7 | — | 70, 78, 84, 89, 80 | 54, 64, 76, 90, 71 | 44, 63, 66, 80, 63 |
| | 8 | — | — | 82, 83, 90, 91, 87 | — |
| 362T3F | 1 | 76, 79, 85, 88, 82 | — | — | — |
| | 2 | — | 46, 59, 66, 76, 61 | 44, 63, 77, 84, 67 | 42, 62, 65, 66, 59 |
| | 3 | — | 49, 68, 73, 83, 68 | 58, 84, 93, 92, 82 | 54, 67, 68, 70, 65 |
| | 4 | — | 83, 90, 96, 100, 93 | 58, 74, 79, 89, 76 | 58, 76, 85, 90, 79 |
| | 5 | — | 58, 66, 73, 85, 70 | 53, 60, 81, 83, 69 | 59, 69, 74, 83, 90 |
| | 6 | — | — | 86, 91, 100, 99, 94 | — |

TABLE 63B-continued

% Weed Control

| | | | | | |
|---|---|---|---|---|---|
| | 7 | — | 70, 80, 85, 90, 81 | 61, 69, 88, 86, 76 | 44, 55, 73, 78, 62 |
| | 8 | — | — | 76, 84, 88, 92, 85 | — |
| 363K9L | 1 | 67, 79, 86, 86, 79 | — | — | — |
| | 2 | — | 45, 59, 72, 72, 62 | 42, 56, 79, 87, 66 | 40, 53, 61, 68, 55 |
| | 3 | — | 54, 65, 76, 85, 71 | 62, 85, 93, 92, 84 | 50, 66, 74, 76, 67 |
| | 4 | — | 86, 93, 99, 100, 94 | 59, 75, 76, 80, 73 | 60, 81, 86, 86, 78 |
| | 5 | — | 61, 73, 76, 86, 74 | 48, 68, 76, 81, 68 | 60, 76, 74, 86, 90 |
| | 6 | — | — | 89, 96, 99, 98, 96 | — |
| | 7 | — | 73, 86, 88, 91, 84 | 54, 81, 84, 84, 76 | 53, 66, 71, 76, 67 |
| | 8 | — | — | 76, 82, 89, 98, 86 | — |
| 364S0N | 1 | 68, 84, 85, 86, 83 | — | — | — |
| | 2 | — | 46, 58, 74, 72, 63 | 48, 63, 81, 83, 69 | 45, 58, 66, 67, 59 |
| | 3 | — | 55, 69, 76, 77, 69 | 63, 81, 96, 93, 83 | 49, 67, 76, 70, 65 |
| | 4 | — | 83, 90, 98, 98, 92 | 61, 71, 76, 86, 74 | 68, 74, 81, 89, 78 |
| | 5 | — | 59, 69, 75, 83, 71 | 51, 63, 83, 83, 70 | 60, 68, 74, 83, 89 |
| | 6 | — | — | 90, 96, 98, 98, 96 | — |
| | 7 | — | 68, 81, 85, 94, 82 | 58, 68, 89, 90, 76 | 48, 55, 73, 85, 65 |
| | 8 | — | — | 82, 88, 89, 94, 88 | — |
| 365Q1L | 1 | 61, 86, 84, 89, 80 | — | — | — |
| | 2 | — | 48, 57, 66, 78, 63 | 43, 63, 78, 87, 69 | 47, 59, 61, 68, 60 |
| | 3 | — | 54, 62, 77, 83, 69 | 51, 78, 92, 94, 79 | 43, 66, 69, 70, 62 |
| | 4 | — | 90, 93, 99, 100, 95 | 71, 76, 75, 84, 77 | 69, 76, 84, 89, 79 |
| | 5 | — | 61, 70, 74, 85, 73 | 56, 64, 75, 80, 69 | 56, 68, 75, 83, 91 |
| | 6 | — | — | 87, 96, 100, 99, 95 | — |
| | 7 | — | 68, 86, 88, 91, 83 | 50, 80, 80, 86, 74 | 44, 58, 76, 83, 65 |
| | 8 | — | — | 81, 81, 85, 94, 85 | — |
| STD4 | 1 | 65, 85, 78, 87, 79 | — | — | — |
| | 2 | — | 43, 59, 68, 77, 62 | 44, 61, 82, 80, 67 | 44, 58, 67, 71, 60 |
| | 3 | — | 55, 63, 73, 88, 70 | 55, 89, 95, 96, 84 | 42, 65, 72, 74, 63 |
| | 4 | — | 84, 90, 98, 100, 93 | 58, 73, 80, 91, 75 | 65, 78, 84, 91, 79 |
| | 5 | — | 58, 69, 71, 81, 70 | 64, 65, 71, 80, 70 | 61, 70, 73, 84, 91 |
| | 6 | — | — | 90, 98, 99, 99, 96 | — |
| | 7 | — | 69, 84, 93, 91, 84 | 58, 75, 85, 90, 77 | 46, 56, 76, 84, 66 |
| | 8 | — | — | 79, 83, 90, 91, 86 | — |
| STD5 | 5 | — | 50, 55, 59, 66, 58 | 50, 54, 75, 76, 64 | 55, 58, 73, 85, 83 |
| | 6 | — | — | — | — |
| | 7 | — | 45, 46, 48, 49, 47 | 48, 61, 68, 75, 63 | 44, 51, 60, 65, 55 |
| | 8 | — | — | 66, 76, 79, 89, 77 | — |
| STD9 | 1 | 71, 85, 85, 92, 83 | — | — | — |
| | 2 | — | 42, 53, 69, 80, 61 | 43, 57, 78, 83, 65 | 40, 56, 61, 63, 55 |
| | 3 | — | 58, 67, 85, 77, 71 | 62, 82, 92, 93, 82 | 53, 68, 75, 66, 65 |
| | 4 | — | 86, 94, 98, 100, 94 | 60, 76, 81, 86, 76 | 65, 75, 81, 88, 77 |
| | 5 | — | 63, 68, 75, 84, 72 | 51, 64, 83, 83, 70 | 53, 65, 76, 83, 91 |
| | 6 | — | — | 88, 97, 100, 100, 96 | — |
| | 7 | — | 69, 84, 89, 90, 83 | 55, 70, 83, 85, 73 | 44, 60, 69, 75, 62 |
| | 8 | — | — | 80, 83, 88, 94, 86 | — |

| Comp. | Titer | SEBEX | SIDSP | ECHCG |
|---|---|---|---|---|
| 634Y7 | 2 | 31, 55, 65, 68, 55 | 41, 65, 90, 89, 71 | — |
| | 3 | 52, 66, 67, 71, 64 | 70, 81, 90, 94, 84 | — |
| | 4 | 55, 80, 81, 93, 77 | 80, 86, 94, 96, 89 | 90, 98, 95, 99, 95 |
| | 5 | 50, 53, 66, 76, 61 | 74, 94, 99, 100, 92 | 88, 100, 100, 99, 97 |
| | 7 | 51, 65, 79, 91, 72 | 85, 96, 100, 100, 95 | 100, 100, 100, 100, 100 |
| 915Z4B | 2 | 34, 54, 63, 75, 56 | 39, 71, 74, 81, 66 | — |
| | 3 | 43, 64, 70, 73, 62 | 69, 73, 89, 91, 81 | — |
| | 4 | 60, 78, 84, 84, 76 | 78, 88, 90, 90, 86 | 86, 95, 95, 100, 94 |
| | 5 | 50, 59, 68, 69, 61 | 83, 95, 98, 100, 94 | 93, 100, 99, 100, 98 |
| | 7 | 46, 64, 74, 85, 67 | 86, 93, 96, 99, 93 | 100, 100, 100, 100, 100 |
| 940V5L | 2 | 41, 60, 65, 75, 60 | 45, 67, 73, 89, 68 | — |
| | 3 | 43, 65, 65, 74, 61 | 60, 76, 82, 86, 76 | — |
| | 4 | 49, 76, 81, 93, 75 | 63, 81, 86, 98, 82 | 84, 98, 95, 100, 94 |
| | 5 | 58, 58, 60, 78, 63 | 74, 89, 100, 100, 91 | 86, 98, 99, 100, 96 |
| | 7 | 45, 59, 78, 79, 65 | 83, 96, 100, 99, 94 | 100, 100, 100, 100, 100 |
| 155L1J | 2 | 39, 55, 67, 73, 59 | 42, 63, 80, 84, 67 | — |
| | 3 | 39, 62, 67, 71, 60 | 58, 77, 84, 85, 76 | — |
| | 4 | 54, 70, 81, 86, 73 | 78, 86, 88, 96, 87 | 84, 98, 96, 99, 94 |
| | 5 | 50, 53, 59, 65, 57 | 78, 84, 99, 95, 89 | 93, 93, 99, 100, 96 |
| | 7 | 44, 63, 80, 81, 67 | 94, 96, 100, 100, 98 | 100, 100, 100, 100, 100 |
| 212R7J | 2 | 36, 52, 67, 65, 55 | 39, 67, 74, 78, 64 | — |
| | 3 | 44, 59, 70, 73, 61 | 67, 75, 89, 92, 82 | — |
| | 4 | 59, 80, 81, 89, 77 | 64, 83, 91, 94, 83 | 86, 96, 98, 100, 95 |
| | 5 | 43, 56, 58, 80, 59 | 71, 91, 100, 100, 91 | 88, 99, 98, 100, 96 |
| | 7 | 43, 63, 76, 78, 65 | 86, 95, 96, 100, 94 | 100, 100, 100, 100, 100 |
| 273B9D | 2 | 46, 57, 65, 75, 61 | 48, 69, 74, 83, 68 | — |
| | 3 | 39, 59, 66, 64, 57 | 55, 74, 84, 89, 75 | — |
| | 4 | 51, 71, 75, 89, 72 | 63, 80, 89, 96, 82 | 78, 94, 91, 94, 89 |

TABLE 63B-continued

| | | % Weed Control | | |
|---|---|---|---|---|
| | 5 | 51, 46, 63, 65, 56 | 79, 95, 98, 98, 92 | 89, 95, 98, 100, 95 |
| | 7 | 44, 56, 75, 78, 63 | 88, 95, 100, 99, 95 | 100, 100, 100, 100, 100 |
| 361H2P | 2 | 41, 54, 68, 70, 58 | 41, 61, 71, 81, 63 | — |
| | 3 | 45, 65, 71, 78, 65 | 62, 76, 92, 90, 80 | — |
| | 4 | 54, 76, 84, 84, 74 | 74, 79, 94, 96, 86 | 85, 98, 96, 100, 95 |
| | 5 | 49, 59, 63, 69, 60 | 81, 85, 100, 100, 92 | 88, 94, 100, 100, 95 |
| | 7 | 46, 59, 70, 78, 63 | 84, 96, 95, 100, 94 | 100, 100, 100, 100, 100 |
| 362T3F | 2 | 36, 57, 64, 63, 55 | 40, 60, 70, 76, 61 | — |
| | 3 | 38, 64, 66, 66, 58 | 57, 78, 86, 87, 77 | — |
| | 4 | 58, 76, 84, 93, 79 | 73, 79, 86, 95, 84 | 83, 94, 96, 100, 94 |
| | 5 | 54, 56, 69, 68, 62 | 79, 90, 95, 98, 90 | 88, 98, 100, 100, 96 |
| | 7 | 49, 59, 76, 78, 65 | 86, 89, 99, 99, 93 | 100, 100, 100, 100, 100 |
| 363K9L | 2 | 38, 54, 69, 76, 59 | 40, 58, 68, 87, 63 | — |
| | 3 | 50, 66, 69, 68, 64 | 70, 77, 85, 90, 81 | — |
| | 4 | 60, 83, 83, 88, 78 | 68, 85, 91, 94, 84 | 88, 100, 98, 100, 96 |
| | 5 | 56, 64, 63, 76, 65 | 74, 88, 98, 100, 90 | 90, 99, 98, 100, 97 |
| | 7 | 45, 71, 71, 78, 66 | 88, 95, 100, 100, 96 | 100, 100, 100, 100, 100 |
| 364S0N | 2 | 41, 61, 68, 76, 61 | 40, 66, 78, 91, 69 | — |
| | 3 | 50, 62, 66, 65, 64 | 63, 84, 84, 91, 84 | — |
| | 4 | 58, 71, 75, 89, 73 | 66, 84, 90, 94, 83 | 85, 94, 95, 100, 93 |
| | 5 | 50, 56, 64, 74, 61 | 71, 91, 94, 100, 89 | 89, 98, 96, 100, 96 |
| | 7 | 46, 61, 70, 81, 65 | 86, 98, 99, 100, 96 | 100, 100, 100, 100, 100 |
| 365Q1L | 2 | 32, 58, 67, 70, 58 | 39, 70, 71, 88, 69 | — |
| | 3 | 42, 62, 68, 72, 61 | 61, 77, 90, 92, 80 | — |
| | 4 | 65, 80, 83, 86, 78 | 76, 81, 91, 96, 86 | 93, 95, 93, 100, 95 |
| | 5 | 45, 61, 66, 66, 60 | 71, 98, 95, 100, 91 | 88, 100, 99, 100, 97 |
| | 7 | 44, 65, 76, 79, 66 | 83, 95, 100, 99, 94 | 100, 100, 100, 100, 100 |
| STD4 | 2 | 38, 56, 68, 86, 62 | 40, 65, 84, 92, 70 | — |
| | 3 | 43, 60, 64, 66, 58 | 56, 72, 82, 85, 74 | — |
| | 4 | 60, 69, 78, 85, 73 | 73, 86, 85, 93, 84 | 81, 98, 95, 98, 93 |
| | 5 | 49, 58, 64, 68, 59 | 74, 90, 99, 100, 91 | 89, 95, 96, 100, 95 |
| | 7 | 51, 65, 80, 80, 69 | 85, 94, 98, 100, 94 | 100, 100, 100, 100, 100 |
| STD5 | 5 | 40, 43, 46, 50, 45 | 75, 73, 88, 95, 83 | 64, 61, 61, 75, 65 |
| | 7 | 29, 30, 31, 36, 32 | 84, 93, 90, 99, 91 | 53, 59, 56, 66, 58 |
| STD9 | 2 | 43, 55, 68, 72, 60 | 43, 64, 77, 84, 67 | — |
| | 3 | 47, 68, 65, 67, 62 | 58, 78, 90, 88, 77 | — |
| | 4 | 54, 79, 76, 84, 73 | 70, 84, 84, 94, 83 | 88, 96, 95, 99, 94 |
| | 5 | 46, 53, 64, 65, 57 | 78, 93, 99, 96, 91 | 88, 96, 99, 100, 96 |
| | 7 | 43, 64, 74, 79, 65 | 85, 100, 100, 100, 96 | 100, 100, 100, 100, 100 |

As applied to AMBTR, 634Y7, 155L1J, 364S0N and STD9 gave the highest efficacy and, with the exception of 273B9D and 940V5L, commercial control at 1261 g a.e. per hectare.

Efficacy results on CASOB are as follows. At Titer 2, 273B9D, 365Q1L, 212R7J, 634Y7 and 364S0N each gave greater efficacy than STD4 and STD9 with commercial control not attained at any titer of application. At Titer 3, 155L1J, 212R7J, 273B9D, 362T3F, 364S0N and 365Q1L each gave slightly lower control than STD4 and STD9; commercial control at 900 g a.e. per hectare was provided by STD4, 915Z4B, 940V5L, 212R7J, 273B9D and 363K9L. At Titer 4, 365Q1L gave the highest control; commercial control was established for all compositions at 500 g a.e. per hectare. At Titer 5, the efficacy for 634Y7, 363K9L and 365Q1L each exceeded that of STD4, STD5 and STD9; commercial control was shown at 1000 g a.e. per hectare for 634Y7, 940V5L, 212R7J, 362T3F, 363K9L and 365Q1L. At Titer 7, 634Y7 and 940V5L were the most efficacious formulations. 155L1J, 363K9L and STD4 were the next efficacious formulations; commercial control was demonstrated at 750 g a.e. per hectare for all formulations except 361H2P and STD5.

Efficacy results on ABUTH are as follows. At Titer 2, only formulations 915Z4B and 363K9L failed to match the efficacy of STD4; 915Z4B, 362T3F, 364S0N, STd4, STD5 and STD9 did not provide commercial control at 800 g a.e./ha. At Titer 3, each of 212R7J and 155L1J and 363K9L were the most efficacious formulations evaluated; commercial control for all compositions was achieved at 700 g a.e. per hectare. At Titer 4, 634Y7, 365Q1L, 940V5L, 155L1J, 212R7J and 362T3F each provided control greater than STD4 and STD9; commercial control was established at 800 g a.e. per hectare for every formulation except 361H2P, 363K9L and 365Q1L. At Titer 5, 155L1J, 634Y7, 915Z4B, 940V5L and 212R7J each gave higher efficacy than STD4, STD5 and STD9; commercial control for 634Y7, 915Z4B, 940V5L, 155L1J and 212R7J was shown at 1000 g a.e. per hectare. At Titer 6, efficacy of all formulations was extremely high; commercial control was established at 395 g a.e./ha, the lowest rate of application in this trial. At Titer 7, 634Y7, 155L1J, 915Z4B and 273B9D were each more efficacious than STD4, with STD5 (monoammonium salt of glyphosate) being the least efficacious composition; commercial control was shown for all formulations except STD5 and 393K9L at 950 g a.e. per hecatare. At Titer 8, 364S0N, 273B9D, 212R7J, 940V5L, 212R7J, 155L1J, 915Z4B and 361H2P each showed greater efficacy than STD4 and STD9 (with STD5 being the least efficacious); commercial control was shown at 1105 g a.e. per hectare.

Efficacy results on IPOLA are as follows. At Titer 2, 273B9D, 365Q1L and STD4 gave the highest efficacy; commercial control was not established at any titer of application. At Titer 3, each of 634Y7, 363K9L, 155L1J, 212R7J, 361H2P and 940V5L were more efficacious than STD4 and STD9; commercial control was not achieved at any titer of application. At Titer 4, 634Y7 and 915Z4B were more efficacious than STD4 and STD9; commercial control was established for all compositions at 800 g a.e. per hectare. At Titer 5, 915Z4B, 273B9D, 634Y7 and 361H2P were each more efficacious than STD4, STD5 and STD9; commercial control for 634Y7, 915Z4B, 940V5L, 155L1J, 212R7J, 273B9D and 363K9L was indicated at 1000 g a.e. per hectare. At Titer 7, 155L1J, 634Y7, 273B9D, 940V5L, 365Q1L and 363K9L each were more efficacious than STD4, STD5 and STD9 (with STD5 showing the lowest efficacy); commercial control was established for 634Y7, 940V5L, 155L1J and 364S0N at 950 g a.e. per hectare.

Efficacy results on SEBEX are as follows. At Titer 2, STD4 gave the highest efficacy; only STD4 achieved commercial control at 800 g a.e. per hectare. At Titer 3, 273B9D was 361H2P, 363K9L, 634Y7, 364S0N and 915Z4B gave the highest efficacy; commercial control was not achieved at any titer of application in this trial. At Titer 4, every experimental formulation except 273B9D was more efficacious than STD4 and STD9; commercial control generally was established at 800 g a.e. per hectare. At Titer 5, 363K9L, 940V5L, 362T3F, 634Y7, 915Z4B, 364S0N, 361H2P and 365Q1L was each more efficacious than STD4, STD5 and STD9; commercial control was not obtained for any formulation evaluated. At Titer 7, 634Y7 was more efficacious than STD4 and STD5 was the least efficacious; commercial control was attained at 950 g a.e. per hectare with only 634Y7 and 915Z4B.

Efficacy results on SIDSP are as follows. At Titer 2, 634Y7 gave the highest efficacy followed by STD4; commercial control for STD4, 634Y7, 940V5L, 363K9L, 364S0N and 365Q1L was achieved at 800 g a.e. per hectare. At Titer 3, 634Y7, 212R7J, 363K9L, 915Z4B, 364S0N, 361H2P AND 365Q1L provided the highest efficacy; commercial control was achieved with all compositions at 900 g a.e. per hectare. At Titer 4, the efficacy of each of 634Y7, 155L1J, 915Z4B, 365Q1L and 361H2P exceeded that of STD4 and STD9; commercial control was obtained at 650 g a.e. per hectare for all formulations except STD9. At Titer 5, 915Z4B, 273B9D, 634Y7 and 361H2P each gave greater control than STD4, STD5 and STD9; commercial control was shown at 600 g a.e. per hectare. At Titer 7, 155L1J was the most efficacious composition followed by STD9; commercial control was shown at 350 g a.e. per hectare for all formulations except 940V5L, 361H2P and 365Q1L.

Efficacy results on ECHCG are as follows. At Titer 4, all formulations were quite effective; commercial control was established at 500 g a.e. per hectare for all formulations. At Titer 5, 915Z4B, 634Y7, 363K9L and 365Q1L each gave greater control than STD4, STD5 and STD9; commercial control was indicated at 400 g a.e. per hectare for all compositions except STD5. At Titer 7, all formulations, except for STD5, gave complete control at each application titer evaluated.

The entire contents of U.S. provisional application No. 60/407,479, entitled, PROCESS FOR THE PREPARATION OF A DRY PESTICIDAL COMPOSITION CONTAINING A DICARBOXYLATE COMPONENT, filed on Aug. 30, 2002, are incorporated herein by reference.

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

What is claimed is:

1. A solid pesticidal concentrate composition that is biologically effective to control growth of a susceptible plant when the composition is diluted in water to form an enhanced application mixture and applied to the foliage of a susceptible plant, comprising:
   a herbicidal component consisting essentially of water-soluble herbicides in a concentration greater than 30% by weight;
   a surfactant component being selected from the group consisting of cationic surfactants, nonionic surfactants, amphoteric surfactants, and mixtures thereof; and
   an efficacy enhancer component comprising a dicarboxylic acid or an anhydride, ester, amide, halide, salt or precursor thereof;
   the molar ratio of said herbicide component to said enhancer component being between about 0.1 and about 16 on an acid equivalent basis.

2. A composition as set forth in claim 1 wherein said herbicidal component comprises a glyphosate component comprising glyphosate acid or an ester or salt thereof in a concentration greater than 30% by weight on an acid equivalent basis; and said enhancer component comprises oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors; the molar ratio of said glyphosate component to said dicarboxylic acid component being between about 0.18 and about 16 on an acid equivalent basis.

3. A composition as set forth in claim 1 wherein the enhancer component comprises oxalic acid or an anhydride, ester, amide, halide, salt or precursor thereof.

4. A composition of claim 2 wherein said glyphosate component is present in a concentration of at least 50% by weight on an acid equivalent basis.

5. A composition as set forth in claim 1 containing less than 5.7% by weight anionic surfactant.

6. A composition as set forth in claim 1 containing at least 28% by weight anionic surfactant.

7. A composition as set forth in claim 1 wherein the weight ratio of said enhancer component to any anionic surfactant contained in the composition is at least 4.8 on an acid equivalent basis.

8. A composition as set forth in claim 1 wherein the weight ratio of said enhancer component to any anionic surfactant contained in the composition is less than 0.25 on an acid equivalent basis.

9. A composition as set forth in claim 1 wherein the weight ratio of said pesticide to any anionic surfactant contained in the composition is greater than 5.7 on an acid equivalent basis.

10. A composition as set forth in claim 1 wherein the weight ratio of said pesticide to any anionic surfactant contained in the composition is no more than 1.7 on an acid equivalent basis.

11. A composition as set forth in claim 1 wherein the concentration of said herbicidal component is greater than 33% by weight on an acid equivalent basis.

12. A composition as set forth in claim 11 containing not greater than 22% by weight anionic surfactant.

13. A composition as set forth in claim 11 containing at least 28% by weight anionic surfactant.

14. A composition as set forth in claim 1 wherein the weight ratio of said enhancer component to any anionic surfactant contained in the composition is greater than 1.1 on an acid equivalent basis.

15. A composition as set forth in claim 1 wherein the weight ratio of said enhancer component to any anionic surfactant contained in the composition is less than 0.25 on an acid equivalent basis.

16. A composition as set forth in claim 1 wherein the weight ratio of said pesticide to any anionic surfactant contained in the composition is at least 2.1 on an acid equivalent basis.

17. A composition as set forth in claim 1 wherein the weight ratio of said pesticide to any anionic surfactant contained in the composition is no more than 1.7 on an acid equivalent basis.

18. A composition as set forth in claim 1 wherein the enhancer component is nonherbicidal, the movement of said herbicide to the phloem being increased in the plant treated with said enhanced application mixture as compared to the plant treated with a reference application mixture devoid of said enhancer component but otherwise having the same composition as the enhanced application mixture.

19. A composition as set forth in claim 1 wherein the enhancer component is not a surfactant or a herbicide.

20. A composition as set forth in claim 1 wherein the enhancer component has two carboxyl functional groups joined by a covalent bond or an alkylene or alkenylene moiety having 1 to about 10 carbon atoms.

21. A solid pesticidal concentrate composition that is biologically effective to control growth of a susceptible plant when the composition is diluted in a suitable volume of water to form an enhanced application mixture and applied to the foliage of a susceptible plant, comprising:
a herbicidal component consisting essentially of water-soluble herbicides in a concentration between 30% and 70% by weight;
an efficacy enhancer component comprising a dicarboxylic acid or an anhydride, ester, amide, halide, salt or precursor thereof;
the molar ratio of said herbicidal component to said efficacy enhancer component being between about 0.1 and about 16 on an acid equivalent basis;
said composition containing less than 5.7% by weight anionic surfactant.

22. A solid pesticidal concentrate composition that is biologically effective to control growth of a susceptible plant when the composition is diluted in a suitable volume of water to form an enhanced application mixture and applied to the foliage of a susceptible plant, comprising:
a herbicidal component consisting essentially of water-soluble herbicides in a concentration between 30% and 70% by weight; and
an efficacy enhancer component comprising a dicarboxylic acid or an anhydride, ester, amide, halide, salt or precursor thereof;
the molar ratio of said herbicidal component to said efficacy enhancer component being between about 0.1 and about 16 on an acid equivalent basis; and either:
(a) the weight ratio of said efficacy enhancer component to any anionic surfactant contained in the composition being at least 4.8 on an acid equivalent basis;
(b) the weight ratio of said efficacy enhancer component to any anionic surfactant contained in the composition is no more than 0.25 on an acid equivalent basis;
(c) the weight ratio of said herbicidal component to any anionic surfactant contained in the composition being greater than 5.7 on an acid equivalent basis; or
(d) the weight ratio of said herbicidal component to any anionic surfactant contained in the composition being no more than 1.7 on an acid equivalent basis.

23. A solid pesticidal concentrate composition that is biologically effective to control growth of a susceptible plant when the composition is diluted in a suitable volume of water to form an enhanced application mixture and applied to the foliage of a susceptible plant, comprising:
a herbicidal component consisting essentially of water-soluble herbicides in a concentration between 30% and 70% by weight;
an efficacy enhancer component comprising a dicarboxylic acid or an anhydride, ester, amide, halide, salt or precursor thereof;
the molar ratio of said herbicidal component to said efficacy enhancer component being between about 0.1 and about 16 on an acid equivalent basis;
said composition containing at least 28% by weight anionic surfactant.

24. A composition as set forth in claim 21 wherein the herbicidal component comprises a glyphosate component comprising glyphosate acid or an ester or salt thereof in a concentration between 30% and 70% by weight on an acid equivalent basis; the efficacy enhancer component comprises oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors; and the molar ratio of said glyphosate component to said efficacy enhancer component is between about 0.18 and about 16 on an acid equivalent basis.

25. A composition as set forth in claim 21 wherein the herbicidal component comprises a glyphosate component comprising glyphosate acid or an ester or salt thereof in a concentration between 33% and 70% by weight on an acid equivalent basis; the molar ratio of said glyphosate component to said efficacy enhancer component being between about 0.2 and about 16 on an acid equivalent basis; said composition containing less than 22% by weight anionic surfactant.

26. A solid pesticidal concentrate composition that is biologically effective to control growth of a susceptible plant when the composition is diluted in a suitable volume of water to form an enhanced application mixture and applied to the foliage of a susceptible plant, comprising:
a herbicidal component consisting essentially of water-soluble herbicides in a concentration between 33% and 70% by weight;
an efficacy enhancer component comprising a dicarboxylic acid or an anhydride, ester, amide, halide, salt or precursor thereof;
the molar ratio of said herbicidal component to said efficacy enhancer component being between about 0.1 and about 16 on an acid equivalent basis; and either:

(a) the weight ratio of said efficacy enhancer component to any anionic surfactant contained in the composition being greater than 1.1 on an acid equivalent basis; or (b) the weight ratio of said herbicidal component to any anionic surfactant contained in the composition being at least 2.1 on an acid equivalent basis.

27. A composition as set forth in claim 26 wherein the herbicidal component comprises a glyphosate component comprising glyphosate acid or an ester or salt thereof; the efficacy enhancer component comprises oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors; and the molar ratio of said glyphosate component to said efficacy enhancer component is between about 0.2 and about 16 on an acid equivalent basis.

28. A composition as set forth in claim 24 substantially free of anionic surfactant.

29. A composition as set forth in claim 21 wherein the weight ratio of said herbicidal component to any anionic surfactant contained in the composition is less than 2.1 on an acid equivalent basis.

30. A composition as set forth in claim 21 wherein the concentration of said herbicidal component is greater than 33% by weight on an acid equivalent basis.

31. A composition as set forth in claim 30 wherein the weight ratio of said herbicidal component to any anionic surfactant contained in the composition is no more than 5.7 on an acid equivalent basis.

32. A composition as set forth in claim 21 wherein the weight ratio of said efficacy enhancer component to any anionic surfactant contained in the composition is less than 4.8 on an acid equivalent basis.

33. A composition as set forth in claim 21 wherein the weight ratio of said efficacy enhancer component to any anionic surfactant contained in the composition is no more than 1.1 on an acid equivalent basis.

34. A solid pesticidal concentrate composition that is biologically effective to control growth of a susceptible plant when the composition is diluted in water to form an enhanced application mixture and applied to the foliage of a susceptible plant, comprising:
   a herbicidal component consisting essentially of water-soluble herbicides;
   a surfactant component selected from the group consisting of cationic surfactants, nonionic surfactants, amphoteric surfactants, and mixtures thereof and
   an efficacy enhancer component in a concentration of greater than 20% by weight, the enhancer component comprising a dicarboxylic acid or an anhydride, ester, amide, halide, salt or precursor thereof.

35. A solid pesticidal concentrate composition that is biologically effective to control growth of a susceptible plant when the composition is diluted in water to form an enhanced application mixture and applied to the foliage of a susceptible plant, comprising:
   a herbicidal component consisting essentially of water-soluble herbicides;
   an efficacy enhancer component comprising a dicarboxylic acid or an anhydride, ester, amide, halide, salt or precursor thereof; and
   a surfactant component comprising one or more surfactants;
   wherein the composition is free of anionic surfactants, and either:
   (a) said herbicidal component is present in a concentration greater than 30 wt. %;
   (b) said enhancer component is present in a concentration greater than 20 wt. %;
   (c) said surfactant component is present in an amount greater than 10 wt. %;
   (d) the molar ratio of said herbicidal component to said enhancer component is greater than 1.1:1 on an acid equivalent basis, or the weight ratio of said herbicidal component to said enhancer component is greater than 1.25:1 on an acid equivalent basis;
   (e) the molar ratio of said herbicidal component to said enhancer component is less than 0.9:1 on an acid equivalent basis, or the weight ratio of said herbicidal component to said enhancer component is less than 1.8 on an acid equivalent basis;
   (f) the weight ratio of glyphosate to surfactant component is greater than 2:1 on an acid equivalent basis; or (g) the weight ratio of glyphosate to surfactant component is less than 2:1 on an acid equivalent basis.

36. A solid pesticidal concentrate composition that is biologically effective to control growth of a susceptible plant when the composition is diluted in of water to form an enhanced application mixture and applied to the foliage of a susceptible plant, comprising:
   a herbicidal component consisting essentially of water-soluble herbicides;
   an efficacy enhancer component comprising a dicarboxylic acid or an anhydride, ester, amide, halide, salt or precursor thereof; and
   wherein the composition is free of anionic surfactants and the concentration of said herbicidal component in the enhanced application mixture is greater than 0.15 wt. %.

37. A composition as set forth in claim 36 wherein the composition further comprises a surfactant component comprising one or more surfactants.

38. A liquid pesticidal concentrate composition that is biologically effective to control growth of a susceptible plant when the composition is diluted in water to form an enhanced application mixture and applied to the foliage of a susceptible plant, comprising:
   at least one water-soluble pesticide;
   a surfactant component comprising one or more surfactants; and
   an enhancer component comprising disodium oxalate, diammonium oxalate or a mixture thereof, said enhancer component being present in an acid equivalent concentration between 2% by weight and maximum percent by weight dictated by the solubility of the enhancer component present.

39. A composition as set forth in claim 38 wherein said pesticide is present in a concentration between 2% and 30% by weight.

40. A composition as set forth in claim 38 wherein said surfactant is selected from the group consisting of cationic surfactants, nonionic surfactants, anionic surfactants, amphoteric surfactants, and mixtures thereof.

41. A composition as set forth in claim 40 wherein said surfactant is selected from the group consisting of cationic surfactants, nonionic surfactants, and mixtures thereof.

42. A composition as set forth in claim 38 wherein said pesticide comprises glyphosate acid or an ester or salt thereof.

43. A composition as set forth in claim 38 wherein said pesticide comprises glyphosate ester or glyphosate salt.

44. A composition as set forth in claim 38 wherein the movement of said enhancer component to the phloem is increased in the plant treated with said enhanced application mixture as compared to the plant treated with a reference application mixture devoid of said enhancer component but otherwise having the same composition as the enhanced application mixture.

45. A composition as set forth in claim 39 wherein the molar ratio of said pesticide to said enhancer component is less than 16:1 on an acid equivalent basis.

46. A composition as set forth in claim 38 wherein said composition has a cloud point of at least about 50° C. and a crystallization point not greater than about 0° C.

47. An aqueous pesticidal composition that is biologically effective to control growth of a susceptible plant when applied to the foliage of a susceptible plant, comprising:
  at least one water-soluble pesticide in a concentration between about 0.0001% and about 3% by weight;
  a surfactant component comprising one or more cationic, anionic or amphoteric surfactants; and
  an enhancer component comprising disodium oxalate, diammonium oxalate or a mixture thereof, said enhancer component being present in an acid equivalent concentration between 2% by weight and maximum percent by weight dictated by the solubility of the enhancer component present.

48. A composition as set forth in claim 47 wherein said pesticide is present in a concentration between about 0.01% and about 3% by weight.

49. A composition as set forth in claim 47 wherein said surfactant is selected from the group consisting of cationic surfactants, nonionic surfactants, anionic surfactants, amphoteric surfactants, and mixtures thereof.

50. A composition as set forth in claim 49 wherein said surfactant is selected from the group consisting of cationic surfactants, nonionic surfactants, and mixtures thereof.

51. A composition as set forth in claim 47 wherein said pesticide comprises glyphosate ester or glyphosate salt.

52. A composition as set forth in claim 47 wherein the movement of said enhancer component to the phloem is increased in the plant treated with said composition as compared to the plant treated with a reference application mixture devoid of said enhancer component but otherwise having the same composition as the enhanced application mixture.

53. A composition as set forth in claim 47 wherein the molar ratio of said pesticide to said enhancer component is less than 2.1:1 on an acid equivalent basis.

54. A composition as set forth in claim 2 wherein the glyphosate is predominantly in the form of the potassium, dipotassium, monoammonium, diammonium, sodium, monoethanolamine, isopropylamine, n-propylamine, ethylamine, ethylenediamine, hexamethylenediamine or trimethylsulfonium salt thereof.

55. A composition as set forth in claim 54 wherein the glyphosate is predominantly in the form of the potassium, dipotassium, monoammonium, diammonium, or sodium salt thereof.

56. A composition as set forth in claim 3 wherein said enhancer component comprises an alkali metal salt, alkanolamine salt, alkylamine salt, tetraalkylammonium salt, or aryltrialkylammonium salt of oxalic acid.

57. A composition as set forth in claim 1 wherein the surfactant component comprises at least one surfactant selected from the group consisting of:

(a) aminated alkoxylated alcohol having the formula:

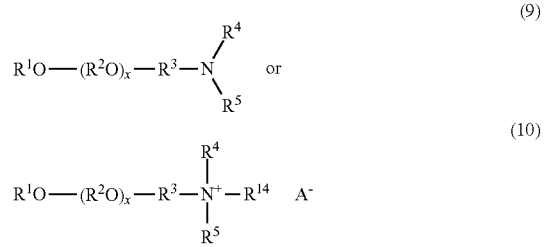

wherein $R^1$ is hydrogen or hydrocarbyl or substituted hydrocarbyl having from 1 to about 30 carbon atoms; $R^2$ in each of the x ($R^2O$) and y ($R^2O$) groups is independently $C_2$-$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, or $-C(=S)NR^{12}R^{13}$, n is 0 or 1, x and y are independently an average number from 1 to about 60, and A- is an agriculturally acceptable anion;

(b) hydroxylated amides having the formula:

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl;

(c) diamines having the formula:

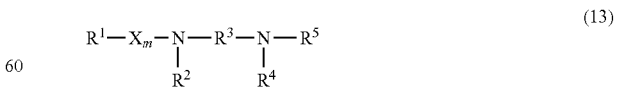

wherein $R^1$, $R^2$ and $R^5$ are independently hydrogen or hydrocarbyl or substituted hydrocarbyl having from 1 to about 30 carbon atoms or $-R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is —C(O)— or —SO$_2$—;

(d) mono- or di-ammonium salts having the formula:

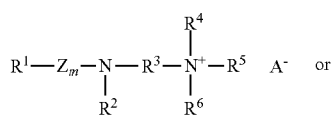

(14)

or

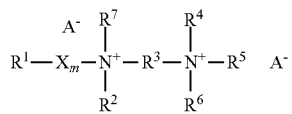

(15)

wherein $R^1$, $R^2$, $R^4$, $R^5$ and $R^7$ are independently hydrogen or hydrocarbyl or substituted hydrocarbyl having from 1 to about 30 carbon atoms or —$R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A$^-$ is an agriculturally acceptable anion;

(e) poly(hydroxyalkyl)amines having the formula:

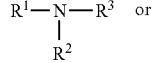

(16)

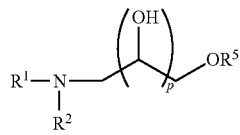

(17)

wherein $R^1$ is hydrocarbyl or substituted hydrocarbyl having from about 4 to about 30 carbon atoms or —$R^4OR^8$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, $R^8$ is hydrogen or hydrocarbyl or substituted hydrocarbyl having from 1 to about 30 carbon atoms, and $R^5$ is —$(R^6O)_yR^7$; $R^6$ in each of the y($R^6O$) groups is independently $C_2$-$C_4$ alkylene; $R^7$ is hydrogen or a linear or branched alkyl group having 1 to about 4 carbon atoms; and y is an average number from 0 to about 30;

(f) alkoxylated poly(hydroxyalkyl)amines having the formula:

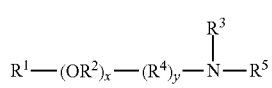

(20)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$-$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1;

(g) di-poly(hydroxyalkyl)amine having the formula:

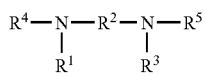

(23)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl;

(h) quaternary poly(hydroxyalkyl)amine salts having the formula:

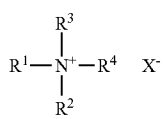

(25)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, and X— is an agriculturally acceptable anion;

(i) triamines having the formula:

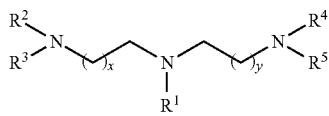

(28)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or —$(R^8)_s(R^7O)_nR^6$; $R^6$ is hydrogen or a linear or branched alkyl group having from 1 to about 4 carbon atoms, $R^7$ in each of the n ($R^7O$) groups is independently $C_2$-$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4;

(j) diamines having the formula:

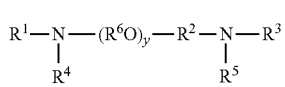

(29)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $C(=NR^{11})NR^{12}R^{13}$—, —$C(=O)NR^{12}R^{13}$—, —$C(=S)NR^{12}R^{13}$—$C(=NR^{12})$—, —$C(S)$— or —$C(O)$—$R^6$ in each of the x $(R^6O)$ and y $(R^6O)$ groups is independently $C_2$-$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60;

(k) mono- or di-quaternary ammonium salts having the formula:

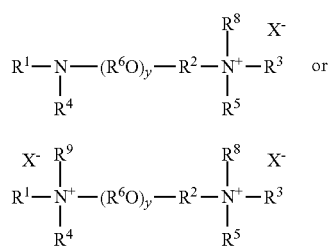

(30)

(31)

wherein $R^1$ $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $R^6$ in each of the x $(R^6O)$ and y $(R^6O)$ groups is independently $C_2$-$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion;

(l) a secondary or tertiary amine having the formula:

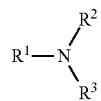

(32)

wherein $R^1$ and $R^2$ are hydrocarbyl having from 1 to about 30 carbon atoms, and $R^3$ is hydrogen or hydrocarbyl having from 1 to about 30 carbon atoms;

(m) monoalkoxylated amines having the formula:

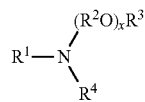

(33)

wherein $R^1$ and $R^4$ are independently hydrocarbyl or substituted hydrocarbyl groups having from 1 to about 30 carbon atoms or —$R^5SR^6$, $R^2$ in each of the x $(R^2O)$ groups is independently $C_2$-$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60;

(n) dialkoxylated quaternary ammonium salts having the formula:

(34)

wherein $R^1$ is hydrocarbyl or substituted hydrocarbyl having from 1 to about 30 carbon atoms, $R^2$ in each of the x $(R^2O)$ and y $(R^2O)$ groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X— is an agriculturally acceptable anion;

(o) monoalkoxylated quaternary ammonium salts having the formula:

(8)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x $(R^2O)$ groups is independently $C_2$-$C_4$ alkylene, $R^3$ is hydrogen, or a linear or branched alkyl group having from 1 to about 30 carbon atoms, x is an average number from 1 to about 60, and X— is an agriculturally acceptable anion;

(p) quaternary ammonium salts having the formula:

(35)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X— is an agriculturally acceptable anion;

(q) etheramines having the formula:

(7)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —(R⁵O)ₓR⁶, R⁵ in each of the x(R⁵—O) groups is independently C₂-C₄ alkylene, R⁶ is hydrogen, or a linear or branched alkyl group having from 1 to about 4 carbon atoms, and x is an average number from 1 to about 50;

(r) diamines having the formula:

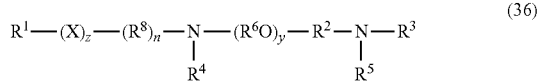
(36)

wherein R¹, R³, R⁴ and R⁵ are independently hydrogen, hydrocarbyl or substituted hydrocarbyl having from 1 to about 30 carbon atoms, or —(R⁶O)ₓR⁷; R² and R⁸ are independently hydrocarbylene or substituted hydrocarbylene having from 2 to about 30 carbon atoms, R⁶ in each of the x (R⁶O) and y (R⁶O) groups is independently C₂-C₄ alkylene, R⁷ is hydrogen, or a linear or branched alkyl group having from 1 to about 30 carbon atoms, x is an average number from 1 to about 30, X is —O—, —N(R⁶)—, —C(O)—, —C(O)O—, —OC(O)—, —N(R⁹)C(O)—, —C(O)N(R⁹)—, —S—, —SO—, or —SO₂—, y is 0 or an average number from 1 to about 30, n and z are independently 0 or 1, and R⁹ is hydrogen or hydrocarbyl or substituted hydrocarbyl;

(s) amine oxides having the formula:

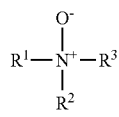
(37)

wherein R¹, R² and R³ are independently hydrogen, hydrocarbyl or substituted hydrocarbyl having from 1 to about 30 carbon atoms, —(R⁴O)ₓR⁵, or —R⁶(OR⁴)ₓOR⁵; R⁴ in each of the x (R⁴ O) groups is independently C₂-C₄ alkylene, R⁵ is hydrogen, or a hydrocarbyl or substituted hydrocarbyl having from 1 to about 30 carbon atoms, R⁶ is a hydrocarbylene or substituted hydrocarbylene having from 1 to about 6 carbon atoms, x is an average number from 1 to about 50, and the total number of carbon atoms in R¹, R² and R³ is at least 8;

(t) alkoxylated amine oxides having the formula:

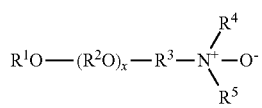
(38)

wherein R¹ is hydrogen or hydrocarbyl or substituted hydrocarbyl having from 1 to about 30 carbon atoms; R² in each of the x (R²O) and y (R²O) groups is independently C₂-C₄ alkylene; R³ is a hydrocarbylene or substituted hydrocarbylene having from 2 to about 6 carbon atoms; R⁴ and R⁵ are each independently hydrogen, hydrocarbyl or substituted hydrocarbyl having from 1 to about 30 carbon atoms, —(R⁶)ₙ—(R²O)ᵧR⁷; R⁶ is hydrocarbylene or substituted hydrocarbylene containing from 1 to about 6 carbon atoms, R⁷ is hydrogen or a linear or branched alkyl group having 1 to about 4 carbon atoms, n is 0 or 1, and x and y are independently an average number from 1 to about 60;

(u) dialkoxylated amines having the formula:

(39)

wherein R¹ is hydrogen or hydrocarbyl or substituted hydrocarbyl having from 1 to about 30 carbon atoms, —R⁴SR⁵, or —(R²O)ᵤR³, R² in each of the x (R²O), y (R²O) and z (R²O) groups is independently C₂-C₄ alkylene, R³ is hydrogen, or a linear or branched alkyl group having from 1 to about 22 carbon atoms, R⁴ is a linear or branched alkyl group having from about 6 to about 30 carbon atoms, R⁵ is a linear or branched alkyl group having from about 4 to about 15 carbon atoms, and x, y and z are independently an average number from 1 to about 40;

(v) aminated alkoxylated alcohols having the following chemical structure:

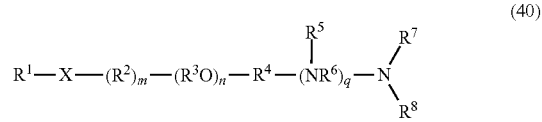
(40)

wherein R¹, R⁷, R⁸, and R⁹ are each independently hydrogen, hydrocarbyl or substituted hydrocarbyl having from 1 to about 30 carbon atoms, or —(R¹¹)ₛ(R³O)ᵥR¹⁰; X is —O—, —OC(O)—, —C(O)O—, —N(R¹²)C(O)—, —C(O)N(R¹²)—, —S—, —SO—, —SO₂— or —N(R⁹)—; R³ in each of the n (R³O) groups and the v (R³O) groups is independently C₂-C₄ alkylene; R¹⁰ is hydrogen, or a linear or branched alkyl group having from 1 to about 30 carbon atoms; n is an average number from 1 to about 60; v is an average number from 1 to about 50; R² and R¹¹ are each independently hydrocarbylene or substituted hydrocarbylene having from 1 to about 6 carbon atoms; R⁴ is hydrocarbylene or substituted hydrocarbylene having from 2 to about 6 carbon atoms; R¹² is hydrogen or hydrocarbyl or substituted hydrocarbyl having from 1 to about 30 carbon atoms; m and s are each independently 0 or 1; R⁶ is hydrocarbylene or substituted hydrocarbylene having from 2 to about 30 carbon atoms, —C(=NR¹²)—, —C(S)—, or —C(O )—; q is an integer from 0 to 5; and R⁵ is hydrogen or hydrocarbyl or substituted hydrocarbyl having from 1 to about 30 carbon atoms;

(w) a quaternary ammonium, sulfonium or sulfoxonium salt having the following chemical structure:

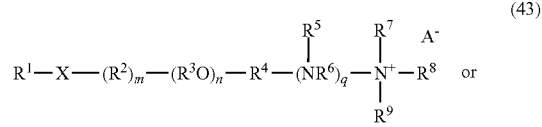
(43)

or

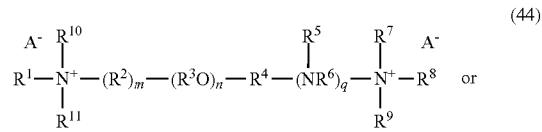
(44)

or

-continued

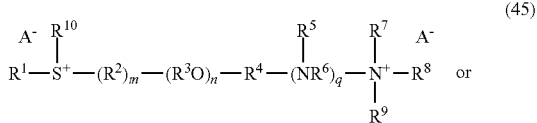
(45)

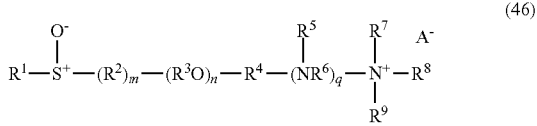
(46)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or $-(R^{13})_s(R^3O)_vR^{12}$; X is $-O-$, $-OC(O)-$, $-N(R^{14})C(O)-$, $-C(O)N(R^{14})-$, $-C(O)O-$, or $-S-$; $R^3$ in each of the n $(R^3O)$ groups and v $(R^3O)$ groups is independently $C_2$-$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, $-C(=NR^{12})-$, $-C(S)-$, or $-C(O)-$; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each $A^-$ is an agriculturally acceptable anion;

(x) a diamine or diammonium salt having the formula:

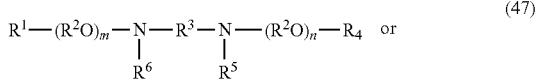
(47)

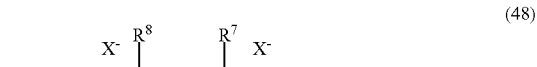
(48)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m $(R^2O)$ and n $(R^2O)$ groups and $R^9$ are independently $C_2$-$C_4$ alkylene, $R^3$ is hydrocarbylene or substituted hydrocarbylene having from about 2 to about 6 carbon atoms or $-(R^2O)_pR_9-$, m and n are individually an average number from 0 to about 50, and p is an average number from 0 to about 60;

(y) an alkoxylated alcohol having the formula:

$$R^1O-(R^2O)_xR^3 \quad (49)$$

wherein $R^1$ is hydrocarbyl or substituted hydrocarbyl having from 1 to about 30 carbon atoms, $R^2$ in each of the x $(R^2O)$ groups is independently $C_2$-$C_4$ alkylene, $R^3$ is hydrogen, or a linear or branched alkyl group having from 1 to about 4 carbon atoms, and x is an average number from 1 to about 60;

(z) dialkoxylated alcohols having the formula:

$$R^1(OR^2)_xO-R^3-O-(R^2O)_yR^1 \quad (50)$$

wherein $R^1$ is independently hydrogen, or a linear or branched alkyl group having from 1 to about 4 carbon atoms, $R^2$ in each of the x $(R^2O)$ and the y $(R^2O)$ groups is independently $C_2$-$C_4$ alkylene, $R^3$ is hydrocarbylene or substituted hydrocarbylene having from 2 to about 30 carbon atoms, and x and y are independently an average number from 1 to about 60;

(aa) alkoxylated dialkylphenols having the formula:

(51)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x $(R^2O)$ groups is independently $C_2$-$C_4$ alkylene, $R^3$ is hydrogen, or a linear or branched alkyl group having from 1 to about 4 carbon atoms, and x is an average number from 1 to about 60;

(bb) a compound of the formula:

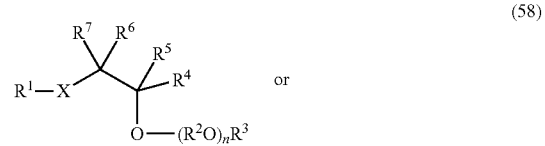
(58)

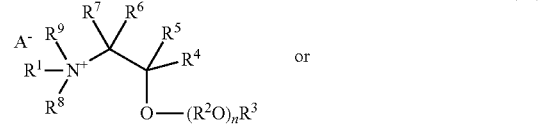
(59)

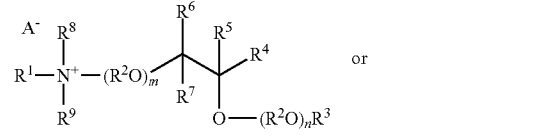
(60)

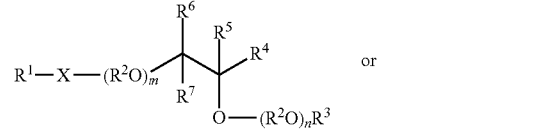
(61)

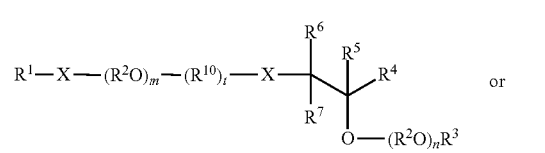
(62)

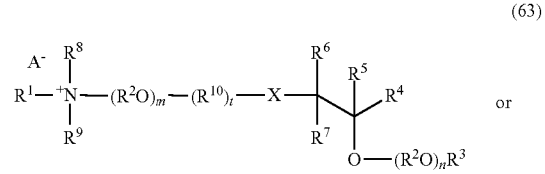
(63)

-continued (64)

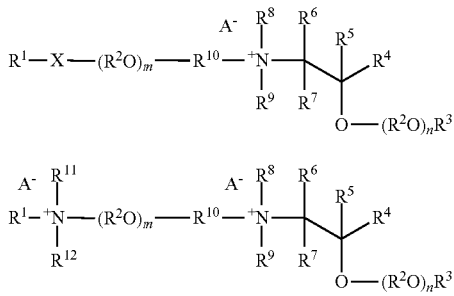

(65)

wherein $R^1$, $R^9$, and $R^{12}$ are independently hydrocarbyl or substituted hydrocarbyl having from 1 to about 30 carbon atoms, or —$(R^2O)_pR^{13}$; $R^2$ in each of the m $(R^2O)$, n $(R^2O)$, p $(R^2O)$ and q $(R^2O)$ groups is independently $C_2$-$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is —$(CH_2)_yOR^{13}$ or —$(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrogen, hydrocarbyl or substituted hydrocarbyl having from 1 to about 30 carbon atoms, or —$(CH_2)_zO(R^2O)_pR^3$; m, n, p and q are independently an average number from 1 to about 50; X is independently —O—, —N($R^{14}$)—, —C(O)—, —C(O)O—, —OC(O)—, —N($R^{15}$)C(O)—, —C(O)N($R^{15}$)—, —S—, —SO—, or —SO$_2$—; t is 0 or 1; A- is an agriculturally acceptable anion; and y and z are independently an integer from 0 to about 30;

(cc) an N-acyl sarcosinate having the formula:

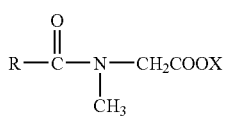

(70)

wherein R is $C_8$ to $C_{22}$ N-acyl, preferably a fatty acid of chain length $C_{10}$ to $C_{18}$, and X is an agriculturally acceptable anion;

(dd) a glycoside having the formula:

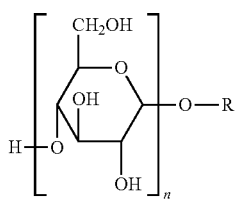

(71)

wherein n is the degree of polymerization, or number of glycose groups, and R is a branched or straight chain alkyl group preferably having from 4 to 18 carbon atoms, or a mixture of alkyl groups having an average value within the given range; or (ee) a polysiloxane having the formula:

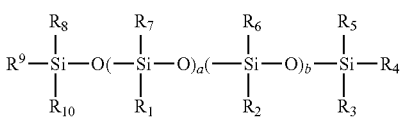

(72)

wherein $R^1$ is —$C_nH_{2n}O(CH_2CH_2O)_m(CH_2CH(CH_3)O)_qX$, n is 0 to 6, a is 0 to about 100, b is 0 to about 10, m is 0 to about 30, q is 0 to about 30, X is hydrogen or a $C_{1-20}$ hydrocarbyl or $C_{2-6}$ acyl group, and $R_2$, $R_3$, $R_4$, $R_5$, $R_6$, $R_7$, $R_8$, $R_9$, $R_{10}$ groups are independently substituted or unsubstituted $C_{1-20}$ hydrocarbyl or nitrogen containing groups;

(ff) a compound having the formula:

$$R_1O(R_2O)_nX_1 \qquad (57)$$

wherein $R_1$ is a hydrocarbyl group having from about 8 to about 22 carbon atoms, each of the n $(R_2O)$ groups is independently $C_2$-$C_4$ alkylene, n is a number from 0 to about 60, and $X_1$ is a carboxylate, sulfate or phosphate;

(gg) a phosphate diester having the formula:

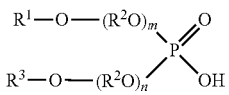

(6)

wherein $R^1$ and $R^3$ are independently a linear or branched alkyl, linear or branched alkenyl, linear or branched alkynyl, aryl, or aralkyl group having from about 4 to about 30 carbon atoms; $R^2$ in each of the m ($R^2$ O) and the n ($R^2$O) groups is independently $C_2$-$C_4$ alkylene; and m and n are independently from 1 to about 30; and (hh) a phosphate ester having the formula:

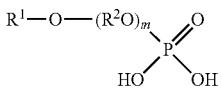

(5)

wherein $R^1$ is a linear or branched alkyl, linear or branched alkenyl, linear or branched alkynyl, aryl, or aralkyl group having from about 4 to about 30 carbon atoms; $R^2$ in each of the m ($R^2$ O) groups is independently $C_2$-$C_4$ alkylene; and m is from 1 to about 30; and (ii) an anionic surfactant selected from the group consisting of fatty soaps, alkyl sulfates, sulfated oils, ether sulfates, sulfonates, sulfosuccinates, sulfonated amides and isethionates.

58. A composition as set forth in claim 57 wherein:
the cationic surfactant is selected from the group consisting of an alkylamine, an alkyl diamine, an alkyl polyamine, a mono- or di-quaternary ammonium salt, a monoalkoxylated amine, a dialkoxylated amine, a monoalkoxylated quaternary ammonium salt, a dialkoxylated quaternary ammonium salt, an etheramine, an amine oxide, an alkoxylated amine oxide, and a fatty imidazoline; and
the nonionic surfactant is selected from the group consisting of an alkoxylated alcohol, a dialkoxylated alcohol, an alkoxylated dialkylphenol, an alkylpolyglycoside, an alkoxylated alkylphenol, an alkoxylated glycol, an alkoxylated mercaptan, a glyceryl or polyglyceryl ester of a natural fatty acid, an alkoxylated glycol ester, an alkoxylated fatty acid, an alkoxylated alkanolamide, a polyalkoxylated silicone, and an N-alkyl pyrrolidone.

59. A method of enhancing control of susceptible plants in a plurality of areas comprising:
providing an enhancer component source, wherein the enhancer component source is a disodium oxalate or diammonium oxalate source, or mixture thereof, for use in preparing the enhanced application mixture of claim 38, wherein the enhanced application mixture comprises a glyphosate component and the enhancer component source for application to a plurality of areas for control of susceptible plants therein;
wherein other application mixtures previously administered to said areas have comprised a glyphosate component in the absence of any enhancer component source.

60. A method as set forth in claim 59 further comprising determining the concentration of the glyphosate component and the ratio of the enhancer component source to said glyphosate component in said enhanced application mixture that are estimated to provide a desired degree of control of said susceptible plants when administered at a defined volumetric rate, wherein said estimated degree of control is enhanced with respect to the degree of control provided by administration at said defined rate of a reference mixture otherwise identical to said enhanced application mixture but devoid of enhancer component source.

61. A method of controlling susceptible plants comprising supplying a disodium oxalate or diammonium oxalate source, or a mixture thereof, for use in preparing the aqueous pesticide composition of claim 47 for application to said susceptible plants, wherein the water-soluble pesticide comprises glyphosate or a salt or ester thereof and the enhancer component, said enhanced application mixture comprising glyphosate anions in a proportion between 0.01% and about 3% by weight and conjugate anions of said disodium oxalate or diammonium oxalate source or mixture thereof, in a proportion between about 2% by weight and the maximum percent by weight dictated by the solubility of the disodium oxalate or diammonium oxalate source or mixture thereof.

62. A method for controlling susceptible plants in an area containing said susceptible plants and containing a growing crop of glyphosate tolerant plants of value or having been planted with or designated for planting with seeds for glyphosate tolerant plants comprising:
applying the enhanced application mixture of claim 38 wherein the water-soluble pesticide component comprises glyphosate acid or a salt or ester thereof.

63. A method as set forth in claim 62 wherein the molar ratio of said glyphosate to said disodium oxalate, diammonium oxalate or mixture thereof in said enhanced application mixture is between about 0.1 and about 16.

64. A method as set forth in claim 62 wherein said enhanced application mixture contains between about 0.01% and about 3% by weight of said glyphosate on an acid equivalent basis.

65. A method for controlling susceptible plants with the aqueous pesticidal composition of claim 47, wherein the water-soluble pesticide component comprises glyphosate or a salt or ester thereof, the method comprising:
obtaining a disodium oxalate or diammonium oxalate source or a mixture thereof;
obtaining a glyphosate source comprising glyphosate acid or a salt or ester thereof;
mixing said disodium oxalate or diammonium oxalate source, or a mixture thereof, said glyphosate source and water to produce the enhanced application mixture containing
between about 0.01% and about 3% by weight, on a glyphosate acid equivalent basis, of said glyphosate source; and
applying said enhanced application mixture to the susceptible plants to be controlled.

66. A method for controlling susceptible plants with the enhanced application mixture of claim 38, wherein the water soluble pesticide component is a glyphosate component, the method comprising:
determining the concentration of the glyphosate component and ratio of the disodium oxalate, diammonium oxalate, or mixture thereof, to said glyphosate component in an enhanced application mixture whose administration at a defined volumetric rate is estimated to provide a desired degree of control of said susceptible plants, wherein said estimated degree of control is enhanced with respect to the degree of control provided by administration at said defined rate of a reference mixture otherwise identical to said enhanced application mixture but devoid of disodium oxalate, diammonium oxalate, or mixture thereof, said glyphosate component comprising glyphosate acid or a salt or ester thereof; and
applying said enhanced application mixture to the susceptible plants to be controlled.

67. A method as set forth in claim 66 wherein said degree of control is estimated from a known relationship for determining the efficacy of enhanced application mixtures containing a glyphosate component and disodium oxalate, diammonium oxalate, or mixture thereof in controlling said susceptible plants as a function of: (i) the ratio of glyphosate component to disodium oxalate, diammonium oxalate, or mixture thereof in such enhanced application mixtures; and (ii) the absolute rate of application of glyphosate contained in such enhanced application mixtures per unit area.

68. A method for preparation of the pesticidal composition of claim 47 comprising:
milling a disodium oxalate or diammonium oxalate source, or mixture thereof to produce a refined source of disodium oxalate, diammonium oxalate, or mixture thereof of reduced average particle size; and
transporting said refined source of disodium oxalate, diammonium oxalate, or mixture thereof to a mixing site for mixing of said refined source of disodium oxalate, diammonium oxalate, or mixture thereof with the water-soluble pesticide wherein the water-soluble pesticide comprises a glyphosate source comprising glyphosate acid or a salt or ester thereof.

69. A composition as set forth in claim 3 wherein the enhancer component comprises the diammonium salt of oxalic acid.

70. A composition as set forth in claim 34 wherein the enhancer component comprises the diammonium salt of oxalic acid.

71. A composition as set forth in claim 35 wherein the enhancer component comprises the diammonium salt of oxalic acid.

72. A composition as set forth in claim 36 wherein the enhancer component comprises the diammonium salt of oxalic acid.

73. A composition as set forth in claim 38 wherein the enhancer component comprises the diammonium salt of oxalic acid.

74. A composition as set forth in claim 47 wherein the enhancer component comprises the diammonium salt of oxalic acid.

75. A solid pesticidal concentrate composition that is biologically effective to control growth of a susceptible plant when the composition is diluted in water to form an enhanced application mixture and applied to the foliage of a susceptible plant, comprising:
- a herbicidal component consisting essentially of water soluble herbicides in a concentration greater than 30% by weight;
- a surfactant component being selected from the group consisting of cationic surfactants, nonionic surfactants, amphoteric surfactants, and mixtures thereof; and
- an efficacy enhancer component comprising a dicarboxylic acid or an anhydride, ester, amide, halide, salt or precursor thereof;
- the molar ratio of said herbicidal component to said enhancer component being between 1.1 and about 16 on an acid equivalent basis.

76. A composition as set forth in claim 75 wherein said herbicidal component comprises a glyphosate component comprising glyphosate acid or an ester or salt thereof in a concentration greater than 30% by weight on an acid equivalent basis; and said enhancer component comprises oxalic acid, malonic acid, succinic acid, malic acid, tartaric acid, fumaric acid, maleic acid, glutaric acid, dimethylglutaric acid, adipic acid, trimethyladipic acid, pimelic acid, tartronic acid, suberic acid, azelaic acid, sebacic acid, 1,12-dodecanedioic acid, 1,13-tridecanedioic acid, glutamic acid, phthalic acid, isophthalic acid, or terephthalic acid, an anhydride, ester, amide, halide, salt or precursor of any of said acids or mixtures of any of said acids, anhydrides, esters, amides, halides, salts or precursors; the molar ratio of said glyphosate component to said dicarboxylic acid component being between about 0.18 and about 16 on an acid equivalent basis.

77. A composition as set forth in claim 76 wherein the enhancer component comprises oxalic acid or an anhydride, ester, amide, halide, salt or precursor thereof.

78. A composition as set forth in claim 76 wherein the molar ratio of said herbicidal component to said enhancer component being between 2 and about 16 on an acid equivalent basis.

* * * * *